US009657050B2

(12) United States Patent
Matsuo et al.

(10) Patent No.: US 9,657,050 B2
(45) Date of Patent: May 23, 2017

(54) ENA NUCLEIC ACID PHARMACEUTICALS CAPABLE OF MODIFYING SPLICING OF MRNA PRECURSORS

(71) Applicants: DAIICHI SANKYO COMPANY, LIMITED, Tokyo (JP); Masafumi Matsuo, Kobe (JP); Yasuhiro Takeshima, Nishinomiya (JP); Orphan Disease Treatment Institute Co., Ltd., Tokyo (JP)

(72) Inventors: Masafumi Matsuo, Kobe (JP); Yasuhiro Takeshima, Nishinomiya (JP); Makoto Koizumi, Tokyo (JP)

(73) Assignees: Matsuo Masafumi, Kobe-shi (JP); Takeshima Yasuhiro, Nishinomiya (JP); Daiichi Sankyo Company, Limited, Tokyo (JP); Orphan Disease Treatment Institute Co., Ltd., Tokyo (JP)

( * ) Notice: Subject to any disclaimer, the term of this patent is extended or adjusted under 35 U.S.C. 154(b) by 0 days.

(21) Appl. No.: 14/858,404

(22) Filed: Sep. 18, 2015

(65) Prior Publication Data

US 2016/0002636 A1    Jan. 7, 2016

Related U.S. Application Data

(62) Division of application No. 14/258,663, filed on Apr. 22, 2014, now Pat. No. 9,243,026, which is a division of application No. 13/673,466, filed on Nov. 9, 2012, which is a division of application No. 12/847,237, filed on Jul. 30, 2010, now Pat. No. 8,624,019, which is a division of application No. 10/536,258, filed as application No. PCT/JP03/14915 on Nov. 21, 2003, now Pat. No. 7,902,160.

(30) Foreign Application Priority Data

Nov. 25, 2002 (JP) .................. 2002-340857
Jul. 31, 2003  (JP) .................. 2003-204381

(51) Int. Cl.
  C07H 21/02    (2006.01)
  C07H 21/04    (2006.01)
  C12N 15/113   (2010.01)
  A61K 38/00    (2006.01)
  A61K 48/00    (2006.01)

(52) U.S. Cl.
  CPC .......... *C07H 21/04* (2013.01); *C12N 15/113* (2013.01); *A61K 38/00* (2013.01); *A61K 48/00* (2013.01); *C12N 2310/11* (2013.01); *C12N 2310/3231* (2013.01); *C12N 2320/33* (2013.01)

(58) Field of Classification Search
  None
  See application file for complete search history.

(56) References Cited

U.S. PATENT DOCUMENTS

| 5,525,470 A | * | 6/1996 | Cohen ............... C12Q 1/6869 |
| | | | 435/6.1 |
| 5,853,990 A | * | 12/1998 | Winger ................ C07H 21/00 |
| | | | 435/6.1 |
| 6,653,467 B1 | | 11/2003 | Matsuo et al. |
| 7,902,160 B2 | | 3/2011 | Matsuo et al. |
| 2001/0056077 A1 | | 12/2001 | Matsuo et al. |
| 2002/0055481 A1 | | 5/2002 | Matsuo et al. |
| 2003/0219770 A1 | | 11/2003 | Eshleman et al. |
| 2003/0235845 A1 | | 12/2003 | van Ommen et al. |
| 2008/0209581 A1 | | 8/2008 | van Ommen et al. |
| 2009/0228998 A1 | | 9/2009 | van Ommen et al. |

FOREIGN PATENT DOCUMENTS

| EP | 1 054 058 | 11/2000 |
| EP | 1 054 058 A1 | 11/2000 |
| EP | 1 152 009 | 11/2001 |
| EP | 1 160 318 | 12/2001 |
| EP | 1 191 097 A1 | 3/2002 |
| EP | 1 191 098 | 3/2002 |
| JP | 2000-297097 | 10/2000 |
| JP | 2000-325085 A | 11/2000 |
| JP | 2002-10790 A | 1/2002 |
| JP | 2002-325582 A | 11/2002 |
| WO | WO 93/20227 A1 | 10/1993 |
| WO | 00/47599 | 8/2000 |
| WO | WO 01/36443 A1 | 5/2001 |
| WO | WO 02/02406 A1 | 3/2002 |
| WO | WO 02/024906 A1 | 3/2002 |
| WO | WO 2004/083432 A1 | 9/2004 |
| WO | WO 2004/083446 A2 | 9/2004 |

OTHER PUBLICATIONS

Morita et al (Nucl. Acids Res. Supp. No. 1 pp. 241-242, 2001).*
Journal Clinical Rehabilitation., vol. 12, No. 10 (Oct. 2003) p. 900-906.
Judith C. T. Van Deutekom, et al., Antisense-induced exon skipping restores dystrophin expression in DMD patient derived muscle cells, Human Molecular Genetics, (2001), vol. 10, No. 15, 1547-1554.
Masafumi Matsuo, "Duchenne and Becker Muscular Dystrophy: From Gene Diagnosis to Molecular Therapy", IUBMB Life, vol. 53, No. 3 (Mar. 2002), p. 147-152.
Yasuhiro Takeshima, et al., "Oligonucleotides against a splicing enhancer sequence led to dystrophin production in muscle cells from a Duchenne muscular dystrophy patient", Brain & Development, vol. 23, No. 8 (2001), p. 788-790.
Zacharias Aloysius Dwi Pramono, et al., "Induction of Exon Skipping of the Dystrophin Transcript in Lymphoblastoid Cells by Transfecting an Antisense Oligodeoxynucleotide Complementary to an Exon Recognition Sequence", Biochemical and Biophysical Research Communications, vol. 226, No. 2 (1996), p. 445-449.

(Continued)

*Primary Examiner* — Richard Schnizer
(74) *Attorney, Agent, or Firm* — Oblon, McClelland, Maier & Neustadt, L.L.P.

(57) ABSTRACT

Oligonucleotides having a nucleotide sequence complementary to nucleotide numbers such as 2571-2607, 2578-2592, 2571-2592, 2573-2592, 2578-2596, 2578-2601 or 2575-2592 of the dystrophin cDNA (Gene Bank accession No. NM_004006.1) and therapeutic agents for muscular dystrophy comprising such oligonucleotides.

18 Claims, 22 Drawing Sheets

(56) References Cited

OTHER PUBLICATIONS

Koji Morita, et al., 2'-O,4'-C-Ethylene-Bridged Nucleic Acids (ENA): Highly Nuclease-Resistant and Thermodynamically Stable Oligonucleotides for Antisense Drug, Bioorganic & Medicinal Chemistry Letters, vol. 12, No. 1 (Jan. 2002), p. 73-76.
Agus Surono et al.: "Circular dystrophin RNAs consisting of exons that were skipped by alternative splicing", Human Molecular Genetics, vol. 8, No. 3, pp. 493-500, 1999.
Harding, PL, et al., "The Influence of Antisense Oligonucleotide Length on Dystrophin Exon Skipping," Molecular Therapy, vol. 15, No. 1, Jan. 2007, pp. 157-166, XP009101408.
Annemieke Aartsma-Rus, et al., "Targeted exon skipping as a potential gene correction therapy for Duchenne muscular dystrophy", Neuromuscular Disorders 12 (2002) S71-S77.
Bremmer-Bout (Mol. Ther. 10(2): 232-240, 2004).
Gebski et al (Hum. Mol. Gen. 12(15): 1801-1811, 2003).
Lu et al (Nature Medicine 9(8) 1009-1014, 2003).
Yokota et al. (Ann. Neurol. 65; 667-676, 2009).
Wahlestedt et al (Proc. Nat. Acad. Sci. USA (May 9, 2000) vol. 97, No. 10, pp. 5633-5638).
Book of reports about studies conducted by the grants for commission of studies on mental and nerve diseases from Ministry of Health, Labour and Welfare on 2002, (Jul. 28, 2003), p. 590 (w/partial English translation).
Matsuo (Brain and Dev. 18: 167-172, 1996).
Fernada Gabriella De Angelis, et al., "Chimeric snRNA molecules carrying antisense sequences against the splice junctions of exon 51 of the dystrophin pre-mRNA induce exon skipping and restoration of a dystrophin synthesis in Δ48-50 DMD cells", PNAS, vol. 99, No. 14, (Jul. 2002), p. 9456-61.
Christopher J. Mann, et al., "Antisense-induced exon skipping and synthesis of dystrophin in the mdx mouse", PNAS, vol. 98, No. 1 (2001),p. 42-47.
Christopher J. Mann, et al., "Improved antisense oligonucleotide induced exon skipping in the mdx mouse model of muscular dystrophy", The Journal of Gene Medicine, vol. 4, No. 6 (Nov.-Dec. 2002), p. 644-654.
D-H. Chen et al.: "A novel deletion of the dystrophin S-promoter region cosegregating with metal", Neurology, vol. 52, pp. 638-640, 1999.
Suryono Yudha Patria et al.: "A simple explanation for a case of incompatibility with the reading frame theory in Duchenne muscular dystrophy: failure to detect an aberrant restriction fragment in Southern blot analysis", Brain & Development, vol. 21, pp. 386-389, 1999.
Yasuhiro Takeshima et al.: "Molecular genetics and problems found in genetic diagnosis of Duchenne/Becker muscular dystrophy", Nihon Rinsho, vol. 55, No. 12, pp. 3120-3125, 1997.
Masafumi Matsuo et al.: "Gene Diagnosis in the Field of Child Neurology: Introductory Remarks", No To Hattatsu, vol. 30, pp. 121-122, 1998.
Surono, A., et al., "Chimeric RNA/Ethylene-Bridged Nucleic Acids Promote Dystrophin Expression in Myocytes of Duchenne Muscular Dystrophy by Inducing Skipping of the Nonsense Mutation-Encoding Exon," Human Gene Therapy, vol. 15, Aug. 2004, pp. 749-757, XP009101403.
Zacharias Aloysius Dwi Pramono et al.: "A Novel Cryptic Exon in Intron 2 of the Human Dystrophin Gene Evolved from an Intron by Acquiring Consensus Sequences for Splicing at Different Stages of Anthropoid Evolution", Biochemical and Biophysical Research Communications, vol. 267, No. 1, pp. 321-328, 2000.
Chieko Ishigaki et al.: Early cardiac failure in a child with Becker muscular dystrophy is due to an abnormally low amount of dystrophin transcript lacking exon 13, Acta Paediatrica Japonica, vol. 39, pp. 685-689, 1997.
Masanori Ino-Ue et al.: "Genotype and Electroretinal Heterogeneity in Duchenne Muscular Dystrophy", Exp. Eye Res., vol. 65, pp. 861-864, 1997.
N. Tachi et al.: "Deficiency of syntrophin, dystroglycan, and merosin in a female infant with a congenital muscular dystrophy phenotype lacking cysteine-rich and C-terminal domains of dystrophin", Neurology, vol. 49, pp. 579-583, 1997.
Nobuyuki Shiga et al.: "Study on Mutations Affecting the Muscle Promoter/First Exon of the Dystrophin Gene in 92 Japanese Dilated Cardiomyopathy Patients", American Journal of Medical Genetics, vol. 79, pp. 226-227, 1998.
Nobuyuki Shiga et al.: "Disruption of the Splicing Enhancer Sequence within Exon 27 of the Dystrophin Gene by a Nonsense Mutation Induces Partial Skipping of the Exon and Is Responsible for Becker Muscular Dystrophy", J. Clin. Invest., vol. 100, No. 9, pp. 2204-2210, Nov. 1997.
Takeshima, et al., Intravenous Infusion of an Antisense Oligonucleotide Results in Exon Skipping in Muscle Dystrophin mRNA of Duchenne Muscular Dystrophy, Pediatric Research, vol. 59, No. 5, 2006, pp. 690-694.
Scheuerbrandt, "Research Approaches for a Therapy of Duchenne Muscular Dystrophy", Parent Project Muscular Dystrophy, action duchenne, TREAT-NMD, pp. 1-20, Apr. 30, 2009, http://www.cureduchenne.org/2009/05/research-approaches-for-a-therapy-of-duchenne-muscular-dystrophy/.
Beroud, et al., "Multiexon Skipping Leading to an Artifical DMD Protein Lacking Amino Acids from Exons 45 Through 55 Could Rescue Up to 63% of Patients With Duchenne Muscular Dystrophy", Human Mutation, 28(2), pp. 196-202, 2007.
Van Deutekom, "Local Dystrophin Restoration with Antisense Oligonucleotide PRO051", The New England Journal of Medicine, vol. 357; 26, pp. 2677-2686, 2007.
Agus Surono et al.: "Six Novel Transcripts That Remove a huge Intron Ranging from 250 to 800 kb Are Produced by Alternative Splicing of the 5' Region of the Dystrophin Gene in Human Skeletal Muscle", Biochemical and Biophysical Research Communications, vol. 239, No. 3, pp. 895-899, 1997.
Yasuhiro Takeshima, et al., "Molecular Therapy for Duchenne Muscular Dystrophy", J. Clin. Rehabil., vol. 12, No. 10, Oct. 2003, pp. 900-906 previously filed submitting English translation only.
Buck et al. (Biotechniques, 1999, 27:528-536).
GenBank Accession M18533 (2000).
Extended European Search Report Issued Aug. 2, 2012 in Patent Application No. 11155689.0.
Annemieke Aartsma-Rus et al., "Functional analysis of 114 Exon-Internal AON's for Targeted DMD Exon Skipping: Indication for Steric Hindrance of SR Protein Binding Sites", Oligonucleotides, XP002406791, vol. 15, No. 4, 2005, pp. 284-297.
Jun-ichi Asakawa et al., "Accurate Detection of Heterozygous Carriers of a Deletion or a Duplication by Combined PCR and HPLC", Tanpakushitsu Kakusan Koso. Protein, Nucleic Acid, Enzyme, XP009158480, vol. 38, No. 16, 1993, pp. 2723-2727.
Rebecca J. Gardner et al., "The Identification of Point Mutations in Duchenne Muscular Dystrophy Patients by Using Reverse-Transcription PCR and the Protein Truncation Test", American Journal of Human Genetics, XP002673980, vol. 57, No. 2, 1995, pp. 311-320.
Luciana C. B. Dolinsky, "Denaturing Gradient Gel Electrophoresis (DGGE) for Mutation Detection in Duchenne Muscular Dystrophy (DMD)", Methods in Molecular Biology, XP002673981, vol. 217, 2003, pp. 165-175.
Judith C. T. van Deutekom et al., "Advances in Duchenne Muscular Dystrophy Gene Therapy", Nature Reviews Genetics, XP002993824, vol. 4, Oct. 2003, pp. 774-783.
Extended European Search Report issued Feb. 11, 2010, in Application No. 09011130.3-2404/2135948.
Office Action issued Jan. 17, 2011, in Canada Patent Application No. 2,507,125.
Yasuhiro Takeshima, et al., "Modulation of in Vitro Splicing of the Upstream Intron by Modifying an Intra-Exon Sequence Which is deleted from the Dystrophln Gene in Dystrophin Kobe", Journal of Clinical Investigation, American Society for Clinical Investigation, vol. 95, No. 2, XP-000939311, Feb. 1, 1995, 6 pages.
Elizabeth M. McNally, et al., "Mild and Severe Muscular Dystrophy Caused by a Single γ-Sarcoglycan Mutation", American Journal of Human Genetics, vol. 59, No. 5, XP009128432, Nov. 1996, pp. 1040-1047.

(56) References Cited

OTHER PUBLICATIONS

K. E. Wells et al., "Enhanced in vivo delivery of antisense oligonucleotides to restore dystrophin expression in adult mdx mouse muscle", FEBS Letters, XP004460888, vol. 552, No. 2-3, 2003, pp. 145-149.

* cited by examiner

SEQUENCE LISTING

```
<160> NUMBER OF SEQ ID NOS: 217

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcctgagctg atctgctggc atcttgcagt t                                       31

<210> SEQ ID NO 2
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 2
gatctgctgg catct                                                         15

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatctgctgg catcttgcag tt                                                 22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agctgatctg ctggcatct                                                     19

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcctgagctg atctgctggc atct                                               24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatctgctgg catcttgcag                                                    20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatctgctgg catcttgc                                                      18

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
gcatgctcaa gaggaacttc c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tagcaactgg cagaattcga t                                              21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agttgagtct tcgaaactga gca                                            23

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaactgagca aatttgct                                                  18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgagtcttc aaaactga                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgcaaagtt gagtcttc                                                  18

<210> SEQ ID NO 14
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
gccgctgccc aatgc                                                      15

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgctgcccaa tgccatcc                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagtttgccg ctgcccaa                                                   18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgttctgaca acagtttg                                                   18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcttttcttt tagttgctgc                                                 20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttttagttg ctgctctttt cc                                              22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 20 tttccaggt tcaagtgg                                                        18

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgcttcctc caacc                                                          15

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gttatctgct tcctccaacc                                                     20

<210> SEQ ID NO 23
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cugcuuccuc caacc                                                          15

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
guuaucugcu uccuccaacc                                                     20

<210> SEQ ID NO 25
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcuuuucuuu uaguugcugc                                                     20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggtatcagta caagaggcag gctg                                    24

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cacttctaat agggcttgtg                                         20

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgaacagt ttctcagaaa gacacaa                                 27

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tccactggag atttgtctgc                                         20

<210> SEQ ID NO 30
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 30
gaaaacgccg ccatuuct                                           18

<210> SEQ ID NO 31
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 31
ctgutagcca ctgattaa                                           18

<210> SEQ ID NO 32
<211> LENGTH: 18

```
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 32
tgagaaactg tucagcut                                                   18

<210> SEQ ID NO 33
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 33
caggaattug tgucuutc                                                   18

<210> SEQ ID NO 34
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 34
gtauttagca tgutccca                                                   18

<210> SEQ ID NO 35
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 35
agcatgttcc caatuctc                                                   18

<210> SEQ ID NO 36
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 36
gccgccatuu cucaacag                                                   18

<210> SEQ ID NO 37
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cataatgaaa acgccgcc                                                  18

<210> SEQ ID NO 38
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 38
tucccaatuc tcaggaat                                                  18

<210> SEQ ID NO 39
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 39
ccautugtau ttagcatg                                                  18

<210> SEQ ID NO 40
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 40
ctcagatcuu ctaacuuc                                                  18

<210> SEQ ID NO 41
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 41
accgcctucc actcagag                                                  18

<210> SEQ ID NO 42
<211> LENGTH: 18
<212> TYPE: DNA
```

```
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 42
tcttgaagta aacggtut                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 43
ggctgcttug ccctcagc                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agtccaggag ctaggtca                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gctccaatag tggtcagt                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 46
gctaggtcag gctgcttu                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
```

```
<223> OTHER INFORMATION: Description of Artificial Sequence: Synthetic
      oligonucleotide

<400> SEQUENCE: 47
gcagccuctc gctcactc                                                    18

<210> SEQ ID NO 48
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 48
tcuuccaaag cagccuct                                                    18

<210> SEQ ID NO 49
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 49
tgcagtaatc uatgagtt                                                    18

<210> SEQ ID NO 50
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 50
gttucagcut ctgtaagc                                                    18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgtaggacat tggcagtt                                                    18

<210> SEQ ID NO 52
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide
```

```
<400> SEQUENCE: 52
tccttacggg tagcaucc                                                 18

<210> SEQ ID NO 53
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 53
agctcututa ctcccttg                                                 18

<210> SEQ ID NO 54
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 54
ccautgutuc aucagctc                                                 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctatgagttt cttccaaa                                                 18

<210> SEQ ID NO 56
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 56
tgtgtcacca gaguaacagt                                               20

<210> SEQ ID NO 57
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 57
```
aggttguguc accagagtaa                                           20

<210> SEQ ID NO 58
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 58
agtaaccaca gguugtgtca                                           20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttgatcaagc agagaaagcc                                           20

<210> SEQ ID NO 60
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 60
cacccucugu gauuutataa                                           20

<210> SEQ ID NO 61
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 61
acccaccauc acccuctgtg                                           20

<210> SEQ ID NO 62
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 62
cctcaagguc acccaccatc                                           20

<210> SEQ ID NO 63
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 63
taacagucug aguaggag                                                 18

<210> SEQ ID NO 64
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 64
ggcatuucua guutggag                                                 18

<210> SEQ ID NO 65
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 65
agccagucgg uaagttct                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 66
agtttggaga uggcagtt                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 67

-continued ctgattctga attcuutc                                                                                     18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcttgtact tcatccca                                                                                     18

<210> SEQ ID NO 69
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 69
ccuccggttc tgaaggtg                                                                                     18

<210> SEQ ID NO 70
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 70
cattucautc aactgttg                                                                                     18

<210> SEQ ID NO 71
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 71
ttccttagct uccagcca                                                                                     18

<210> SEQ ID NO 72
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 72
taagacctgc tcagcutc                                                                                     18

```
<210> SEQ ID NO 73
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 73
cttggctctg gcctgucc                                                 18

<210> SEQ ID NO 74
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 74
ctcctuccat gactcaag                                                 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctgaaggtgt tcttgtac                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttccagccat tgtgttga                                                 18

<210> SEQ ID NO 77
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 77
ctcagctuct tccttagc                                                 18

<210> SEQ ID NO 78
<211> LENGTH: 18
<212> TYPE: DNA
<213> ORGANISM: Artificial Sequence
```

<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 78
gcttcutccu tagcutcc                                                  18

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tagtctacaa caaagctcag gt                                             22

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cttccccagt tgcattcaat                                                20

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caaggagaaa ttgaagctca a                                              21

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgatccgtaa tgattgttct agc                                            23

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tggacagaac ttaccgactg g                                              21

<210> SEQ ID NO 84
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggcggaggtc tttggccaac                                              20

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaggattcaa cacaatggct gg                                           22

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtaacaggac tgcatcatcg                                              20

<210> SEQ ID NO 87
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 87
ggcattucta guttggag                                                18

<210> SEQ ID NO 88
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 88
agtutggaga tggcagtt                                                18

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
```
tgagtcttcg                                                          10

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttgagtcttc g                                                        11

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gttgagtctt cg                                                       12

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gcaaatttgc                                                          10

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcaaatttgc t                                                        11

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttgagtcttc                                                          10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgctgcccaa                                                          10

```
<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gttctgacaa                                                          10

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgttctgaca a                                                        11

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccgctgccca                                                          10

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ccgctgccca a                                                        11

<210> SEQ ID NO 100
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttttagttg ctgc                                                     14

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gttgctgctc                                                          10
```

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
agttgctgct c                                                          11

<210> SEQ ID NO 103
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tagttgctgc tc                                                         12

<210> SEQ ID NO 104
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ttagttgctg ctc                                                        13

<210> SEQ ID NO 105
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tttagttgct gctc                                                       14

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ttttagttgc tgctc                                                      15

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cttttagttg ctgctc                                                     16

-continued

```
<210> SEQ ID NO 108
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aggttcaagt                                                            10

<210> SEQ ID NO 109
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aggttcaagt g                                                          11

<210> SEQ ID NO 110
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aggttcaagt gg                                                         12

<210> SEQ ID NO 111
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atttgtattt                                                            10

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
catttgtatt t                                                          11

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ccatttgtat tt                                                         12

<210> SEQ ID NO 114
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ttcccaattc                                                            10

<210> SEQ ID NO 115
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ttcccaattc t                                                          11

<210> SEQ ID NO 116
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ttcccaattc tc                                                         12

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
taatgaaaac                                                            10

<210> SEQ ID NO 118
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ataatgaaaa c                                                          11

<210> SEQ ID NO 119
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cataatgaaa ac                                                         12

<210> SEQ ID NO 120
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
atttctcaac                                                          10

<210> SEQ ID NO 121
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
atttctcaac a                                                        11

<210> SEQ ID NO 122
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
atttctcaac ag                                                       12

<210> SEQ ID NO 123
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttgtttcatc                                                          10

<210> SEQ ID NO 124
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
attgtttcat c                                                        11

<210> SEQ ID NO 125
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cattgtttca tc                                                       12

<210> SEQ ID NO 126
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 126
ccattgtttc atc                                                          13

<210> SEQ ID NO 127
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ttttactccc                                                              10

<210> SEQ ID NO 128
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttttactccc t                                                            11

<210> SEQ ID NO 129
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ttttactccc tt                                                           12

<210> SEQ ID NO 130
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ttttactccc ttg                                                          13

<210> SEQ ID NO 131
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gtcaccagag                                                              10

<210> SEQ ID NO 132
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 132
tgtcaccaga g                                                              11

<210> SEQ ID NO 133
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtgtcaccag ag                                                             12

<210> SEQ ID NO 134
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tgtgtcacca gag                                                            13

<210> SEQ ID NO 135
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ctgagtagga                                                                10

<210> SEQ ID NO 136
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ctgagtagga g                                                              11

<210> SEQ ID NO 137
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tgtgtcacca gagtaa                                                         16

<210> SEQ ID NO 138
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 138
aggttgtgtc a                                                              11

<210> SEQ ID NO 139
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
caccctctgt g                                                              11

<210> SEQ ID NO 140
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cctcaaggtc                                                                10

<210> SEQ ID NO 141
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
acccaccatc                                                                10

<210> SEQ ID NO 142
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
aagcagagaa                                                                10

<210> SEQ ID NO 143
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
caagcagaga a                                                              11

<210> SEQ ID NO 144
<211> LENGTH: 12
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 144
tcaagcagag aa                                                            12

<210> SEQ ID NO 145
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
atcaagcaga gaa                                                           13

<210> SEQ ID NO 146
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gatcaagcag agaa                                                          14

<210> SEQ ID NO 147
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tgatcaagca gagaa                                                         15

<210> SEQ ID NO 148
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttgatcaagc agagaa                                                        16

<210> SEQ ID NO 149
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agtcggtaag                                                               10

<210> SEQ ID NO 150
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
agtcggtaag t                                                                                    11

<210> SEQ ID NO 151
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
agtcggtaag tt                                                                                   12

<210> SEQ ID NO 152
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
agtcggtaag ttc                                                                                  13

<210> SEQ ID NO 153
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
agtcggtaag ttct                                                                                 14

<210> SEQ ID NO 154
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcttcttcct tagc                                                                                 14

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gaaaacgccg ccatttct                                                                             18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 156
ctgttagcca ctgattaa                                                   18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgagaaactg ttcagctt                                                   18

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
caggaatttg tgtctttc                                                   18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gtatttagca tgttccca                                                   18

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
agcatgttcc caattctc                                                   18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gccgccattt ctcaacag                                                   18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
```
ttcccaattc tcaggaat                                                         18

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccatttgtat ttagcatg                                                         18

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ctcagatctt ctaacttc                                                         18

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
accgccttcc actcagag                                                         18

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tcttgaagta aacggttt                                                         18

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggctgctttg ccctcagc                                                         18

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
gctaggtcag gctgcttt                                                 18

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gcagcctctc gctcactc                                                 18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tcttccaaag cagcctct                                                 18

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tgcagtaatc tatgagtt                                                 18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtttcagctt ctgtaagc                                                 18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tccttacggg tagcatcc                                                 18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
agctctttta ctcccttg                                                 18
```

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ccattgtttc atcagctc                                                   18

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tgtgtcacca gagtaacagt                                                 20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aggttgtgtc accagagtaa                                                 20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agtaaccaca ggttgtgtca                                                 20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
caccctctgt gattttataa                                                 20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
acccaccatc accctctgtg                                                 20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cctcaaggtc acccaccatc                                                   20

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
taacagtctg agtaggag                                                     18

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggcatttcta gtttggag                                                     18

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
agccagtcgg taagttct                                                     18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
agtttggaga tggcagtt                                                     18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ctgattctga attctttc                                                     18

```
<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cctccggttc tgaaggtg                                                 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
catttcattc aactgttg                                                 18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttccttagct tccagcca                                                 18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
taagacctgc tcagcttc                                                 18

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cttggctctg gcctgtcc                                                 18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ctccttccat gactcaag                                                 18

<210> SEQ ID NO 193
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctcagcttct tccttagc                                                     18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gcttcttcct tagcttcc                                                     18

<210> SEQ ID NO 195
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 195
catttcautc aactgttg                                                     18

<210> SEQ ID NO 196
<211> LENGTH: 31
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 196
gcctgagcug aucugcuggc aucuugcagt t                                      31

<210> SEQ ID NO 197
<211> LENGTH: 15
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 197
gatctgcugg catct                                                        15

<210> SEQ ID NO 198
<211> LENGTH: 22
<212> TYPE: DNA
<213> ORGANISM: Artificial Sequence
<220> FEATURE:
<223> OTHER INFORMATION: Description of combined DNA/RNA molecule:
```

```
          Synthetic oligonucleotide
<220> FEATURE:
<223> OTHER INFORMATION: Description of Artificial Sequence: Synthetic
      oligonucleotide

<400> SEQUENCE: 198
gatctgcugg caucuugcag tt                                              22

<210> SEQ ID NO 199
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 199
gatctgcugg caucttgcag                                                 20

<210> SEQ ID NO 200
<211> LENGTH: 19
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 200
agctgatcug cuggcatct                                                  19

<210> SEQ ID NO 201
<211> LENGTH: 24
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 201
gcctgagcug aucugcuggc atct                                            24

<210> SEQ ID NO 202
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 202
gatctgcugg caucttgc                                                   18

<210> SEQ ID NO 203
<211> LENGTH: 23
<212> TYPE: DNA
<213> ORGANISM: Artificial Sequence
<220> FEATURE:
```

```
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 203
agttgagucu ucgaaacuga gca                                            23

<210> SEQ ID NO 204
<211> LENGTH: 23
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 204
agttgagtcu ucgaaactga gca                                            23

<210> SEQ ID NO 205
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 205
aaactgagca aauttgct                                                  18

<210> SEQ ID NO 206
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 206
ttgagucuuc aaaactga                                                  18

<210> SEQ ID NO 207
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 207
gtgcaaaguu gagtcttc                                                  18

<210> SEQ ID NO 208
<211> LENGTH: 15
<212> TYPE: DNA
<213> ORGANISM: Artificial Sequence
```

```
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 208
gccgcugccc aatgc                                                    15

<210> SEQ ID NO 209
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 209
cgctgcccaa tgccaucc                                                 18

<210> SEQ ID NO 210
<211> LENGTH: 18
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 210
cagttugccg ctgcccaa                                                 18

<210> SEQ ID NO 211
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 211
gctttucuuu uaguugctgc                                               20

<210> SEQ ID NO 212
<211> LENGTH: 22
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 212
cuuuuagttg ctgctctuuu cc                                            22

<210> SEQ ID NO 213
<211> LENGTH: 18
<212> TYPE: DNA
```

<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 213
ttttccaggu ucaagtgg                                                        18

<210> SEQ ID NO 214
<211> LENGTH: 15
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 214
ctgctuccuc caacc                                                           15

<210> SEQ ID NO 215
<211> LENGTH: 20
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 215
gttatcugcu uccuccaacc                                                      20

<210> SEQ ID NO 216
<211> LENGTH: 22
<212> TYPE: DNA
<213> ORGANISM: Artificial Sequence
<220> FEATURE:
<223> OTHER INFORMATION: Description of combined DNA/RNA molecule:
      Synthetic oligonucleotide
<220> FEATURE:
<223> OTHER INFORMATION: Description of Artificial Sequence: Synthetic
      oligonucleotide

<400> SEQUENCE: 216
cttttaguug cugcucuttt cc                                                   22

<210> SEQ ID NO 217
<211> LENGTH: 13993
<212> TYPE: DNA
<213> ORGANISM: Homo sapiens

<400> SEQUENCE: 217
tcctggcatc agttactgtg ttgactcact cagtgttggg atcactcact ttcccctac           60 aggactcaga tctgggaggc aattaccttc ggagaaaaac gaataggaaa aactgaagtg         120
ttactttttt taaagctgct gaagtttgtt ggtttctcat tgtttttaag cctactggag         180
caataaagtt tgaagaactt ttaccaggtt ttttttatcg ctgccttgat atacactttt         240
caaaatgctt tggtgggaag aagtagagga ctgttatgaa agagaagatg ttcaaaagaa         300
aacattcaca aaatgggtaa atgcacaatt ttctaagttt gggaagcagc atattgagaa         360

```
cctcttcagt gacctacagg atgggaggcg cctcctagac ctcctcgaag gcctgacagg    420
gcaaaaactg ccaaaagaaa aaggatccac aagagttcat gccctgaaca atgtcaacaa    480
ggcactgcgg gttttgcaga acaataatgt tgatttagtg aatattggaa gtactgacat    540
cgtagatgga aatcataaac tgactcttgg tttgatttgg aatataatcc tccactggca    600
ggtcaaaaat gtaatgaaaa atatcatggc tggattgcaa caaaccaaca gtgaaaagat    660
tctcctgagc tgggtccgac aatcaactcg taattatcca caggttaatg taatcaactt    720
caccaccagc tggtctgatg gcctggcttt gaatgctctc atccatagtc ataggccaga    780
cctatttgac tggaatagtg tggtttgcca gcagtcagcc acacaacgac tggaacatgc    840
attcaacatc gccagatatc aattaggcat agagaaacta ctcgatcctg aagatgttga    900
taccacctat ccagataaga agtccatctt aatgtacatc acatcactct tccaagtttt    960
gcctcaacaa gtgagcattg aagccatcca ggaagtggaa atgttgccaa ggccacctaa   1020
agtgactaaa aagaacatt ttcagttaca tcatcaaatg cactattctc aacagatcac   1080
ggtcagtcta gcacagggat atgagagaac ttcttcccct aagcctcgat tcaagagcta   1140
tgcctacaca caggctgctt atgtcaccac ctctgaccct acacggagcc catttccttc   1200
acagcatttg gaagctcctg aagacaagtc atttggcagt tcattgatgg agagtgaagt   1260
aaacctggac cgttatcaaa cagctttaga agaagtatta tcgtggcttc tttctgctga   1320
ggacacattg caagcacaag gagagatttc taatgatgtg gaagtggtga agaccagtt   1380 tcatactcat gaggggtaca tgatggattt gacagcccat cagggccggg ttggtaatat   1440
tctacaattg ggaagtaagc tgattggaac aggaaaatta tcagaagatg aagaaactga   1500
agtacaagag cagatgaatc tcctaaattc aagatgggaa tgcctcaggg tagctagcat   1560
ggaaaaacaa agcaatttac atagagtttt aatggatctc cagaatcaga aactgaaaga   1620
gttgaatgac tggctaacaa aaacagaaga agaacaagg aaaatggagg aagagcctct   1680
tggacctgat cttgaagacc taaaacgcca agtacaacaa cataaggtgc ttcaagaaga   1740
tctagaacaa gaacaagtca gggtcaattc tctcactcac atggtggtgg tagttgatga   1800
atctagtgga gatcacgcaa ctgctgcttt ggaagaacaa cttaaggtat tgggagatcg   1860
atgggcaaac atctgtagat ggacagaaga ccgctgggtt cttttacaag acatccttct   1920
caaatggcaa cgtcttactg aagaacagtg ccttttttagt gcatggcttt cagaaaaaga   1980
agatgcagtg aacaagattc acacaactgg ctttaaagat caaaatgaaa tgttatcaag   2040
tcttcaaaaa ctggccgttt taaaagcgga tctagaaaag aaaagcaat ccatgggcaa   2100 actgtattca ctcaaacaag atcttctttc aacactgaag aataagtcag tgacccagaa   2160
gacggaagca tggctggata ctttgcccg gtgttgggat aatttagtcc aaaaacttga   2220
aaagagtaca gcacagattt cacaggctgt caccaccact cagccatcac taacacagac   2280
aactgtaatg gaaacagtaa ctacggtgac cacaagggaa cagatcctgg taaagcatgc   2340
tcaagaggaa cttccaccac cacctcccca aaagaagagg cagattactg tggattctga   2400
aattaggaaa aggttggatg ttgatataac tgaacttcac agctggatta ctcgctcaga   2460
agctgtgttg cagagtcctg aatttgcaat ctttcggaag gaaggcaact tctcagactt   2520
aaaagaaaaa gtcaatgcca tagagcgaga aaaagctgag aagttcagaa aactgcaaga   2580
tgccagcaga tcagctcagg ccctggtgga acagatggtg aatgagggtg ttaatgcaga   2640
tagcatcaaa caagcctcag aacaactgaa cagccggtgg atcgaattct gccagttgct   2700
```

```
aagtgagaga cttaactggc tggagtatca gaacaacatc atcgctttct ataatcagct    2760
acaacaattg gagcagatga caactactgc tgaaaactgg ttgaaaatcc aacccaccac    2820
cccatcagag ccaacagcaa ttaaaagtca gttaaaaatt tgtaaggatg aagtcaaccg    2880
gctatcaggt cttcaacctc aaattgaacg attaaaaatt caaagcatag ccctgaaaga    2940
gaaaggacaa ggacccatgt tcctggatgc agactttgtg gcctttacaa atcattttaa    3000
gcaagtcttt tctgatgtgc aggccagaga gaaagagcta cagacaattt ttgacacttt    3060
gccaccaatg cgctatcagg agaccatgag tgccatcagg acatgggtcc agcagtcaga    3120
aaccaaactc tccatacctc aacttagtgt caccgactat gaaatcatgg agcagagact    3180
cggggaattg caggctttac aaagttctct gcaagagcaa caaagtggcc tatactatct    3240
cagcaccact gtgaaagaga tgtcgaagaa agcgccctct gaaattagcc ggaaatatca    3300
atcagaattt gaagaaattg agggacgctg gaagaagctc tcctcccagc tggttgagca    3360
ttgtcaaaag ctagaggagc aaatgaataa actccgaaaa attcagaatc acatacaaac    3420
cctgaagaaa tggatggctg aagttgatgt ttttctgaag gaggaatggc ctgcccttgg    3480
ggattcagaa attctaaaaa agcagctgaa acagtgcaga ctttttagtca gtgatattca    3540 gacaattcag cccagtctaa acagtgtcaa tgaaggtggg cagaagataa agaatgaagc    3600
agagccagag tttgcttcga gacttgagac agaactcaaa gaacttaaca ctcagtggga    3660
tcacatgtgc caacaggtct atgccagaaa ggaggccttg aagggaggtt tggagaaaac    3720
tgtaagcctc cagaaagatc tatcagagat gcacgaatgg atgacacaag ctgaagaaga    3780
gtatcttgag agagattttg aatataaaac tccagatgaa ttacagaaag cagttgaaga    3840
gatgaagaga gctaaagaag aggcccaaca aaaagaagcg aaagtgaaac tccttactga    3900
gtctgtaaat agtgtcatag ctcaagctcc acctgtagca caagaggcct taaaaaagga    3960
acttgaaact ctaaccacca actaccagtg gctctgcact aggctgaatg ggaaatgcaa    4020
gactttggaa gaagtttggg catgttggca tgagttattg tcatacttgg agaaagcaaa    4080
caagtggcta aatgaagtag aatttaaact taaaaccact gaaaacattc ctggcggagc    4140
tgaggaaatc tctgaggtgc tagattcact tgaaaatttg atgcgacatt cagaggataa    4200
cccaaatcag attcgcatat tggcacagac cctaacagat ggcggagtca tggatgagct    4260
aatcaatgag gaacttgaga catttaattc tcgttggagg gaactacatg aagaggctgt    4320
aaggaggcaa aagttgcttg aacagagcat ccagtctgcc caggagactg aaaaatcctt    4380
acacttaatc caggagtccc tcacattcat tgacaagcag ttggcagctt atattgcaga    4440
caaggtggac gcagctcaaa tgcctcagga agcccagaaa atccaatctg atttgacaag    4500
tcatgagatc agtttagaag aaatgaagaa acataatcag gggaaggagg ctgcccaaag    4560
agtcctgtct cagattgatg ttgcacagaa aaaattacaa gatgtctcca tgaagtttcg    4620
attattccag aaaccagcca attttgagca gcgtctacaa gaaagtaaga tgatttaga    4680 tgaagtgaag atgcacttgc ctgcattgga acaaagagt gtggaacagg aagtagtaca    4740
gtcacagcta atcattgtg tgaacttgta taaaagtctg agtgaagtga agtctgaagt    4800
ggaaatggtg ataaagactg gacgtcagat tgtacagaaa aagcagacgg aaaatcccaa    4860
agaacttgat gaaagagtaa cagctttgaa attgcattat aatgagctgg gagcaaaggt    4920
aacagaaaga aagcaacagt tggagaaaatg cttgaaattg tcccgtaaga tgcgaaagga    4980
aatgaatgtc ttgacagaat ggctggcagc tacagatatg gaattgacaa agagatcagc    5040
agttgaagga atgcctagta atttggattc tgaagttgcc tggggaaagg ctactcaaaa    5100
```

```
agagattgag aaacagaagg tgcacctgaa gagtatcaca gaggtaggag aggccttgaa   5160
aacagttttg ggcaagaagg agacgttggt ggaagataaa ctcagtcttc tgaatagtaa   5220
ctggatagct gtcacctccc gagcagaaga gtggttaaat cttttgttgg aataccagaa   5280
acacatggaa acttttgacc agaatgtgga ccacatcaca aagtggatca ttcaggctga   5340
cacacttttg gatgaatcag agaaaaagaa accccagcaa aaagaagacg tgcttaagcg   5400
tttaaaggca gaactgaatg acatacgccc aaaggtggac tctacacgtg accaagcagc   5460
aaacttgatg gcaaaccgcg gtgaccactg caggaaatta gtagagcccc aaatctcaga   5520
gctcaaccat cgatttgcag ccatttcaca cagaattaag actggaaagg cctccattcc   5580
tttgaaggaa ttggagcagt ttaactcaga tatacaaaaa ttgcttgaac cactggaggc   5640
tgaaattcag caggggtga atctgaaaga ggaagacttc aataaagata tgaatgaaga   5700
caatgagggt actgtaaaag aattgttgca agaggagac aacttacaac aaagaatcac   5760
agatgagaga aagcgagagg aaataaagat aaaacagcag ctgttacaga caaaacataa   5820
tgctctcaag gatttgaggt ctcaaagaag aaaaaaggct ctagaaattt ctcatcagtg   5880
gtatcagtac aagaggcagg ctgatgatct cctgaaatgc ttggatgaca ttgaaaaaaa   5940
attagccagc ctacctgagc ccagagatga aaggaaaata aaggaaattg atcgggaatt   6000
gcagaagaag aaagaggagc tgaatgcagt gcgtaggcaa gctgagggct tgtctgagga   6060
tggggccgca atggcagtgg agccaactca gatccagctc agcaagcgct ggcgggaaat   6120
tgagagcaaa tttgctcagt ttcgaagact caactttgca caaattcaca ctgtccgtga   6180
agaaacgatg atggtgatga ctgaagacat gcctttggaa atttcttatg tgccttctac   6240
ttatttgact gaaatcactc atgtctcaca agccctatta gaagtggaac aacttctcaa   6300
tgctcctgac ctctgtgcta aggactttga agatctcttt aagcaagagg agtctctgaa   6360
gaatataaaa gatagtctac aacaaagctc aggtcggatt gacattattc atagcaagaa   6420
gacagcagca ttgcaaagtg caacgcctgt ggaaagggtg aagctacagg aagctctctc   6480
ccagcttgat ttccaatggg aaaaagttaa caaaatgtac aaggaccgac aagggcgatt   6540
tgacagatct gttgagaaat ggcggcgttt tcattatgat ataaagatat ttaatcagtg   6600
gctaacagaa gctgaacagt ttctcagaaa gacacaaatt cctgagaatt gggaacatgc   6660
taaatacaaa tggtatctta aggaactcca ggatggcatt gggcagcggc aaactgttgt   6720
cagaacattg aatgcaactg gggaagaaat aattcagcaa tcctcaaaaa cagatgccag   6780
tattctacag gaaaaattgg gaagcctgaa tctgcggtgg caggaggtct gcaaacagct   6840
gtcagacaga aaaagaggc tagaagaaca aaagaatatc ttgtcagaat ttcaaagaga   6900
tttaaatgaa tttgttttat ggttggagga agcagataac attgctagta tcccacttga   6960
acctggaaaa gagcagcaac taaagaaaa gcttgagcaa gtcaagttac tggtggaaga   7020 gttgccctg cgccagggaa ttctcaaaca attaaatgaa actggaggac ccgtgcttgt   7080
aagtgctccc ataagcccag aagagcaaga taaacttgaa aataagctca agcagacaaa   7140
tctccagtgg ataaaggttt ccagagcttt acctgagaaa caaggagaaa ttgaagctca   7200
aataaaagac ctgggcagc ttgaaaaaaa gcttgagac cttgaagagc agttaaatca   7260
tctgctgctg tggttatctc ctattaggaa tcagttggaa atttataacc aaccaaacca   7320
agaaggacca tttgacgttc aggaaactga aatagcagtt caagctaaac aaccggatgt   7380
ggaagagatt ttgtctaaag ggcagcattt gtacaaggaa aaaccagcca ctcagccagt   7440
```

```
gaagaggaag ttagaagatc tgagctctga gtggaaggcg gtaaaccgtt tacttcaaga    7500
gctgagggca aagcagcctg acctagctcc tggactgacc actattggag cctctcctac    7560
tcagactgtt actctggtga cacaacctgt ggttactaag gaaactgcca tctccaaact    7620
agaaatgcca tcttccttga tgttggaggt acctgctctg gcagatttca accgggcttg    7680
gacagaactt accgactggc tttctctgct tgatcaagtt ataaaatcac agagggtgat    7740
ggtgggtgac cttgaggata tcaacgagat gatcatcaag cagaaggcaa caatgcagga    7800
tttggaacag aggcgtcccc agttggaaga actcattacc gctgcccaaa atttgaaaaa    7860
caagaccagc aatcaagagg ctagaacaat cattacggat cgaattgaaa gaattcagaa    7920
tcagtgggat gaagtacaag aacaccttca gaaccggagg caacagttga atgaaatgtt    7980
aaaggattca acacaatggc tggaagctaa ggaagaagct gagcaggtct taggacaggc    8040
cagagccaag cttgagtcat ggaaggaggg tccctataca gtagatgcaa tccaaaagaa    8100
aatcacagaa accaagcagt tggccaaaga cctccgccag tggcagacaa atgtagatgt    8160
ggcaaatgac ttggccctga aacttctccg ggattattct gcagatgata ccagaaaagt    8220
ccacatgata acagagaata tcaatgcctc ttggagaagc attcataaaa gggtgagtga    8280
gcgagaggct gctttggaag aaactcatag attactgcaa cagttccccc tggacctgga    8340
aaagtttctt gcctggctta cagaagctga acaactgcc aatgtcctac aggatgctac    8400
ccgtaaggaa aggctcctag aagactccaa gggagtaaaa gagctgatga acaatggca    8460 agacctccaa ggtgaaattg aagctcacac agatgtttat cacaacctgg atgaaaacag    8520
ccaaaaaatc ctgagatccc tggaaggttc cgatgatgca gtcctgttac aaagacgttt    8580
ggataacatg aacttcaagt ggagtgaact tcggaaaaag tctctcaaca ttaggtccca    8640
tttggaagcc agttctgacc agtggaagcg tctgcacctt tctctgcagg aacttctggt    8700
gtggctacag ctgaaagatg atgaattaag ccggcaggca cctattggag gcgactttcc    8760
agcagttcag aagcagaacg atgtacatag ggccttcaag agggaattga aaactaaaga    8820
acctgtaatc atgagtactc ttgagactgt acgaatattt ctgacagagc agcctttgga    8880
aggactagag aaactctacc aggagcccag agagctgcct cctgaggaga gagcccagaa    8940
tgtcactcgg cttctacgaa agcaggctga ggaggtcaat actgagtggg aaaaattgaa    9000
cctgcactcc gctgactggc agagaaaaat agatgagacc cttgaaagac tccaggaact    9060
tcaagaggcc acggatgagc tggacctcaa gctgcgccaa gctgaggtga tcaagggatc    9120
ctggcagccc gtgggcgatc tcctcattga ctctctccaa gatcacctcg agaaagtcaa    9180
ggcacttcga ggagaaattg cgcctctgaa agagaacgtg agccacgtca atgaccttgc    9240
tcgccagctt accactttgg gcattcagct ctcaccgtat aacctcagca ctctggaaga    9300
cctgaacacc agatggaagc ttctgcaggt ggccgtcgag gaccgagtca ggcagctgca    9360
tgaagcccac agggactttg gtccagcatc tcagcacttt ctttccacgt ctgtccaggg    9420
tccctgggag agagccatct cgccaaacaa agtgccctac tatatcaacc acgagactca    9480
aacaacttgc tggaccatcc caaaatgaca gagctctac cagtctttag ctgacctgaa    9540
taatgtcaga ttctcagctt ataggactgc catgaaactc cgaagactgc agaaggccct    9600
ttgcttggat ctcttgagcc tgtcagctgc atgtgatgcc ttggaccagc acaacctcaa    9660
gcaaaatgac cagcccatgg atatcctgca gattattaat tgtttgacca ctatttatga    9720
ccgcctggag caagagcaca acaatttggt caacgtccct ctctgcgtgg atatgtgtct    9780
gaactggctg ctgaatgttt atgatacggg acgaacaggg aggatccgtg tcctgtctttt    9840
```

```
taaaactggc atcatttccc tgtgtaaagc acatttggaa gacaagtaca gataccttt      9900 caagcaagtg gcaagttcaa caggattttg tgaccagcgc aggctgggcc tccttctgca     9960
tgattctatc caaattccaa gacagttggg tgaagttgca tcctttgggg gcagtaacat    10020
tgagccaagt gtccggagct gcttccaatt tgctaataat aagccagaga tcgaagcggc    10080
cctcttccta gactggatga gactggaacc ccagtccatg gtgtggctgc ccgtcctgca    10140
cagagtggct gctgcagaaa ctgccaagca tcaggccaaa tgtaacatct gcaaagagtg    10200
tccaatcatt ggattcaggt acaggagtct aaagcacttt aattatgaca tctgccaaag    10260 ctgcttttt tctggtcgag ttgcaaaagg ccataaaatg cactatccca tggtggaata    10320
ttgcactccg actacatcag gagaagatgt tcgagacttt gccaaggtac taaaaaacaa    10380
atttcgaacc aaaaggtatt tgcgaagca tccccgaatg ggctacctgc cagtgcagac    10440
tgtcttagag ggggacaaca tggaaactcc cgttactctg atcaacttct ggccagtaga    10500
ttctgcgcct gcctcgtccc ctcagctttc acacgatgat actcattcac gcattgaaca    10560
ttatgctagc aggctagcag aaatggaaaa cagcaatgga tcttatctaa atgatagcat    10620
ctctcctaat gagagcatag atgatgaaca tttgttaatc cagcattact gccaaagttt    10680
gaaccaggac tcccccctga gccagcctcg tagtcctgcc cagatcttga tttccttaga    10740
gagtgaggaa agaggggagc tagagagaat cctagcagat cttgaggaag aaaacaggaa    10800
tctgcaagca gaatatgacc gtctaaagca gcagcacgaa cataaaggcc tgtccccact    10860
gccgtcccct cctgaaatga tgcccacctc tccccagagt ccccgggatg ctgagctcat    10920
tgctgaggcc aagctactgc gtcaacacaa aggccgcctg gaagccagga tgcaaatcct    10980
ggaagaccac aataaacagc tggagtcaca gttacacagg ctaaggcagc tgctggagca    11040
accccaggca gaggccaaag tgaatggcac aacggtgtcc tctccttcta cctctctaca    11100
gaggtccgac agcagtcagc ctatgctgct ccgagtggtt ggcagtcaaa cttcggactc    11160
catgggtgag gaagatcttc tcagtcctcc ccaggacaca agcacagggt tagaggaggt    11220
gatggagcaa ctcaacaact ccttccctag ttcaagagga agaaatacccc ctggaaagcc    11280 aatgagagag gacacaatgt aggaagtctt ttccacatgg cagatgattt gggcagagcg    11340
atggagtcct tagtatcagt catgacagat gaagaaggag cagaataaat gttttacaac    11400
tcctgattcc cgcatggttt ttataatatt catcaacaa agaggattag acagtaagag    11460
tttacaagaa ataaatctat attttttgtga agggtagtgg tattatactg tagatttcag    11520
tagtttctaa gtctgttatt gttttgttaa caatggcagg ttttacacgt ctatgcaatt    11580
gtacaaaaaa gttataagaa aactacatgt aaaatcttga tagctaaata acttgccatt    11640 tcttttatatg gaacgcattt tgggttgttt aaaaatttat aacagttata agaaagatt    11700 gtaaactaaa gtgtgcttta taaaaaaaag ttgtttataa aaaccctaa aaacaaaaca    11760 aacacacaca cacacacata cacacacaca cacaaaactt tgaggcagcg cattgttttg    11820
catccttttg gcgtgatatc catatgaaat tcatggcttt ttcttttttt gcatattaaa    11880
gataagactt cctctaccac cacaccaaat gactactaca cactgctcat ttgagaactg    11940
tcagctgagt ggggcaggct tgagttttca tttcatatat ctatatgtct ataagtatat    12000
aaatactata gttatataga taaagagata cgaatttccta tagactgact ttttccattt    12060
```

```
tttaaatgtt catgtcacat cctaatagaa agaaattact tctagtcagt catccaggct    12120
tacctgcttg gtctagaatg gattttccc ggagccggaa gccaggagga aactacacca    12180
cactaaaaca ttgtctacag ctccagatgt ttctcatttt aaacaactt ccactgacaa    12240 cgaaagtaaa gtaaagtatt ggattttttt aaagggaaca tgtgaatgaa tacacaggac   12300
ttattatatc agagtgagta atcggttggt tggttgattg attgattgat tgatacattc   12360
agcttcctgc tgctagcaat gccacgattt agatttaatg atgcttcagt ggaaatcaat   12420
cagaaggtat tctgaccttg tgaacatcag aaggtatttt ttaactccca agcagtagca   12480
ggacgatgat agggctggag ggctatggat tcccagccca tccctgtgaa ggagtaggcc   12540
actctttaag tgaaggattg gatgattgtt cataatacat aaagttctct gtaattacaa   12600
ctaaattatt atgccctctt ctcacagtca aaaggaactg ggtggtttgg tttttgttgc   12660 tttttttagat ttattgtccc atgtgggatg agtttttaaa tgccacaaga cataatttaa 12720
aataaataaa ctttgggaaa aggtgtaaga cagtagcccc atcacatttg tgatactgac   12780
aggtatcaac ccagaagccc atgaactgtg tttccatcct ttgcatttct ctgcgagtag   12840
ttccacacag gtttgtaagt aagtaagaaa gaaggcaaat tgattcaaat gttacaaaaa   12900
aacccttctt ggtggattag acaggttaaa tatataaaca aacaaacaaa aattgctcaa   12960
aaaagaggag aaaagctcaa gaggaaaagc taaggactgg taggaaaaag ctttactctt   13020
tcatgccatt ttatttcttt ttgattttta aatcattcat tcaatagata ccaccgtgtg   13080
acctataatt ttgcaaatct gttacctctg acatcaagtg taattagctt ttggagagtg   13140
ggctgacatc aagtgtaatt agcttttgga gagtgggttt tgtccattat taataattaa   13200
ttaattaaca tcaaacacgg cttctcatgc tatttctacc tcactttggt tttgggtgt    13260 tcctgataat tgtgcacacc tgagttcaca gcttcaccac ttgtccattg cgttattttc   13320
tttttccttt ataattcttt cttttttcctt cataatttc aaaagaaaac ccaaagctct    13380
aaggtaacaa attaccaaat tacatgaaga tttggttttt gtcttgcatt tttttccttt   13440
atgtgacgct ggaccttttc tttacccaag gatttttaaa actcagattt aaaacaaggg   13500
gttactttac atcctactaa gaagtttaag taagtaagtt tcattctaaa atcagaggta   13560
aatagagtgc ataaataatt ttgttttaat ctttttgttt ttcttttaga cacattagct   13620
ctggagtgag tctgtcataa tatttgaaca aaaattgaga gctttattgc tgcattttaa   13680
gcataattaa tttggacatt atttcgtgtt gtgttcttta taaccaccga gtattaaact   13740
gtaaatcata atgtaactga agcataaaca tcacatggca tgttttgtca ttgtttttcag 13800 gtactgagtt cttacttgag tatcataata tattgtgttt taacaccaac actgtaacat   13860
ttacgaatta ttttttttaaa cttcagtttt actgcatttt cacaacatat cagacttcac   13920
caaatatatg ccttactatt gtattatagt actgctttac tgtgtatctc aataaagcac   13980
gcagttatgt tac                                                      13993
```

ENA NUCLEIC ACID PHARMACEUTICALS CAPABLE OF MODIFYING SPLICING OF MRNA PRECURSORS

CROSS-REFERENCE TO RELATED APPLICATIONS

The present application is a division of U.S. Ser. No. 14/258,663, filed Apr. 22, 2014, which is a division of U.S. Ser. No. 13/673,466, filed Nov. 9, 2012, which is a division of U.S. Ser. No. 12/847,237, filed Jul. 30, 2010, which is a division of U.S. Ser. No. 10/536,258, filed Dec. 13, 2005, which is a National Stage (371) of PCT/JP03/14915, filed Nov. 21, 2003, and claims priority to JP 2003-204381, filed Jul. 31, 2003, and JP 2002-340857, filed Nov. 25, 2002.

TECHNICAL FIELD

The present invention relates to ENA nucleic acid pharmaceuticals capable of modifying splicing of mRNA precursors. More specifically, the present invention relates to antisense oligonucleotide compounds to splicing enhancer sequences within exon 19, 41, 45, 46, 44, 50, 55, 51 or 53 of the dystrophin gene, as well as therapeutic agents for muscular dystrophy comprising the compounds.

BACKGROUND ART

Muscular dystrophy, which is a genetic muscular disease, is roughly classified into Duchenne muscular dystrophy (DMD) and Becker muscular dystrophy (BMD). DMD is the most frequently occurring genetic muscular disease and occurs at a ratio of 1 per 3,500 male births. DMD patients show symptoms of weakening of muscles in their childhood; thereafter, muscular atrophy progresses consistently and results in death at the age of around 20. Currently, there is no effective therapeutic for DMD. Development of therapeutics is strongly demanded by DMD patients throughout the world. BMD in many cases occurs in adulthood and most of the patients are capable of normal survival though slight weakening of muscles is observed. Mutations of deletions in the dystrophin gene have been identified in ⅔ of DMD and BMD cases. The progress of clinical symptoms in DMD or BMD patients is predictable depending on whether such deletions disrupt the translational reading frame of mRNA or maintain that reading frame (Monaco A. P. et al., Genomics 1988: 2:90-95). Although molecular biological understanding of DMD has been thus deepened, no effective method for treating DMD has been established yet.

When DMD patients have a frame shift mutation, dystrophin protein disappears completely from patients' skeletal muscles. On the other hand, dystrophin protein is produced from in-frame mRNA in BMD patient-derived muscle tissues, though the protein is incomplete. As a method for treating DMD, there is known a method in which an out-frame mutation (the reading frame of amino acids is shifted) is converted to an in-frame mutation (the reading frame is maintained) by modifying dystrophin mRNA (Matsuo M., Brain Dev 1996; 18:167-172). Recently, it has been reported that the mdx mouse synthesized a deletion-containing dystrophin as a result of induction of exon skipping with an oligonucleotide complementary to the splicing consensus sequence of the dystrophin gene (Wilton S. D. et al., Neuromusc Disord 1999: 9:330-338; Mann C. J. et al., Proc Natl Acad Sci USA 2001: 98:42-47). In these studies, exon skipping is induced using as a target the splicing consensus sequence located on the border between two exons.

It is asserted that splicing is regulated by splicing enhancer sequences (SESs). In fact, it has been demonstrated that by disrupting the SES within exon 19 of the dystrophin gene with an antisense oligonucleotide complementary thereto, complete skipping of exon 19 occurs in normal lymphoblastoid cells (Takeshima Y. et al., J Clin Invest 1995: 95:515-520; Pramono Z. A. et al., Biochem Biophys Res Commun 1996: 226:445-449).

It has been also reported that by introducing an oligonucleotide complementary to the SES within exon 19 of the dystrophin gene to thereby induce exon skipping, a deletion-containing dystrophin was successfully produced in muscular cells derived from DMD patients carrying exon 20 deletion (Takeshima Y et al., Brain & Development 2001: 23:788-790; Japanese Unexamined Patent Publication No. H11-140930; Japanese Unexamined Patent Publication No. 2002-10790). This indicates that repairing of the reading frame shift by inducing exon 19 skipping with an antisense oligonucleotide complementary to the SES within exon 19 of the dystrophin gene results in production of a dystrophin protein whose function is partially restored; and thus it is possible to change DMD to BMD. If it is possible to convert DMD, a severe myoatrophy, to slight BMD, prolonging patients' lives can be expected.

At present, oligonucleotide analogues having stable and excellent antisense activity are being developed (Japanese Unexamined Patent Publication No. 2000-297097).

It is an object of the present invention to provide therapeutics with broader applicable range and higher efficacy, by improving antisense oligonucleotides to the SES within exon 19, 41, 45, 46, 44, 50, 55, 51 or 53 of the dystrophin gene.

DISCLOSURE OF THE INVENTION

As a result of extensive and intensive researches toward the achievement of the above-described object, the present inventors have succeeded in designing and synthesizing those nucleotide sequences and antisense oligonucleotide compounds which have higher exon skipping effect on exon 19, 41, 45, 46, 44, 50, 55, 51 or 53 of the dystrophin gene. Thus, the present invention has been achieved.

The present invention may be summarized as follows.

[1] An oligonucleotide having the nucleotide sequence as shown in any one of SEQ ID NOS: 2-6, 10-22, 30-78, 87 or 88 in the SEQUENCE LISTING, or a pharmacologically acceptable salt thereof.

[2] The oligonucleotide of [1] above or a pharmacologically acceptable salt thereof, wherein at least one of the sugars and/or the phosphates constituting the oligonucleotide is modified.

[3] The oligonucleotide of [2] above or a pharmacologically acceptable salt thereof, wherein the sugar constituting the oligonucleotide is D-ribofuranose and the modification of the sugar is modification of the hydroxyl group at position 2' of D-ribofuranose.

[4] The oligonucleotide of [3] above or a pharmacologically acceptable salt thereof, wherein the modification of the sugar is 2'-O-alkylation and/or 2'-O,4'-C-alkylenation of the D-ribofuranose.

[5] The oligonucleotide of [2] above or a pharmacologically acceptable salt thereof, wherein the modification of the phosphate is thioation of the phosphate group.

[6] A compound represented by the following general formula (I) or a pharmacologically acceptable salt thereof:

$$B_T\text{-}B_M\text{-}B_B \quad (I)$$

where $B_T$ is a group represented by any one of the following (1a) to (1k):

(1a) HO-, (1b) HO-Bt-, (1c) HO-Bc-Bt-, (1d) HO-Bg-Bc-Bt-, (1e) HO-Ba-Bg-Bc-Bt-, (1f) HO-Bg-Ba-Bg-Bc-Bt-, (1g) HO-Bt-Bg-Ba-Bg-Bc-Bt-, (1h) HO-Bc-Bt-Bg-Ba-Bg-Bc-Bt-, (1j) HO-Bc-Bc-Bt-Bg-Ba-Bg-Bc-Bt-, or (1k) HO-Bg-Bc-Bc-Bt-Bg-Ba-Bg-Bc-Bt-;

where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

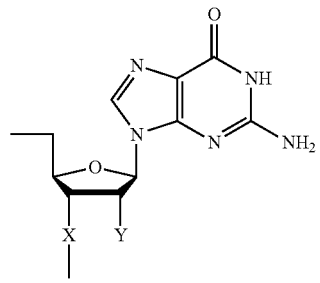

(G1)

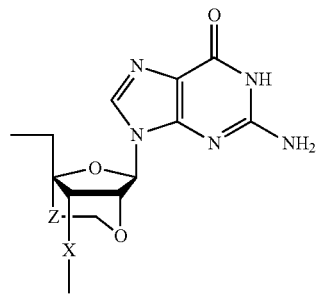

(G2)

(A1)

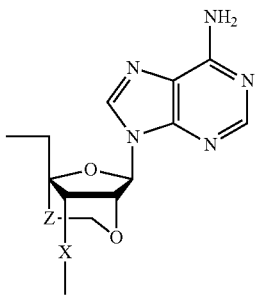

(A2)

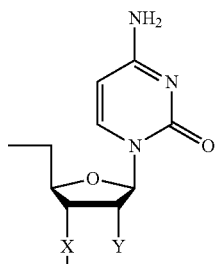

(C1)

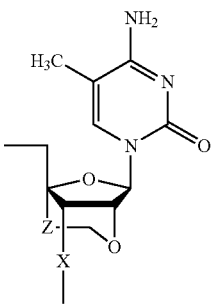

(C2)

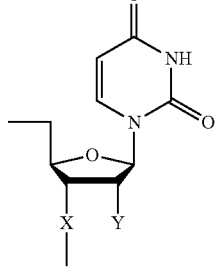

(U1)

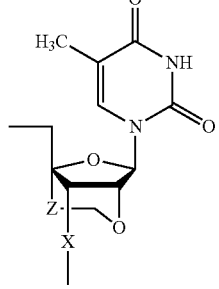

(T2)

where X is individually and independently a group represented by the following formula (X1) or (X2):

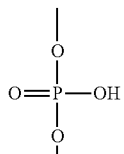
(X1)

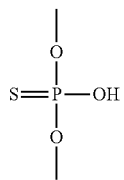
(X2)

Y is individually and independently a hydrogen atom, a hydroxyl group or an alkoxy group with 1-6 carbon atoms; and Z is individually and independently a single bond or an alkylene group with 1-5 carbon atoms;

$B_M$ is a group represented by the following formula (2):

(2)
(SEQ ID NO: 2)
-Bg-Ba-Bt-Bc-Bt-Bg-Bc-Bt-Bg-Bg-Bc-Ba-Bt-Bc-Btwhere Bg, Ba, Bt and Bc are as defined above;

$B_B$ is a group represented by any one of the following (2a) to (2h):

(2a) -CH₂CH₂OH, (2b) -Bt-CH₂CH₂OH, (2c) -Bt-Bg-CH₂CH₂OH, (2d) -Bt-Bg-Bc-CH₂CH₂OH, (2e) -Bt-Bg-Bc-Ba-CH₂CH₂OH, (2f) -Bt-Bg-Bc-Ba-Bg-CH₂CH₂OH, (2g) -Bt-Bg-Bc-Ba-Bg-Bt-CH₂CH₂OH, or (2h) -Bt-Bg-Bc-Ba-Bg-Bt-Bt-CH₂CH₂OH where Bg, Ba, Bt and Bc are as defined above;

provided that at least one of the nucleosides constituting the compound represented by formula (I) has 2'-O,4'-C-alkylene group.

[7] The compound according to claim 6 which is selected from the group consisting of the following compounds (i) to (vi), or a pharmacologically acceptable salt thereof:

(i) a compound where $B_T$ is a group represented by (1k) and $B_B$ is a group represented by (2h), (ii) a compound where $B_T$ is a group represented by (1a) and $B_B$ is a group represented by (2a), (iii) a compound where $B_T$ is a group represented by (1a) and $B_B$ is a group represented by (2h), (iv) a compound where $B_T$ is a group represented by (1e) and $B_B$ is a group represented by (2a), (v) a compound where $B_T$ is a group represented by (1k) and $B_B$ is a group represented by (2a), (vi) a compound where $B_T$ is a group represented by (1a) and $B_B$ is a group represented by (2f), and (vii) a compound where $B_T$ is a group represented by (1a) and $B_B$ is a group represented by (2d).

[8] The compound of [6] above which is selected from the group consisting of the following compounds (I1) to (I7), or a pharmacologically acceptable salt thereof:

(SEQ ID NO: 1)
HO-Bg\*\*-Bc\*\*-Bc\*\*-Bt\*\*-Bg\*\*-Ba\*-Bg\*-Bc\*-Bt\*-Bg\*-Ba\*-Bt\*-Bc\*-Bt\*-Bg\*-

Bc\*-Bt\*-Bg\*-Bg\*-Bc\*-Ba\*-Bt\*-Bc\*-Bt\*-Bt\*-Bg\*-Bc\*\*-Ba\*\*-Bg\*\*-

Bt\*\*-Bt\*\*-CH₂CH₂OH  (I1)

(SEQ ID NO: 2)
HO-Bg\*\*-Ba\*\*-Bt\*\*-Bc\*\*-Bt\*\*-Bg\*-Bc\*-Bt\*-Bg\*-Bg\*-Bc\*\*-Ba\*\*-Bt\*\*-

Bc\*\*-Bt\*\*-CH₂CH₂OH  (I2)

(SEQ ID NO: 3)
HO-Bg\*\*-Ba\*\*-Bt\*\*-Bc\*\*-Bt\*\*-Bg\*-Bc\*-Bt\*-Bg\*-Bg\*-Bc\*-Ba\*-Bt\*-Bc\*-Bt\*-Bt\*-

Bg\*-Bc\*\*-Ba\*\*-Bg\*\*-Bt\*\*-Bt\*\*-CH₂CH₂OH  (I3)

(SEQ ID NO: 4)
HO-Ba\*-Bg\*\*-Bc\*\*-Bt\*\*-Bg\*\*-Ba\*-Bt\*\*-Bc\*-Bt\*-Bg\*-Bc\*-Bt\*-Bg\*-Bg\*\*-Bc\*\*-

Ba\*-Bt\*\*-Bc\*\*-Bt\*\*-CH₂CH₂OH  (I4)

(SEQ ID NO: 5)
HO-Bg\*\*-Bc\*\*-Bc\*\*-Bt\*\*-Bg\*\*-Ba\*-Bg\*-Bc\*-Bt\*-Bg\*-Ba\*-Bt\*-Bc\*-Bt\*-Bg\*-Bc\*-

Bt\*-Bg\*-Bg\*\*-Bc\*\*-Ba\*-Bt\*\*-Bc\*\*-Bt\*\*-CH₂CH₂OH  (I5)

(SEQ ID NO: 6)
HO-Bg\*\*-Ba\*-Bt\*\*-Bc\*\*-Bt\*\*-Bg\*\*-Bc\*-Bt\*-Bg\*-Bg\*-Bc\*-Ba\*-Bt\*-Bc\*-Bt\*\*-

Bt\*\*-Bg\*\*-Bc\*\*-Ba\*-Bg\*\*-CH₂CH₂OH  (I6)

(SEQ ID NO: 4)
HO-Ba\*\*-Bg\*\*-Bc\*\*-Bt\*\*-Bg\*\*-Ba\*\*-Bt\*\*-Bc\*\*-Bt\*\*-Bg\*\*-Bc\*\*-Bt\*\*-

Bg\*\*-Bg\*\*-Bc\*\*-Ba\*\*-Bt\*\*-Bc\*\*-Bt\*\*-CH$_2$CH$_2$OH  (I7)

(SEQ ID NO: 7)
HO-Bg\*\*-Ba\*\*-Bt\*\*-Bc\*\*-Bt\*\*-Bg\*-Bc\*-Bt\*-Bg\*-Bg\*-Bc\*-Ba\*-Bt\*-Bc\*\*-Bt\*\*-

Bt\*\*-Bg\*\*-Bc\*\*-CH$_2$CH$_2$OH  (I8)

(SEQ ID NO: 2)
HO-Bg\*\*-Ba\*\*-Bt\*\*-Bc\*\*-Bt\*\*-Bg\*\*-Bc\*\*-Bt\*\*-Bg\*\*-Bg\*\*-Bc\*\*-Ba\*\*-

Bt\*\*-Bc\*\*-Bt\*\*-CH$_2$CH$_2$OH  (I9)

where Bg* is a group represented by the following formula (G1$^a$), Ba* is a group represented by the following formula (A1$^a$); Bc* is a group represented by the following formula (C1$^a$), Bt* is a group represented by the following formula (U1$^a$), Bg is a group represented by formula (G2); Ba is a group represented by formula (A2); Bc is a group represented by formula (C2); and Bt is a group represented by formula (T2):

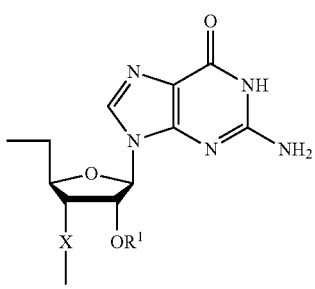
(G1$^a$)

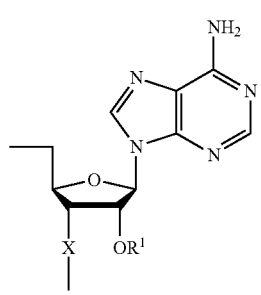
(A1$^a$)

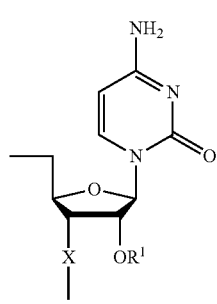
(C1$^a$)

-continued

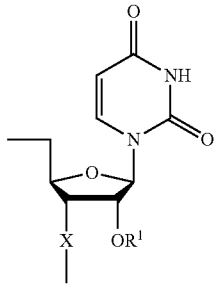
(U1$^a$)

where X is individually and independently a group represented by the following formula (X1) or (X2):

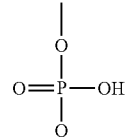
(X1)

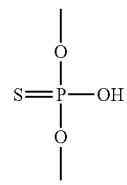
(X2)

and R$^1$ is individually and independently an alkyl group with 1-6 carbon atoms.)

[9] The compound of [8] above where X in formulas (G1$^a$), (A1$^a$), (C1$^a$) and (U1$^a$) is a group represented by formula (X2) and X in formulas (G2), (A2), (C2) and (T2) is a group represented by formula (X1), or a pharmacologically acceptable salt thereof.

[10] The compound of [8] above where X in all the formulas (G1$^a$), (A1$^a$), (C1$^a$), (U1$^a$), (G2), (A2), (C2) and (T2) is a group represented by formula (X2), or a pharmacologically acceptable salt thereof.

[11] The compound of [8] above which is represented by any one of the following formulas (I1-a), (I2-a), (I3-a), (I6-a), (I7-a), (I8-a) and (I9-a), or a pharmacologically acceptable salt thereof:

(SEQ ID NO: 1)
HO-Bg\*\*-Bc\*\*-Bc\*\*-Bt\*\*-Bg\*\*-Ba\*-Bg\*-Bc\*-Bt\*-Bg\*-Ba\*-Bt\*-Bg\*-Bc\*-Bt\*-Bg\*-Bg\*-Bc\*-Ba\*-Bt\*-Bc\*-Bt\*-Bg\*-Bc\*\*-Ba\*\*-Bg\*\*-Bt\*\*-Bt\*\*-CH₂CH₂OH (I1-a)

(SEQ ID NO: 2)
HO-Bg\*\*-Ba\*\*-Bt\*\*-Bc\*\*-Bt\*\*-Bg\*-Bc\*-Bt\*-Bg\*-Bg\*-Bc\*\*-Ba\*\*-Bt\*\*-Bc\*\*-Bt\*\*-CH₂CH₂OH (I2-a)

(SEQ ID NO: 3)
HO-Bg\*\*-Ba\*\*-Bt\*\*-Bc\*\*-Bt\*\*-Bg\*-Bc\*-Bt\*-Bg\*-Bg\*-Bc\*-Ba\*-Bt\*-Bc\*-Bt\*-Bt\*-Bg\*-Bc\*\*-Ba\*\*-Bg\*\*-Bt\*\*-Bt\*\*-CH₂CH₂OH (I3-a)

(SEQ ID NO: 4)
HO-Ba\*-Bg\*\*-Bc\*\*-Bt\*\*-Bg\*\*-Ba\*-Bt\*-Bc\*-Bt\*-Bg\*-Bc\*-Bt\*-Bg\*-Bg\*\*-Bc\*\*-Ba\*-Bt\*\*-Bc\*\*-Bt\*\*-CH₂CH₂OH (I4-a)

(SEQ ID NO: 5)
HO-Bg\*\*-Bc\*\*-Bc\*\*-Bt\*\*-Bg\*\*-Ba\*-Bg\*-Bc\*-Bt\*-Bg\*-Ba\*-Bt\*-Bc\*-Bt\*-Bg\*-Bc\*-Bt\*-Bg\*-Bg\*\*-Bc\*\*-Ba\*-Bt\*\*-Bc\*\*-Bt\*\*-CH₂CH₂OH (I5-a)

(SEQ ID NO: 6)
HO-Bg\*\*-Ba\*-Bt\*\*-Bc\*\*-Bt\*\*-Bg\*-Bc\*-Bt\*-Bg\*-Bg\*-Bc\*-Ba\*-Bt\*-Bc\*-Bt\*\*-Bt\*\*-Bg\*\*-Bc\*\*-Ba\*-Bg\*\*-CH₂CH₂OH (I6-a)

(SEQ ID NO: 4)
HO-Ba\*\*-Bg\*\*-Bc\*\*-Bt\*\*-Bg\*\*-Ba\*\*-Bt\*\*-Bc\*\*-Bt\*\*-Bg\*\*-Bc\*\*-Bt\*\*-Bg\*\*-Bg\*\*-Bc\*\*-Ba\*\*-Bt\*\*-Bc\*\*-Bt\*\*-CH₂CH₂OH (I7-a)

(SEQ ID NO: 7)
HO-Bg\*\*-Ba\*\*-Bt\*\*-Bc\*\*-Bt\*\*-Bg\*-Bc\*-Bt\*-Bg\*-Bg\*-Bc\*-Ba\*-Bt\*-Bc\*\*-Bt\*\*-Bt\*\*-Bg\*\*-Bc\*\*-CH₂CH₂OH (I8-a)

(SEQ ID NO: 2)
HO-Bg\*\*-Ba\*\*-Bt\*\*-Bc\*\*-Bt\*\*-Bg\*\*-Bc\*\*-Bt\*\*-Bg\*\*-Bg\*\*-Bc\*\*-Ba\*\*-Bt\*\*-Bc\*\*-Bt\*\*-CH₂CH₂OH (I9-a)

where Bg* is a group represented by formula (G1$^a$); Ba* is a group represented by formula (A1$^a$); Bc* is a group represented by formula (C1$^a$); Bt* is a group represented by formula (U1$^a$); Bg is a group represented by formula (G2); Ba is a group represented by formula (A2); Bc is a group represented by formula (C2); Bt is a group represented by formula (T2); and in individual formulas, at least one of Bg*, Ba*, Bc*, Bt*, Bg, Ba, Bc and Bt has a group represented by formula (X2) as X and all of ☐, Bg*, Bc*, Bt*, Bg, Ba, Bc and Bt have a group represented by formula (X1) as X.

[12] The compound of any one of [6] to [11] above where Y in formulas (G1), (A1), (C1) and (U1) is a methoxy group and Z in formulas (G2), (A2), (C2) and (T2) is an ethylene group, or a pharmacologically acceptable salt thereof.

[13] A compound represented by the following general formula (I') or a pharmacologically acceptable salt thereof:

$$B_{T'1}-B_{M'1}-B_{B'1} \quad (I')$$

where $B_{T'1}$ is a group represented by any one of the following (1a') to (1o'):

(1a') HO-, (1b') HO-Bg-, (1c') HO-Bc-Bg-, (1d') HO-Bt-Bc-Bg-, (1e') HO-Bt-Bt-Bc-Bg-, (1f') HO-Bc-Bt-Bt-Bc-Bg-, (1g') HO-Bt-Bc-Bt-Bt-Bc-Bg-, (1h') HO-Bg-Bt-Bc-Bt-Bt-Bc-Bg-,

-continued (1j') HO-Ba-Bg-Bt-Bc-Bt-Bt-Bc-Bg-, (1k') HO-Bg-Ba-Bg-Bt-Bc-Bt-Bt-Bc-Bg-, (SEQ ID NO: 89)
(1l') HO-Bt-Bg-Ba-Bg-Bt-Bc-Bt-Bt-Bc-Bg-, (SEQ ID NO: 90)
(1m') HO-Bt-Bt-Bg-Ba-Bg-Bt-Bc-Bt-Bt-Bc-Bg-, (SEQ ID NO: 91)
(1n') HO-Bg-Bt-Bt-Bg-Ba-Bg-Bt-Bc-Bt-Bt-Bc-Bg-, or (SEQ ID NO: 2)
(1o') HO-Ba-Bg-Bt-Bt-Bg-Ba-Bg-Bt-Bc-Bt-Bt-Bc-Bg-, where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

(G1)

[Chemical structure of guanine nucleoside with X and Y substituents at 2' and 3' positions]

11
-continued (G2)
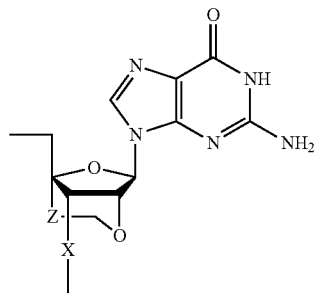

(A1)
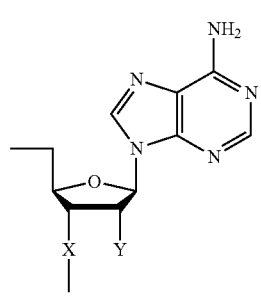

(A2)
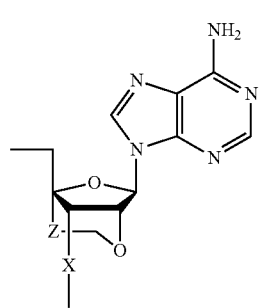

(C1)
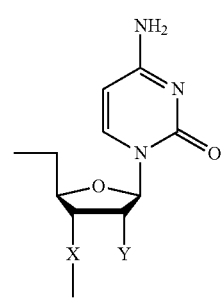

(C2)
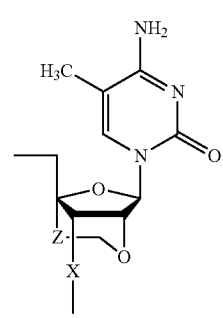

12
-continued (U1)
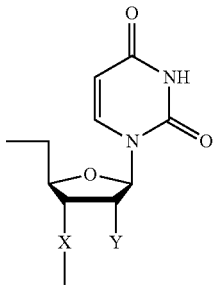

(T2)
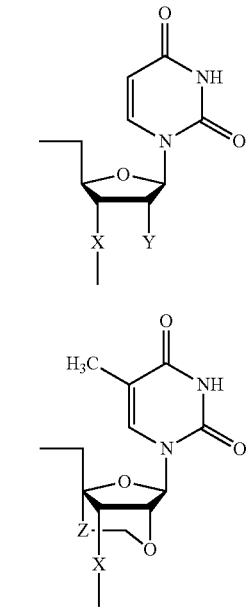

where X is individually and independently a group represented by the following formula (X1) or (X2):

(X1)
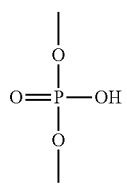

(X2)
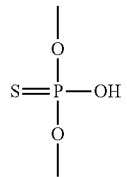

Y is individually and independently a hydrogen atom, a hydroxyl group or an alkoxy group with 1-6 carbon atoms; and Z is individually and independently a single bond or an alkylene group with 1-5 carbon atoms;

$B_{M'1}$ is a group represented by the following formula (1'):

-Ba-Ba-Ba-Bc-Bt-Bg-Ba- (1')

where Bg, Ba, Bt and Bc are as defined above;
$B_{B'1}$ is a group represented by any one of the following (12a') to (12l'):

(12a') -CH₂CH₂OH, (12b') -Bg-CH₂CH₂OH, (12c') -Bg-Bc-CH₂CH₂OH, (12d') -Bg-Bc-Ba-CH₂CH₂OH,

-continued (12e')-Bg-Bc-Ba-Ba-CH₂CH₂OH, (12f')-Bg-Bc-Ba-Ba-Ba-CH₂CH₂OH, (12g')-Bg-Bc-Ba-Ba-Ba-Bt-CH₂CH₂OH, (12h')-Bg-Bc-Ba-Ba-Ba-Bt-Bt-CH₂CH₂OH, (12i')-Bg-Bc-Ba-Ba-Ba-Bt-Bt-Bt-CH₂CH₂OH, (12j')-Bg-Bc-Ba-Ba-Ba-Bt-Bt-Bt-Bg-CH₂CH₂OH, (SEQ ID NO: 92)
(12k')-Bg-Bc-Ba-Ba-Ba-Bt-Bt-Bt-Bg-Bc-CH₂CH₂OH,
or (SEQ ID NO: 93)
(12l')-Bg-Bc-Ba-Ba-Ba-Bt-Bt-Bt-Bg-Bc-Bt-CH₂CH₂OH, where Bg, Ba, Bt and Bc are as defined above;

provided that at least one of the nucleosides constituting the compound represented by formula (I') has 2'-O,4'-C-alkylene group.

[14] A compound represented by the following general formula (II') or a pharmacologically acceptable salt thereof:

$$B_{T'2}\text{-}B_{M'2}\text{-}B_{B'2} \quad (II')$$

where $B_{T'2}$ is a group represented by any one of the following (2a') to (2j'):

(2a') HO-, (2b') HO-Bg-, (2c') HO-Ba-Bg-, (2d') HO-Ba-Ba-Bg-, (2e') HO-Ba-Ba-Ba-Bg-, (2f') HO-Bc-Ba-Ba-Ba-Bg-, (2g') HO-Bg-Bc-Ba-Ba-Ba-Bg-, (2h') HO-Bt-Bg-Bc-Ba-Ba-Ba-Bg-,
or (2j') HO-Bg-Bt-Bg-Bc-Ba-Ba-Ba-Bgwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

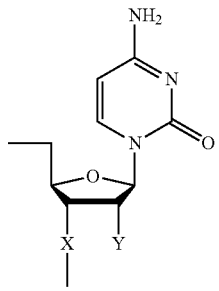
(G1)

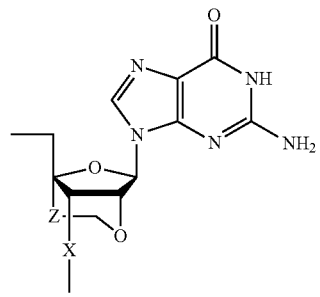
(G2)

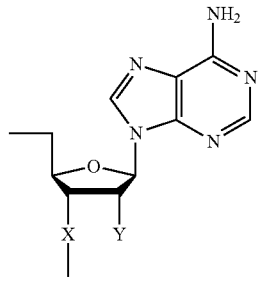
(A1)

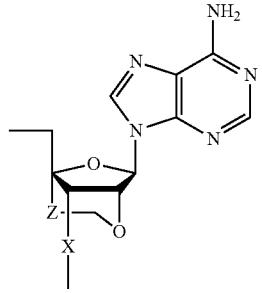
(A2)

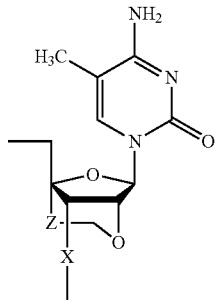
(C1)

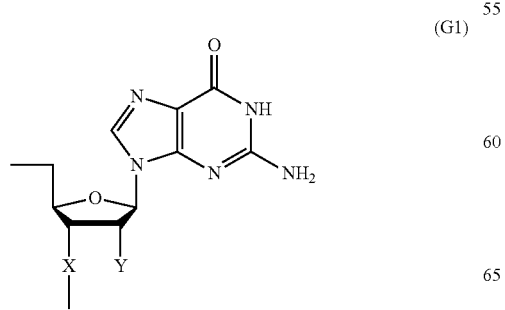
(C2)

-continued

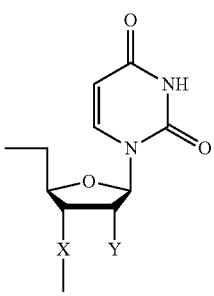
(U1)

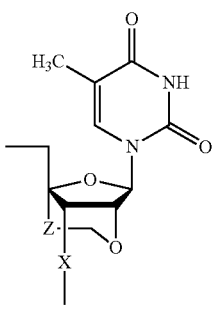
(T2)

where X is individually and independently a group represented by the following formula (X1) or (X2):

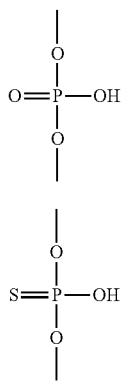

Y is individually and independently a hydrogen atom, a hydroxyl group or an alkoxy group with 1-6 carbon atoms; and Z is individually and independently a single bond or an alkylene group with 1-5 carbon atoms;

$B_{M'2}$ is a group represented by the following formula (2'):

(SEQ ID NO: 94)
-Bt-Bt-Bg-Ba-Bg-Bt-Bc-Bt-Bt-Bc-    (2')

where Bg, Ba, Bt and Bc are as defined above;

$B_{B'2}$ is a group represented by any one of the following (22a') to (22i'):

(22a')-CH₂CH₂OH, (22b')-Ba-CH₂CH₂OH, (22c')-Ba-Ba-CH₂CH₂OH, (22d')-Ba-Ba-Ba-CH₂CH₂OH, (22e')-Ba-Ba-Ba-Ba-CH₂CH₂OH, (22f')-Ba-Ba-Ba-Ba-Bc-CH₂CH₂OH, (22g')-Ba-Ba-Ba-Ba-Bc-Bt-CH₂CH₂OH, (22h')-Ba-Ba-Ba-Ba-Bc-Bt-Bg-CH₂CH₂OH,
or (22i')-Ba-Ba-Ba-Ba-Bc-Bt-Bg-Ba-CH₂CH₂OH where Bg, Ba, Bt and Bc are as defined above;

provided that at least one of the nucleosides constituting the compound represented by formula (II') has 2'-O,4'-C-alkylene group.

[15] A compound represented by the following general formula (III') or a pharmacologically acceptable salt thereof:

$$B_{T'3}\text{-}B_{M'3}\text{-}B_{B'3} \quad (III')$$

where $B_{T'3}$ is a group represented by any one of the following (3a') to (3c'):

(3a') HO-, (3b') HO-Bc-,
or (3c') HO-Bg-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

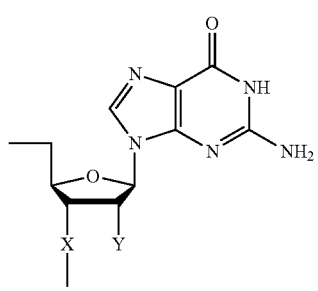
(G1)

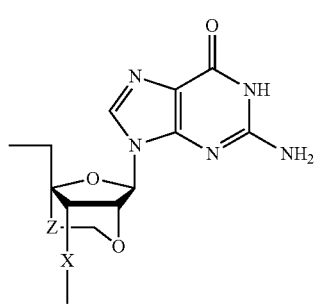
(G2)

17
-continued (A1) 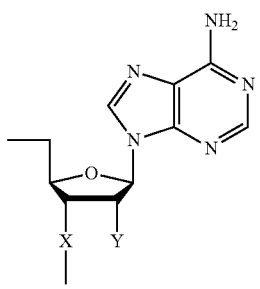

(A2) 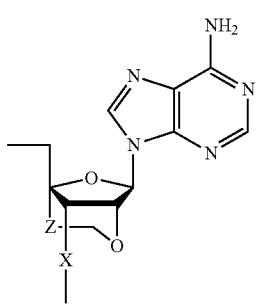

(C1) 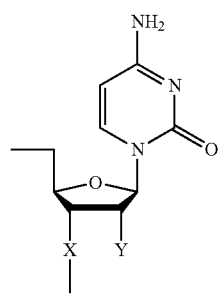

(C2) 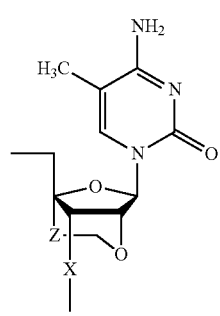

(U1) 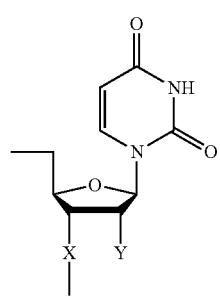

18
-continued (T2) 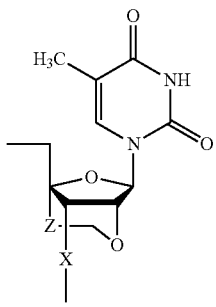

where X is individually and independently a group represented by the following formula (X1) or (X2):

(X1) 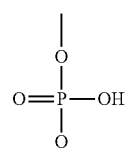

(X2) 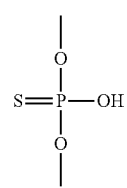

Y is individually and independently a hydrogen atom, a hydroxyl group or an alkoxy group with 1-6 carbon atoms; and Z is individually and independently a single bond or an alkylene group with 1-5 carbon atoms;

$B_{M3}$ is a group represented by the following formula (3'):

```
                               (SEQ ID NO: 95)
-Bc-Bg-Bc-Bt-Bg-Bc-Bc-Ba-Ba-  (3')
``` where Bg, Ba, Bt and Bc are as described above;)

$B_{B3}$ is a group represented by any one of the following (32a') to (32i'):

```
(32a')-CH₂CH₂OH, (32b')-Bt-CH₂CH₂OH, (32c')-Bt-Bg-CH₂CH₂OH, (32d')-Bt-Bg-Bc-CH₂CH₂OH, (32e')-Bt-Bg-Bc-Bc-CH₂CH₂OH, (32f')-Bt-Bg-Bc-Bc-Ba-CH₂CH₂OH, (32g')-Bt-Bg-Bc-Bc-Ba-Bt-CH₂CH₂OH, (32h')-Bt-Bg-Bc-Bc-Ba-Bt-Bc-CH₂CH₂OH,
or (32i')-Bt-Bg-Bc-Bc-Ba-Bt-Bc-Bc-CH₂CH₂OH,
``` where Bg, Ba, Bt and Bc are as described above;

provided that at least one of the nucleosides constituting the compound represented by formula (III') has 2'-O,4'-C-alkylene group.

[16] A compound represented by the following general formula (IV') or a pharmacologically acceptable salt thereof:

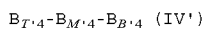

where $B_{T'4}$ is a group represented by any one of the following (4a') to (4m'):

(4a') HO-, (4b') HO-Ba-, (4c') HO-Ba-Ba-, (4d') HO-Bc-Ba-Ba-, (4e') HO-Ba-Bc-Ba-Ba-, (4f') HO-Bg-Ba-Bc-Ba-Ba-, (4g') HO-Bt-Bg-Ba-Bc-Ba-Ba-, (4h') HO-Bc-Bt-Bg-Ba-Bc-Ba-Ba-, (4j') HO-Bt-Bc-Bt-Bg-Ba-Bc-Ba-Ba-, (4k') HO-Bt-Bt-Bc-Bt-Bg-Ba-Bc-Ba-Ba-, (SEQ ID NO: 96)
(4l') HO-Bg-Bt-Bt-Bc-Bt-Bg-Ba-Bc-Ba-Ba-,
or (SEQ ID NO: 97)
(4m') HO-Bt-Bg-Bt-Bt-Bc-Bt-Bg-Ba-Bc-Ba-Bawhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

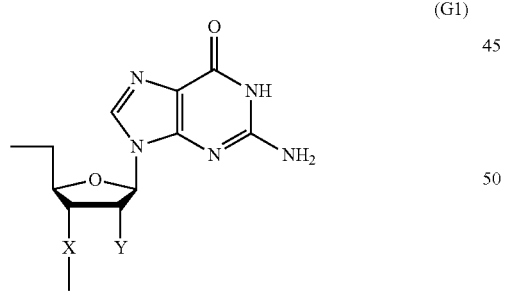
(G1)

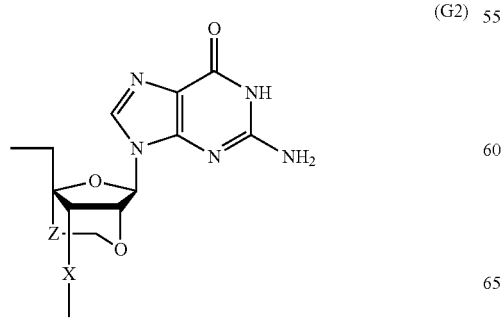
(G2)

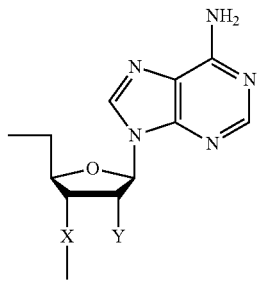
(A1)

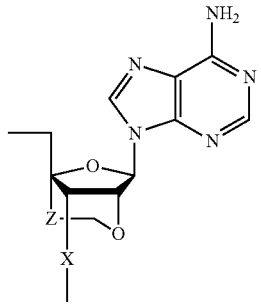
(A2)

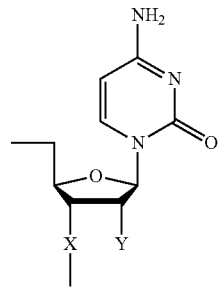
(C1)

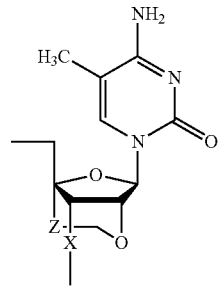
(C2)

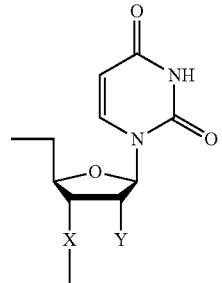
(U1)

(T2) 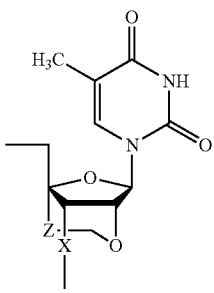

where X is individually and independently a group represented by the following formula (X1) or (X2):

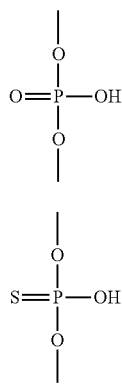 (X1)

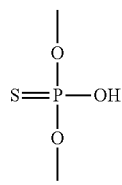 (X2)

Y is individually and independently a hydrogen atom, a hydroxyl group or an alkoxy group with 1-6 carbon atoms; and Z is individually and independently a single bond or an alkylene group with 1-5 carbon atoms;

$B_{M'4}$ is a group represented by the following formula (4'):

-Bc-Ba-Bg-Bt-Bt-Bt-Bg- (4')

where Bg, Ba, Bt and Bc are as described above;
$B_{B'4}$ is a group represented by any one of the following (42a') to (42l'):

(42a') -CH₂CH₂OH, (42b') -Bc-CH₂CH₂OH, (42c') -Bc-Bc-CH₂CH₂OH, (42d') -Bc-Bc-Bg-CH₂CH₂OH, (42e') -Bc-Bc-Bg-Bc-CH₂CH₂OH, (42f') -Bc-Bc-Bg-Bc-Bt-CH₂CH₂OH, (42g') -Bc-Bc-Bg-Bc-Bt-Bg-CH₂CH₂OH, (42h') -Bc-Bc-Bg-Bc-Bt-Bg-Bc-CH₂CH₂OH, (42i') -Bc-Bc-Bg-Bc-Bt-Bg-Bc-Bc-CH₂CH₂OH, (42j') -Bc-Bc-Bg-Bc-Bt-Bg-Bc-Bc-Bc-CH₂CH₂OH, (SEQ ID NO: 98)
(42k') -Bc-Bc-Bg-Bc-Bt-Bg-Bc-Bc-Bc-Ba-CH₂CH₂OH, or (SEQ ID NO: 99)
(42l') -Bc-Bc-Bg-Bc-Bt-Bg-Bc-Bc-Bc-Ba-Ba-CH₂CH₂OH, where Bg, Ba, Bt and Bc are as described above;

provided that at least one of the nucleosides constituting the compound represented by formula (IV') has 2'-O,4'-C-alkylene group.

[17] A compound represented by the following general formula (V') or a pharmacologically acceptable salt thereof:

$B_{T'5}$-$B_{M'5}$-$B_{B'5}$  (V')

where $B_{T'5}$ is a group represented by any one of the following (5a') to (5g'):

(5a') HO-, (5b') HO-Bt-, (5c') HO-Bt-Bt-, (5d') HO-Bt-Bt-Bt-, (5e') HO-Bt-Bt-Bt-Bt-, (5f') HO-Bc-Bt-Bt-Bt-Bt-, or (5g') HO-Bg-Bc-Bt-Bt-Bt-Btwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

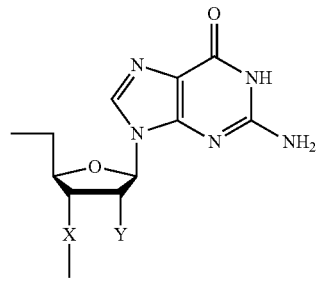 (G1)

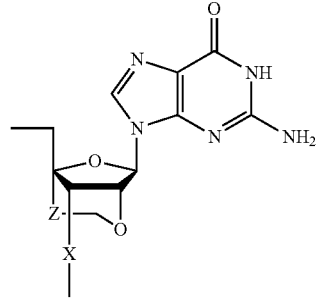 (G2)

-continued (A1)
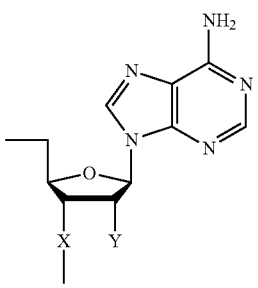

(A2)
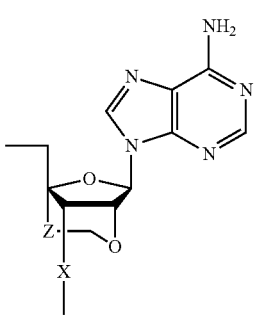

(C1)
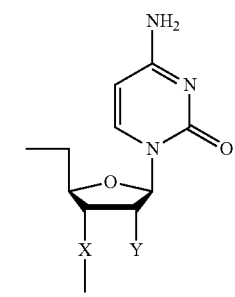

(C2)
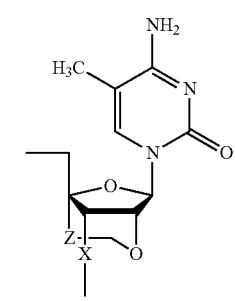

(U1)
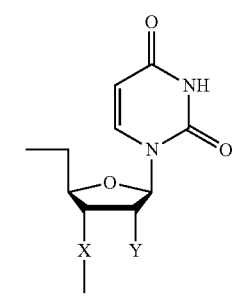

-continued (T2)
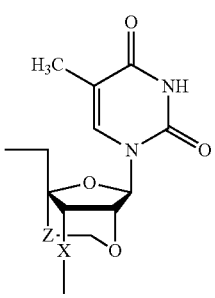

where X is individually and independently a group represented by the following formula (X1) or (X2):

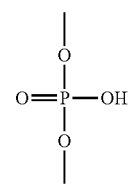
(X1)

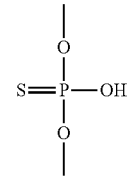
(X2)

Y is individually and independently a hydrogen atom, a hydroxyl group or an alkoxy group with 1-6 carbon atoms; and Z is individually and independently a single bond or an alkylene group with 1-5 carbon atoms;

$B_{M'5}$ is a group represented by the following formula (5'):

```
                                    (SEQ ID NO: 100)
  -Bc-Bt-Bt-Bt-Bt-Ba-Bg-Bt-Bt-Bg-Bc-Bt-Bg-Bc-  (5')
``` where Bg, Ba, Bt and Bc are as described above;
$B_{B'5}$ is a group represented by any one of the following (52a') to (52i'):

```
(52a')-CH₂CH₂OH, (52b')-Bt-CH₂CH₂OH, (52c')-Bt-Bc-CH₂CH₂OH, (52d')-Bt-Bc-Bt-CH₂CH₂OH, (52e')-Bt-Bc-Bt-Bt-CH₂CH₂OH, (52f')-Bt-Bc-Bt-Bt-Bt-CH₂CH₂OH, (52g')-Bt-Bc-Bt-Bt-Bt-Bt-CH₂CH₂OH, (52h')-Bt-Bc-Bt-Bt-Bt-Bt-Bc-CH₂CH₂OH,
or (52i')-Bt-Bc-Bt-Bt-Bt-Bt-Bc-Bc-CH₂CH₂OH
``` where Bg, Ba, Bt and Bc are as described above;
provided that at least one of the nucleosides constituting the compound represented by formula (V') has 2'-O,4'-C-alkylene group.

[18] A compound represented by the following general formula (VI') or a pharmacologically acceptable salt thereof:

$$B_{T'6}\text{-}B_{M'6}\text{-}B_{B'6} \quad (VI')$$

where $B_{T'6}$ is a group represented by any one of the following (6a') to (6r'):

(6a') HO-, (6b') HO-Bc-, (6c') HO-Bt-Bc-, (6d') HO-Bc-Bt-Bc-, (6e') HO-Bg-Bc-Bt-Bc-, (6f') HO-Bt-Bg-Bc-Bt-Bc-, (6g') HO-Bc-Bt-Bg-Bc-Bt-Bc-, (6h') HO-Bg-Bc-Bt-Bg-Bc-Bt-Bc-, (6j') HO-Bt-Bg-Bc-Bt-Bg-Bc-Bt-Bc-, (6k') HO-Bt-Bt-Bg-Bc-Bt-Bg-Bc-Bt-Bc-, (SEQ ID NO: 101)
(6l') HO-Bg-Bt-Bt-Bg-Bc-Bt-Bg-Bc-Bt-Bc-, (SEQ ID NO: 102)
(6m') HO-Ba-Bg-Bt-Bt-Bg-Bc-Bt-Bg-Bc-Bt-Bc-, (SEQ ID NO: 103)
(6n') HO-Bt-Ba-Bg-Bt-Bt-Bg-Bc-Bt-Bg-Bc-Bt-Bc-, (SEQ ID NO: 104)
(6o') HO-Bt-Bt-Ba-Bg-Bt-Bt-Bg-Bc-Bt-Bg-Bc-Bt-Bc-, (SEQ ID NO: 105)
(6p') HO-Bt-Bt-Bt-Ba-Bg-Bt-Bt-Bg-Bc-Bt-Bg-Bc-Bt-Bc-, (SEQ ID NO: 106)
(6q') HO-Bt-Bt-Bt-Bt-Ba-Bg-Bt-Bt-Bg-Bc-Bt-Bg-Bc-Bt-Bc-,
or (SEQ ID NO: 107)
(6r') HO-Bc-Bt-Bt-Bt-Bt-Ba-Bg-Bt-Bt-Bg-Bc-Bt-Bg-Bc-Bt-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

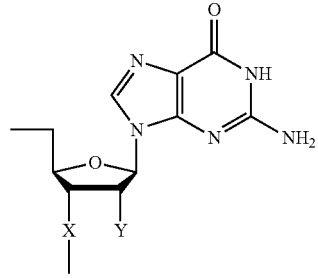
(G1)

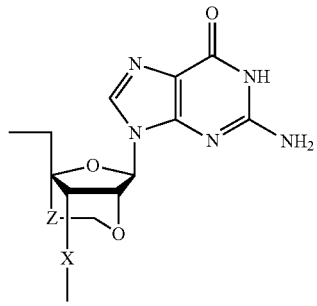
(G2)

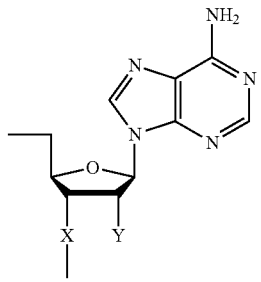
(A1)

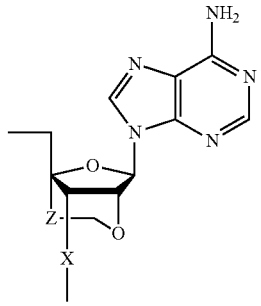
(A2)

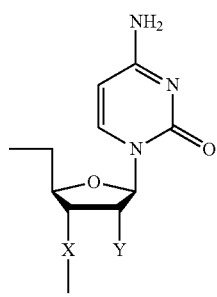
(C1)

(C2)

(U1)
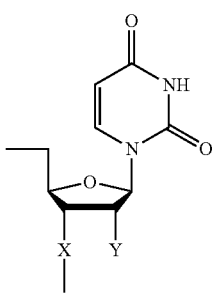

(T2)
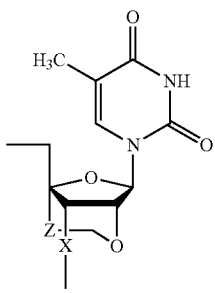

where X is individually and independently a group represented by the following formula (X1) or (X2):

(X1)
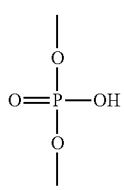

(X2)
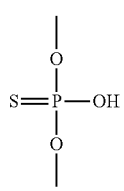

Y is individually and independently a hydrogen atom, a hydroxyl group or an alkoxy group with 1-6 carbon atoms; and Z is individually and independently a single bond or an alkylene group with 1-5 carbon atoms;

$B_{M'6}$ is a group represented by the following formula (6'):

```
-Bt-Bt-Bt-Bt-Bc-Bc- (6')
``` where Bg, Ba, Bt and Bc are as described above;
$B_{B'6}$ is a group represented by any one of the following (62a') to (62m'):

```
(62a')-CH2CH2OH,
(62b')-Ba-CH2CH2OH,
(62c')-Ba-Bg-CH2CH2OH,
(62d')-Ba-Bg-Bg-CH2CH2OH,
(62e')-Ba-Bg-Bg-Bt-CH2CH2OH,
(62f')-Ba-Bg-Bg-Bt-Bt-CH2CH2OH,
(62g')-Ba-Bg-Bg-Bt-Bt-Bc-CH2CH2OH,
(62h')-Ba-Bg-Bg-Bt-Bt-Bc-Ba-CH2CH2OH,
(62i')-Ba-Bg-Bg-Bt-Bt-Bc-Ba-Ba-CH2CH2OH,
(62j')-Ba-Bg-Bg-Bt-Bt-Bc-Ba-Ba-Bg-CH2CH2OH,
                                                (SEQ ID NO: 108)
(62k')-Ba-Bg-Bg-Bt-Bt-Bc-Ba-Ba-Bg-Bt-CH2CH2OH,
                                                (SEQ ID NO: 109)
(62l')-Ba-Bg-Bg-Bt-Bt-Bc-Ba-Ba-Bg-Bt-Bg-CH2CH2OH,
or
                                                (SEQ ID NO: 110)
(62m')-Ba-Bg-Bg-Bt-Bt-Bc-Ba-Ba-Bg-Bt-Bg-Bg-CH2CH2OH
``` where Bg, Ba, Bt and Bc are as described above;
provided that at least one of the nucleosides constituting the compound represented by formula (VI') has 2'-O,4'-C-alkylene group.

[19] A compound represented by the following general formula (VII') or a pharmacologically acceptable salt thereof:

where $B_{T'7}$ is a group represented by any one of the following (7a') to (7f'):

```
(7a')HO-,
(7b')HO-Bt-,
(7c')HO-Ba-Bt-,
(7d')HO-Bt-Ba-Bt-,
(7e')HO-Bt-Bt-Ba-Bt-,
or
(7f')HO-Bg-Bt-Bt-Ba-Bt-
``` where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

(G1)
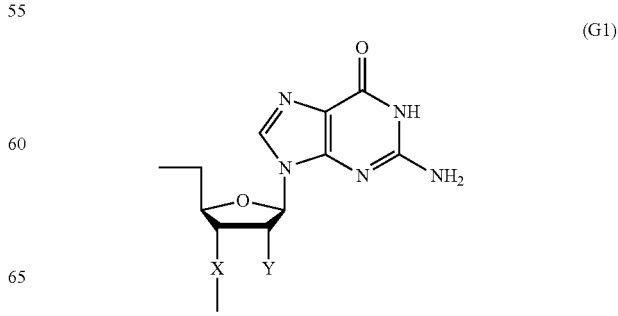

(G2) 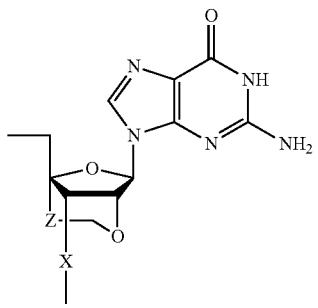

(A1) 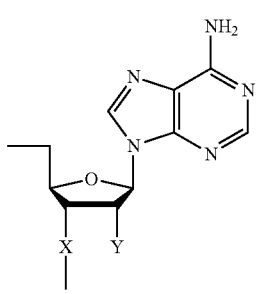

(A2) 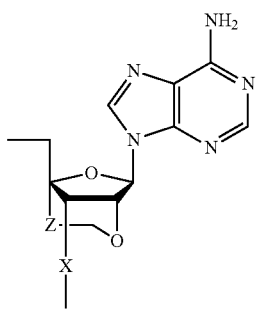

(C1) 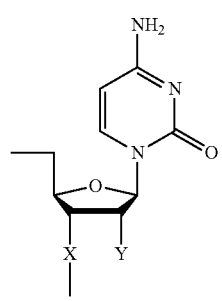

(C2) 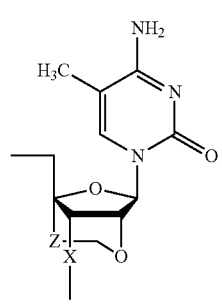

(U1) 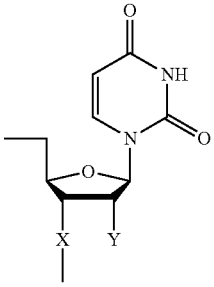

(T2) 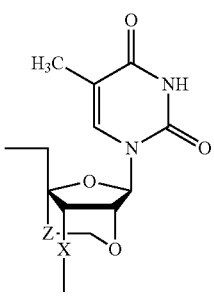

where X is individually and independently a group represented by the following formula (X1) or (X2):

(X1) 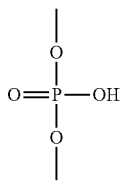

(X2) 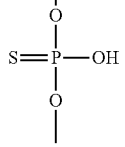

Y is individually and independently a hydrogen atom, a hydroxyl group or an alkoxy group with 1-6 carbon atoms; and Z is individually and independently a single bond or an alkylene group with 1-5 carbon atoms;

$B_{M7}$ is a group represented by the following formula (7'):

(SEQ ID NO: 21)
-Bc-Bt-Bg-Bc-Bt-Bt-Bc-Bc-Bt-Bc-Bc-Ba-Ba-Bc-Bc- (7')

where Bg, Ba, Bt and Bc are as described above;

$B_{B7}$ is a group represented by the following (72a'):

(72a') -CH₂CH₂OH provided that at least one of the nucleosides constituting the compound represented by formula (VII') has 2'-O,4'-C-alkylene group.

[20] The compound of any one of [13] to [19] above which is selected from the group consisting of the following compounds (i') to (xiii'), or a pharmacologically acceptable salt thereof:

(i') a compound represented by the following formula (i'):

(SEQ ID NO: 10)
HO-Ba-Bg-Bt-Bt-Bg-Ba-Bg-Bt-Bc-Bt-Bt-Bc-Bg-Ba-Ba-

Ba-Bc-Bt-Bg-Ba-Bg-Bc-Ba-CH₂CH₂OH (i')

(ii') a compound represented by the following formula (ii'):

(SEQ ID NO: 11)
HO-Ba-Ba-Ba-Bc-Bt-Bg-Ba-Bg-Bc-Ba-Ba-Ba-Bt-Bt-Bt-

Bg-Bc-Bt-CH₂CH₂OH (ii')

(iii') a compound represented by the following formula (iii'):

(SEQ ID NO: 12)
HO-Bt-Bt-Bg-Ba-Bg-Bt-Bc-Bt-Bt-Bc-Ba-Ba-Ba-Ba-Bc-

Bt-Bg-Ba-CH₂CH₂OH (iii')

(iv') a compound represented by the following formula (iv'):

(SEQ ID NO: 13)
HO-Bg-Bt-Bg-Bc-Ba-Ba-Ba-Bg-Bt-Bt-Bg-Ba-Bg-Bt-Bc-

Bt-Bt-Bc-CH₂CH₂OH (iv')

(v') a compound represented by the following formula (v'):

(SEQ ID NO: 14)
HO-Bg-Bc-Bc-Bg-Bc-Bt-Bg-Bc-Bc-Bc-Ba-Ba-Bt-Bg-Bc-

CH₂CH₂OH (v')

(vi') a compound represented by the following formula (vi'):

(SEQ ID NO: 15)
HO-Bc-Bg-Bc-Bt-Bg-Bc-Bc-Bc-Ba-Ba-Bt-Bg-Bc-Bc-Ba-

Bt-Bc-Bc-CH₂CH₂OH (vi')

(vii') a compound represented by the following formula (vii'):

(SEQ ID NO: 16)
HO-Bc-Ba-Bg-Bt-Bt-Bt-Bg-Bc-Bc-Bg-Bc-Bt-Bg-Bc-Bc-

Bc-Ba-Ba-CH₂CH₂OH (vii')

(viii') a compound represented by the following formula (viii'):

(SEQ ID NO: 17)
HO-Bt-Bg-Bt-Bt-Bt-Bg-Ba-Bc-Ba-Ba-Bc-Ba-Bg-Bt-

Bt-Bt-Bg-CH₂CH₂OH (viii')

(ix') a compound represented by the following formula (ix'):

(SEQ ID NO: 18)
HO-Bg-Bc-Bt-Bt-Bt-Bt-Bc-Bt-Bt-Bt-Bt-Ba-Bg-Bt-Bt-

Bg-Bc-Bt-Bg-Bc-CH₂CH₂OH (ix')

(x') a compound represented by the following formula (x'):

(SEQ ID NO: 19)
HO-Bc-Bt-Bt-Bt-Bt-Ba-Bg-Bt-Bt-Bg-Bc-Bt-Bg-Bc-Bt-

Bc-Bt-Bt-Bt-Bt-Bc-Bc-CH₂CH₂OH (x')

(xi') a compound represented by the following formula (xi'):

(SEQ ID NO: 20)
HO-Bt-Bt-Bt-Bt-Bc-Bc-Ba-Bg-Bg-Bt-Bt-Bc-Ba-Ba-Bg-

Bt-Bg-Bg-CH₂CH₂OH (xi')

(xii') a compound represented by the following formula (xii'):

(SEQ ID NO: 21)
HO-Bc-Bt-Bg-Bc-Bt-Bt-Bc-Bc-Bt-Bc-Bc-Ba-Ba-Bc-Bc-

CH₂CH₂OH (xii')

(xiii') a compound represented by the following formula (xiii'):

(SEQ ID NO: 22)
HO-Bg-Bt-Bt-Ba-Bt-Bc-Bt-Bg-Bc-Bt-Bt-Bc-Bc-Bt-Bc-

Bc-Ba-Ba-Bc-Bc-CH₂CH₂OH (xiii')

where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

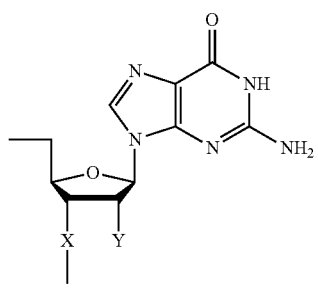

(G1)

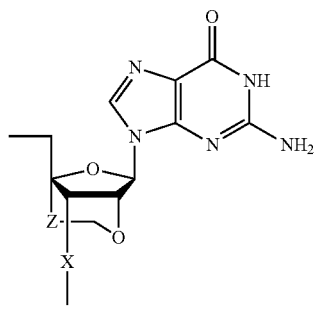

(G2)

(A1) 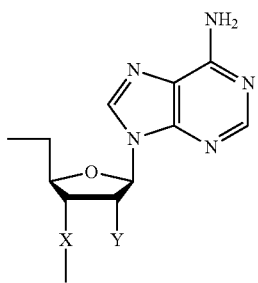

(A2) 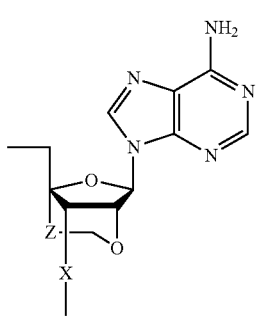

(C1) 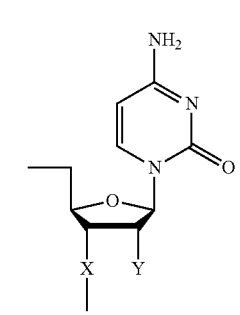

(C2) 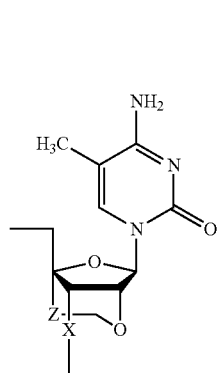

(U1) 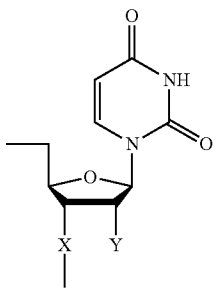

(T2) 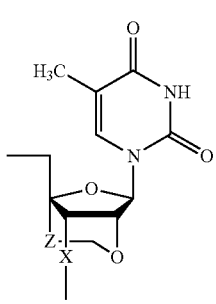

where X is individually and independently a group represented by the following formula (X1) or (X2):

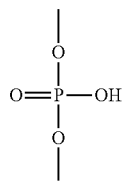
(X1)

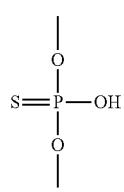
(X2)

Y is individually and independently a hydrogen atom, a hydroxyl group or an alkoxy group with 1-6 carbon atoms; and Z is individually and independently a single bond or an alkylene group with 1-5 carbon atoms.

[21] The compound of any one of [13] to [20] above which is represented by any one of the following compounds (I'1) to (I'20), or a pharmacologically acceptable salt thereof:

```
                                                       (SEQ ID NO: 10)
HO-Ba**-Bg**-Bt**-Bt**-Bg**-Ba*-Bg*-Bt*-Bc*-Bt*-Bt*-Bc*-

Bg*-Ba*-Ba*-Ba*-Bc*-Bt*-Bg-Ba-Bg-Bc-Ba**-CH₂CH₂OH (I'1)
```

```
                                                       (SEQ ID NO: 10)
HO-Ba**-Bg**-Bt**-Bt**-Bg**-Ba**-Bg**-Bt**-Bc**-Bt*-Bt*-Bc*-

Bg*-Ba*-Ba*-Ba**-Bc**-Bt**-Bg**-Ba**-Bg**-Bc**-Ba**-

CH₂CH₂OH  (I'2)
```

-continued (SEQ ID NO: 11)
HO-Ba\*\*-Ba\*\*-Ba\*\*-Bc\*\*-Bt\*\*-Bg\*-Ba\*-Bg\*-Bc\*-Ba\*-Ba\*-Ba\*-Bt\*-Bt\*\*-Bt\*\*-Bg\*\*-Bc\*\*-Bt\*\*-CH$_2$CH$_2$OH (I'3)

(SEQ ID NO: 12)
HO-Bt\*\*-Bt\*\*-Bg\*\*-Ba\*\*-Bg\*\*-Bt\*-Bc\*-Bt\*-Bt\*-Bc\*-Ba\*-Ba\*-Ba\*\*-Bc\*\*-Bt\*\*-Bg\*\*-Ba\*\*-CH$_2$CH$_2$OH (I'4)

(SEQ ID NO: 13)
HO-Bg\*\*-Bt\*\*-Bg\*\*-Bc\*\*-Ba\*\*-Ba\*-Ba\*-Bg\*-Bt\*-Bt\*-Bg\*-Ba\*-Bg\*-Bt\*\*-Bc\*\*-Bt\*\*-Bt\*\*-Bc\*\*-CH$_2$CH$_2$OH (I'5)

(SEQ ID NO: 12)
HO-Bt\*\*-Bt\*\*-Bg\*-Ba\*-Bg\*-Bt\*\*-Bc\*\*-Bt\*\*-Bt\*\*-Bc\*\*-Ba\*-Ba\*-Ba\*-Ba\*-Bc\*\*-Bt\*\*-Bg\*-Ba\*-CH$_2$CH$_2$OH (I'6)

(SEQ ID NO: 13)
HO-Bg\*-Bt\*\*-Bg\*-Bc\*\*-Ba\*-Ba\*-Ba\*-Bg\*-Bt\*\*-Bt\*\*-Bg\*-Bg\*-Bt\*\*-Bc\*\*-Bt\*\*-Bt\*\*-Bc\*\*-CH$_2$CH$_2$OH (I'7)

(SEQ ID NO: 14)
HO-Bg\*\*-Bc\*\*-Bc\*\*-Bg\*\*-Bc\*\*-Bt\*-Bg\*-Bc\*-Bc\*-Ba\*\*-Ba\*\*-Bt\*\*-Bg\*\*-Bc\*\*-CH$_2$CH$_2$OH (I'8)

(SEQ ID NO: 15)
HO-Bc\*\*-Bg\*-Bc\*\*-Bt\*\*-Bg\*-Bc\*-Bc\*\*-Bc\*\*-Ba\*-Ba\*-Bt\*\*-Bg\*-Bc\*\*-Bc\*\*-Ba\*-Bt\*-Bc\*\*-Bc\*\*-CH$_2$CH$_2$OH (I'9)

(SEQ ID NO: 16)
HO-Bc\*\*-Ba\*-Bg\*-Bt\*\*-Bt\*-Bt\*-Bg\*-Bc\*\*-Bc\*\*-Bg\*-Bc\*\*-Bt\*\*-Bg\*-Bc\*\*-Bc\*\*-Bc\*\*-Ba\*-Ba\*-CH$_2$CH$_2$OH (I'10)

(SEQ ID NO: 17)
HO-Bt\*\*-Bg\*-Bt\*\*-Bt\*\*-Bc\*\*-Bt\*\*-Bg\*-Ba\*-Bc\*\*-Ba\*-Ba\*-Bc\*\*-Ba\*-Bg\*-Bt\*\*-Bt\*\*-Bt\*\*-Bg\*-CH$_2$CH$_2$OH (I'11)

(SEQ ID NO: 15)
HO-Bc\*\*-Bg\*-Bc\*\*-Bt\*\*-Bg\*-Bc\*-Bc\*\*-Bc\*\*-Ba\*-Ba\*-Bt\*\*-Bg\*-Bc\*\*-Bc\*\*-Ba\*-Bt\*-Bc\*\*-Bc\*\*-CH$_2$CH$_2$OH (I'12)

(SEQ ID NO: 18)
HO-Bg\*\*-Bc\*\*-Bt\*\*-Bt\*\*-Bt\*\*-Bt\*-Bc\*-Bt\*-Bt\*-Bt\*-Bt\*-Ba\*-Bg\*-Bt\*-Bt\*-Bg\*\*-Bc\*\*-Bt\*\*-Bg\*\*-Bc\*\*-CH$_2$CH$_2$OH (I'13)

(SEQ ID NO: 19)
HO-Bc\*-Bt\*-Bt\*-Bt\*-Bt\*-Ba\*\*-Bg\*\*-Bt\*\*-Bt\*\*-Bg\*\*-Bc\*\*-Bt\*\*-Bg\*\*-Bc\*\*-Bt\*\*-Bc\*\*-Bt\*\*-Bt\*-Bt\*-Bc\*-Bc\*-CH$_2$CH$_2$OH (I'14)

(SEQ ID NO: 21)
HO-Bc\*\*-Bt\*\*-Bg\*\*-Bc\*\*-Bt\*\*-Bt\*-Bc\*-Bt\*-Bc\*-Bc\*\*-Ba\*\*-Ba\*\*-Bc\*\*-Bc\*\*-CH$_2$CH$_2$OH (I'15)

(SEQ ID NO: 22)
HO-Bg\*\*-Bt\*\*-Bt\*\*-Ba\*\*-Bt\*\*-Bc\*-Bt\*-Bg\*-Bc\*-Bt\*-Bt\*-Bc\*-Bc\*-Bt\*-Bc\*-Bc\*\*-Ba\*\*-Ba\*\*-Bc\*\*-Bc\*\*-CH$_2$CH$_2$OH (I'16)

(SEQ ID NO: 19)
HO-Bc\*\*-Bt\*\*-Bt\*\*-Bt\*\*-Bt\*\*-Ba\*-Bg\*-Bt\*\*-Bt\*\*-Bg\*-Bc\*\*-Bt\*-Bg\*-Bc\*-Bt\*-Bc\*-Bt\*-Bt\*\*-Bt\*\*-Bt\*\*-Bc\*\*-Bc\*\*-CH$_2$CH$_2$OH (I'17)

(SEQ ID NO: 20)
HO-Bt\*\*-Bt\*\*-Bt\*\*-Bt\*\*-Bc\*\*-Bc\*-Ba\*-Bg\*-Bg\*-Bt\*-Bt\*-Bc\*-Ba\*-Ba\*\*-Bg\*\*-Bt\*\*-Bg\*\*-Bg\*\*-CH$_2$CH$_2$OH (I'18)

```
                                                       (SEQ ID NO: 21)
HO-Bc**-Bt*-Bg*-Bc**-Bt*-Bt*-Bc**-Bc**-Bt*-Bc**-Bc**-Ba*-Ba*-Bc**-

Bc**-CH2CH2OH  (I'19)

(SEQ ID NO: 21)
HO-Bc**-Bt**-Bg*-Bc**-Bt**-Bt*-Bc*-Bc**-Bt*-Bc*-Bc**-Ba*-Ba*-Bc**-

Bc**-CH2CH2OH  (I'20)
``` where Bg* is a group represented by the following formula (G1$^a$); Ba* is a group represented by the following formula (A1$^a$); Bc* is a group represented by the following formula (C1$^a$); Bt* is a group represented by the following formula (U1$^a$); Bg is a group represented by the following formula (G2); Ba is a group represented by the following formula (A2); Bc is a group represented by the following formula (C2); and Bt is a group represented by the following formula (T2):

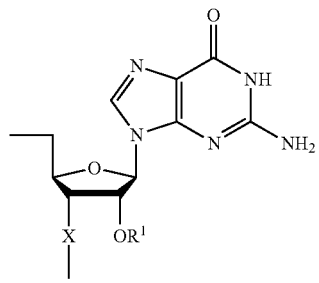

(G1$^a$)

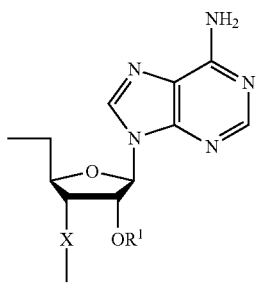

(A1$^a$)

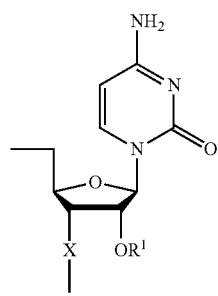

(C1$^a$)

-continued

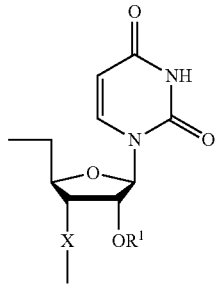

(U1$^a$)

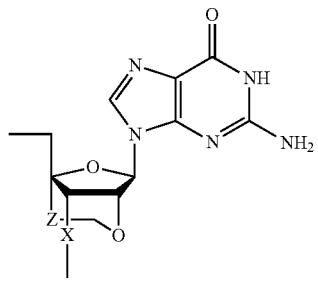

(G2)

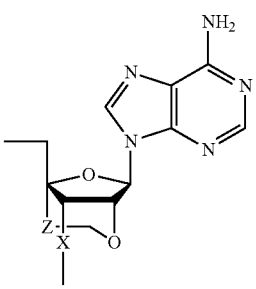

(A2)

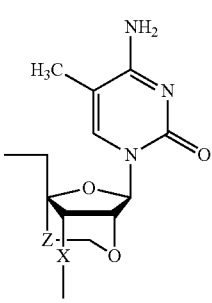

(C2)

(T2) 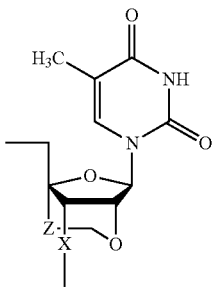

where X is individually and independently a group represented by the following formula (X1) or (X2); $R^1$ is individually and independently an alkyl group with 1-6 carbon atoms; and Z is individually and independently a single bond or an alkylene group with 1-5 carbon atoms:

(X1)

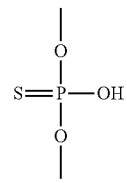 (X2)

[22] The compound of [21] above where X in formulas $(G1^a)$, $(A1^a)$, $(C1^a)$ and $(U1^a)$ is a group represented by formula (X2) and X in formulas (G2), (A2), (C2) and (T2) is a group represented by formula (X1), or a pharmacologically acceptable salt thereof.

[23] The compound of [21] above where X in all the formulas $(G1^a)$, $(A1^a)$, $(C1^a)$, $(U1^a)$, (G2), (A2), (C2) and (T2) is a group represented by formula (X2), or a pharmacologically acceptable salt thereof.

[24] The compound of [21] above which is represented by any one of the following formulas (I'1-a) to (I'20-b), or a pharmacologically acceptable salt thereof:

(SEQ ID NO: 10)
HO-Ba\*\*-Bg\*\*-Bt\*\*-Bt\*\*-Bg\*\*-Ba\*-Bg\*-Bt\*-Bc\*-Bt\*-Bt\*-Bc\*-Bg\*-Ba\*-Ba\*-Ba\*-Bc\*-Bt\*-Bg\*\*-Ba\*\*-Bg\*\*-Bc\*\*-Ba\*\*-CH₂CH₂OH (I'1-a)

(SEQ ID NO: 10)
HO-Ba\*\*-Bg\*\*-Bt\*\*-Bt\*\*-Bg\*\*-Ba\*\*-Bg\*\*-Bt\*\*-Bc\*\*-Bt\*-Bt\*-Bc\*-Bg\*-Ba\*-Ba\*-Ba\*\*-Bc\*\*-Bt\*\*-Bg\*\*-Ba\*\*-Bg\*\*-Bc\*\*-Ba\*\*-CH₂CH₂OH (I'2-a)

(SEQ ID NO: 11)
HO-Ba\*\*-Ba\*\*-Ba\*\*-Bc\*\*-Bt\*\*-Bg\*-Ba\*-Bg\*-Bc\*-Ba\*-Ba\*-Ba\*-Bt\*-Bt\*\*-Bt\*\*-Bg\*-Bc\*-Bt\*\*-CH₂CH₂OH (I'3-a)

(SEQ ID NO: 12)
HO-Bt\*\*-Bt\*\*-Bg\*\*-Ba\*\*-Bg\*\*-Bt\*-Bc\*-Bt\*-Bt\*-Bc\*-Ba\*-Ba\*-Ba\*-Ba\*\*-Bc\*\*-Bt\*\*-Bg\*\*-Ba\*\*-CH₂CH₂OH (I'4-a)

(SEQ ID NO: 13)
HO-Bg\*\*-Bt\*\*-Bg\*\*-Bc\*\*-Ba\*\*-Ba\*-Ba\*-Bg\*-Bt\*-Bt\*-Bg\*-Ba\*-Bg\*\*-Bt\*\*-Bc\*\*-Bt\*\*-Bt\*\*-Bc\*\*-CH₂CH₂OH (I'5-a)

(SEQ ID NO: 12)
HO-Bt\*\*-Bt\*\*-Bg\*-Ba\*-Bg\*-Bt\*\*-Bc\*\*-Bt\*\*-Bt\*\*-Bc\*\*-Ba\*-Ba\*-Ba\*-Ba\*-Bc\*\*-Bt\*\*-Bg\*-Ba\*-CH₂CH₂OH (I'6-a)

(SEQ ID NO: 12)
HO-Bt\*\*-Bt\*\*-Bg\*-Ba\*-Bg\*-Bt\*\*-Bc\*\*-Bt\*\*-Bt\*\*-Bc\*\*-Ba\*-Ba\*-Ba\*-Ba\*-Bc\*\*-Bt\*\*-Bg\*-Ba\*-CH₂CH₂OH (I'6-b)

(SEQ ID NO: 12)
HO-Bt\*\*-Bt\*\*-Bg\*-Ba\*-Bg\*-Bt\*\*-Bc\*\*-Bt\*\*-Bt\*\*-Bc\*\*-Ba\*-Ba\*-Ba\*-Ba\*-Bc\*\*-Bt\*\*-Bg\*-Ba\*-CH₂CH₂OH (I'6-c)

(SEQ ID NO: 13)
HO-Bg\*-Bt\*\*-Bg\*-Bc\*\*-Ba\*-Ba\*-Ba\*-Bg\*-Bt\*\*-Bt\*\*-Bg\*-Ba\*-Bg\*-Bt\*\*-Bc\*\*-Bt\*\*-Bt\*\*-Bc\*\*-CH₂CH₂OH (I'7-a)

(SEQ ID NO: 13)
HO-Bg\*-Bt\*\*-Bg\*-Bc\*\*-Ba\*-Ba\*-Ba\*-Bg\*-Bt\*\*-Bt\*\*-Bg\*-Ba\*-Bg\*-Bt\*\*-Bc\*\*-Bt\*\*-Bt\*\*-Bc\*\*-CH₂CH₂OH (I'7-b)

(SEQ ID NO: 13)
HO-Bg\*-Bt\*\*-Bg\*-Bc\*\*-Ba\*-Ba\*-Ba\*-Bg\*-Bt\*\*-Bt\*\*-Bg\*-Ba\*-Bg\*-Bt\*\*-Bc\*\*-Bt\*\*-Bq\*\*-Bc\*\*-CH₂CH₂OH (I'7-c)

(SEQ ID NO: 14)
HO-Bg\*\*-Bc\*\*-Bc\*\*-Bg\*\*-Bc\*\*-Bt\*-Bg\*-Bc\*-Bc\*-Ba\*\*-Ba\*\*-Bt\*\*-Bg\*\*-Bc\*\*-CH₂CH₂OH (I'8-a)

-continued (SEQ ID NO: 15)
HO-Bc**-Bg*-Bc-Bt-Bg*-Bc*-Bc-Bc-Ba*-Ba*-Bt*-Bg*-Bc-Bc-Ba*-Bt*-Bc-Bc-CH$_2$CH$_2$OH (I'9-a)

(SEQ ID NO: 16)
HO-Bc**-Ba*-Bg*-Bt-Bt-Bt**-Bg*-Bc-Bc-Bg*-Bc-Bt-Bg*-Bc-Bc-Bc**-Ba*-Ba*-CH$_2$CH$_2$OH (I'10-a)

(SEQ ID NO: 17)
HO-Bt*-Bg*-Bt-Bt-Bc-Bt-Bg*-Ba*-Bc**-Ba*-Ba*-Bc**-Ba*-Bg*-Bt-Bt-Bt**-Bg*-CH$_2$CH$_2$OH (I'11-a)

(SEQ ID NO: 15)
HO-Bc**-Bg*-Bc-Bt-Bg*-Bc*-Bc-Bc-Ba*-Ba*-Bt*-Bg*-Bc-Bc-Ba*-Bt*-Bc-Bc-CH$_2$CH$_2$OH (I'12-a)

(SEQ ID NO: 18)
HO-Bg-Bc-Bt-Bt-Bt-Bt-Bc*-Bt*-Bt*-Bt*-Bt*-Ba*-Bg*-Bt*-Bt*-Bg-Bc-Bt-Bg-Bc**-CH$_2$CH$_2$OH (I'13-a)

(SEQ ID NO: 19)
HO-Bc*-Bt*-Bt*-Bt*-Bt*-Ba*-Bg-Bt-Bt-Bg-Bc-Bt-Bg-Bc-Bt-Bc-Bt**-Bt*-Bt*-Bc*-Bc*-CH$_2$CH$_2$OH (I'14-a)

(SEQ ID NO: 21)
HO-Bc-Bt-Bg-Bc-Bt**-Bt*-Bc*-Bc*-Bt*-Bc*-Bc-Ba-Ba-Bc-Bc**-CH$_2$CH$_2$OH (I'15-a)

(SEQ ID NO: 22)
HO-Bg-Bt-Bt**-Ba*-Bt**-Bc*-Bt*-Bg*-Bc*-Bt*-Bt*-Bc*-Bc*-Bt*-Bc*-Bc**-Ba*-Ba-Bc-Bc**-CH$_2$CH$_2$OH (I'16-a)

(SEQ ID NO: 19)
HO-Bc**-Bt*-Bt**-Bt*-Bt**-Ba*-Bg*-Bt*-Bt*-Bg*-Bc*-Bt*-Bg*-Bc*-Bt*-Bc*-Bt*-Bt-Bt-Bc-Bc-CH$_2$CH$_2$OH (I'17-a)

(SEQ ID NO: 20)
HO-Bt-Bt-Bt-Bt-Bc**-Bc*-Ba*-Bg*-Bg*-Bt*-Bt*-Bc*-Ba*-Ba-Bg-Bt-Bg-Bg**-CH$_2$CH$_2$OH (I'18-a)

(SEQ ID NO: 21)
HO-Bc-Bt-Bg-Bc-Bt**-Bt*-Bc*-Bc*-Bt*-Bc*-Bc-Ba-Ba-Bc-Bc**-CH$_2$CH$_2$OH (I'18-b)

(SEQ ID NO: 21)
HO-Bc-Bt-Bg*-Bc**-Bt*-Bt*-Bc-Bc-Bt*-Bc-Bc-Ba*-Ba*-Bc-Bc-CH$_2$CH$_2$OH (I'19-a)

(SEQ ID NO: 21)
HO-Bc**-Bt*-Bg*-Bc*-Bt*-Bt*-Bc-Bc-Bt*-Bc-Bc-Ba*-Ba*-Bc-Bc-CH$_2$CH$_2$OH (I'19-b)

(SEQ ID NO: 21)
HO-Bc-Bt-Bg*-Bc-Bt-Bt*-Bc*-Bc*-Bt*-Bc*-Bc**-Ba*-Ba*-Bc-Bc-CH$_2$CH$_2$OH (I'20-a)

(SEQ ID NO: 21)
HO-Bc-Bt-Bg*-Bc-Bt-Bt*-Bc*-Bc**-Bt*-Bc*-Bc**-Ba*-Ba*-Bc-Bc-CH$_2$CH$_2$OH (I'20-b)

where Bg* is a group represented by formula (G1$^a$), Ba* is a group represented by formula (A1$^a$); Bc* is a group represented by formula (C1$^a$); Bt* is a group represented by formula (U1$^a$); Bg is a group represented by formula (G2); Ba is a group represented by formula (A2); Bc is a group represented by formula (C2); Bt is a group represented by formula (T2); and in individual formulas, at least one of Bg*, Ba*, Bc*, Bt*, Bg, Ba, Bc and Bt has a group represented by formula (X2) as X and all of Bg**, Ba*, Bc*, Bt*, Bg, Bc, Bc, and Bt have a group represented by formula (X1) as X.

[25] The compound of any one of [13] to [24] above where Y in formulas (G1), (A1), (C1) and (U1) is a methoxy group and Z in formulas (G2), (A2), (C2) and (T2) is an ethylene group, or a pharmacologically acceptable salt thereof.

[26] A compound represented by the following general formula (I'') or a pharmacologically acceptable salt thereof:

$$B_{T''1}\text{-}B_{M''1}\text{-}B_{B''1} \quad (I'')$$

where $B_{T''1}$ is a group represented by any one of the following (1a'') to (1m''):

(1a'') HO-, (1b'') HO-Bt-, (1c'') HO-Bt-Bt-, (1d'') HO-Bt-Bt-Bt-, (1e'') HO-Ba-Bt-Bt-Bt-, (1f'') HO-Bt-Ba-Bt-Bt-, (1g'') HO-Bg-Bt-Ba-Bt-Bt-Bt-, (1h'') HO-Bt-Bg-Bt-Ba-Bt-Bt-Bt-, (1i'') HO-Bt-Bt-Bg-Bt-Ba-Bt-Bt-Bt-, (1j'') HO-Bt-Bt-Bt-Bg-Bt-Ba-Bt-Bt-Bt-, (1k″)HO-Ba-Bt-Bt-Bt-Bg-Bt-Ba-Bt-Bt-Bt-, (SEQ ID NO: 111)

(1l″)HO-Bc-Ba-Bt-Bt-Bt-Bg-Bt-Ba-Bt-Bt-Bt-, (SEQ ID NO: 112)

or (1m″)HO-Bc-Bc-Ba-Bt-Bt-Bt-Bg-Bt-Ba-Bt-Bt-Bt-, (SEQ ID NO: 113)

where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

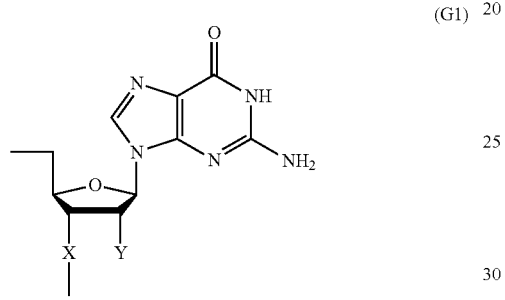

(G1)

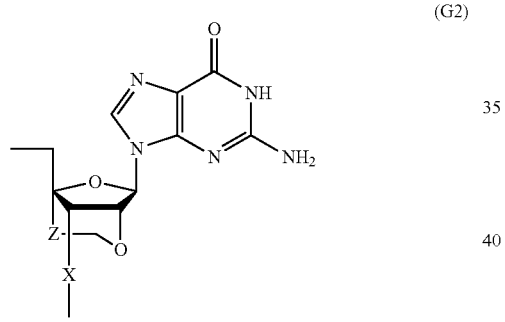

(G2)

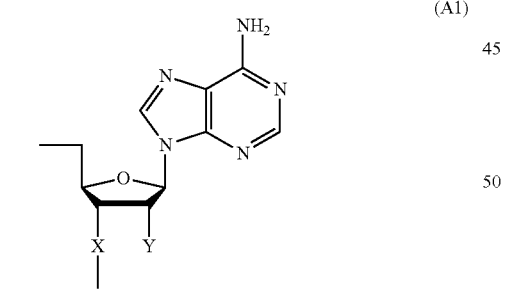

(A1)

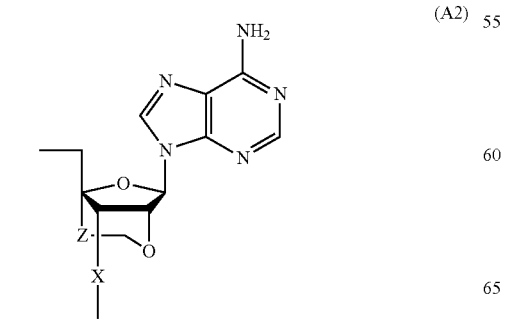

(A2)

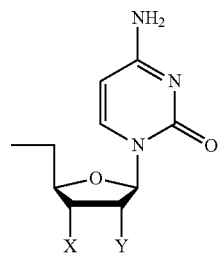

(C1)

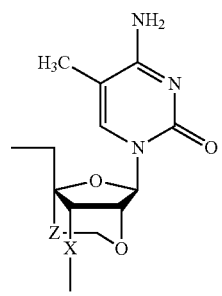

(C2)

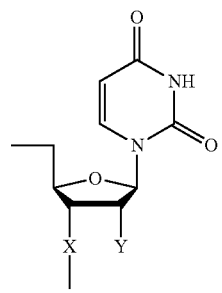

(U1)

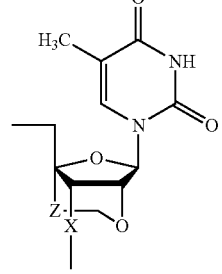

(T2)

where X is individually and independently a group represented by the following formula (X1) or (X2):

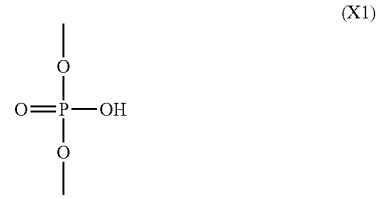

(X1)

-continued

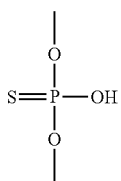
(X2)

Y is individually and independently a hydrogen atom, a hydroxyl group or an alkoxy group with 1-6 carbon atoms; and Z is individually and independently a single bond or an alkylene group with 1-5 carbon atoms;
$B_{M''1}$ is a group represented by the following formula (1''):

-Ba-Bg-Bc-Ba-Bt-Bg- (1'')

where Bg, Ba, Bt and Bc are as defined above;
$B_{B''1}$ is a group represented by any one of the following (101a'') to (101m''):

(101a'')-CH₂CH₂OH, (101b'')-Bt-CH₂CH₂OH, (101c'')-Bt-Bt-CH₂CH₂OH, (101d'')-Bt-Bt-Bc-CH₂CH₂OH, (101e'')-Bt-Bt-Bc-Bc-CH₂CH₂OH, (101f'')-Bt-Bt-Bc-Bc-Bc-CH₂CH₂OH, (101g'')-Bt-Bt-Bc-Bc-Bc-Ba-CH₂CH₂OH, (101h'')-Bt-Bt-Bc-Bc-Bc-Ba-Ba-CH₂CH₂OH, (101i'')-Bt-Bt-Bc-Bc-Bc-Ba-Ba-Bt-CH₂CH₂OH, (101j'')-Bt-Bt-Bc-Bc-Bc-Ba-Ba-Bt-Bt-CH₂CH₂OH, (SEQ ID NO: 114)
(101k'')-Bt-Bt-Bc-Bc-Bc-Ba-Ba-Bt-Bt-Bc-CH₂CH₂OH, (SEQ ID NO: 115)
(101l'')-Bt-Bt-Bc-Bc-Bc-Ba-Ba-Bt-Bt-Bc-Bt-CH₂CH₂OH,
or (SEQ ID NO: 116)
(101m'')-Bt-Bt-Bc-Bc-Bc-Ba-Ba-Bt-Bt-Bc-Bt-Bc-CH₂CH₂OH, where Bg, Ba, Bt and Bc are as defined above;
provided that at least one of the nucleosides constituting the compound represented by formula (I'') has 2''-O,4''-C-alkylene group.
[27] A compound represented by the following general formula (II'') or a pharmacologically acceptable salt thereof:

$B_{T''2}$-$B_{M''2}$-$B_{B''2}$ (II'')

where $B_{T''2}$ is a group represented by any one of the following (2a'') to (2g''):

(2a'')HO-, (2b'')HO-Bg-, (2c'')HO-Bt-Bg-, (2d'')HO-Ba-Bt-Bg-, (2e'')HO-Bc-Ba-Bt-Bg-, (2f'')HO-Bg-Bc-Ba-Bt-Bg-,
or (2g'')HO-Ba-Bg-Bc-Ba-Bt-Bg-, where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

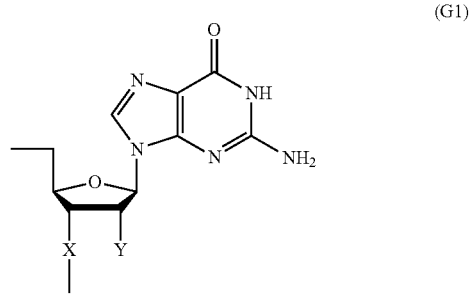
(G1)

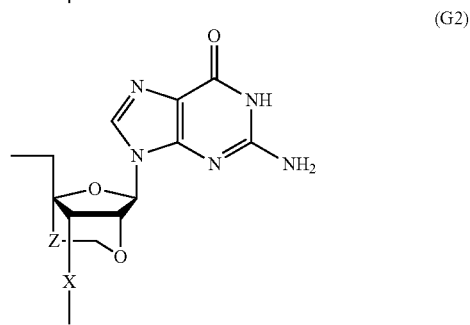
(G2)

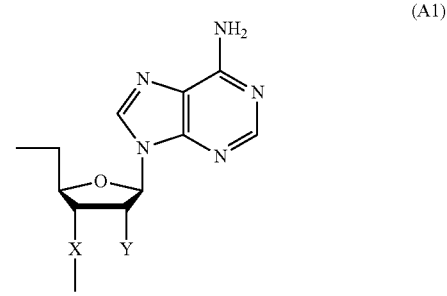
(A1)

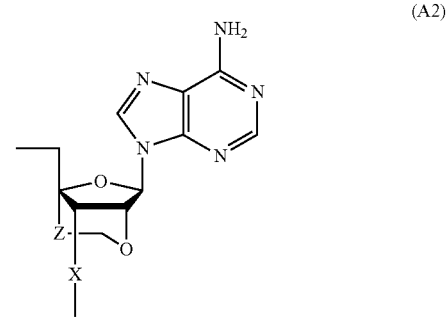
(A2)

(C1) 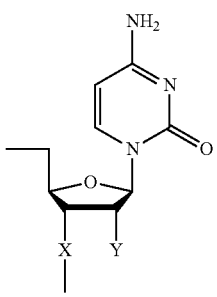

(C2) 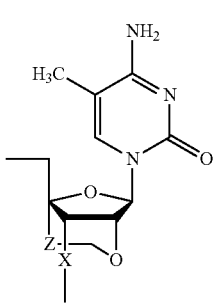

(U1) 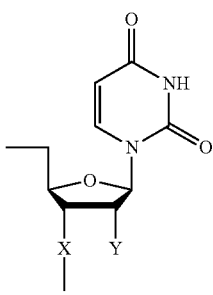

(T2) 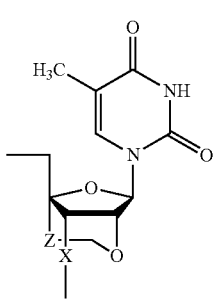

where X is individually and independently a group represented by the following formula (X1) or (X2):

(X1) 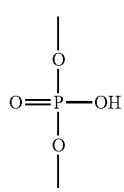

(X2) 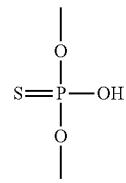

Y is individually and independently a hydrogen atom, a hydroxyl group or an alkoxy group with 1-6 carbon atoms; and Z is individually and independently a single bond or an alkylene group with 1-5 carbon atoms;

$B_{M''2}$ is a group represented by the following formula (2''):

```
                                          (SEQ ID NO: 116)
        -Bt-Bt-Bc-Bc-Bc-Ba-Ba-Bt-Bt-Bc-Bt-Bc-   (2")
``` where Bg, Ba, Bt and Bc are as defined above;

$B_{B''2}$ is a group represented by any one of the following (102a'') to (102g''):

```
(102a") -CH2CH2OH, (102b") -Ba-CH2CH2OH, (102c") -Ba-Bg-CH2CH2OH, (102d") -Ba-Bg-Bg-CH2CH2OH, (102e") -Ba-Bg-Bg-Ba-CH2CH2OH, (102f") -Ba-Bg-Bg-Ba-Ba-CH2CH2OH,
or (102g") -Ba-Bg-Bg-Ba-Ba-Bt-CH2CH2OH,
``` where Bg, Ba, Bt and Bc are as defined above;

provided that at least one of the nucleosides constituting the compound represented by formula (II'') has 2''-O,4''-C-alkylene group.

[28] A compound represented by the following general formula (III'') or a pharmacologically acceptable salt thereof:

$$B_{T''3}-B_{M''3}-B_{B''3} \quad (III'')$$

where $B_{T''3}$ is a group represented by any one of the following (3a'') to (3m''):

```
(3a") HO-, (3b") HO-Bc-, (3c") HO-Ba-Bc-, (3d") HO-Ba-Ba-Bc-, (3e") HO-Ba-Ba-Ba-Bc-, (3f") HO-Ba-Ba-Ba-Ba-Bc-, (3g") HO-Bg-Ba-Ba-Ba-Ba-Bc-, (3h") HO-Bt-Bg-Ba-Ba-Ba-Ba-Bc-, (3i") HO-Ba-Bt-Bg-Ba-Ba-Ba-Ba-Bc-, (3j") HO-Ba-Ba-Bt-Bg-Ba-Ba-Ba-Ba-Bc-,
```

(3k″) HO-Bt-Ba-Ba-Bt-Bg-Ba-Ba-Ba-Ba-Bc-, (SEQ ID NO: 117)

(3l″) HO-Ba-Bt-Ba-Ba-Bt-Bg-Ba-Ba-Ba-Ba-Bc-, (SEQ ID NO: 118)

or (3m″) HO-Bc-Ba-Bt-Ba-Ba-Bt-Bg-Ba-Ba-Ba-Ba-Bc- (SEQ ID NO: 119)

where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

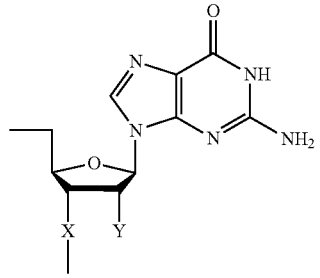

(G1)

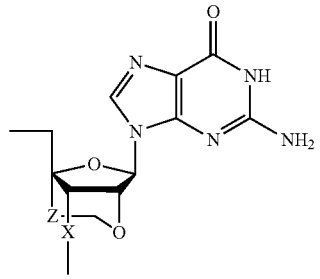

(G2)

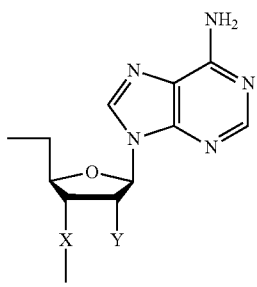

(A1)

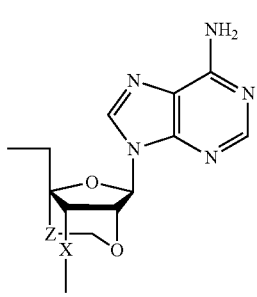

(A2)

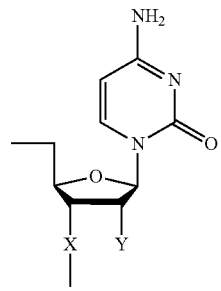

(C1)

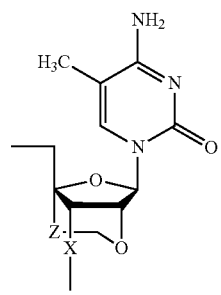

(C2)

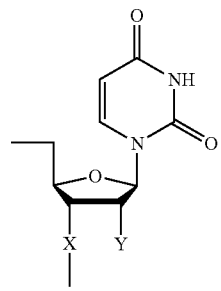

(U1)

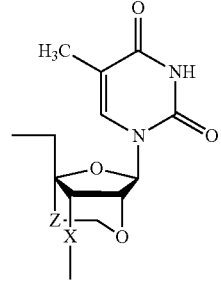

(T2)

where X is individually and independently a group represented by the following formula (X1) or (X2):

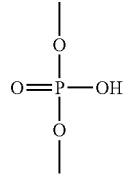

(X1)

-continued

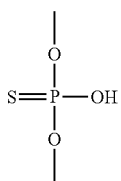
(X2)

Y is individually and independently a hydrogen atom, a hydroxyl group or an alkoxy group with 1-6 carbon atoms; and Z is individually and independently a single bond or an alkylene group with 1-5 carbon atoms;

$B_{M''3}$ is a group represented by the following formula (3"):

-Bg-Bc-Bc-Bg-Bc-Bc- (3")

where Bg, Ba, Bt and Bc are as defined above;
$B_{B''3}$ is a group represented by any one of the following (103a") to (103m"):

(103a") -CH$_2$CH$_2$OH, (103b") -Ba-CH$_2$CH$_2$OH, (103c") -Ba-Bt-CH$_2$CH$_2$OH, (103d") -Ba-Bt-Bt-CH$_2$CH$_2$OH, (103e") -Ba-Bt-Bt-Bt-CH$_2$CH$_2$OH, (103f") -Ba-Bt-Bt-Bt-Bc-CH$_2$CH$_2$OH, (103g") -Ba-Bt-Bt-Bt-Bc-Bt-CH$_2$CH$_2$OH, (103h") -Ba-Bt-Bt-Bt-Bc-Bt-Bc-CH$_2$CH$_2$OH, (103i") -Ba-Bt-Bt-Bt-Bc-Bt-Bc-Ba-CH$_2$CH$_2$OH, (103j") -Ba-Bt-Bt-Bt-Bc-Bt-Bc-Ba-Ba-CH$_2$CH$_2$OH, (SEQ ID NO: 120)
(103k") -Ba-Bt-Bt-Bt-Bc-Bt-Bc-Ba-Ba-Bc-CH$_2$CH$_2$OH, (SEQ ID NO: 121)
(103l") -Ba-Bt-Bt-Bt-Bc-Bt-Bc-Ba-Ba-Bc-Ba-CH$_2$CH$_2$OH,
or (SEQ ID NO: 122)
(103m") -Ba-Bt-Bt-Bt-Bc-Bt-Bc-Ba-Ba-Bc-Ba-Bg-CH$_2$CH$_2$OH where Bg, Ba, Bt and Bc are as defined above;
provided that at least one of the nucleosides constituting the compound represented by formula (III") has 2"-O,4"-C-alkylene group.

[29] A compound represented by the following general formula (IV") or a pharmacologically acceptable salt thereof:

$B_{T''4}$-$B_{M''4}$-$B_{B''4}$ (IV")

where $B_{T''4}$ is a group represented by any one of the following (4a") to (4j"):

(4a") HO-, (4b") HO-Ba-, (4c") HO-Bc-Ba-, (4d") HO-Bt-Bc-Ba-, (4e") HO-Bg-Bt-Bc-Ba-, (4f") HO-Bg-Bg-Bt-Bc-Ba-, (4g") HO-Ba-Bg-Bg-Bt-Bc-Ba-, (4h") HO-Bt-Ba-Bg-Bg-Bt-Bc-Ba-, (4i") HO-Bc-Bt-Ba-Bg-Bg-Bt-Bc-Ba-,
or (4j") HO-Bg-Bc-Bt-Ba-Bg-Bg-Bt-Bc-Bawhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

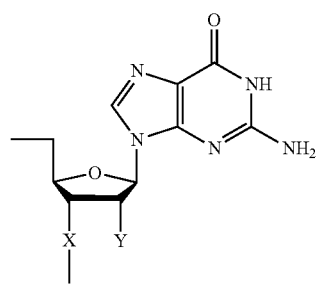
(G1)

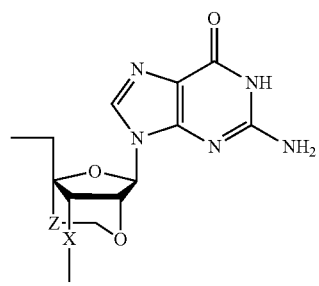
(G2)

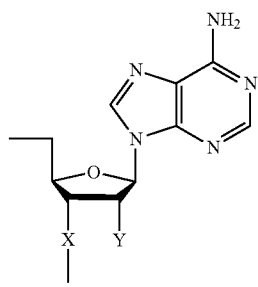
(A1)

-continued (A2) 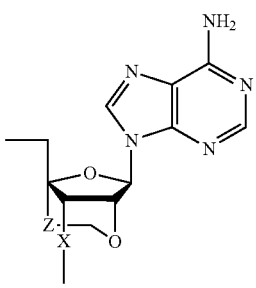

(C1) 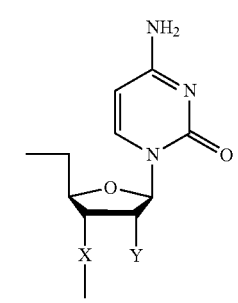

(C2) 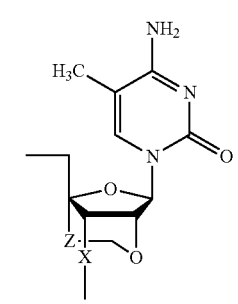

(U1) 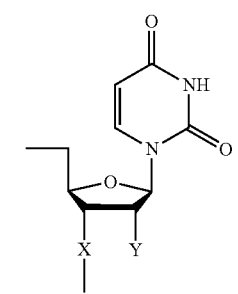

(T2) 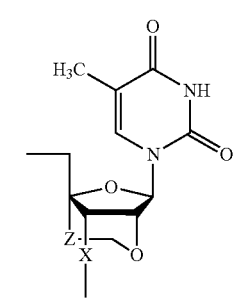

where X is individually and independently a group represented by the following formula (X1) or (X2):

(X1) 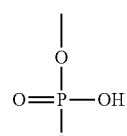

(X2) 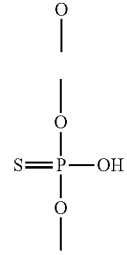

Y is individually and independently a hydrogen atom, a hydroxyl group or an alkoxy group with 1-6 carbon atoms; and Z is individually and independently a single bond or an alkylene group with 1-5 carbon atoms;

$B_{M''4}$ is a group represented by the following formula (4"):

```
-Bg-Bg-Bc-Bt-Bg-Bc-Bt-Bt-Bt-   (4")
``` where Bg, Ba, Bt and Bc are as defined above;

$B_{B''4}$ is a group represented by any one of the following (104a") to (104j"):

```
(104a")-CH2CH2OH, (104b")-Bg-CH2CH2OH, (104c")-Bg-Bc-CH2CH2OH, (104d")-Bg-Bc-Bc-CH2CH2OH, (104e")-Bg-Bc-Bc-Bc-CH2CH2OH, (104f")-Bg-Bc-Bc-Bc-Bt-CH2CH2OH, (104g")-Bg-Bc-Bc-Bc-Bt-Bc-CH2CH2OH, (104h")-Bg-Bc-Bc-Bc-Bt-Bc-Ba-CH2CH2OH, (104i")-Bg-Bc-Bc-Bc-Bt-Bc-Ba-Bg-CH2CH2OH,
or (104j")-Bg-Bc-Bc-Bc-Bt-Bc-Ba-Bg-Bc-CH2CH2OH
``` where Bg, Ba, Bt and Bc are as defined above; provided that at least one of the nucleosides constituting the compound represented by formula (IV") has 2"-O,4"-C-alkylene group.

[30] A compound represented by the following general formula (V") or a pharmacologically acceptable salt thereof:

$$B_{T''5}\text{-}B_{M''5}\text{-}B_{B''5} \quad (V'')$$

where $B_{T''5}$ is a group represented by any one of the following (5a") to (5j"):

```
(5a")HO-, (5b")HO-Ba-, (5c")HO-Bg-Ba-,
```

-continued (5d") HO-Bg-Bg-Ba-, (5e") HO-Ba-Bg-Bg-Ba-, (5f") HO-Bc-Ba-Bg-Bg-Ba-, (5g") HO-Bc-Bc-Ba-Bg-Bg-Ba-, (5h") HO-Bt-Bc-Bc-Ba-Bg-Bg-Ba-, (5i") HO-Bg-Bt-Bc-Bc-Ba-Bg-Bg-Ba-, or (5j") HO-Ba-Bg-Bt-Bc-Bc-Ba-Bg-Bg-Bawhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

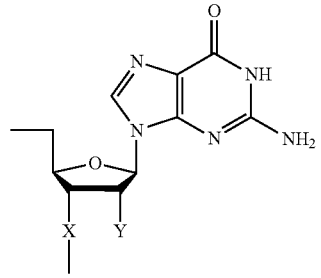
(G1)

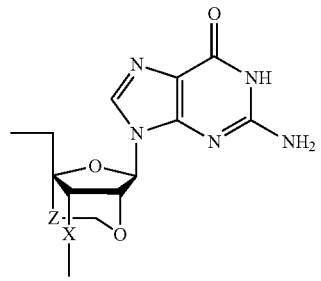
(G2)

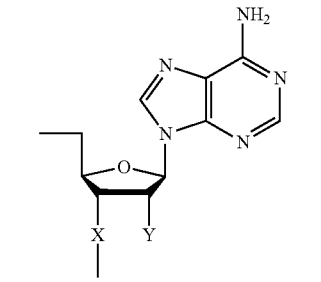
(A1)

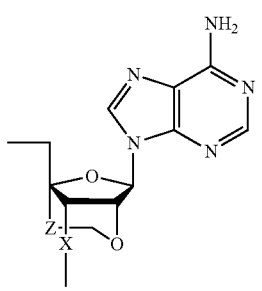
(A2)

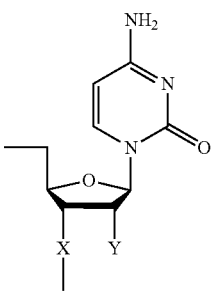
(C1)

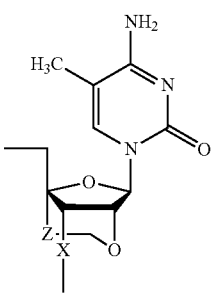
(C2)

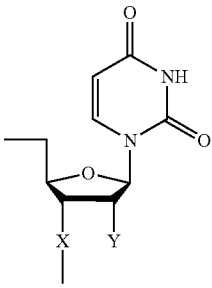
(U1)

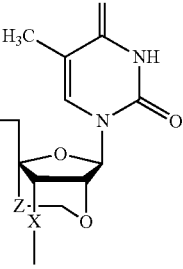
(T2)

where X is individually and independently a group represented by the following formula (X1) or (X2):

(X1)

$$O=\overset{\displaystyle |}{\underset{\displaystyle |}{P}}-OH$$

-continued

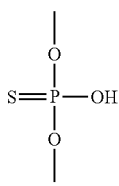
(X2)

Y is individually and independently a hydrogen atom, a hydroxyl group or an alkoxy group with 1-6 carbon atoms; and Z is individually and independently a single bond or an alkylene group with 1-5 carbon atoms;

$B_{M''5}$ is a group represented by the following formula (5"):

-Bg-Bc-Bt-Ba-Bg-Bg-Bt-Bc-Ba- (5")

where Bg, Ba, Bt and Bc are as defined above;
$B_{B''5}$ is a group represented by any one of the following (105a") to (105j"):

(105a") -CH₂CH₂OH, (105b") -Bg-CH₂CH₂OH, (105c") -Bg-Bg-CH₂CH₂OH, (105d") -Bg-Bg-Bc-CH₂CH₂OH, (105e") -Bg-Bg-Bc-Bt-CH₂CH₂OH, (105f") -Bg-Bg-Bc-Bt-Bg-CH₂CH₂OH, (105g") -Bg-Bg-Bc-Bt-Bg-Bc-CH₂CH₂OH, (105h") -Bg-Bg-Bc-Bt-Bg-Bc-Bt-CH₂CH₂OH, (105i") -Bg-Bg-Bc-Bt-Bg-Bc-Bt-Bt-CH₂CH₂OH, or (105j") -Bg-Bg-Bc-Bt-Bg-Bc-Bt-Bt-Bt-CH₂CH₂OH where Bg, Ba, Bt and Bc are as defined above;
provided that at least one of the nucleosides constituting the compound represented by formula (V") has 2"-O,4"-C-alkylene group.

[31] A compound represented by the following general formula (VI") or a pharmacologically acceptable salt thereof:

$B_{T''6}$-$B_{M''6}$-$B_{B''6}$ (VI")

where $B_{T''6}$ is a group represented by any one of the following (6a") to (6j"):

(6a") HO-, (6b") HO-Ba-, (6c") HO-Ba-Ba-, (6d") HO-Ba-Ba-Ba-, (6e") HO-Bc-Ba-Ba-Ba-, (6f") HO-Bc-Bc-Ba-Ba-Ba-, (6g") HO-Bt-Bc-Bc-Ba-Ba-Ba-, (6h") HO-Bt-Bt-Bc-Bc-Ba-Ba-Ba-, (6i") HO-Bc-Bt-Bt-Bc-Bc-Ba-Ba-Ba-, or (6j") HO-Bt-Bc-Bt-Bt-Bc-Bc-Ba-Ba-Bawhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

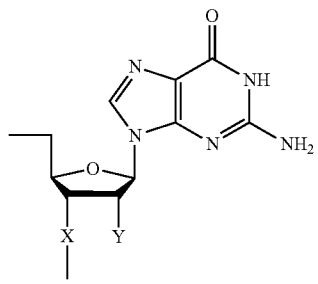
(G1)

(G2)

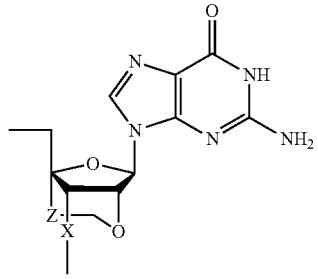

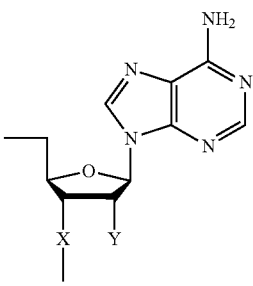
(A1)

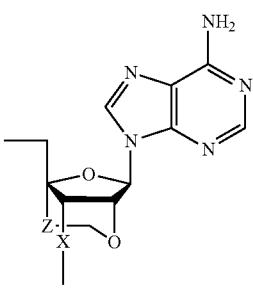
(A2)

-continued (C1) 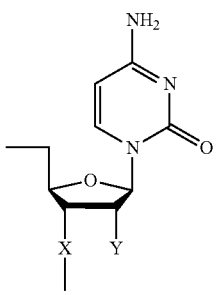

(C2) 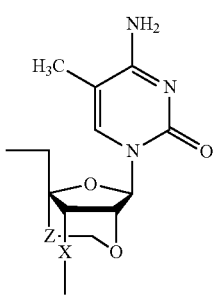

(U1) 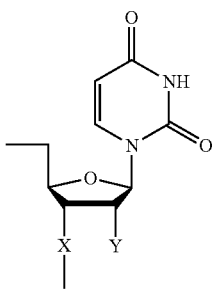

(T2) 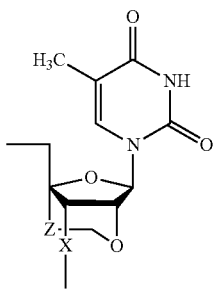

where X is individually and independently a group represented by the following formula (X1) or (X2):

(X1) 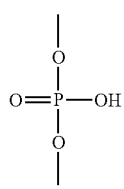

(X2) 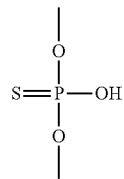

Y is individually and independently a hydrogen atom, a hydroxyl group or an alkoxy group with 1-6 carbon atoms; and Z is individually and independently a single bond or an alkylene group with 1-5 carbon atoms;

$B_{M''6}$ is a group represented by the following formula (6"):

-Bg-Bc-Ba-Bg-Bc-Bc-Bt-Bc-Bt- (6")

where Bg, Ba, Bt and Bc are as defined above;

$B_{B''6}$ is a group represented by any one of the following (106a") to (106j"):

(106a") -CH₂CH₂OH, (106b") -Bc-CH₂CH₂OH, (106c") -Bc-Bg-CH₂CH₂OH, (106d") -Bc-Bg-Bc-CH₂CH₂OH, (106e") -Bc-Bg-Bc-Bt-CH₂CH₂OH, (106f") -Bc-Bg-Bc-Bt-Bc-CH₂CH₂OH, (106g") -Bc-Bg-Bc-Bt-Bc-Ba-CH₂CH₂OH, (106h") -Bc-Bg-Bc-Bt-Bc-Ba-Bc-CH₂CH₂OH, (106i") -Bc-Bg-Bc-Bt-Bc-Ba-Bc-Bt-CH₂CH₂OH, or (106j") -Bc-Bg-Bc-Bt-Bc-Ba-Bc-Bt-Bc-CH₂CH₂OH, where Bg, Ba, Bt and Bc are as defined above;

provided that at least one of the nucleosides constituting the compound represented by formula (VI") has 2"-O,4"-C-alkylene group.

[32] A compound represented by the following general formula (VII") or a pharmacologically acceptable salt thereof:

$B_{T''7}$-$B_{M''7}$-$B_{B''7}$ (VII")

where $B_{T''7}$ is a group represented by any one of the following (7a") to (7j"):

(7a") HO-, (7b") HO-Bt-, (7c") HO-Bt-Bt-, (7d") HO-Bg-Bt-Bt-, (7e") HO-Ba-Bg-Bt-Bt-, (7f") HO-Bg-Ba-Bg-Bt-Bt-, (7g") HO-Bt-Bg-Ba-Bg-Bt-Bt-,

-continued (7h″) HO-Ba-Bt-Bg-Ba-Bg-Bt-Bt-, (7i″) HO-Bt-Ba-Bt-Bg-Ba-Bg-Bt-Bt-,
or (7j″) HO-Bc-Bt-Ba-Bt-Bg-Ba-Bg-Bt-Btwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

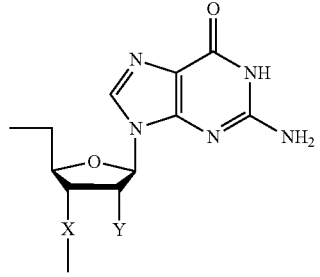
(G1)

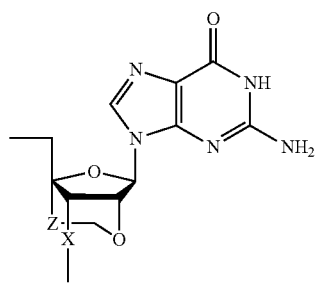
(G2)

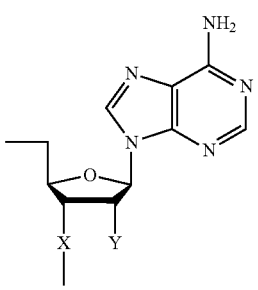
(A1)

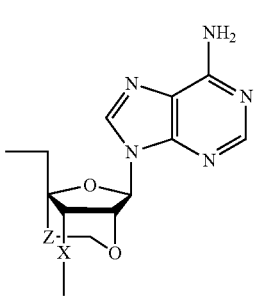
(A2)

-continued

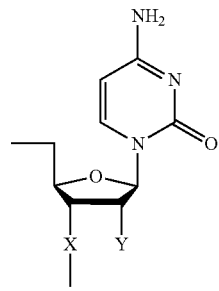
(C1)

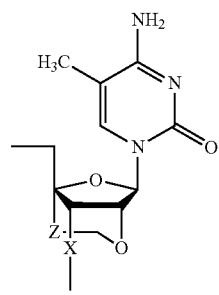
(C2)

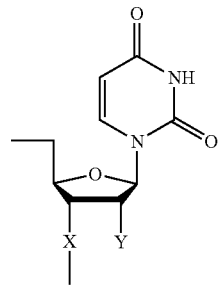
(U1)

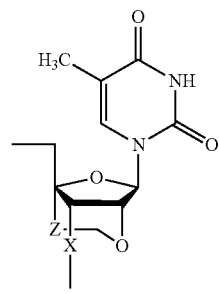
(T2)

where X is individually and independently a group represented by the following formula (X1) or (X2):

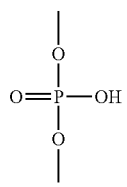
(X1)

-continued

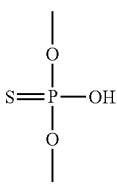

Y is individually and independently a hydrogen atom, a hydroxyl group or an alkoxy group with 1-6 carbon atoms; and Z is individually and independently a single bond or an alkylene group with 1-5 carbon atoms;

$B_{M'''7}$ is a group represented by the following formula (7"):

-Bt-Bc-Bt-Bt-Bc-Bc-Ba-Ba-Ba- (7")

where Bg, Ba, Bt and Bc are as defined above;
$B_{B'''7}$ is a group represented by any one of the following (107a") to (107j"):

(107a") -CH₂CH₂OH, (107b") -Bg-CH₂CH₂OH, (107c") -Bg-Bc-CH₂CH₂OH, (107d") -Bg-Bc-Ba-CH₂CH₂OH, (107e") -Bg-Bc-Ba-Bg-CH₂CH₂OH, (107f") -Bg-Bc-Ba-Bg-Bc-CH₂CH₂OH, (107g") -Bg-Bc-Ba-Bg-Bc-Bc-CH₂CH₂OH, (107h") -Bg-Bc-Ba-Bg-Bc-Bc-Bt-CH₂CH₂OH, (107i") -Bg-Bc-Ba-Bg-Bc-Bc-Bt-Bc-CH₂CH₂OH, or (107j") -Bg-Bc-Ba-Bg-Bc-Bc-Bt-Bc-Bt-CH₂CH₂OH where Bg, Ba, Bt and Bc are as defined above;
provided that at least one of the nucleosides constituting the compound represented by formula (VII") has 2"-O,4"-C-alkylene group.

[33] A compound represented by the following general formula (VIII") or a pharmacologically acceptable salt thereof:

$B_{T''8}$-$B_{M''8}$-$B_{B''8}$ (VIII")

where $B_{T''8}$ is a group represented by any one of the following (8a") to (8n"):

(8a") HO-, (8b") HO-Bc-, (8c") HO-Bt-Bc-, (8d") HO-Ba-Bt-Bc-, (8e") HO-Bc-Ba-Bt-Bc-, (8f") HO-Bt-Bc-Ba-Bt-Bc-, (8g") HO-Bt-Bt-Bc-Ba-Bt-Bc-, (8h") HO-Bt-Bt-Bt-Bc-Ba-Bt-Bc-, (8i") HO-Bg-Bt-Bt-Bt-Bc-Ba-Bt-Bc-, (8j") HO-Bt-Bg-Bt-Bt-Bt-Bc-Ba-Bt-Bc-, (SEQ ID NO: 123)
(8k") HO-Bt-Bt-Bg-Bt-Bt-Bt-Bc-Ba-Bt-Bc-, (SEQ ID NO: 124)
(8l") HO-Ba-Bt-Bt-Bg-Bt-Bt-Bt-Bc-Ba-Bt-Bc-, (SEQ ID NO: 125)
(8m") HO-Bc-Ba-Bt-Bt-Bg-Bt-Bt-Bt-Bc-Ba-Bt-Bc-,
or (SEQ ID NO: 126)
(8n") HO-Bc-Bc-Ba-Bt-Bt-Bg-Bt-Bt-Bt-Bc-Ba-Bt-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

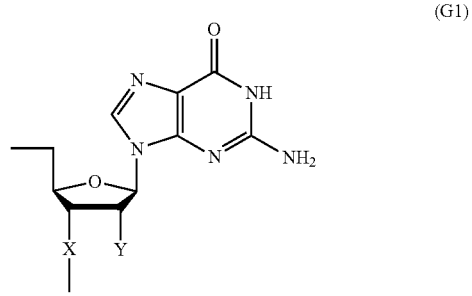

(G1)

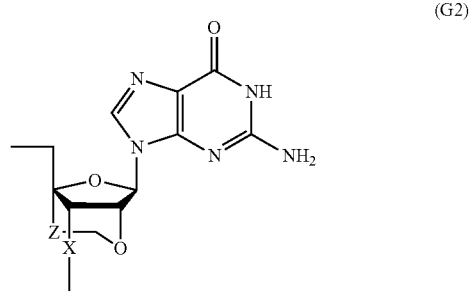

(G2)

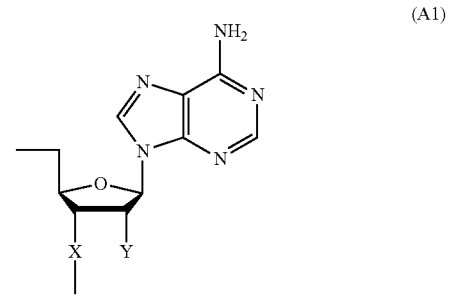

(A1)

-continued (A2)
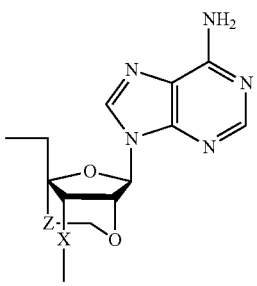

(C1)
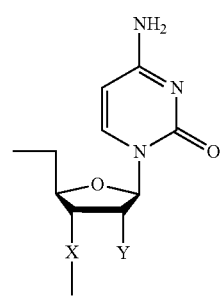

(C2)
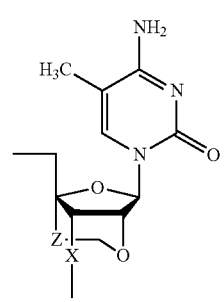

(U1)
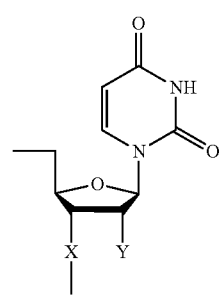

(T2)
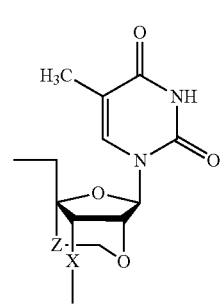

where X is individually and independently a group represented by the following formula (X1) or (X2):

(X1)
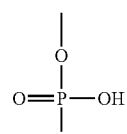

(X2)
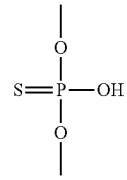

Y is individually and independently a hydrogen atom, a hydroxyl group or an alkoxy group with 1-6 carbon atoms; and Z is individually and independently a single bond or an alkylene group with 1-5 carbon atoms;

$B_{M''8}$ is a group represented by the following formula (8"):

-Ba-Bg-Bc-Bt-Bc- (8")

where Bg, Ba, Bt and Bc are as defined above;

$B_{B''8}$ is a group represented by any one of the following (108a") to (108n"):

(108a") -CH₂CH₂OH, (108b") -Bt-CH₂CH₂OH, (108c") -Bt-Bt-CH₂CH₂OH, (108d") -Bt-Bt-Bt-CH₂CH₂OH, (108e") -Bt-Bt-Bt-Bt-CH₂CH₂OH, (108f") -Bt-Bt-Bt-Bt-Ba-CH₂CH₂OH, (108g") -Bt-Bt-Bt-Bt-Ba-Bc-CH₂CH₂OH, (108h") -Bt-Bt-Bt-Bt-Ba-Bc-Bt-CH₂CH₂OH, (108i") -Bt-Bt-Bt-Bt-Ba-Bc-Bt-Bc-CH₂CH₂OH, (108j") -Bt-Bt-Bt-Bt-Ba-Bc-Bt-Bc-Bc-CH₂CH₂OH, (SEQ ID NO: 127)
(108k") -Bt-Bt-Bt-Bt-Ba-Bc-Bt-Bc-Bc-Bc-CH₂CH₂OH, (SEQ ID NO: 128)
(108l") -Bt-Bt-Bt-Bt-Ba-Bc-Bt-Bc-Bc-Bc-Bt-CH₂CH₂OH, (SEQ ID NO: 129)
(108m") -Bt-Bt-Bt-Bt-Ba-Bc-Bt-Bc-Bc-Bc-Bt-Bt-CH₂CH₂OH,
or (SEQ ID NO: 130)
(108n") -Bt-Bt-Bt-Bt-Ba-Bc-Bt-Bc-Bc-Bc-Bt-Bt-Bg-CH₂CH₂OH, where Bg, Ba, Bt and Bc are as defined above;

provided that at least one of the nucleosides constituting the compound represented by formula (VIII") has 2"-O,4"-C-alkylene group.

[34] A compound represented by the following general formula (IX″) or a pharmacologically acceptable salt thereof:

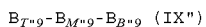

where $B_{T″9}$ is a group represented by any one of the following (9a″) to (9n″):

(9a″) D-, (9b″) D-Bg-, (9c″) D-Ba-Bg-, (9d″) D-Bg-Ba-Bg-, (9e″) D-Ba-Bg-Ba-Bg-, (9f″) D-Bc-Ba-Bg-Ba-Bg-, (9g″) D-Bc-Bc-Ba-Bg-Ba-Bg-, (9h″) D-Ba-Bc-Bc-Ba-Bg-Ba-Bg-, (9i″) D-Bc-Ba-Bc-Bc-Ba-Bg-Ba-Bg-, (9j″) D-Bt-Bc-Ba-Bc-Bc-Ba-Bg-Ba-Bg-, (SEQ ID NO: 131)
(9k″) D-Bg-Bt-Bc-Ba-Bc-Bc-Ba-Bg-Ba-Bg-, (SEQ ID NO: 132)
(9l″) D-Bt-Bg-Bt-Bc-Ba-Bc-Bc-Ba-Bg-Ba-Bg-, (SEQ ID NO: 133)
(9m″) D-Bg-Bt-Bg-Bt-Bc-Ba-Bc-Bc-Ba-Bg-Ba-Bg-,
or (SEQ ID NO: 134)
(9n″) D-Bt-Bg-Bt-Bg-Bt-Bc-Ba-Bc-Bc-Ba-Bg-Ba-Bgwhere Bg is a group represented by the following formula (G1) or (G2); Ba is a group represented by the following formula (A1) or (A2); Bc is a group represented by the following formula (C1) or (C2); Bt is a group represented by the following formula (U1) or (T2); and D is HO— or Ph- wherein Ph- is a group represented by the following first formula:

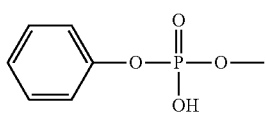

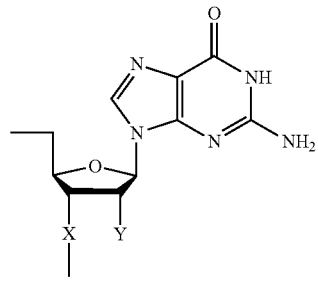

(G1)

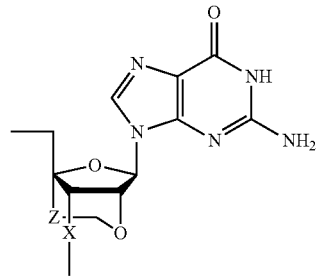

(G2)

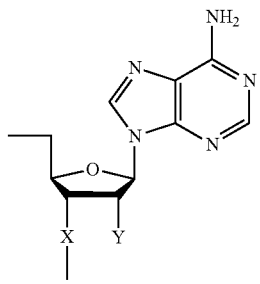

(A1)

(A2)

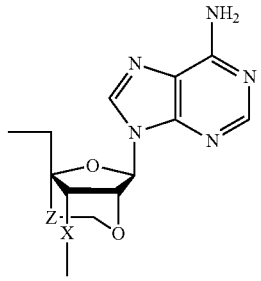

(C1)

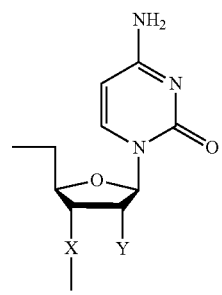

(C2)

-continued (U1)
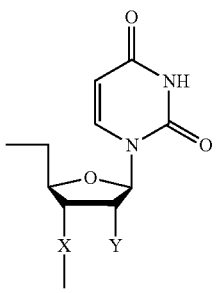

(T2)
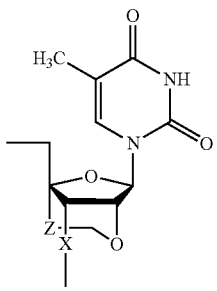

where X is individually and independently a group represented by the following formula (X1) or (X2):

(X1)
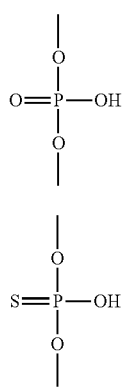

(X2)
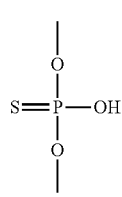

Y is individually and independently a hydrogen atom, a hydroxyl group or an alkoxy group with 1-6 carbon atoms; and Z is individually and independently a single bond or an alkylene group with 1-5 carbon atoms;

$B_{M''9}$ is a group represented by the following formula (9"):

(9")  -Bt-Ba-Ba-Bc-Ba-Bg-Btwhere Bg, Ba, Bt and Bc are as defined above;
$B_{B''9}$ is a group represented by any one of the following (109a") to (109l"):

(109a") -CH₂CH₂OH, (109b") -Bc-CH₂CH₂OH, (109c") -Bc-Bt-CH₂CH₂OH, (109d") -Bc-Bt-Bg-CH₂CH₂OH, (109e") -Bc-Bt-Bg-Ba-CH₂CH₂OH, (109f") -Bc-Bt-Bg-Ba-Bg-CH₂CH₂OH, (109g") -Bc-Bt-Bg-Ba-Bg-Bt-CH₂CH₂OH, (109h") -Bc-Bt-Bg-Ba-Bg-Bt-Ba-CH₂CH₂OH, (109i") -Bc-Bt-Bg-Ba-Bg-Bt-Ba-Bg-CH₂CH₂OH, (109j") -Bc-Bt-Bg-Ba-Bg-Bt-Ba-Bg-Bg-CH₂CH₂OH, (SEQ ID NO: 135)
(109k") -Bc-Bt-Bg-Ba-Bg-Bt-Ba-Bg-Bg-Ba-CH₂CH₂OH, or (SEQ ID NO: 136)
(109l") -Bc-Bt-Bg-Ba-Bg-Bt-Ba-Bg-Bg-Ba-Bg-CH₂CH₂OH where Bg, Ba, Bt and Bc are as defined above;
provided that at least one of the nucleosides constituting the compound represented by formula (IX") has 2"-O,4"-C-alkylene group.

[35] A compound represented by the following general formula (X") or a pharmacologically acceptable salt thereof:

$B_{T''10}$-$B_{M''10}$-$B_{B''10}$  (X")

where $B_{T''10}$ is a group represented by any one of the following (10a") to (10e").

(10a") D-, (10b") D-Bt-, (10c") D-Bg-Bt-, (10d") D-Bg-Bg-Bt-, or (10e") D-Ba-Bg-Bg-Btwhere Bg is a group represented by the following formula (G1) or (G2); Ba is a group represented by the following formula (A1) or (A2); Bc is a group represented by the following formula (C1) or (C2); Bt is a group represented by the following formula (U1) or (T2); and D is HO— or Ph— wherein Ph- is a group represented by the following first formula:

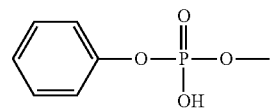

(G1)
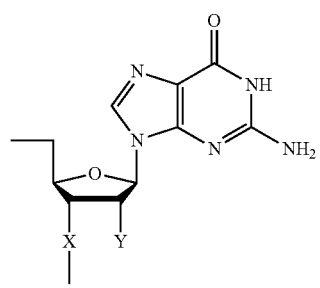

(G2) 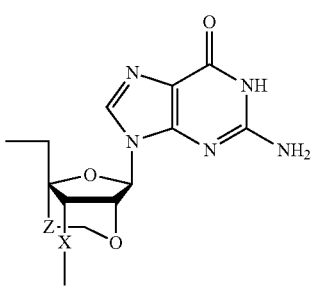

(A1) 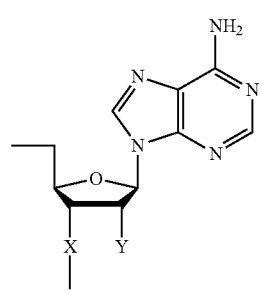

(A2) 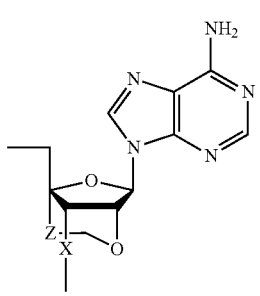

(C1) 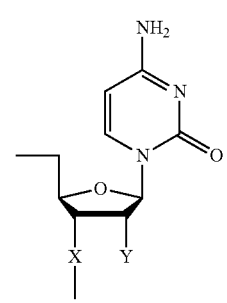

(C2) 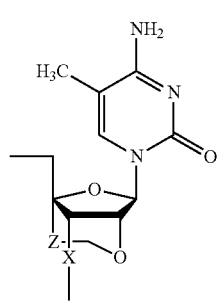

(U1) 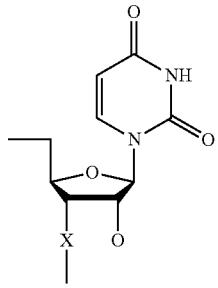

(T2) 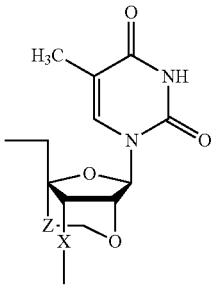

where X is individually and independently a group represented by the following formula (X1) or (X2):

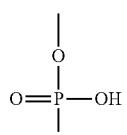 (X1)

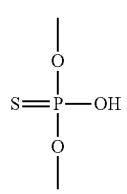 (X2)

Y is individually and independently a hydrogen atom, a hydroxyl group or an alkoxy group with 1-6 carbon atoms; and Z is individually and independently a single bond or an alkylene group with 1-5 carbon atoms;

$B_{M''10}$ is a group represented by the following formula (10''):

```
                                     (SEQ ID NO: 137)
-Bt-Bg-Bt-Bg-Bt-Bc-Ba-Bc-Bc-Ba-Bg-Ba-Bg-Bt-

Ba-Ba-  (10")
``` where Bg, Ba, Bt and Bc are as defined above;

$B_{B''10}$ is a group represented by any one of the following (110a'') to (110e''):

(110a'') -CH₂CH₂OH, (110b'') -Bc-CH₂CH₂OH, (110c'') -Bc-Ba-CH₂CH₂OH, (110d") -Bc-Ba-Bg-CH₂CH₂OH,
or (110e") -Bc-Ba-Bg-Bt-CH₂CH₂OH where Bg, Ba, Bt and Bc are as defined above;

provided that at least one of the nucleosides constituting the compound represented by formula (X") has 2"-O,4"-C-alkylene group.

[36] A compound represented by the following general formula (XI") or a pharmacologically acceptable salt thereof:

$$B_{T''11}\text{-}B_{M''11}\text{-}B_{B''11} \quad (XI'')$$

where $B_{T''11}$ is a group represented by any one of the following (11a") to (11j"):

(11a") D-, (11b") D-Bc-, (11c") D-Ba-Bc-, (11d") D-Bc-Ba-Bc-, (11e") D-Bc-Bc-Ba-Bc-, (11f") D-Ba-Bc-Bc-Ba-Bc-, (11g") D-Ba-Ba-Bc-Bc-Ba-Bc-, (11h") D-Bt-Ba-Ba-Bc-Bc-Ba-Bc-, (11i") D-Bg-Bt-Ba-Ba-Bc-Bc-Ba-Bc-,
or (11j") D-Ba-Bg-Bt-Ba-Ba-Bc-Bc-Ba-Bcwhere Bg is a group represented by the following formula (G1) or (G2); Ba is a group represented by the following formula (A1) or (A2); Bc is a group represented by the following formula (C1) or (C2); Bt is a group represented by the following formula (U1) or (T2); and D is HO— or Ph- wherein Ph- is a group represented by the following first formula:

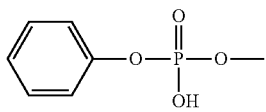

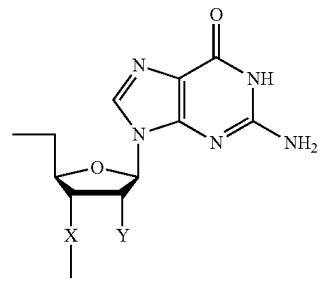

(G1)

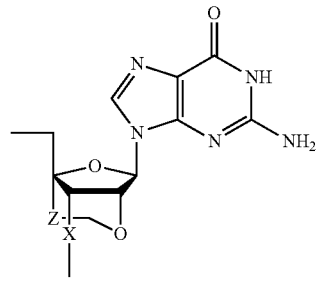

(G2)

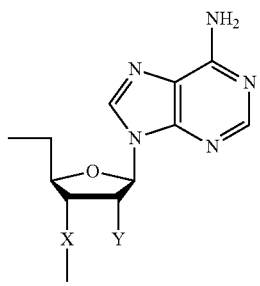

(A1)

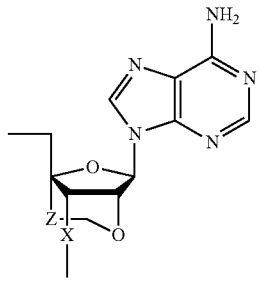

(A2)

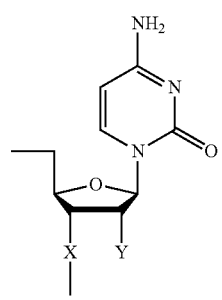

(C1)

(C2)

-continued (U1)
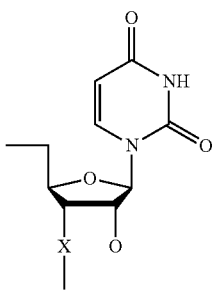

(T2)
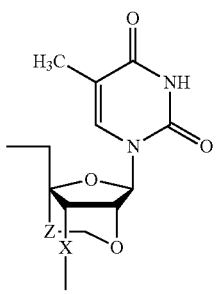

where X is individually and independently a group represented by the following formula (X1) or (X2):

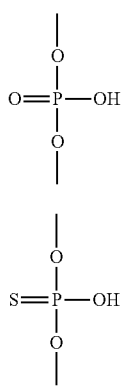

Y is individually and independently a hydrogen atom, a hydroxyl group or an alkoxy group with 1-6 carbon atoms; and Z is individually and independently a single bond or an alkylene group with 1-5 carbon atoms;

$B_{M''11}$ is a group represented by the following formula (11"):

(SEQ ID NO: 138)
-Ba-Bg-Bg-Bt-Bt-Bg-Bt-Bg-Bt-Bc-Ba- (11")

where Bg, Ba, Bt and Bc are as defined above;

$B_{B''11}$ is a group represented by any one of the following (111a") to (111j"):

(111a") -CH₂CH₂OH, (111b") -Bc-CH₂CH₂OH, (111c") -Bc-Bc-CH₂CH₂OH, (111d") -Bc-Bc-Ba-CH₂CH₂OH, (111e") -Bc-Bc-Ba-Bg-CH₂CH₂OH, (111f") -Bc-Bc-Ba-Bg-Ba-CH₂CH₂OH, (111g") -Bc-Bc-Ba-Bg-Ba-Bg-CH₂CH₂OH, (111h") -Bc-Bc-Ba-Bg-Ba-Bg-Bt-CH₂CH₂OH, (111i") -Bc-Bc-Ba-Bg-Ba-Bg-Bt-Ba-CH₂CH₂OH,
or (111j") -Bc-Bc-Ba-Bg-Ba-Bg-Bt-Ba-Ba-CH₂CH₂OH where Bg, Ba, Bt and Bc are as defined above;
provided that at least one of the nucleosides constituting the compound represented by formula (XI") has 2"-O,4"-C-alkylene group.

[37] A compound represented by the following general formula (XII") or a pharmacologically acceptable salt thereof:

$$B_{T''12}-B_{M''12}-B_{B''12} \quad (XII'')$$

where $B_{T''12}$ is a group represented by any one of the following (12a") to (12j"):

(12a") D-, (12b") D-Bt-, (12c") D-Ba-Bt-, (12d") D-Bc-Ba-Bt-, (12e") D-Bc-Bc-Ba-Bt-, (12f") D-Ba-Bc-Bc-Ba-Bt-, (12g") D-Bc-Ba-Bc-Bc-Ba-Bt-, (12h") D-Bc-Bc-Ba-Bc-Bc-Ba-Bt-, (12i") D-Bc-Bc-Bc-Ba-Bc-Bc-Ba-Bt-,
or (12j") D-Ba-Bc-Bc-Bc-Ba-Bc-Bc-Ba-Btwhere Bg is a group represented by the following formula (G1) or (G2); Ba is a group represented by the following formula (A1) or (A2); Bc is a group represented by the following formula (C1) or (C2); Bt is a group represented by the following formula (U1) or (T2); and D is HO— or Ph- wherein Ph- is a group represented by the following first formula:

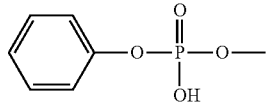

-continued (G1) 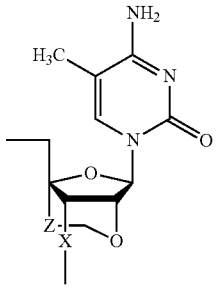

(G2) 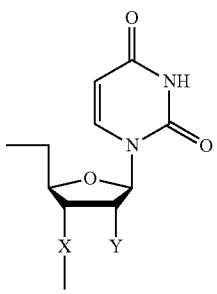

(A1) 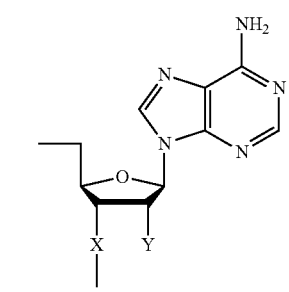

(A2) 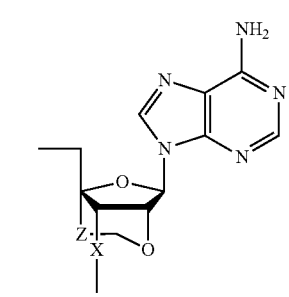

(C1) 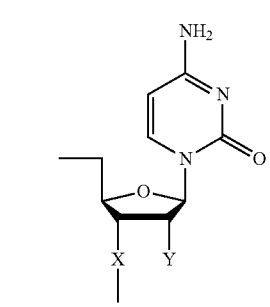

(C2) 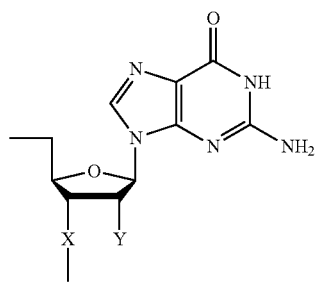

(U1) 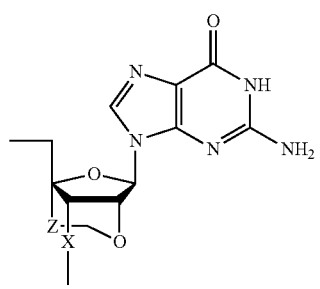

(T2) 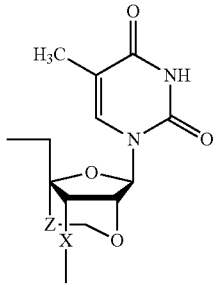

where X is individually and independently a group represented by the following formula (X1) or (X2):

(X1) 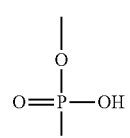

(X2) 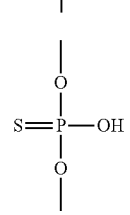

Y is individually and independently a hydrogen atom, a hydroxyl group or an alkoxy group with 1-6 carbon atoms; and Z is individually and independently a single bond or an alkylene group with 1-5 carbon atoms;

$B_{M'''12}$ is a group represented by the following formula (12"):

(SEQ ID NO: 139)
-Bc-Ba-Bc-Bc-Bc-Bt-Bc-Bt-Bg-Bt-Bg- (12")

where Bg, Ba, Bt and Bc are as defined above;

$B_{B''12}$ is a group represented by any one of the following (112a")~(112j"):

(112a") -CH₂CH₂OH, (112b") -Ba-CH₂CH₂OH, (112c") -Ba-Bt-CH₂CH₂OH, (112d") -Ba-Bt-Bt-CH₂CH₂OH, (112e") -Ba-Bt-Bt-Bt-CH₂CH₂OH, (112f") -Ba-Bt-Bt-Bt-Bt-CH₂CH₂OH, (112g") -Ba-Bt-Bt-Bt-Bt-Ba-CH₂CH₂OH, (112h") -Ba-Bt-Bt-Bt-Bt-Ba-Bt-CH₂CH₂OH, (112i") -Ba-Bt-Bt-Bt-Bt-Ba-Bt-Ba-CH₂CH₂OH, or (SEQ ID NO: 140)
(112j") -Ba-Bt-Bt-Bt-Bt-Ba-Bt-Ba-Ba-CH₂CH₂OH where Bg, Ba, Bt and Bc are as defined above;

provided that at least one of the nucleosides constituting the compound represented by formula (XII") has 2"-O,4"-C-alkylene group.

[38] A compound represented by the following general formula (XIII") or a pharmacologically acceptable salt thereof:

$B_{T''13}$-$B_{M''13}$-$B_{B''13}$  (XIII")

where $B_{T''13}$ is a group represented by any one of the following (13a") to (13k"):

(13a") HO-, (13b") HO-Bc-, (13c") HO-Bt-Bc-, (13d") HO-Bg-Bt-Bc-, (13e") HO-Bg-Bg-Bt-Bc-, (13f") HO-Ba-Bg-Bg-Bt-Bc-, (13g") HO-Ba-Ba-Bg-Bg-Bt-Bc-, (13h") HO-Bc-Ba-Ba-Bg-Bg-Bt-Bc-, (13i") HO-Bt-Bc-Ba-Ba-Bg-Bg-Bt-Bc-, (13j") HO-Bc-Bt-Bc-Ba-Ba-Bg-Bg-Bt-Bc-, or (13k") HO-Bc-Bc-Bt-Bc-Ba-Ba-Bg-Bg-Bt-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

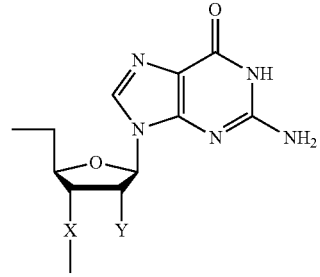
(G1)

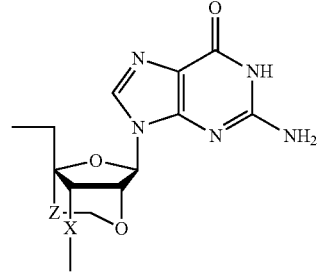
(G2)

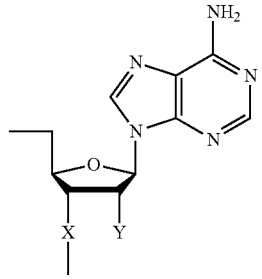
(A1)

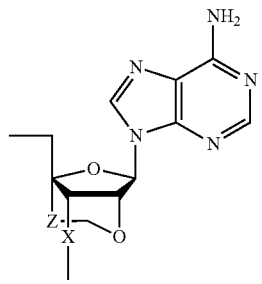
(A2)

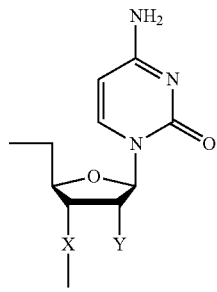
(C1)

-continued

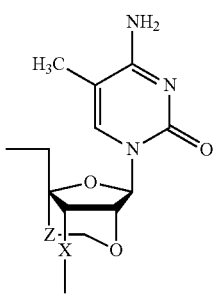
(C2)

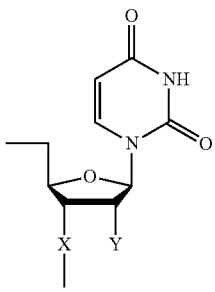
(U1)

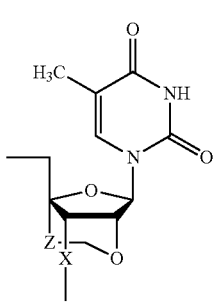
(T2)

where X is individually and independently a group represented by the following formula (X1) or (X2):

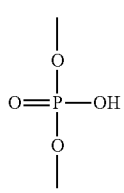
(X1)

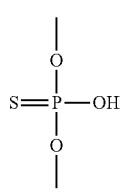
(X2)

Y is individually and independently a hydrogen atom, a hydroxyl group or an alkoxy group with 1-6 carbon atoms; and Z is individually and independently a single bond or an alkylene group with 1-5 carbon atoms;
$B_{M''13}$ is a group represented by the following formula (13''):

(SEQ ID NO: 141)
-Ba-Bc-Bc-Bc-Ba-Bc-Bc-Ba-Bt-Bc-  (13'')

where Bg, Ba, Bt and Bc are as defined above;

$B_{B''13}$ is a group represented by the following (113a''):

(113a'') -CH₂CH₂OH provided that at least one of the nucleosides constituting the compound represented by formula (XIII'') has 2''-O,4''-C-alkylene group.

[39] A compound represented by the following general formula (XIV'') or a pharmacologically acceptable salt thereof:

$B_{T''14}$-$B_{M''14}$-$B_{B''14}$  (XIV'')

where $B_{T''14}$ is a group represented by any one of the following (14a'') to (14q''):

(14a'') HO-, (14b'') HO-Ba-, (14c'') HO-Ba-Ba-, (14d'') HO-Bg-Ba-Ba-, (14e'') HO-Ba-Bg-Ba-Ba-, (14f'') HO-Bg-Ba-Bg-Ba-Ba-, (14g'') HO-Ba-Bg-Ba-Bg-Ba-Ba-, (14h'') HO-Bc-Ba-Bg-Ba-Bg-Ba-Ba-, (14i'') HO-Bg-Bc-Ba-Bg-Ba-Bg-Ba-Ba-, (14j'') HO-Ba-Bg-Bc-Ba-Bg-Ba-Bg-Ba-Ba-, (SEQ ID NO: 142)
(14k'') HO-Ba-Ba-Bg-Bc-Ba-Bg-Ba-Bg-Ba-Ba-, (SEQ ID NO: 143)
(14l'') HO-Bc-Ba-Ba-Bg-Bc-Ba-Bg-Ba-Bg-Ba-Ba-, (SEQ ID NO: 144)
(14m'') HO-Bt-Bc-Ba-Ba-Bg-Bc-Ba-Bg-Ba-Bg-Ba-Ba-, (SEQ ID NO: 145)
(14n'') HO-Ba-Bt-Bc-Ba-Ba-Bg-Bc-Ba-Bg-Ba-Bg-Ba-Ba-, (SEQ ID NO: 146)
(14o'') HO-Bg-Ba-Bt-Bc-Ba-Ba-Bg-Bc-Ba-Bg-Ba-Bg-Ba-Ba-, (SEQ ID NO: 147)
(14p'') HO-Bt-Bg-Ba-Bt-Bc-Ba-Ba-Bg-Bc-Ba-Bg-Ba-Bg-Ba-Ba-,
or (SEQ ID NO: 148)
(14q'') HO-Bt-Bt-Bg-Ba-Bt-Bc-Ba-Ba-Bg-Bc-Ba-Bg-Ba-Bg-Ba-Bawhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

(G1) 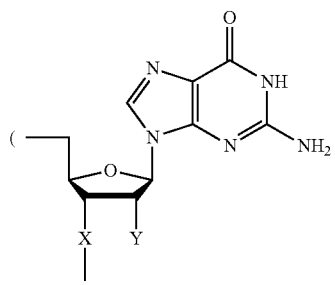

(G2) 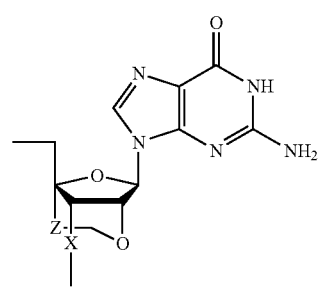

(A1) 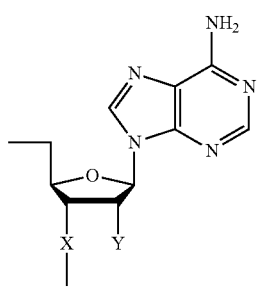

(A2) 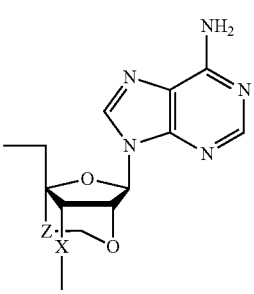

(C1) 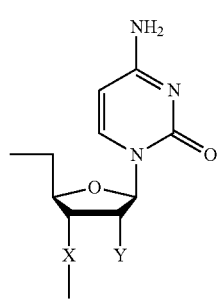

(C2) 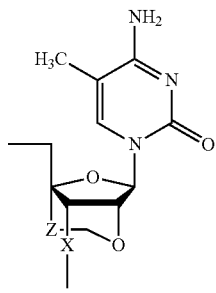

(U1) 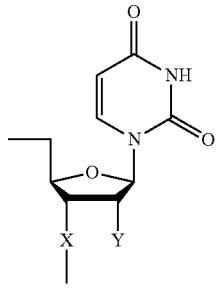

(T2) 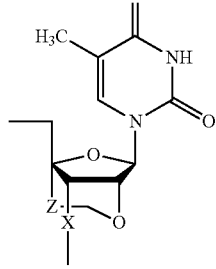

where X is individually and independently a group represented by the following formula (X1) or (X2):

(X1) 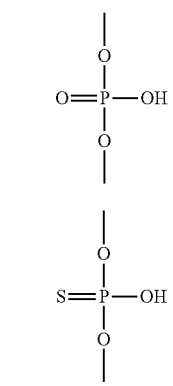

(X2)

Y is individually and independently a hydrogen atom, a hydroxyl group or an alkoxy group with 1-6 carbon atoms; and Z is individually and independently a single bond or an alkylene group with 1-5 carbon atoms;

$B_{M''14}$ is a group represented by the following formula (14''):

-Ba-Bg-Bc-Bc-  (14'')

where Bg, Ba, Bt and Bc are as defined above;

$B_{B''14}$ is a group represented by any one of the following (114a") to (114o"):

(114a") -CH$_2$CH$_2$OH, (114b") -Ba-CH$_2$CH$_2$OH, (114c") -Ba-Bg-CH$_2$CH$_2$OH, (114d") -Ba-Bg-Bt-CH$_2$CH$_2$OH, (114e") -Ba-Bg-Bt-Bc-CH$_2$CH$_2$OH, (114f") -Ba-Bg-Bt-Bc-Bg-CH$_2$CH$_2$OH, (114g") -Ba-Bg-Bt-Bc-Bg-Bg-CH$_2$CH$_2$OH, (114h") -Ba-Bg-Bt-Bc-Bg-Bg-Bt-CH$_2$CH$_2$OH, (114i") -Ba-Bg-Bt-Bc-Bg-Bg-Bt-Ba-CH$_2$CH$_2$OH, (114j") -Ba-Bg-Bt-Bc-Bg-Bg-Bt-Ba-Ba-CH$_2$CH$_2$OH, (SEQ ID NO: 149)
(114k") -Ba-Bg-Bt-Bc-Bg-Bg-Bt-Ba-Ba-Bg-CH$_2$CH$_2$OH, (SEQ ID NO: 150)
(114l") -Ba-Bg-Bt-Bc-Bg-Bg-Bt-Ba-Ba-Bg-Bt-CH$_2$CH$_2$OH, (SEQ ID NO: 151)
(114m") -Ba-Bg-Bt-Bc-Bg-Bg-Bt-Ba-Ba-Bg-Bt-Bt-CH$_2$CH$_2$OH, (SEQ ID NO: 152)
(114n") -Ba-Bg-Bt-Bc-Bg-Bg-Bt-Ba-Ba-Bg-Bt-Bt-Bc-CH$_2$CH$_2$OH,
or (SEQ ID NO: 153)
(114o") -Ba-Bg-Bt-Bc-Bg-Bg-Bt-Ba-Ba-Bg-Bt-Bt-Bc-Bt-CH$_2$CH$_2$OH where Bg, Ba, Bt and Bc are as defined above;

provided that at least one of the nucleosides constituting the compound represented by formula (XIV") has 2"-O,4"-C-alkylene group.

[40] A compound represented by the following general formula (XV") or a pharmacologically acceptable salt thereof:

$$B_{T''15}\text{-}B_{M''15}\text{-}B_{B''15} \quad (XV'')$$

where $B_{T''15}$ is a group represented by any one of the following (15a") to (15j"):

(15a") HO-, (15b") HO-Bt-, (15c") HO-Bc-Bt-, (15d") HO-Bt-Bc-Bt-, (15e") HO-Bt-Bt-Bc-Bt-, (15f") HO-Bt-Bt-Bt-Bc-Bt-, (15g") HO-Ba-Bt-Bt-Bt-Bc-Bt-, (15h") HO-Bc-Ba-Bt-Bt-Bt-Bc-Bt-, (15i") HO-Bg-Bc-Ba-Bt-Bt-Bt-Bc-Bt-,
or (15j") HO-Bg-Bg-Bc-Ba-Bt-Bt-Bt-Bc-Btwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

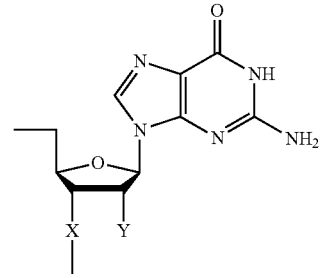
(G1)

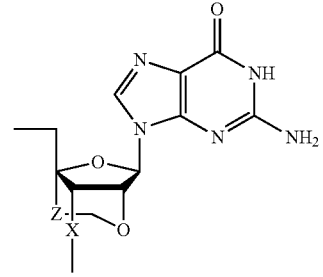
(G2)

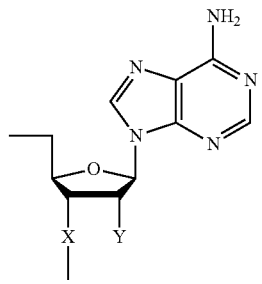
(A1)

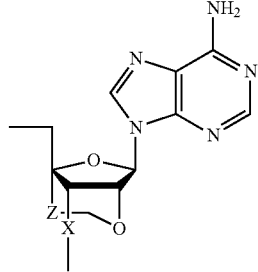
(A2)

-continued (C1) 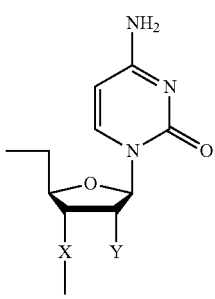

(C2) 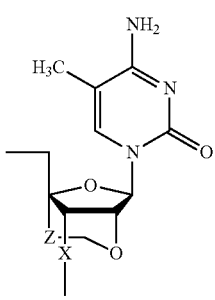

(U1) 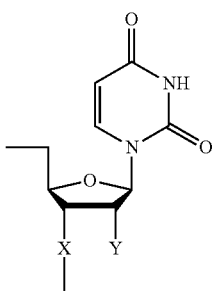

(T2) 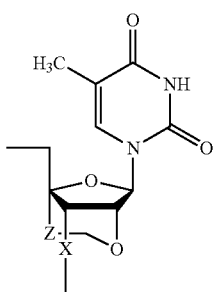

where X is individually and independently a group represented by the following formula (X1) or (X2):

(X1) 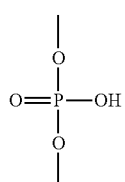

(X2) 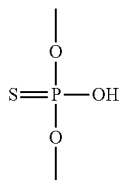

Y is individually and independently a hydrogen atom, a hydroxyl group or an alkoxy group with 1-6 carbon atoms; and Z is individually and independently a single bond or an alkylene group with 1-5 carbon atoms;

$B_{M''15}$ is a group represented by the following formula (15''):

-Ba-Bg-Bt-Bt-Bt-Bg-Bg-Ba-Bg- (15'')

where Bg, Ba, Bt and Bc are as defined above;
$B_{B''15}$ is a group represented by any one of the following (115a'') to (115j''):

(115a'')-CH₂CH₂OH, (115b'')-Ba-CH₂CH₂OH, (115c'')-Ba-Bt-CH₂CH₂OH, (115d'')-Ba-Bt-Bg-CH₂CH₂OH, (115e'')-Ba-Bt-Bg-Bg-CH₂CH₂OH, (115f'')-Ba-Bt-Bg-Bg-Bc-CH₂CH₂OH, (115g'')-Ba-Bt-Bg-Bg-Bc-Ba-CH₂CH₂OH, (115h'')-Ba-Bt-Bg-Bg-Bc-Ba-Bg-CH₂CH₂OH, (115i'')-Ba-Bt-Bg-Bg-Bc-Ba-Bg-Bt-CH₂CH₂OH, or (115j'')-Ba-Bt-Bg-Bg-Bc-Ba-Bg-Bt-Bt-CH₂CH₂OH where Bg, Ba, Bt and Bc are as defined above;
provided that at least one of the nucleosides constituting the compound represented by formula (XV'') has 2''-O,4''-C-alkylene group.

[41] A compound represented by the following general formula (XVI'') or a pharmacologically acceptable salt thereof:

$B_{T''16}$-$B_{M''16}$-$B_{B''16}$ (XVI'')

where $B_{T''16}$ is a group represented by any one of the following (16a'') to (16j''):

(16a'')HO-, (16b'')HO-Bg-, (16c'')HO-Bt-Bg-, (16d'')HO-Bg-Bt-Bg-, (16e'')HO-Bg-Bg-Bt-Bg-, (16f'')HO-Ba-Bg-Bg-Bt-Bg-, (16g'')HO-Ba-Ba-Bg-Bg-Bt-Bg-,

-continued (16h″) HO-Bg-Ba-Ba-Bg-Bg-Bt-Bg-, (16i″) HO-Bt-Bg-Ba-Ba-Bg-Bg-Bt-Bg-, or (16j″) HO-Bc-Bt-Bg-Ba-Ba-Bg-Bg-Bt-Bgwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

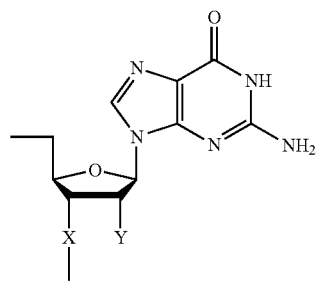
(G1)

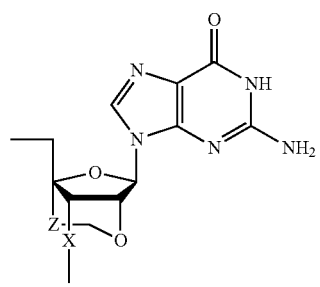
(G2)

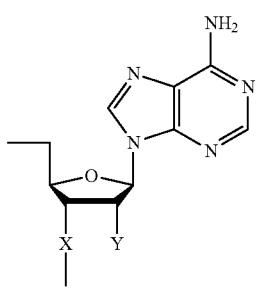
(A1)

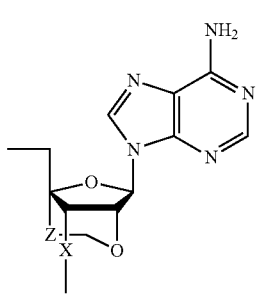
(A2)

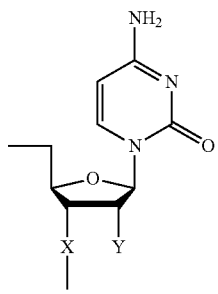
(C1)

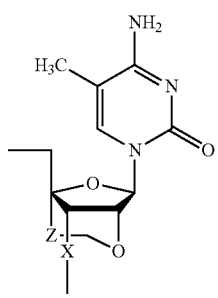
(C2)

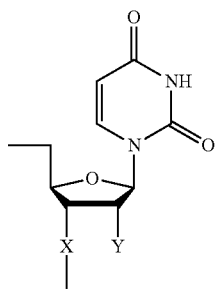
(U1)

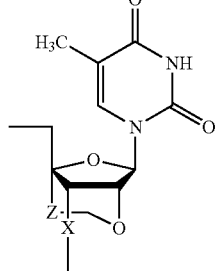
(T2)

where X is individually and independently a group represented by the following formula (X1) or (X2):

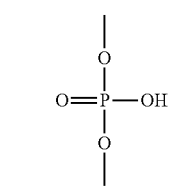
(X1)

-continued

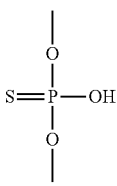
(X2)

Y is individually and independently a hydrogen atom, a hydroxyl group or an alkoxy group with 1-6 carbon atoms; and Z is individually and independently a single bond or an alkylene group with 1-5 carbon atoms;
$B_{M''16}$ is a group represented by the following formula (16''):

```
-Bt-Bt-Bc-Bt-Bt-Bg-Bt-Ba-Bc-   (16")
``` where Bg, Ba, Bt and Bc are as defined above;
$B_{B''16}$ is a group represented by any one of the following (116a'') to (116j''):

```
(116a") -CH2CH2OH,
(116b") -Bt-CH2CH2OH,
(116c") -Bt-Bt-CH2CH2OH,
(116d") -Bt-Bt-Bc-CH2CH2OH,
(116e") -Bt-Bt-Bc-Ba-CH2CH2OH,
(116f") -Bt-Bt-Bc-Ba-Bt-CH2CH2OH,
(116g") -Bt-Bt-Bc-Ba-Bt-Bc-CH2CH2OH,
(116h") -Bt-Bt-Bc-Ba-Bt-Bc-Bc-CH2CH2OH,
(116i") -Bt-Bt-Bc-Ba-Bt-Bc-Bc-Bc-CH2CH2OH,
or
(116j") -Bt-Bt-Bc-Ba-Bt-Bc-Bc-Bc-Ba-CH2CH2OH
``` where Bg, Ba, Bt and Bc are as defined above;
provided that at least one of the nucleosides constituting the compound represented by formula (XVI'') has 2''-O,4''-C-alkylene group.

[42] A compound represented by the following general formula (XVII'') or a pharmacologically acceptable salt thereof:

$$B_{T''17}\text{-}B_{M''17}\text{-}B_{B''17} \quad (XVII'')$$

where $B_{T''17}$ is a group represented by any one of the following (17a'') to (17j''):

```
(17a") HO-,
(17b") HO-Bt-,
(17c") HO-Bt-Bt-,
(17d") HO-Bg-Bt-Bt-,
(17e") HO-Bg-Bg-Bt-Bt-,
(17f") HO-Bc-Bg-Bg-Bt-Bt-,
(17g") HO-Bc-Bc-Bg-Bg-Bt-Bt-,
(17h") HO-Bt-Bc-Bc-Bg-Bg-Bt-Bt-,
(17i") HO-Bc-Bt-Bc-Bc-Bg-Bg-Bt-Bt-,
or
(17j") HO-Bc-Bc-Bt-Bc-Bc-Bg-Bg-Bt-Bt-
``` where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

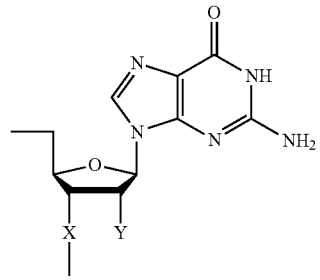
(G1)

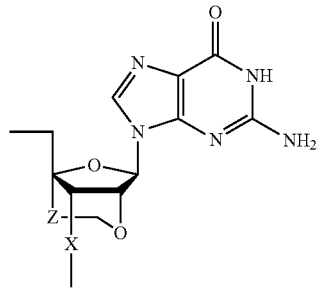
(G2)

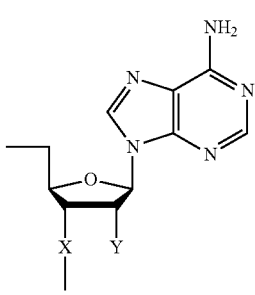
(A1)

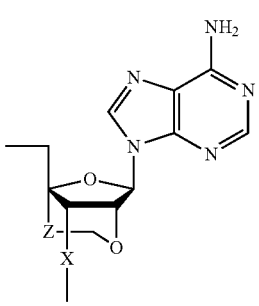
(A2)

-continued (C1)
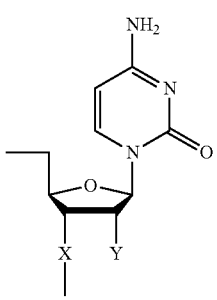

(C2)
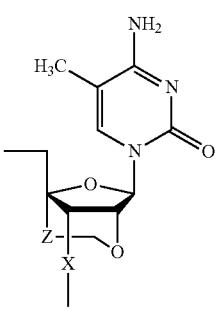

(U1)
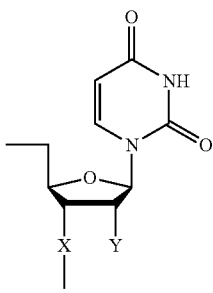

(T2)
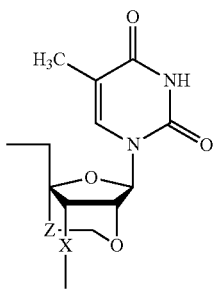

where X is individually and independently a group represented by the following formula (X1) or (X2):

(X1)
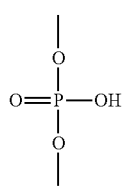

(X2)
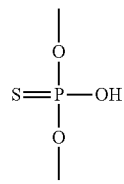

Y is individually and independently a hydrogen atom, a hydroxyl group or an alkoxy group with 1-6 carbon atoms; and Z is individually and independently a single bond or an alkylene group with 1-5 carbon atoms;

$B_{M''17}$ is a group represented by the following formula (17''):

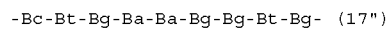
-Bc-Bt-Bg-Ba-Ba-Bg-Bg-Bt-Bg- (17'')

where Bg, Ba, Bt and Bc are as defined above;
$B_{B''17}$ is a group represented by any one of the following (117a'') to (117j''):

(117a'')-CH$_2$CH$_2$OH, (117b'')-Bt-CH$_2$CH$_2$OH, (117c'')-Bt-Bt-CH$_2$CH$_2$OH, (117d'')-Bt-Bt-Bc-CH$_2$CH$_2$OH, (117e'')-Bt-Bt-Bc-Bt-CH$_2$CH$_2$OH, (117f'')-Bt-Bt-Bc-Bt-Bt-CH$_2$CH$_2$OH, (117g'')-Bt-Bt-Bc-Bt-Bt-Bg-CH$_2$CH$_2$OH, (117h'')-Bt-Bt-Bc-Bt-Bt-Bg-Bt-CH$_2$CH$_2$OH, (117i'')-Bt-Bt-Bc-Bt-Bt-Bg-Bt-Ba-CH$_2$CH$_2$OH, or (117j'')-Bt-Bt-Bc-Bt-Bt-Bg-Bt-Ba-Bc-CH$_2$CH$_2$OH where Bg, Ba, Bt and Bc are as defined above;
provided that at least one of the nucleosides constituting the compound represented by formula (XVII'') has 2''-O,4''-C-alkylene group.

[43] A compound represented by the following general formula (XVIII'') or a pharmacologically acceptable salt thereof:

$B_{T''18}-B_{M''18}-B_{B''18}$ (XVIII'')

where $B_{T''18}$ is a group represented by any one of the following (18a'') to (18j''):

(18a'')HO-, (18b'')HO-Bg-, (18c'')HO-Bt-Bg-, (18d'')HO-Bc-Bt-Bg-, (18e'')HO-Bc-Bc-Bt-Bg-, (18f'')HO-Ba-Bc-Bc-Bt-Bg-, (18g'')HO-Bg-Ba-Bc-Bc-Bt-Bg-,

-continued (18h″)HO-Ba-Bg-Ba-Bc-Bc-Bt-Bg-, (18i″)HO-Ba-Ba-Bg-Ba-Bc-Bc-Bt-Bg-,
or (18j″)HO-Bt-Ba-Ba-Bg-Ba-Bc-Bc-Bt-Bgwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

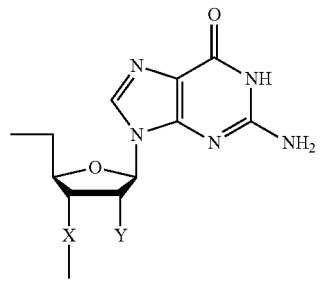
(G1)

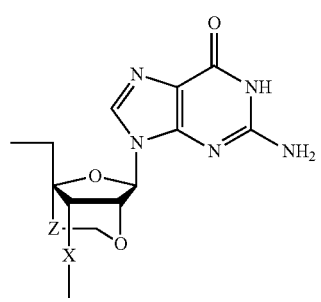
(G2)

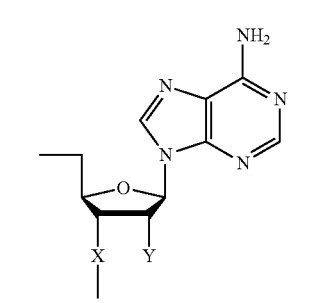
(A1)

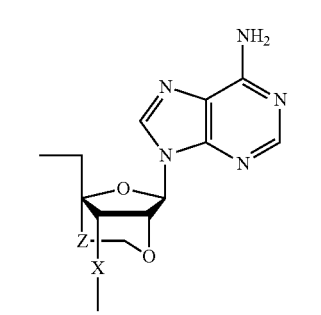
(A2)

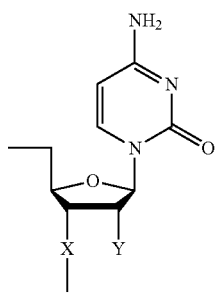
(C1)

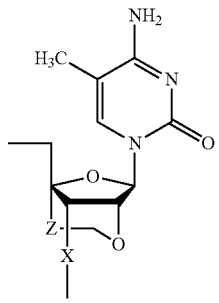
(C2)

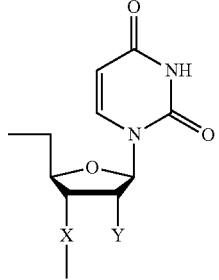
(U1)

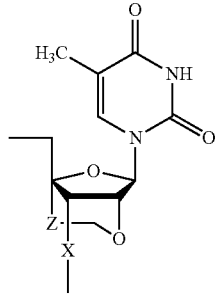
(T2)

where X is individually and independently a group represented by the following formula (X1) or (X2):

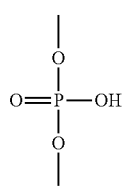
(X1)

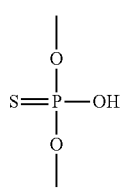
(X2)

Y is individually and independently a hydrogen atom, a hydroxyl group or an alkoxy group with 1-6 carbon atoms; and Z is individually and independently a single bond or an alkylene group with 1-5 carbon atoms;

$B_{M''18}$ is a group represented by the following formula (18''):

(18'')   -Bc-Bt-Bc-Ba-Bg-Bc-Bt-Bt-Bcwhere Bg, Ba, Bt and Bc are as defined above;
$B_{B''18}$ is a group represented by any one of the following (118a'') to (118j''):

(118a'') -CH$_2$CH$_2$OH, (118b'') -Bt-CH$_2$CH$_2$OH, (118c'') -Bt-Bt-CH$_2$CH$_2$OH, (118d'') -Bt-Bt-Bc-CH$_2$CH$_2$OH, (118e'') -Bt-Bt-Bc-Bc-CH$_2$CH$_2$OH, (118f'') -Bt-Bt-Bc-Bc-Bt-CH$_2$CH$_2$OH, (118g'') -Bt-Bt-Bc-Bc-Bt-Bt-CH$_2$CH$_2$OH, (118h'') -Bt-Bt-Bc-Bc-Bt-Bt-Ba-CH$_2$CH$_2$OH, (118i'') -Bt-Bt-Bc-Bc-Bt-Bt-Ba-Bg-CH$_2$CH$_2$OH, or (118j'') -Bt-Bt-Bc-Bc-Bt-Bt-Ba-Bg-Bc-CH$_2$CH$_2$OH where Bg, Ba, Bt and Bc are as defined above;
provided that at least one of the nucleosides constituting the compound represented by formula (XVIII'') has 2''-O,4''-C-alkylene group.

[44] A compound represented by the following general formula (XIX'') or a pharmacologically acceptable salt thereof:

$B_{T''19}$-$B_{M''19}$-$B_{B''19}$   (XIX'')

where $B_{T''19}$ is a group represented by any one of the following (19a'') to (19j''):

(19a'') HO-, (19b'') HO-Bc-, (19c'') HO-Bg-Bc-, (19d'') HO-Ba-Bg-Bc-, (19e'') HO-Bt-Ba-Bg-Bc-, (19f'') HO-Bt-Bt-Ba-Bg-Bc-, (19g'') HO-Bc-Bt-Bt-Ba-Bg-Bc-, (19h'') HO-Bc-Bc-Bt-Bt-Ba-Bg-Bc-, (19i'') HO-Bt-Bc-Bc-Bt-Bt-Ba-Bg-Bc-, or (19j'') HO-Bt-Bt-Bc-Bc-Bt-Bt-Ba-Bg-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

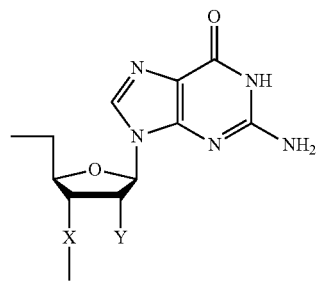
(G1)

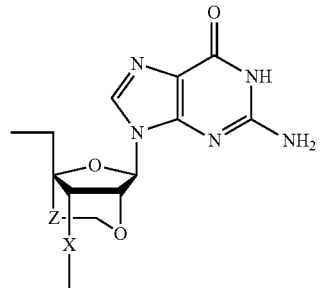
(G2)

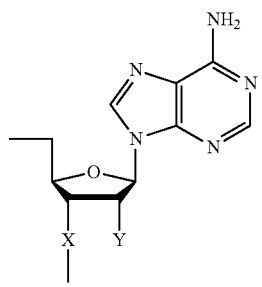
(A1)

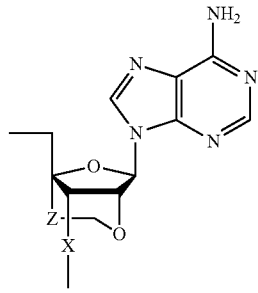
(A2)

-continued (C1) 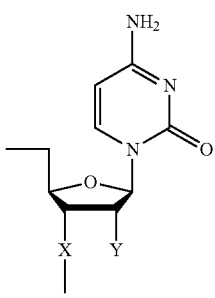

(C2) 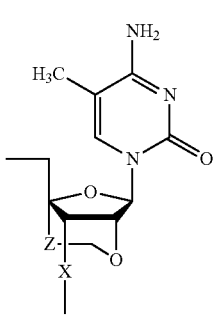

(U1) 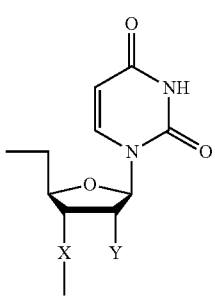

(T2) 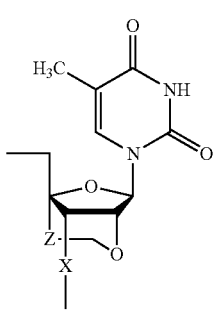

where X is individually and independently a group represented by the following formula (X1) or (X2):

(X1) 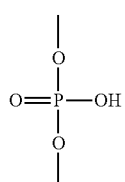

-continued (X2) 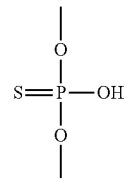

Y is individually and independently a hydrogen atom, a hydroxyl group or an alkoxy group with 1-6 carbon atoms; and Z is individually and independently a single bond or an alkylene group with 1-5 carbon atoms;

$B_{M''19}$ is a group represented by the following formula (19''):

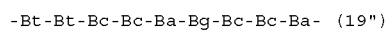
-Bt-Bt-Bc-Bc-Ba-Bg-Bc-Bc-Ba-  (19'')

where Bg, Ba, Bt and Bc are as defined above;

$B_{B''19}$ is a group represented by any one of the following (119a'') to (119j''):

(119a'')-CH₂CH₂OH, (119b'')-Bt-CH₂CH₂OH, (119c'')-Bt-Bt-CH₂CH₂OH, (119d'')-Bt-Bt-Bg-CH₂CH₂OH, (119e'')-Bt-Bt-Bg-Bt-CH₂CH₂OH, (119f'')-Bt-Bt-Bg-Bt-Bg-CH₂CH₂OH, (119g'')-Bt-Bt-Bg-Bt-Bg-Bt-CH₂CH₂OH, (119h'')-Bt-Bt-Bg-Bt-Bg-Bt-Bt-CH₂CH₂OH, (119i'')-Bt-Bt-Bg-Bt-Bg-Bt-Bt-Bg-CH₂CH₂OH, or (119j'')-Bt-Bt-Bg-Bt-Bg-Bt-Bt-Bg-Ba-CH₂CH₂OH where Bg, Ba, Bt and Bc are as defined above;
provided that at least one of the nucleosides constituting the compound represented by formula (XIX'') has 2''-O,4''-C-alkylene group.

[45] A compound represented by the following general formula (XX'') or a pharmacologically acceptable salt thereof:

$B_{T''20}$-$B_{M''20}$-$B_{B''20}$  (XX'')

where $B_{T''20}$ is a group represented by any one of the following (20a'') to (20j''):

(20a'')HO-, (20b'')HO-Bc-, (20c'')HO-Bt-Bc-, (20d'')HO-Bt-Bt-Bc-, (20e'')HO-Bc-Bt-Bt-Bc-, (20f'')HO-Bg-Bc-Bt-Bt-Bc-, (20g'')HO-Ba-Bg-Bc-Bt-Bt-Bc-,

101

-continued (20h") HO-Bc-Ba-Bg-Bc-Bt-Bt-Bc-, (20i") HO-Bt-Bc-Ba-Bg-Bc-Bt-Bt-Bc-,
or (20j") HO-Bc-Bt-Bc-Ba-Bg-Bc-Bt-Bt-Bcwhere Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

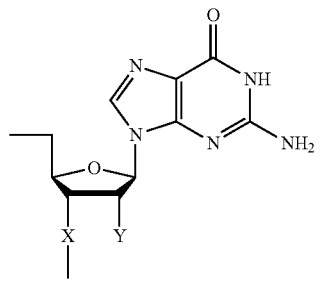
(G1)

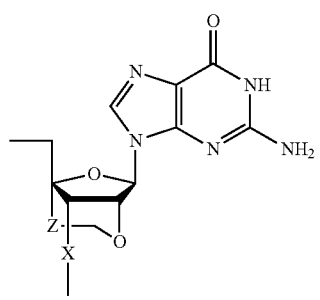
(G2)

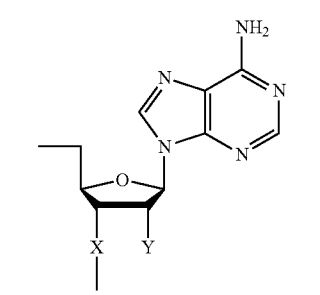
(A1)

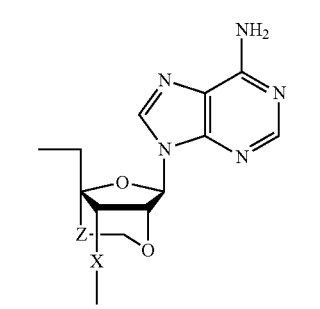
(A2)

102

-continued

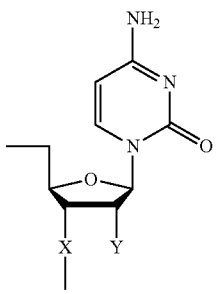
(C1)

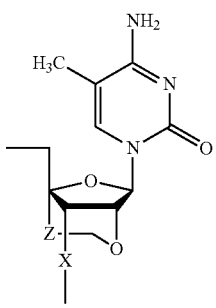
(C2)

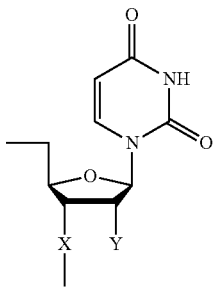
(U1)

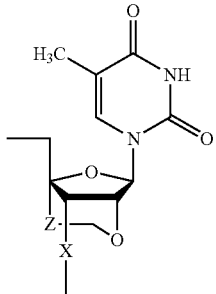
(T2)

where X is individually and independently a group represented by the following formula (X1) or (X2):

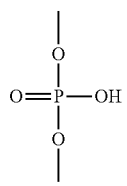
(X1)

-continued

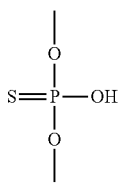
(X2)

Y is individually and independently a hydrogen atom, a hydroxyl group or an alkoxy group with 1-6 carbon atoms; and Z is individually and independently a single bond or an alkylene group with 1-5 carbon atoms;
$B_{M''20}$ is a group represented by the following formula (20''):

```
-Bt-Bt-Bc-Bc-Bt-Bt-Ba-Bg-Bc-   (20")
``` where Bg, Ba, Bt and Bc are as defined above;
$B_{B''20}$ is a group represented by any one of the following (120a'') to (120j''):

```
(120a")  -CH2CH2OH,
(120b")  -Bt-CH2CH2OH,
(120c")  -Bt-Bt-CH2CH2OH,
(120d")  -Bt-Bt-Bc-CH2CH2OH,
(120e")  -Bt-Bt-Bc-Bc-CH2CH2OH,
(120f")  -Bt-Bt-Bc-Bc-Ba-CH2CH2OH,
(120g")  -Bt-Bt-Bc-Bc-Ba-Bg-CH2CH2OH,
(120h")  -Bt-Bt-Bc-Bc-Ba-Bg-Bc-CH2CH2OH,
(120i")  -Bt-Bt-Bc-Bc-Ba-Bg-Bc-Bc-CH2CH2OH,
or
(120j")  -Bt-Bt-Bc-Bc-Ba-Bg-Bc-Bc-Ba-CH2CH2OH
``` where Bg, Ba, Bt and Bc are as defined above;
provided that at least one of the nucleosides constituting the compound represented by formula (XX'') has 2''-O,4''-C-alkylene group.

[46] A compound represented by the following general formula (XXI'') or a pharmacologically acceptable salt thereof:

$$B_{T''21}\text{-}B_{M''21}\text{-}B_{B''21} \quad (XXI'')$$

where $B_{T''21}$ is a group represented by any one of the following (21a'') to (21e''):

```
(21a")  HO-,
(21b")  HO-Ba-,
(21c")  HO-Bc-Ba-,
(21d")  HO-Bt-Bc-Ba-,
or
(21e")  HO-Bc-Bt-Bc-Ba-
``` where Bg is a group represented by the following formula (G1) or (G2); Ba is a group represented by the following formula (A1) or (A2); Bc is a group represented by the following formula (C1) or (C2); and Bt is a group represented by the following formula (U1) or (T2):

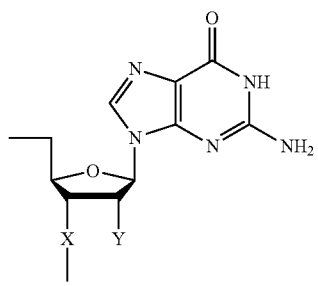

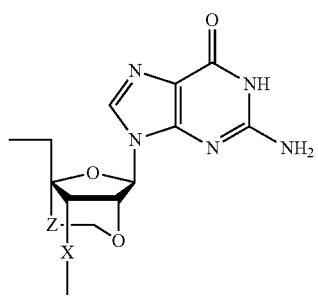

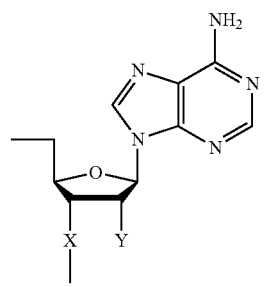

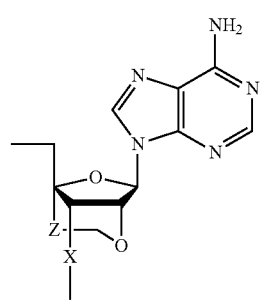

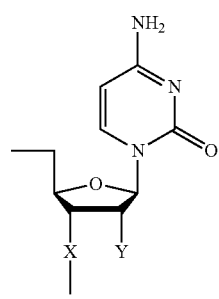

-continued (C2) 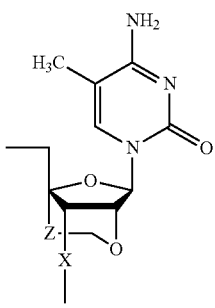

(U1) 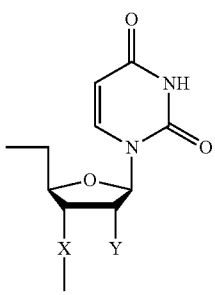

(T2) 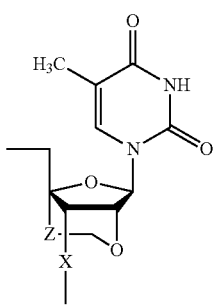

where X is individually and independently a group represented by the following formula (X1) or (X2):

(X1) 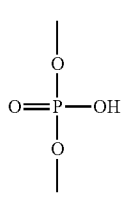

(X2) 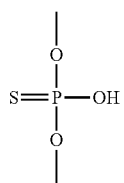

Y is individually and independently a hydrogen atom, a hydroxyl group or an alkoxy group with 1-6 carbon atoms; and Z is individually and independently a single bond or an alkylene group with 1-5 carbon atoms;

$B_{M''21}$ is a group represented by the following formula (21"):

(SEQ ID NO: 154)
-Bg-Bc-Bt-Bt-Bc-Bt-Bt-Bc-Bc-Bt-Bt-Ba-Bg-Bc- (21")

where Bg, Ba, Bt and Bc are as defined above;

$B_{B''21}$ is a group represented by any one of the following (121a") to (121e"):

(121a") -CH₂CH₂OH, (121b") -Bt-CH₂CH₂OH, (121c") -Bt-Bt-CH₂CH₂OH, (121d") -Bt-Bt-Bc-CH₂CH₂OH, or (121e") -Bt-Bt-Bc-Bc-CH₂CH₂OH where Bg, Ba, Bt and Bc are as defined above;

provided that at least one of the nucleosides constituting the compound represented by formula (XXI") has 2"-O,4"-C-alkylene group.

[47] The compound of any one of [26] to [46] above which is selected from the group consisting of the following compounds (i") to (xlix"), or a pharmacologically acceptable salt thereof:

(i") a compound represented by the following formula (i"):

(SEQ ID NO: 155)
HO-Bg-Ba-Ba-Ba-Ba-Bc-Bg-Bc-Bc-Bg-Bc-Bc-Ba-Bt-Bt-

Bt-Bc-Bt-CH₂CH₂OH (i")

(ii") a compound represented by the following formula (ii"):

(SEQ ID NO: 156)
HO-Bc-Bt-Bg-Bt-Bt-Ba-Bg-Bc-Bc-Ba-Bc-Bt-Bg-Ba-Bt-

Bt-Ba-Ba-CH₂CH₂OH (ii")

(iii") a compound represented by the following formula (iii")

(SEQ ID NO: 157)
HO-Bt-Bg-Ba-Bg-Ba-Ba-Ba-Bc-Bt-Bg-Bt-Bt-Bc-Ba-Bg-

Bc-Bt-Bt-CH₂CH₂OH (iii")

(iv") a compound represented by the following formula (iv"):

(SEQ ID NO: 158)
HO-Bc-Ba-Bg-Bg-Ba-Ba-Bt-Bt-Bt-Bg-Bt-Bg-Bt-Bc-Bt-

Bt-Bt-Bc-CH₂CH₂OH (iv")

(v") a compound represented by the following formula (v"):

(SEQ ID NO: 159)
HO-Bg-Bt-Ba-Bt-Bt-Bt-Ba-Bg-Bc-Ba-Bt-Bg-Bt-Bt-Bc-

Bc-Bc-Ba-CH₂CH₂OH (v")

(vi") a compound represented by the following formula (vi"):

(SEQ ID NO: 160)
HO-Ba-Bg-Bc-Ba-Bt-Bg-Bt-Bt-Bc-Bc-Bc-Ba-Ba-Bt-Bt-

Bc-Bt-Bc-CH$_2$CH$_2$OH (vi")

(vii") a compound represented by the following formula (vii"):

(SEQ ID NO: 161)
HO-Bg-Bc-Bc-Bg-Bc-Bc-Ba-Bt-Bt-Bt-Bc-Bt-Bc-Ba-Ba-

Bc-Ba-Bg-CH$_2$CH$_2$OH (vii")

(viii") a compound represented by the following formula (viii"):

(SEQ ID NO: 37)
HO-Bc-Ba-Bt-Ba-Ba-Bt-Bg-Ba-Ba-Ba-Ba-Bc-Bg-Bc-Bc-

Bg-Bc-Bc-CH$_2$CH$_2$OH (viii")

(ix") a compound represented by the following formula (ix"):

(SEQ ID NO: 162)
HO-Bt-Bt-Bc-Bc-Bc-Ba-Ba-Bt-Bt-Bc-Bt-Bc-Ba-Bg-Bg-

Ba-Ba-Bt-CH$_2$CH$_2$OH (ix")

(x") a compound represented by the following formula (x"):

(SEQ ID NO: 163)
HO-Bc-Bc-Ba-Bt-Bt-Bt-Bg-Bt-Ba-Bt-Bt-Bt-Ba-Bg-Bc-

Ba-Bt-Bg-CH$_2$CH$_2$OH (x")

(xi") a compound represented by the following formula (xi"):

(SEQ ID NO: 164)
HO-Bc-Bt-Bc-Ba-Bg-Ba-Bt-Bc-Bt-Bt-Bc-Bt-Ba-Ba-Bc-

Bt-Bt-Bc-CH$_2$CH$_2$OH (xi")

(xii") a compound represented by the following formula (xii"):

(SEQ ID NO: 165)
HO-Ba-Bc-Bc-Bg-Bc-Bc-Bt-Bt-Bc-Bc-Ba-Bc-Bt-Bc-Ba-

Bg-Ba-Bg-CH$_2$CH$_2$OH (xii")

(xiii") a compound represented by the following formula (xiii"):

(SEQ ID NO: 166)
HO-Bt-Bc-Bt-Bt-Bg-Ba-Ba-Bg-Bt-Ba-Ba-Ba-Bc-Bg-Bg-

Bt-Bt-Bt-CH$_2$CH$_2$OH (xiii")

(xiv") a compound represented by the following formula (xiv"):

(SEQ ID NO: 167)
HO-Bg-Bg-Bc-Bt-Bg-Bc-Bt-Bt-Bt-Bg-Bc-Bc-Bc-Bt-Bc-

Ba-Bg-Bc-CH$_2$CH$_2$OH (xiv")

(xv") a compound represented by the following formula (xv"):

(SEQ ID NO: 44)
HO-Ba-Bg-Bt-Bc-Bc-Ba-Bg-Bg-Ba-Bg-Bc-Bt-Ba-Bg-Bg-

Bt-Bc-Ba-CH$_2$CH$_2$OH (xv")

(xvi") a compound represented by the following formula (xvi"):

(SEQ ID NO: 45)
HO-Bg-Bc-Bt-Bc-Bc-Ba-Ba-Bt-Ba-Bg-Bt-Bg-Bg-Bt-Bc-

Ba-Bg-Bt-CH$_2$CH$_2$OH (xvi")

(xvii") a compound represented by the following formula (xvii"):

(SEQ ID NO: 168)
HO-Bg-Bc-Bt-Ba-Bg-Bg-Bt-Bc-Ba-Bg-Bg-Bc-Bt-Bg-Bc-

Bt-Bt-Bt-CH$_2$CH$_2$OH (xvii")

(xviii") a compound represented by the following formula (xviii"):

(SEQ ID NO: 169)
HO-Bg-Bc-Ba-Bg-Bc-Bc-Bt-Bc-Bt-Bc-Bg-Bc-Bt-Bc-Ba-

Bc-Bt-Bc-CH$_2$CH$_2$OH (xviii")

(xix") a compound represented by the following formula (xix"):

(SEQ ID NO: 170)
HO-Bt-Bc-Bt-Bt-Bc-Bc-Ba-Ba-Ba-Bg-Bc-Ba-Bg-Bc-Bc-

Bt-Bc-Bt-CH$_2$CH$_2$OH (xix")

(xx") a compound represented by the following formula (xx"):

(SEQ ID NO: 171)
HO-Bt-Bg-Bc-Ba-Bg-Bt-Ba-Ba-Bt-Bc-Bt-Ba-Bt-Bg-Ba-

Bg-Bt-Bt-CH$_2$CH$_2$OH (xx")

(xxi") a compound represented by the following formula (xxi"):

(SEQ ID NO: 172)
HO-Bg-Bt-Bt-Bt-Bc-Ba-Bg-Bc-Bt-Bt-Bc-Bt-Bg-Bt-Ba-

Ba-Bg-Bc-CH$_2$CH$_2$OH (xxi")

(xxii") a compound represented by the following formula (xxii"):

(SEQ ID NO: 51)
HO-Bt-Bg-Bt-Ba-Bg-Bg-Ba-Bc-Ba-Bt-Bt-Bg-Bg-Bc-Ba-

Bg-Bt-Bt-CH₂CH₂OH (xxii")

(xxiii") a compound represented by the following formula (xxiii"):

(SEQ ID NO: 173)
HO-Bt-Bc-Bc-Bt-Bt-Ba-Bc-Bg-Bg-Bg-Bt-Ba-Bg-Bc-Ba-

Bt-Bc-Bc-CH₂CH₂OH (xxiii")

(xxiv") a compound represented by the following formula (xxiv"):

(SEQ ID NO: 174)
HO-Ba-Bg-Bc-Bt-Bc-Bt-Bt-Bt-Ba-Bc-Bt-Bc-Bc-Bc-

Bt-Bt-Bg-CH₂CH₂OH (xxiv")

(xxv") a compound represented by the following formula (xxv"):

(SEQ ID NO: 175)
HO-Bc-Bc-Ba-Bt-Bt-Bg-Bt-Bt-Bt-Bc-Ba-Bt-Bc-Ba-Bg-

Bc-Bt-Bc-CH₂CH₂OH (xxv")

(xxvi") a compound represented by the following formula (xxvi"):

(SEQ ID NO: 55)
HO-Bc-Bt-Ba-Bt-Bg-Ba-Bg-Bt-Bt-Bt-Bc-Bt-Bt-Bc-Bc-

Ba-Ba-Ba-CH₂CH₂OH (xxvi")

(xxvii") a compound represented by the following formula (xxvii"):

(SEQ ID NO: 176)
D-Bt-Bg-Bt-Bg-Bt-Bc-Ba-Bc-Bc-Ba-Bg-Ba-Bg-Bt-Ba-Ba-

Bc-Ba-Bg-Bt-CH₂CH₂OH (xxvii")

(xxviii") a compound represented by the following formula (xxviii"):

(SEQ ID NO: 177)
D-Ba-Bg-Bg-Bt-Bt-Bg-Bt-Bg-Bt-Bc-Ba-Bc-Bc-Ba-Bg-Ba-

Bg-Bt-Ba-Ba-CH₂CH₂OH (xxviii")

(xxix") a compound represented by the following formula (xxix"):

(SEQ ID NO: 178)
D-Ba-Bg-Bt-Ba-Ba-Bc-Bc-Ba-Bc-Ba-Bg-Bg-Bt-Bt-Bg-Bt-

Bg-Bt-Bc-Ba-CH₂CH₂OH (xxix")

(xxx") a compound represented by the following formula (xxx"):

(SEQ ID NO: 59)
D-Bt-Bt-Bg-Ba-Bt-Bc-Ba-Ba-Bg-Bc-Ba-Bg-Ba-Bg-Ba-Ba-

Ba-Bg-Bc-Bc-CH₂CH₂OH (xxx")

(xxxi") a compound represented by the following formula (xxxi"):

(SEQ ID NO: 179)
D-Bc-Ba-Bc-Bc-Bc-Bt-Bc-Bt-Bg-Bt-Bg-Ba-Bt-Bt-Bt-

Ba-Bt-Ba-Ba-CH₂CH₂OH (xxxi")

(xxxii") a compound represented by the following formula (xxxii"):

(SEQ ID NO: 180)
D-Ba-Bc-Bc-Bc-Ba-Bc-Bc-Ba-Bt-Bc-Ba-Bc-Bc-Bt-Bc-

Bt-Bg-Bt-Bg-CH₂CH₂OH (xxxii")

(xxxiii") a compound represented by the following formula (xxxiii"):

(SEQ ID NO: 181)
D-Bc-Bc-Bt-Bc-Ba-Ba-Bg-Bg-Bt-Bc-Bc-Bc-Bc-Ba-Bc-

Bc-Ba-Bt-Bc-CH₂CH₂OH (xxxiii")

(xxxiv") a compound represented by the following formula (xxxiv"):

(SEQ ID NO: 182)
HO-Bt-Ba-Ba-Bc-Ba-Bg-Bt-Bc-Bt-Bg-Ba-Bg-Bt-Ba-Bg-

Bg-Ba-Bg-CH₂CH₂OH (xxxiv")

(xxxv") a compound represented by the following formula (xxxv"):

(SEQ ID NO: 183)
HO-Bg-Bg-Bc-Ba-Bt-Bt-Bt-Bc-Bt-Ba-Bg-Bt-Bt-Bt-Bg-

Bg-Ba-Bg-CH₂CH₂OH (xxxv")

(xxxvi") a compound represented by the following formula (xxxvi"):

(SEQ ID NO: 184)
HO-Ba-Bg-Bc-Bc-Ba-Bg-Bt-Bc-Bg-Bg-Bt-Ba-Ba-Bg-Bt-

Bt-Bc-Bt-CH₂CH₂OH (xxxvi")

(xxxvii") a compound represented by the following formula (xxxvii"):

(SEQ ID NO: 185)
HO-Ba-Bg-Bt-Bt-Bg-Bg-Ba-Bg-Ba-Bt-Bg-Bg-Bc-Ba-

Bg-Bt-Bt-CH₂CH₂OH (xxxvii")

(xxxviii") a compound represented by the following formula (xxxviii"):

(SEQ ID NO: 186)
HO-Bc-Bt-Bg-Ba-Bt-Bt-Bc-Bt-Bg-Ba-Ba-Bt-Bt-Bc-Bt-

Bt-Bt-Bc-CH₂CH₂OH (xxxviii")

(xxxix") a compound represented by the following formula (xxxix"):

(SEQ ID NO: 68)
HO-Bt-Bt-Bc-Bt-Bt-Bg-Bt-Ba-Bc-Bt-Bt-Bc-Ba-Bt-Bc-

Bc-Bc-Ba-CH₂CH₂OH (xxxix")

(xl") a compound represented by the following formula (xl").

(SEQ ID NO: 187)
HO-Bc-Bc-Bt-Bc-Bc-Bg-Bg-Bt-Bt-Bc-Bt-Bg-Ba-Ba-Bg-

Bg-Bt-Bg-CH₂CH₂OH (xl")

(xli") a compound represented by the following formula (xli"):

(SEQ ID NO: 188)
HO-Bc-Ba-Bt-Bt-Bt-Bc-Ba-Bt-Bt-Bc-Ba-Ba-Bc-Bt-Bg-

Bt-Bt-Bg-CH₂CH₂OH (xli")

(xlii") a compound represented by the following formula (xlii"):

(SEQ ID NO: 189)
HO-Bt-Bt-Bc-Bc-Bt-Bt-Ba-Bg-Bc-Bt-Bt-Bc-Bc-Ba-Bg-

Bc-Bc-Ba-CH₂CH₂OH (xlii")

(xliii") a compound represented by the following formula (xliii"):

(SEQ ID NO: 190)
HO-Bt-Ba-Ba-Bg-Ba-Bc-Bc-Bt-Bg-Bc-Bt-Bc-Ba-Bg-Bc-

Bt-Bt-Bc-CH₂CH₂OH (xliii")

(xliv") a compound represented by the following formula (xliv"):

(SEQ ID NO: 191)
HO-Bc-Bt-Bt-Bg-Bg-Bc-Bt-Bc-Bt-Bg-Bg-Bc-Bc-Bt-Bg-

Bt-Bc-Bc-CH₂CH₂OH (xliv")

(xlv") a compound represented by the following formula (xlv"):

(SEQ ID NO: 192)
HO-Bc-Bt-Bc-Bc-Bt-Bt-Bc-Bc-Ba-Bt-Bg-Ba-Bc-Bt-Bc-

Ba-Ba-Bg-CH₂CH₂OH (xlv")

(xlvi") a compound represented by the following formula (xlvi"):

(SEQ ID NO: 75)
HO-Bc-Bt-Bg-Ba-Ba-Bg-Bg-Bt-Bg-Bt-Bt-Bc-Bt-Bt-Bg-

Bt-Ba-Bc-CH₂CH₂OH (xlvi")

(xlvii") a compound represented by the following formula (xlvii"):

(SEQ ID NO: 76)
HO-Bt-Bt-Bc-Bc-Ba-Bg-Bc-Bc-Ba-Bt-Bt-Bg-Bt-Bg-Bt-

Bt-Bg-Ba-CH₂CH₂OH (xlvii")

(xlviii") a compound represented by the following formula (xlviii"):

(SEQ ID NO: 193)
HO-Bc-Bt-Bc-Ba-Bg-Bc-Bt-Bt-Bc-Bt-Bt-Bc-Bc-Bt-Bt-

Ba-Bg-Bc-CH₂CH₂OH (xlviii")

(xlix") a compound represented by the following formula (xlix"):

(SEQ ID NO: 194)
HO-Bg-Bc-Bt-Bt-Bc-Bt-Bt-Bc-Bc-Bt-Bt-Ba-Bg-Bc-Bt-

Bt-Bc-Bc-CH₂CH₂OH (xlix")

where Bg is a group represented by the following formula (G1) or (G2); Ba is a group represented by the following formula (A1) or (A2); Bc is a group represented by the following formula (C1) or (C2); Bt is a group represented by the following formula (U1) or (T2); and D is HO— or Ph- wherein Ph- is a group represented by the following first formula:

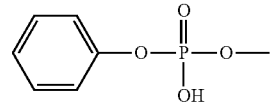

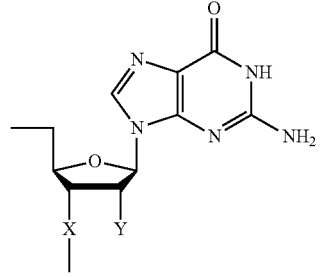
(G1)

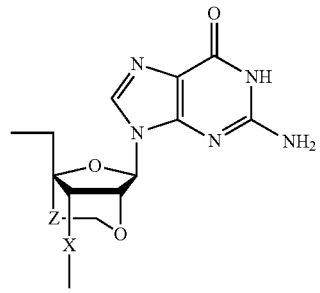
(G2)

(A1) 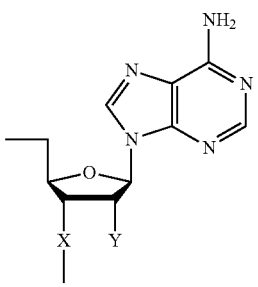

(A2) 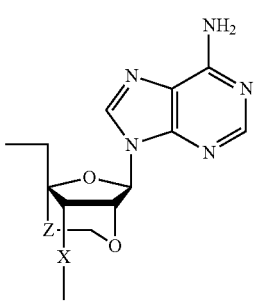

(C1) 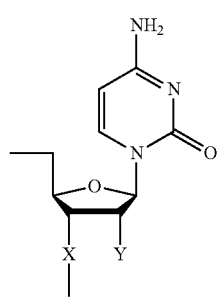

(C2) 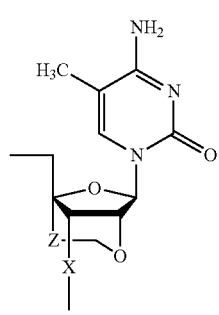

(U1) 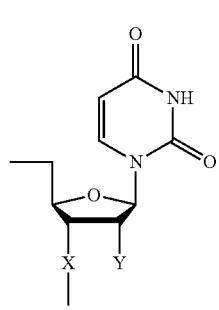

(T2) 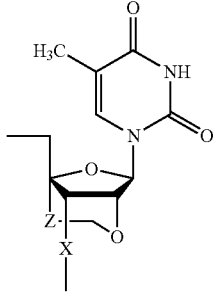

where X is individually and independently a group represented by the following formula (X1) or (X2):

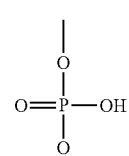 (X1)

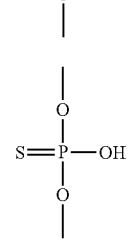 (X2)

Y is individually and independently a hydrogen atom, a hydroxyl group or an alkoxy group with 1-6 carbon atoms; and Z is individually and independently a single bond or an alkylene group with 1-5 carbon atoms.

[48] The compound of any one of [26] to [46] above which is selected from the group consisting of the following compounds (i″-a) to (li″-a) or a pharmacologically acceptable salt thereof:

(i″-a) a compound represented by the following formula (i″-a):

```
                                          (SEQ ID NO: 30)
HO-Bg-Ba-Ba-Ba-Ba-Bc-Bg-Bc-Bc-Bg-Bc-Bc-Ba-B't-

B'u-B'u-Bc-B't-CH2CH2OH  (i"-a)
```

(ii″-a) a compound represented by the following formula (ii″-a):

```
                                          (SEQ ID NO: 31)
HO-Bc-B't-Bg-B'u-B't-Ba-Bg-Bc-Bc-Ba-Bc-B't-Bg-

Ba-B't-B't-Ba-Ba-CH2CH2OH  (ii"-a)
```

(iii″-a) a compound represented by the following formula (iii″-a):

```
                                          (SEQ ID NO: 32)
HO-B't-Bg-Ba-Bg-Ba-Ba-Ba-Bc-B't-Bg-B't-B'u-Bc-Ba-

Bg-Bc-B'u-B't-CH2CH2OH  (iii"-a)
```

(iv"-a) a compound represented by the following formula (iv"-a):

(SEQ ID NO: 33)
HO-Bc-Ba-Bg-Bg-Ba-Ba-B't-B't-B'u-Bg-B't-Bg-B'u-Bc-B'u-B'u-B't-Bc-CH₂CH₂OH (iv"-a)

(v"-a) a compound represented by the following formula (v"-a):

(SEQ ID NO: 34)
HO-Bg-B't-Ba-B'u-B't-B't-Ba-Bg-Bc-Ba-B't-Bg-B'u-B't-Bc-Bc-Bc-Ba-CH₂CH₂OH (v"-a)

(vi"-a) a compound represented by the following formula (vi"-a):

(SEQ ID NO: 35)
HO-Ba-Bg-Bc-Ba-B't-Bg-B't-B't-Bc-Bc-Bc-Ba-Ba-B't-B'u-Bc-B't-Bc-CH₂CH₂OH (vi"-a)

(vii"-a) a compound represented by the following formula (vii"-a):

(SEQ ID NO: 36)
HO-Bg-Bc-Bc-Bg-Bc-Bc-Ba-B't-B'u-B'u-Bc-B'u-Bc-Ba-Ba-Bc-Ba-Bg-CH₂CH₂OH (vii"-a)

(viii"-a) a compound represented by the following formula (viii"-a):

(SEQ ID NO: 37)
HO-Bc-Ba-B't-Ba-Ba-B't-Bg-Ba-Ba-Ba-Ba-Bc-Bg-Bc-Bc-Bg-Bc-Bc-CH₂CH₂OH (viii"-a)

(ix"-a) a compound represented by the following formula (ix"-a):

(SEQ ID NO: 38)
HO-B't-B'u-Bc-Bc-Bc-Ba-Ba-B't-B'u-Bc-B't-Bc-Ba-Bg-Bg-Ba-Ba-B't-CH₂CH₂OH (ix"-a)

(x"-a) a compound represented by the following formula (x"-a):

(SEQ ID NO: 39)
HO-Bc-Bc-Ba-B'u-B't-B'u-Bg-B't-Ba-B'u-B't-B't-Ba-Bg-Bc-Ba-B't-Bg-CH₂CH₂OH (x"-a)

(xi"-a) a compound represented by the following formula (xi"-a):

(SEQ ID NO: 40)
HO-Bc-B't-Bc-Ba-Bg-Ba-B't-Bc-B'u-B'u-Bc-B't-Ba-Ba-Bc-B'u-B'u-Bc-CH₂CH₂OH (xi"-a)

(xii"-a) a compound represented by the following formula (xii"-a):

(SEQ ID NO: 41)
HO-Ba-Bc-Bc-Bg-Bc-Bc-B't-B'u-Bc-Bc-Ba-Bc-B't-Bc-Ba-Bg-Ba-Bg-CH₂CH₂OH (xii"-a)

(xiii"-a) a compound represented by the following formula (xiii"-a):

(SEQ ID NO: 42)
HO-B't-Bc-B't-B't-Bg-Ba-Ba-Bg-B't-Ba-Ba-Ba-Bc-Bg-Bg-B't-B'u-B't-CH₂CH₂OH (xiii"-a)

(xiv"-a) a compound represented by the following formula (xiv"-a):

(SEQ ID NO: 43)
HO-Bg-Bg-Bc-B't-Bg-Bc-B't-B't-B'u-Bg-Bc-Bc-Bc-B't-Bc-Ba-Bg-Bc-CH₂CH₂OH (xiv"-a)

(xv"-a) a compound represented by the following formula (xv"-a):

(SEQ ID NO: 44)
HO-Ba-Bg-B't-Bc-Bc-Ba-Bg-Bg-Ba-Bg-Bc-B't-Ba-Bg-Bg-B't-Bc-Ba-CH₂CH₂OH (xv"-a)

(xvi"-a) a compound represented by the following formula (xvi"-a):

(SEQ ID NO: 45)
HO-Bg-Bc-B't-Bc-Bc-Ba-Ba-B't-Ba-Bg-B't-Bg-Bg-B't-Bc-Ba-Bg-B't-CH₂CH₂OH (xvi"-a)

(xvii"-a) a compound represented by the following formula (xvii"-a):

(SEQ ID NO: 46)
HO-Bg-Bc-B't-Ba-Bg-Bg-B't-Bc-Ba-Bg-Bg-Bc-B't-Bg-Bc-B't-B't-B'u-CH₂CH₂OH (xvii"-a)

(xviii"-a) a compound represented by the following formula (xviii"-a):

(SEQ ID NO: 47)
HO-Bg-Bc-Ba-Bg-Bc-Bc-B'u-Bc-B't-Bc-Bg-Bc-B't-Bc-Ba-Bc-B't-Bc-CH₂CH₂OH (xviii"-a)

(xix"-a) a compound represented by the following formula (xix"-a):

(SEQ ID NO: 48)
HO-B't-Bc-B'u-B'u-Bc-Bc-Ba-Ba-Ba-Bg-Bc-Ba-Bg-Bc-Bc-B'u-Bc-B't-CH₂CH₂OH (xix"-a)

(xx"-a) a compound represented by the following formula (xx"-a):

(SEQ ID NO: 49)
HO-B't-Bg-Bc-Ba-Bg-B't-Ba-Ba-B't-Bc-B'u-Ba-B't-Bg-

Ba-Bg-B't-B't-CH₂CH₂OH (xx"-a)

(xxi"-a) a compound represented by the following formula (xxi"-a):

(SEQ ID NO: 50)
HO-Bg-B't-B't-B'u-Bc-Ba-Bg-Bc-B'u-B't-Bc-B't-Bg-

B't-Ba-Ba-Bg-Bc-CH₂CH₂OH (xxi"-a)

(xxii"-a) a compound represented by the following formula (xxii"-a):

(SEQ ID NO: 51)
HO-B't-Bg-B't-Ba-Bg-Bg-Ba-Bc-Ba-B't-B't-Bg-Bg-Bc-

Ba-Bg-B't-B't-CH₂CH₂OH (xxii"-a)

(xxiii"-a) a compound represented by the following formula (xxiii"-a):

(SEQ ID NO: 52)
HO-B't-Bc-Bc-B't-B't-Ba-Bc-Bg-Bg-Bg-B't-Ba-Bg-Bc-

Ba-B'u-Bc-Bc-CH₂CH₂OH (xxiii"-a)

(xxiv"-a) a compound represented by the following formula (xxiv"-a):

(SEQ ID NO: 53)
HO-Ba-Bg-Bc-B't-Bc-B'u-B't-B'u-B't-Ba-Bc-B't-Bc-

Bc-Bc-B't-B't-Bg-CH₂CH₂OH (xxiv"-a)

(xxv"-a) a compound represented by the following formula (xxv"-a):

(SEQ ID NO: 54)
HO-Bc-Bc-Ba-B'u-B't-Bg-B'u-B't-B'u-Bc-Ba-B'u-Bc-

Ba-Bg-Bc-B't-Bc-CH₂CH₂OH (xxv"-a)

(xxvi"-a) a compound represented by the following formula (xxvi"-a):

(SEQ ID NO: 55)
HO-Bc-B't-Ba-B't-Bg-Ba-Bg-B't-B't-B't-Bc-B't-B't-

Bc-Bc-Ba-Ba-Ba-CH₂CH₂OH (xxvi"-a)

(xxvii"-a) a compound represented by the following formula (xxvii"-a):

(SEQ ID NO: 56)
D-B't-Bg-B't-Bg-B't-Bc-Ba-Bc-Bc-Ba-Bg-Ba-Bg-B'u-

Ba-Ba-Bc-Ba-Bg-B't-CH₂CH₂OH (xxvii"-a)

(xxviii"-a) a compound represented by the following formula (xxviii"-a):

(SEQ ID NO: 57)
D-Ba-Bg-Bg-B't-B't-Bg-B'u-Bg-B'u-Bc-Ba-Bc-Bc-Ba-

Bg-Ba-Bg-B't-Ba-Ba-CH₂CH₂OH (xxviii"-a)

(xxix"-a) a compound represented by the following formula (xxix"-a):

(SEQ ID NO: 58)
D-Ba-Bg-B't-Ba-Ba-Bc-Bc-Ba-Bc-Ba-Bg-Bg-B'u-B'u-Bg-

B't-Bg-B't-Bc-Ba-CH₂CH₂OH (xxix"-a)

(xxx"-a) a compound represented by the following formula (xxx"-a):

(SEQ ID NO: 59)
D-B't-B't-Bg-Ba-B't-Bc-Ba-Ba-Bg-Bc-Ba-Bg-Ba-Bg-Ba-

Ba-Ba-Bg-Bc-Bc-CH₂CH₂OH (xxx"-a)

(xxxi"-a) a compound represented by the following formula (xxxi"-a):

(SEQ ID NO: 60)
D-Bc-Ba-Bc-Bc-Bc-B'u-Bc-B'u-Bg-B'u-Bg-Ba-B'u-B'u-

B'u-B't-Ba-B't-Ba-Ba-CH₂CH₂OH (xxxi"-a)

(xxxii"-a) a compound represented by the following formula (xxxii"-a):

(SEQ ID NO: 61)
D-Ba-Bc-Bc-Bc-Ba-Bc-Bc-Ba-B'u-Bc-Ba-Bc-Bc-Bc-B'u-

Bc-B't-Bg-B't-Bg-CH₂CH₂OH (xxxii"-a)

(xxxiii"-a) a compound represented by the following formula (xxxiii"-a):

(SEQ ID NO: 62)
D-Bc-Bc-B't-Bc-Ba-Ba-Bg-Bg-B'u-Bc-Ba-Bc-Bc-Bc-Ba-

Bc-Bc-Ba-B't-Bc-CH₂CH₂OH (xxxiii"-a)

(xxxiv"-a) a compound represented by the following formula (xxxiv"-a):

(SEQ ID NO: 63)
HO-B't-Ba-Ba-Bc-Ba-Bg-B'u-Bc-B'u-Bg-Ba-Bg-B'u-Ba-

Bg-Bg-Ba-Bg-CH₂CH₂OH (xxxiv"-a)

(xxxv"-a) a compound represented by the following formula (xxxv"-a):

(SEQ ID NO: 64)
HO-Bg-Bg-Bc-Ba-B't-B'u-B'u-Bc-B'u-Ba-Bg-B'u-B'u-

B't-Bg-Bg-Ba-Bg-CH₂CH₂OH (xxxv"-a)

(xxxvi"-a) a compound represented by the following formula (xxxvi"-a):

(SEQ ID NO: 65)
HO-Ba-Bg-Bc-Bc-Ba-Bg-B'u-Bc-Bg-Bg-B'u-Ba-Ba-Bg-

B't-B't-Bc-B't-CH₂CH₂OH (xxxvi"-a)

(xxxvii"-a) a compound represented by the following formula (xxxvii"-a):

(SEQ ID NO: 66)
HO-Ba-Bg-B't-B't-B't-Bg-Bg-Ba-Bg-Ba-B'u-Bg-Bg-Bc-

Ba-Bg-B't-B't-CH₂CH₂OH (xxxvii"-a)

(xxxviii"-a) a compound represented by the following formula (xxxviii"-a):

(SEQ ID NO: 67)
HO-Bc-B't-Bg-Ba-B't-B't-Bc-B't-Bg-Ba-Ba-B't-B't-

Bc-B'u-B'u-B't-Bc-CH₂CH₂OH (xxxviii"-a)

(xxxix"-a) a compound represented by the following formula (xxxix"-a):

(SEQ ID NO: 68)
HO-B't-B't-Bc-B't-B't-Bg-B't-Ba-Bc-B't-B't-Bc-Ba-

B't-Bc-Bc-Bc-Ba-CH₂CH₂OH (xxxix"-a)

(xl"-a) a compound represented by the following formula (xl"-a):

(SEQ ID NO: 187)
HO-Bc-Bc-B't-Bc-Bc-Bg-Bg-B't-B't-Bc-B't-Bg-Ba-Ba-

Bg-Bg-B't-Bg-CH₂CH₂OH (xl"-a)

(xli"-a) a compound represented by the following formula (xli"-a):

(SEQ ID NO: 195)
HO-Bc-Ba-B't-B't-B't-Bc-Ba-B'u-B't-Bc-Ba-Ba-Bc-

B't-Bg-B't-B't-Bg-CH₂CH₂OH (xli"-a)

(xlii"-a) a compound represented by the following formula (xlii"-a):

(SEQ ID NO: 71)
HO-B't-B't-Bc-Bc-B't-B't-Ba-Bg-Bc-B't-B'u-Bc-Bc-

Ba-Bg-Bc-Bc-Ba-CH₂CH₂OH (xlii"-a)

(xliii"-a) a compound represented by the following formula (xliii"-a):

(SEQ ID NO: 72)
HO-B't-Ba-Ba-Bg-Ba-Bc-Bc-B't-Bg-Bc-B't-Bc-Ba-Bg-

Bc-B'u-B't-Bc-CH₂CH₂OH (xliii"-a)

(xliv"-a) a compound represented by the following formula (xliv"-a):

(SEQ ID NO: 73)
HO-Bc-B't-B't-Bg-Bg-Bc-B't-Bc-B't-Bg-Bg-Bc-Bc-

B't-Bg-B'u-Bc-Bc-CH₂CH₂OH (xliv"-a)

(xlv"-a) a compound represented by the following formula (xlv"-a):

(SEQ ID NO: 74)
HO-Bc-B't-Bc-Bc-B't-B'u-Bc-Bc-Ba-B't-Bg-Ba-Bc-

B't-Bc-Ba-Ba-Bg-CH₂CH₂OH (xlv"-a)

(xlvi"-a) a compound represented by the following formula (xlvi"-a):

(SEQ ID NO: 75)
HO-Bc-B't-Bg-Ba-Ba-Bg-Bg-B't-Bg-B't-B't-Bc-B't-

B't-Bg-B't-Ba-Bc-CH₂CH₂OH (xlvi"-a)

(xlvii"-a) a compound represented by the following formula (xlvii"-a):

(SEQ ID NO: 76)
HO-B't-B't-Bc-Bc-Ba-Bg-Bc-Bc-Ba-B't-B't-Bg-B't-Bg-

B't-B't-Bg-Ba-CH₂CH₂OH (xlvii"-a)

(xlviii"-a) a compound represented by the following formula (xlviii"-a):

(SEQ ID NO: 77)
HO-Bc-B't-Bc-Ba-Bg-Bc-B't-B'u-Bc-B't-B't-Bc-Bc-

B't-B't-Ba-Bg-Bc-CH₂CH₂OH (xlviii"-a)

(xlix"-a) a compound represented by the following formula (xlix"-a):

(SEQ ID NO: 78)
HO-Bg-Bc-B't-B't-Bc-B'u-B't-Bc-Bc-B'u-B't-Ba-Bg-

Bc-B'u-B't-Bc-Bc-CH₂CH₂OH (xlix"-a)

(l"-a) a compound represented by the following formula (l"-a):

(SEQ ID NO: 87)
HO-Bg-Bg-Bc-Ba-B't-B't-B'u-Bc-B't-Ba-Bg-B'u-B't-

B't-Bg-Bg-Ba-Bg-CH₂CH₂OH (l"-a)

(li"-a) a compound represented by the following formula (li"-a):

(SEQ ID NO: 88)
HO-Ba-Bg-B't-B'u-B't-Bg-Bg-Ba-Bg-Ba-B't-Bg-Bg-

Bc-Ba-Bg-B't-B't-CH₂CH₂OH (li"-a)

where Bg is a group represented by the following formula (G1) or (G2); Ba is a group represented by the following formula (A1) or (A2); Bc is a group represented by the following formula (C1) or (C2); B't is a group represented by the following formula (T2); B'u is a formula represented by the following formula (U1); and D is HO— or Ph- wherein Ph- is a group represented by the following first formula:
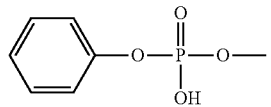
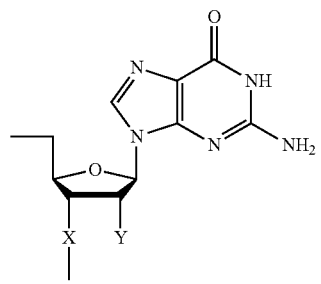
(G1)
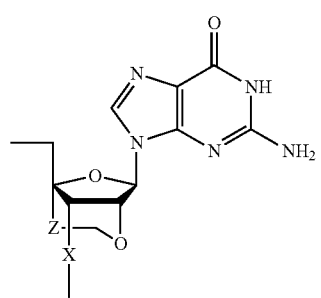
(G2)
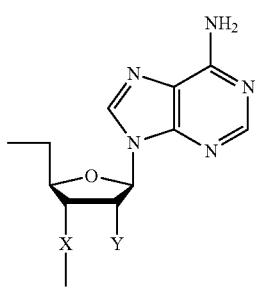
(A1)
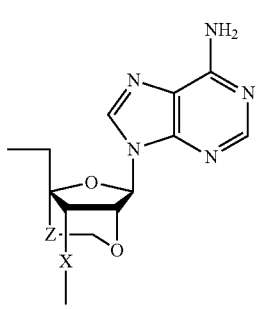
(A2)
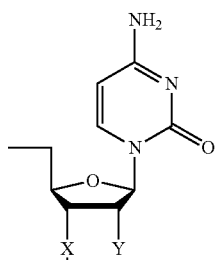
(C1)
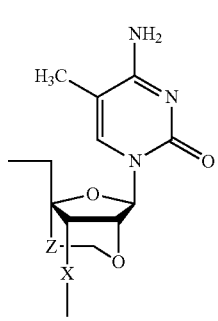
(C2)
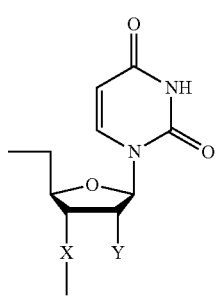
(U1)
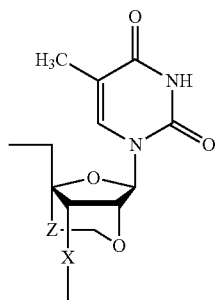
(T2)
where X is individually and independently a group represented by the following formula (X1) or (X2):
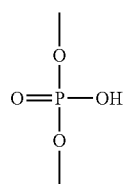
(X1)

-continued

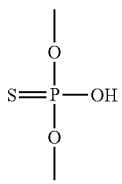
(X2)

Y is individually and independently a hydrogen atom, a hydroxyl group or an alkoxy group with 1-6 carbon atoms; and Z is individually and independently a single bond or an alkylene group with 1-5 carbon atoms.

[49] The compound of any one of [26] to [48] above which is represented by any one of the following formulas (I"1) to (I"51), or a pharmacologically acceptable salt thereof:

```
                                                    (SEQ ID NO: 30)
HO-Bg*-Ba**-Ba*-Ba*-Ba*-Bc**-Bg*-Bc**-Bc**-Bg*-Bc*-Bc**-Ba*-Bt**-
Bu*-Bu*-Bc**-Bt**-CH2CH2OH (I"1)

(SEQ ID NO: 31)
HO-Bc**-Bt**-Bg*-Bu*-Bt**-Ba*-Bg*-Bc**-Bc**-Ba*-Bc**-Bt**-Bg*-Ba*-
Bt**-Bt**-Ba*-Ba*-CH2CH2OH (I"2)

(SEQ ID NO: 32)
HO-Bt**-Bg*-Ba*-Bg*-Ba**-Ba*-Ba*-Bc**-Bt**-Bg*-Bt**-Bu*-Bc**-Ba*-
Bg*-Bc**-Bu*-Bt**-CH2CH2OH (I"3)

(SEQ ID NO: 33)
HO-Bc**-Ba*-Bg*-Bg*-Ba**-Ba*-Bt**-Bt**-Bu*-Bg*-Bt**-Bg*-Bu*-Bc**-
Bu*-Bu*-Bt**-Bc**-CH2CH2OH (I"4)

(SEQ ID NO: 34)
HO-Bg*-Bt**-Ba*-Bu*-Bt**-Bt**-Ba*-Bg*-Bc**-Ba*-Bt**-Bg*-Bu*-Bt**-Bc*-
Bc**-Bc**-Ba*-CH2CH2OH (I"5)

(SEQ ID NO: 35)
HO-Ba*-Bg*-Bc**-Ba*-Bt**-Bg*-Bt**-Bt**-Bc*-Bc*-Bc**-Ba*-Ba*-Bt**-
Bu*-Bc*-Bt**-Bc**-CH2CH2OH (I"6)

(SEQ ID NO: 36)
HO-Bg*-Bc**-Bc**-Bg*-Bc**-Bc*-Ba*-Bt**-Bu*-Bu*-Bc**-
Bu*-Bc**-Ba*-Ba*-Bc**-Ba**-Bg*-CH2CH2OH (I"7)

(SEQ ID NO: 37)
HO-Bc**-Ba*-Bt**-Ba*-Ba*-Bt**-Bg*-Ba*-Ba**-Ba*-Ba*-Bc**-Bg*-Bc*-
Bc**-Bg*-Bc**-Bc**-CH2CH2OH (I"8)

(SEQ ID NO: 38)
HO-Bt**-Bu*-Bc**-Bc*-Bc**-Ba*-Ba*-Bt**-Bu*-Bc*-Bt**-Bc**-Ba*-Bg*-
Bg*-Ba**-Ba*-Bt**-CH2CH2OH (I"9)

(SEQ ID NO: 39)
HO-Bc**-Bc**-Ba*-Bu*-Bt**-Bu*-Bg*-Bt**-Ba*-Bu*-Bt**-Bt**-Ba*-Bg*-Bc**-
Ba*-Bt**-Bg*-CH2CH2OH (I"10)

(SEQ ID NO: 40)
HO-Bc*-Bt**-Bc**-Ba*-Bg*-Ba*-Bt**-Bc**-Bu*-Bu*-Bc**-Bt**-Ba*-Ba*-Bc**-
Bu*-Bu*-Bc**-CH2CH2OH (I"11)

(SEQ ID NO: 41)
HO-Ba*-Bc**-Bc**-Bg*-Bc*-Bc**-Bt**-Bu*-Bc*-Bc**-Ba*-Bc**-Bt**-Bc**-Ba*-
Bg*-Ba**-Bg*-CH2CH2OH (I"12)

(SEQ ID NO: 42)
HO-Bt**-Bc*-Bt**-Bt**-Bg*-Ba*-Ba*-Bg*-Bt**-Ba*-Ba**-Ba*-Bc**-Bg*-
Bg*-Bt**-Bu*-Bt**-CH2CH2OH (I"13)
```

(SEQ ID NO: 43)
HO-Bg*-Bg*-Bc-Bt-Bg*-Bc*-Bt-Bt-Bu*-Bg*-Bc**-Bc*-Bc*-Bt-Bc-Ba*-Bg*-Bc**-CH₂CH₂OH (I"14)

(SEQ ID NO: 44)
HO-Ba*-Bg*-Bt-Bc-Bc**-Ba*-Bg*-Bg*-Ba**-Bg*-Bc-Bt-Ba*-Bg*-Bg*-Bt-Bc-Ba*-CH₂CH₂OH (I"15)

(SEQ ID NO: 45)
HO-Bg*-Bc-Bt-Bc**-Bc*-Ba*-Ba*-Bt**-Ba*-Bg*-Bt**-Bg*-Bg*-Bt-Bc-Ba*-Bg*-Bt**-CH₂CH₂OH (I"16)

(SEQ ID NO: 46)
HO-Bg*-Bc-Bt-Ba*-Bg*-Bg*-Bt-Bc-Ba*-Bg*-Bg*-Bc-Bt-Bg*-Bc*-Bt-Bt-Bu*-CH₂CH₂OH (I"17)

(SEQ ID NO: 47)
HO-Bg*-Bc**-Ba*-Bg*-Bc-Bc-Bu*-Bc*-Bt**-Bc*-Bg*-Bc-Bt-Bc*-Ba*-Bc-Bt-Bc*-CH₂CH₂OH (I"18)

(SEQ ID NO: 48)
HO-Bt-Bc-Bu*-Bu*-Bc-Bc-Ba*-Ba*-Ba*-Bg*-Bc**-Ba*-Bg*-Bc**-Bc*-Bu*-Bc-Bt-CH₂CH₂OH (I"19)

(SEQ ID NO: 49)
HO-Bt**-Bg*-Bc**-Ba*-Bg*-Bt**-Ba*-Ba*-Bt-Bc-Bu*-Ba*-Bt**-Bg*-Ba*-Bg*-Bt-Bt-CH₂CH₂OH (I"20)

(SEQ ID NO: 50)
HO-Bg*-Bt-Bt-Bu*-Bc**-Ba*-Bg*-Bc**-Bu*-Bt-Bc-Bt**-Bg*-Bt**-Ba*-Ba*-Bg*-Bc**-CH₂CH₂OH (I"21)

(SEQ ID NO: 51)
HO-Bt**-Bg*-Bt**-Ba*-Bg*-Bg*-Ba*-Bc**-Ba*-Bt-Bt-Bg*-Bg*-Bc**-Ba*-Bg*-Bt-Bt-CH₂CH₂OH (I"22)

(SEQ ID NO: 52)
HO-Bt**-Bc*-Bc*-Bt-Bt-Ba*-Bc**-Bg*-Bg*-Bg*-Bt**-Ba*-Bg*-Bc**-Ba*-Bu*-Bc-Bc-CH₂CH₂OH (I"23)

(SEQ ID NO: 53)
HO-Ba*-Bg*-Bc-Bt-Bc**-Bu*-Bt**-Bu*-Bt**-Ba*-Bc-Bt-Bc**-Bc*-Bc*-Bt-Bt-Bg*-CH₂CH₂OH (I"24)

(SEQ ID NO: 54)
HO-Bc-Bc-Ba*-Bu*-Bt**-Bg*-Bu*-Bt**-Bu*-Bc**-Ba*-Bu*-Bc**-Ba*-Bg*-Bc-Bt-Bc**-CH₂CH₂OH (I"25)

(SEQ ID NO: 55)
HO-Bc*-Bt**-Ba*-Bt**-Bg*-Ba*-Bg*-Bt-Bt-Bt-Bc-Bt-Bt-Bc*-Bc*-Ba*-Ba**-Ba*-CH₂CH₂OH (I"26)

(SEQ ID NO: 56)
Ph-Bt-Bg-Bt-Bg-Bt**-Bc*-Ba*-Bc*-Bc*-Ba*-Bg*-Ba*-Bg*-Bu*-Ba*-Ba-Bc-Ba-Bg-Bt**-CH₂CH₂OH (I"27)

(SEQ ID NO: 57)
Ph-Ba*-Bg**-Bg*-Bt-Bt-Bg*-Bu*-Bg*-Bu*-Bc**-Ba*-Bc*-Bc*-Ba*-Bg*-Ba-Bg-Bt-Ba-Ba**-CH₂CH₂OH (I"28)

(SEQ ID NO: 58)
Ph-Ba-Bg-Bt-Ba-Ba**-Bc*-Bc*-Ba*-Bc*-Ba*-Bg*-Bg*-Bu*-Bu*-Bg*-Bt-Bg-Bt-Bc-Ba**-CH₂CH₂OH (I"29)

-continued (SEQ ID NO: 59)
Ph-Bt-Bt-Bg-Ba-Bt**-Bc*-Ba*-Ba*-Bg*-Bc*-Ba*-Bg*-Ba*-
Bg*-Ba*-Ba*-Ba-Bg-Bc-Bc-CH$_2$CH$_2$OH  (I"30)

(SEQ ID NO: 60)
Ph-Bc-Ba-Bc-Bc-Bc**-Bu*-Bc*-Bu*-Bg*-Bu*-Bg*-Ba*-Bu*-
Bu*-Bu*-Bt-Ba-Bt-Ba-Ba**-CH$_2$CH$_2$OH  (I"31)

(SEQ ID NO: 61)
Ph-Ba-Bc-Bc-Bc-Ba**-Bc*-Bc*-Ba*-Bu*-Bc*-Ba*-Bc*-Bc*-
Bc*-Bu*-Bc-Bt-Bg-Bt-Bg**-CH$_2$CH$_2$OH  (I"32)

(SEQ ID NO: 62)
Ph-Bc-Bc-Bt-Bc-Ba**-Ba*-Bg*-Bg*-Bu*-Bc*-Ba*-Bc*-Bc*-
Bc*-Ba*-Bc-Bc-Ba-Bt-Bc**-CH$_2$CH$_2$OH  (I"33)

(SEQ ID NO: 63)
HO-Bt-Ba-Ba-Bc-Ba**-Bg*-Bu*-Bc*-Bu*-Bg*-Ba*-Bg*-Bu*-
Ba-Bg-Bg-Ba-Bg**-CH$_2$CH$_2$OH  (I"34)

(SEQ ID NO: 64)
HO-Bg-Bg-Bc-Ba-Bt**-Bu*-Bu*-Bc*-Bu*-Ba*-Bg*-Bu*-Bu*-
Bt-Bg-Bg-Ba-Bg**-CH$_2$CH$_2$OH  (I"35)

(SEQ ID NO: 65)
HO-Ba-Bg-Bc-Bc-Ba**-Bg*-Bu*-Bc*-Bg*-Bg*-Bu*-Ba*-Ba*-
Bg-Bt-Bt-Bc-Bt**-CH$_2$CH$_2$OH  (I"36)

(SEQ ID NO: 66)
HO-Ba-Bg-Bt-Bt-Bt**-Bg*-Bg*-Ba*-Bg*-Ba*-Bu*-Bg*-Bg*-
Bc-Ba-Bg-Bt-Bt**-CH$_2$CH$_2$OH  (I"37)

(SEQ ID NO: 67)
HO-Bc-Bt-Bg*-Ba*-Bt-Bt-Bc*-Bt**-Bg*-Ba*-Ba*-Bt-Bt-
Bc**-Bu*-Bu*-Bt-Bc-CH$_2$CH$_2$OH  (I"38)

(SEQ ID NO: 68)
HO-Bt-Bt-Bc*-Bt-Bt-Bg*-Bt**-Ba*-Bc*-Bt-Bt-Bc*-Ba*-
Bt**-Bc*-Bc-Bc-Ba*-CH$_2$CH$_2$OH  (I"39)

(SEQ ID NO: 69)
HO-Bc-Bc-Bu*-Bc-Bc-Bg*-Bg*-Bt-Bt-Bc-Bt-Bg*-Ba*-
Ba*-Bg*-Bg*-Bt**-Bg*-CH$_2$CH$_2$OH  (I"40)

(SEQ ID NO: 70)
HO-Bc**-Ba*-Bt-Bt-Bu*-Bc**-Ba*-Bu*-Bt-Bc-Ba*-Ba*-Bc**-
Bt**-Bg*-Bt-Bt-Bg*-CH$_2$CH$_2$OH  (I"41)

(SEQ ID NO: 71)
HO-Bt-Bt-Bc*-Bc*-Bt-Bt-Ba*-Bg*-Bc-Bt-Bu*-Bc-Bc-
Ba*-Bg*-Bc-Bc-Ba*-CH$_2$CH$_2$OH  (I"42)

(SEQ ID NO: 72)
HO-Bt**-Ba*-Ba*-Bg*-Ba*-Bc-Bc-Bt**-Bg*-Bc-Bt-Bc**-Ba*-
Bg*-Bc**-Bu*-Bt-Bc-CH$_2$CH$_2$OH  (I"43)

(SEQ ID NO: 73)
HO-Bc-Bt-Bt**-Bg*-Bg*-Bc-Bt-Bc-Bt-Bg*-Bg*-Bc*-Bc**-
Bt**-Bg*-Bu*-Bc-Bc-CH$_2$CH$_2$OH  (I"44)

(SEQ ID NO: 74)
HO-Bc-Bt-Bc*-Bc-Bt-Bu*-Bc-Bc-Ba*-Bt**-Bg*-Ba*-Bc**-
Bt-Bc-Ba*-Ba*-Bg*-CH$_2$CH$_2$OH  (I"45)

-continued (SEQ ID NO: 75)
HO-Bc-Bt-Bg*-Ba*-Ba*-Bg*-Bg*-Bt**-Bg*-Bt-Bt-Bc-Bt-Bt**-Bg*-Bt**-Ba*-Bc**-$CH_2CH_2OH$ (I"46)

(SEQ ID NO: 76)
HO-Bt-Bt-Bc*-Bc**-Ba*-Bg*-Bc-Bc-Ba*-Bt-Bt-Bg*-Bt**-Bg*-Bt-Bt-Bg*-Ba*-$CH_2CH_2OH$ (I"47)

(SEQ ID NO: 77)
HO-Bc-Bt-Bc**-Ba*-Bg*-Bc-Bt-Bu*-Bc*-Bt-Bt-Bc*-Bc*-Bt-Bt-Ba*-Bg*-Bc**-$CH_2CH_2OH$ (I"48)

(SEQ ID NO: 78)
HO-Bg*-Bc-Bt-Bt**-Bc*-Bu*-Bt-Bc-Bc*-Bu*-Bt**-Ba*-Bg*-Bc**-Bu*-Bt-Bc-Bc**-$CH_2CH_2OH$ (I"49)

(SEQ ID NO: 87)
HO-Bg*-Bg*-Bc**-Ba*-Bt-Bt-Bu*-Bc-Bt-Ba*-Bg*-Bu*-Bt-Bt-Bg*-Bg*-Ba**-Bg*-$CH_2CH_2OH$ (I"50)

(SEQ ID NO: 88)
HO-Ba**-Bg*-Bt**-Bu*-Bt**-Bg*-Bg*-Ba**-Bg*-Ba*-Bt**-Bg*-Bg*-Bc-Ba-Bg*-Bt-Bt-$CH_2CH_2OH$ (I"51)

where Bg* is a group represented by the following formula (G1[a]), Ba* is a group represented by the following formula (A1[a]); Bc* is a group represented by the following formula (C1[a]), Bu* is a group represented by the following formula (U1[a]), Bg is a group represented by the following formula (G2); Ba is a group represented by the following formula (A2); Bc is a group represented by the following formula (C2); Bt is a group represented by the following formula (T2); and Ph- is a group represented by the following first formula:

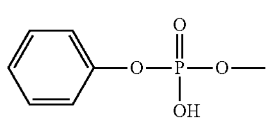

(G1[a])

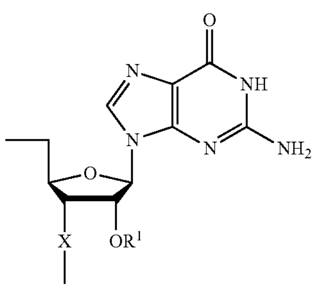

(A1[a])

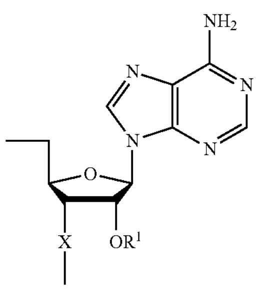

-continued (C1[a])

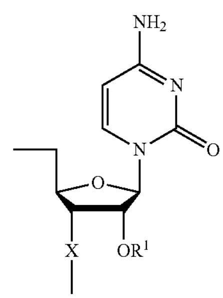

(U1[a])

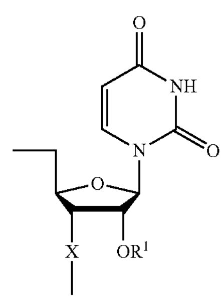

(G2)

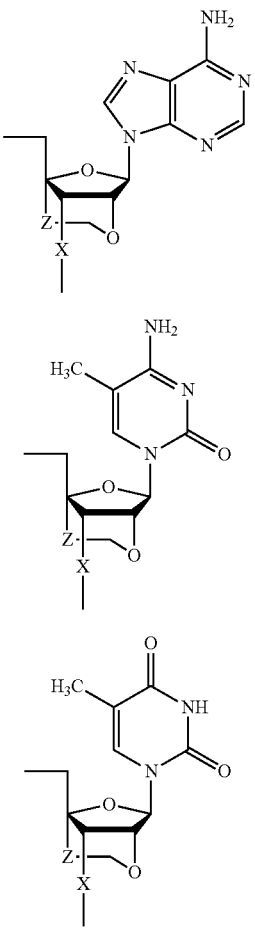

(A2)

(C2)

(T2)

where X is individually and independently a group represented by the following formula (X1) or (X2); $R^1$ is individually and independently an alkyl group with 1-6 carbon atoms; and Z is individually and independently a single bond or an alkylene group with 1-5 carbon atoms:

(X1)

$$\begin{array}{c} | \\ O \\ | \\ O = P - OH \\ | \\ O \\ | \end{array}$$

(X2)

$$\begin{array}{c} | \\ O \\ | \\ S = P - OH \\ | \\ O \\ | \end{array}$$

[50] The compound of [49] above where X in formulas (G1$^a$), (A1$^a$), (C1$^a$) and (U1$^a$) is a group represented by formula (X2) and X in formulas (G2), (A2), (C2) and (T2) is a group represented by formula (X1), or a pharmacologically acceptable salt thereof.

[51] The compound of [49] above where X in all the formulas (G1$^a$), (A1$^a$), (C1$^a$), (U1$^a$), (G2), (A2), (C2) and (T2) is a group represented by formula (X2), or a pharmacologically acceptable salt thereof.

[52] The compound of [49] above which is represented by any one of the following formulas (I″50-a) to (I″51-b), or a salt thereof:

(SEQ ID NO: 87)

(SEQ ID NO: 87)
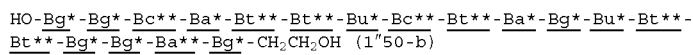

(SEQ ID NO: 78)
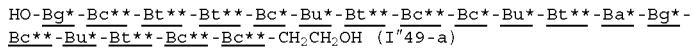

(SEQ ID NO: 30)
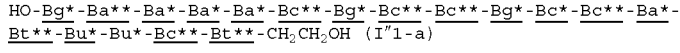

(SEQ ID NO: 41)
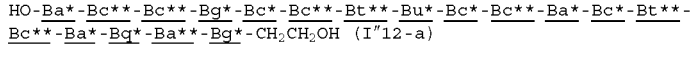

(SEQ ID NO: 47)
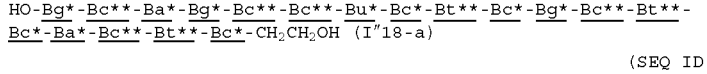

(SEQ ID NO: 48)
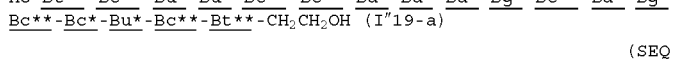

(SEQ ID NO: 88)
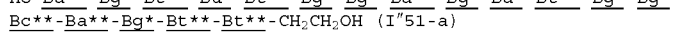

-continued (SEQ ID NO: 88)

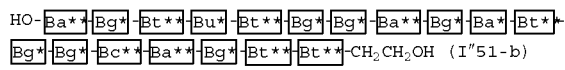-CH₂CH₂OH (I"51-b)

where Bg* is a group represented by formula (G1$^a$), Ba* is a group represented by formula (A1$^a$); Bc* is a group represented by formula (C1$^a$), Bu* is a group represented by formula (U1$^a$); Bg is a group represented by formula (G2); Ba is a group represented by formula (A2); Bc is a group represented by formula (C2); Bt is a group represented by formula (T2); and in individual formulas, at least one of Bg*, Ba*, Bc*, Bu*, Bg, Ba, Bc and Bt has a group represented by formula (X2) as X and all of Bg*, Ba*, Bc*, Bt*, Bg, Ba, Bc and Bt have a group represented by formula (X1) as X.

[53] The compound of any one of [26] to [52] above where Y in formulas (G1), (A1), (C1) and (U1) is a methoxy group and Z in formulas (G2), (A2), (C2) and (T2) is an ethylene group, or a pharmacologically acceptable salt thereof.

[54] A therapeutic agent for muscular dystrophy, comprising the oligonucleotide of [1] above or a pharmacologically acceptable salt thereof, or the compound of any one of [6], [13] to [19] and [26] to [46] or a pharmacologically acceptable salt thereof.

[55] The therapeutic agent of [54] above, which is an agent for treating Duchenne muscular dystrophy.

[56] The therapeutic agent of [54] above, whose target of treatment is those patients in which the total number of the amino acids in the open reading frame of the dystrophin gene will be a multiple of 3 when exon 19, 41, 45, 46, 44, 50, 55, 51 or 53 of the dystrophin gene has been skipped.

The term "oligonucleotide" used in the present invention encompasses not only oligo DNA or oligo RNA, but also an oligonucleotide in which at least one D-ribofuranose constituting the oligonucleotide is 2'-O-alkylated; an oligonucleotide in which at least one D-ribofuranose constituting the oligonucleotide is 2'-O,4'-C-alkylenated; an oligonucleotide in which at least one phosphate constituting the oligonucleotide is thioated; or a combination thereof. Such oligonucleotides in which at least one D-ribofuranose constituting the oligonucleotides is 2'-O-alkylated or 2'-O,4'-C-alkylenated have high binding strength to RNA and high resistance to nuclease. Thus, they are expected to produce higher therapeutic effect than natural nucleotides (i.e. oligo DNA or oligo RNA). Further, an oligonucleotide in which at least one phosphate constituting the oligonucleotide is thioated also has high resistance to nuclease and, thus, is expected to produce higher therapeutic effect than natural nucleotides (i.e. oligo DNA or oligo RNA). An oligonucleotide comprising both the modified sugar and the modified phosphate as described above has still higher resistance to nuclease and, thus, is expected to produce still higher therapeutic effect.

With respect to the oligonucleotide of the present invention, examples of the modification of sugar include, but are not limited to, 2'-O-alkylation (e.g. 2'-O-methylation, 2'-O-aminoethylation, 2'-O-propylation, 2'-O-allylation, 2'-O-methoxyethylation, 2'-O-butylation, 2'-O-pentylation, or 2'-O-propargylation) of D-ribofuranose; 2'-O,4'-C-alkylenation (e.g. 2'-O,4'-C-ethylenation, 2'-O,4'-C-methylenation, 2'-O,4'-C-propylenation, 2'-O,4'-C-tetramethylation, or 2'-O,4'-C-pentamethylation) of D-ribofuranose; 3'-deoxy-3'-amino-2'-deoxy-D-ribofuranose; and 3'-deoxy-3'-amino-2'-deoxy-2'-fluoro-D-ribofuranose.

With respect to the oligonucleotide of the present invention, examples of the modification of phosphate include, but are not limited to, phosphorothioate, methylphosphonate, methylthiophosphonate, phosphorodithioate and phosphoroamidate.

With respect to Y in formulas (G1), (A1), (C1) and (U1), examples of the alkoxy group with 1-6 carbon atoms include, but are not limited to, methoxy group, aminoethoxy group, propoxy group, allyloxy group, methoxyethoxy group, butoxy group, pentyloxy group, and propargyloxy group.

With respect to Z in formulas (G2), (A2), (C2) and (T2), examples of the alkylene group with 1-5 carbon atoms include, but are not limited to, methylene group, ethylene group, propylene group, tetramethylene group and pentamethylene group.

With respect to $R^1$ in formulas (G1$^a$), (A1$^a$), (C1$^a$) and (U1$^a$), examples of the alkyl group with 1-6 carbon atoms include, but are not limited to, methyl group, aminoethyl group, propyl group, allyl group, methoxyethyl group, butyl group, pentyl group and propargyl group.

Preferable examples of the compound represented by general formula (I) include the following compounds.

(SEQ ID NO: 196)

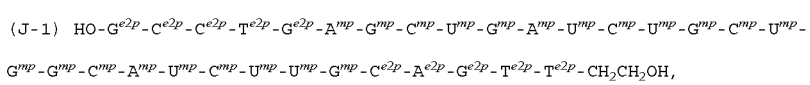

(SEQ ID NO: 197)

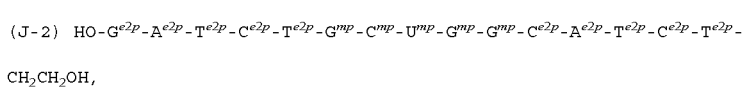

(SEQ ID NO: 198)

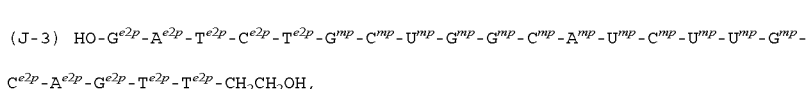

(SEQ ID NO: 199)

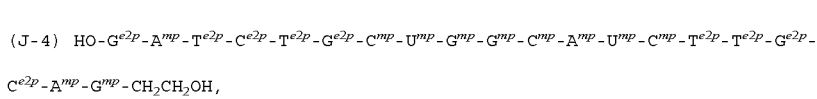

-continued (J-5) HO-A$^{mp}$-G$^{e2p}$-C$^{e2p}$-T$^{e2p}$-G$^{e2p}$-A$^{mp}$-T$^{e2p}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$OH, (SEQ ID NO: 200)

(J-6) HO-G$^{e2p}$-C$^{e2p}$-C$^{e2p}$-T$^{e2p}$-G$^{e2p}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$OH, (SEQ ID NO: 201)

(J-7) HO-A$^{e2p}$-G$^{e2p}$-C$^{e2p}$-T$^{e2p}$-G$^{e2p}$-A$^{e2p}$-T$^{e2p}$-C$^{e2p}$-T$^{e2p}$-G$^{e2p}$-C$^{e2p}$-T$^{e2p}$-G$^{e2p}$-G$^{e2p}$-C$^{e2p}$-A$^{e2p}$-T$^{e2p}$-C$^{e2p}$-T$^{e2p}$-CH$_2$CH$_2$OH, (SEQ ID NO: 4)

(J-8) HO-A$^{ms}$-G$^{e2s}$-C$^{e2s}$-T$^{e2s}$-G$^{e2s}$-A$^{ms}$-T$^{e2s}$-C$^{ms}$-U$^{ms}$-G$^{ms}$-C$^{ms}$-U$^{ms}$-G$^{ms}$-G$^{e2s}$-C$^{e2s}$-A$^{ms}$-T$^{e2s}$-C$^{e2s}$-T$^{e2s}$-CH$_2$CH$_2$OH, (SEQ ID NO: 200)

(J-9) HO-A$^{ms}$-G$^{e2p}$-C$^{e2p}$-T$^{e2p}$-G$^{e2p}$-A$^{ms}$-T$^{e2p}$-C$^{ms}$-U$^{ms}$-G$^{ms}$-C$^{ms}$-U$^{ms}$-G$^{ms}$-G$^{e2p}$-C$^{e2p}$-A$^{ms}$-T$^{e2p}$-C$^{e2p}$-T$^{e2p}$-CH$_2$CH$_2$OH, (SEQ ID NO: 200)

(J-10) HO-A$^{mp}$-G$^{mp}$-C$^{e2p}$-T$^{e2p}$-G$^{mp}$-A$^{mp}$-T$^{e2p}$-C$^{e2p}$-T$^{e2p}$-G$^{mp}$-C$^{e2p}$-T$^{e2p}$-G$^{mp}$-G$^{mp}$-C$^{e2p}$-A$^{mp}$-T$^{e2p}$-C$^{e2p}$-T$^{e2p}$-CH$_2$CH$_2$OH, (SEQ ID NO: 4)

(J-11) HO-A$^{ms}$-G$^{ms}$-C$^{e2s}$-T$^{e2s}$-G$^{ms}$-A$^{ms}$-T$^{e2s}$-C$^{e2s}$-T$^{e2s}$-G$^{ms}$-C$^{e2s}$-T$^{e2s}$-G$^{ms}$-G$^{ms}$-C$^{e2s}$-A$^{ms}$-T$^{e2s}$-C$^{e2s}$-T$^{e2s}$-CH$_2$CH$_2$OH, (SEQ ID NO: 4)

(J-12) HO-A$^{ms}$-G$^{ms}$-C$^{e2p}$-T$^{e2p}$-G$^{ms}$-A$^{ms}$-T$^{e2p}$-C$^{e2p}$-T$^{e2p}$-G$^{ms}$-C$^{e2p}$-T$^{e2p}$-G$^{ms}$-G$^{ms}$-C$^{e2p}$-A$^{ms}$-T$^{e2p}$-C$^{e2p}$-T$^{e2p}$-CH$_2$CH$_2$OH, (SEQ ID NO: 4)

(J-13) HO-G$^{elp}$-C$^{elp}$-C$^{elp}$-T$^{elp}$-G$^{elp}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{mp}$-C$^{mp}$-A$^{mp}$-U$^{mp}$-C$^{mp}$-U$^{mp}$-U$^{mp}$-G$^{mp}$-C$^{elp}$-A$^{elp}$-G$^{elp}$-T$^{elp}$-T$^{elp}$-CH$_2$CH$_2$OH, (SEQ ID NO: 196)

(J-14) HO-G$^{elp}$-A$^{elp}$-T$^{elp}$-C$^{elp}$-T$^{elp}$-G$^{mp}$-C$^{mp}$-U$^{mp}$-G$^{mp}$-G$^{mp}$-C$^{elp}$-A$^{elp}$-T$^{elp}$-C$^{elp}$-T$^{elp}$-CH$_2$CH$_2$OH, (SEQ ID NO: 197)

(J-15) HO-G$^{elp}$-A$^{elp}$-T$^{elp}$-C$^{elp}$-T$^{elp}$-G$^{mp}$-C$^{mp}$-U$^{mp}$-G$^{mp}$-G$^{mp}$-C$^{mp}$-A$^{mp}$-U$^{mp}$-C$^{mp}$-U$^{mp}$-U$^{mp}$-G$^{mp}$-C$^{elp}$-A$^{elp}$-G$^{elp}$-T$^{elp}$-T$^{elp}$-CH$_2$CH$_2$OH, (SEQ ID NO: 198)

(J-16) HO-G$^{elp}$-A$^{mp}$-T$^{elp}$-C$^{elp}$-T$^{elp}$-G$^{elp}$-C$^{mp}$-U$^{mp}$-G$^{mp}$-G$^{mp}$-C$^{mp}$-A$^{mp}$-U$^{mp}$-C$^{mp}$-T$^{elp}$-T$^{elp}$-G$^{elp}$-C$^{elp}$-A$^{mp}$-G$^{mp}$-CH$_2$CH$_2$OH, (SEQ ID NO: 198)

(J-17) HO-A$^{mp}$-G$^{elp}$-C$^{elp}$-T$^{elp}$-G$^{elp}$-A$^{mp}$-T$^{elp}$-C$^{mp}$-U$^{mp}$-G$^{mp}$-C$^{mp}$-U$^{mp}$-G$^{mp}$-G$^{elp}$-C$^{elp}$-A$^{mp}$-T$^{elp}$-C$^{elp}$-T$^{elp}$-CH$_2$CH$_2$OH, (SEQ ID NO: 200)

(J-18) HO-G$^{elp}$-C$^{elp}$-C$^{elp}$-T$^{elp}$-G$^{elp}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{elp}$-C$^{elp}$-A$^{mp}$-T$^{elp}$-C$^{elp}$-T$^{elp}$-CH$_2$CH$_2$OH, (SEQ ID NO: 201)

(J-19) HO-A$^{elp}$-G$^{elp}$-C$^{elp}$-T$^{elp}$-G$^{elp}$-A$^{elp}$-T$^{elp}$-C$^{elp}$-T$^{elp}$-G$^{elp}$-C$^{elp}$-T$^{elp}$-G$^{elp}$-G$^{elp}$-C$^{elp}$-A$^{elp}$-T$^{elp}$-C$^{elp}$-T$^{elp}$-CH$_2$CH$_2$OH, (SEQ ID NO: 4)

(J-20) HO-A$^{ms}$-G$^{els}$-C$^{els}$-T$^{els}$-G$^{els}$-A$^{ms}$-T$^{els}$-C$^{ms}$-U$^{ms}$-G$^{ms}$-C$^{ms}$-U$^{ms}$-G$^{ms}$-G$^{els}$-C$^{els}$-A$^{ms}$-T$^{els}$-C$^{els}$-T$^{els}$-CH$_2$CH$_2$OH, (SEQ ID NO: 200)

-continued (J-21)  HO-A$^{ms}$-G$^{e1p}$-C$^{e1p}$-T$^{e1p}$-G$^{e1p}$-A$^{ms}$-T$^{e1p}$-C$^{ms}$-U$^{ms}$-G$^{ms}$-C$^{ms}$-U$^{ms}$-G$^{ms}$-G$^{e1p}$-C$^{e1p}$-A$^{ms}$-T$^{e1p}$-C$^{e1p}$-T$^{e1p}$-CH$_2$CH$_2$OH, (SEQ ID NO: 200)

(J-22)  HO-A$^{mp}$-G$^{mp}$-C$^{e1p}$-T$^{e1p}$-G$^{mp}$-A$^{mp}$-T$^{e1p}$-C$^{e1p}$-T$^{e1p}$-G$^{mp}$-C$^{e1p}$-T$^{e1p}$-G$^{mp}$-G$^{mp}$-C$^{e1p}$-A$^{mp}$-T$^{e1p}$-C$^{e1p}$-T$^{e1p}$-CH$_2$CH$_2$OH, (SEQ ID NO: 4)

(J-23)  HO-A$^{ms}$-G$^{ms}$-C$^{e1s}$-T$^{e1s}$-G$^{ms}$-A$^{ms}$-T$^{e1s}$-C$^{e1s}$-T$^{e1s}$-G$^{ms}$-C$^{e1s}$-T$^{e1s}$-G$^{ms}$-G$^{ms}$-C$^{e1s}$-A$^{ms}$-T$^{e1s}$-C$^{e1s}$-T$^{e1s}$-CH$_2$CH$_2$OH, (SEQ ID NO: 4)

(J-24)  HO-A$^{ms}$-G$^{ms}$-C$^{e1p}$-T$^{e1p}$-G$^{ms}$-A$^{ms}$-T$^{e1p}$-C$^{e1p}$-T$^{e1p}$-G$^{ms}$-C$^{e1p}$-T$^{e1p}$-G$^{ms}$-G$^{ms}$-C$^{e1p}$-A$^{ms}$-T$^{e1p}$-C$^{e1p}$-T$^{e1p}$-CH$_2$CH$_2$OH, (SEQ ID NO: 4)

(J-25)  HO-G$^{e2p}$-C$^{e2p}$-C$^{e2p}$-T$^{e2p}$-G$^{e2p}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{mp}$-C$^{mp}$-A$^{mp}$-U$^{mp}$-C$^{mp}$-U$^{mp}$-U$^{mp}$-G$^{mp}$-C$^{e2p}$-A$^{e2p}$-G$^{e2p}$-T$^{e2p}$-T$^{e2p}$-CH$_2$CH$_2$CH$_2$OH, (SEQ ID NO: 196)

(J-26)  HO-G$^{e2p}$-A$^{e2p}$-T$^{e2p}$-C$^{e2p}$-T$^{e2p}$-G$^{mp}$-C$^{mp}$-U$^{mp}$-G$^{mp}$-G$^{mp}$-C$^{e2p}$-A$^{e2p}$-T$^{e2p}$-C$^{e2p}$-T$^{e2p}$-CH$_2$CH$_2$CH$_2$OH, (SEQ ID NO: 197)

(J-27)  HO-G$^{e2p}$-A$^{e2p}$-T$^{e2p}$-C$^{e2p}$-T$^{e2p}$-G$^{mp}$-C$^{mp}$-U$^{mp}$-G$^{mp}$-G$^{mp}$-C$^{mp}$-A$^{mp}$-U$^{mp}$-C$^{mp}$-U$^{mp}$-U$^{mp}$-G$^{mp}$-C$^{e2p}$-A$^{e2p}$-G$^{e2p}$-T$^{e2p}$-T$^{e2p}$-CH$_2$CH$_2$CH$_2$OH, (SEQ ID NO: 198)

(J-28)  HO-G$^{e2p}$-A$^{mp}$-T$^{e2p}$-C$^{e2p}$-T$^{e2p}$-G$^{e2p}$-C$^{mp}$-U$^{mp}$-G$^{mp}$-G$^{mp}$-C$^{mp}$-A$^{mp}$-U$^{mp}$-C$^{mp}$-T$^{e2p}$-T$^{e2p}$-G$^{e2p}$-C$^{e2p}$-A$^{mp}$-G$^{mp}$-CH$_2$CH$_2$CH$_2$OH, (SEQ ID NO: 199)

(J-29)  HO-A$^{mp}$-G$^{e2p}$-C$^{e2p}$-T$^{e2p}$-G$^{e2p}$-A$^{mp}$-T$^{e2p}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$CH$_2$OH, (SEQ ID NO: 200)

(J-30)  HO-G$^{e2p}$-C$^{e2p}$-C$^{e2p}$-T$^{e2p}$-G$^{e2p}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$CH$_2$OH, (SEQ ID NO: 201)

(J-31)  HO-A$^{e2p}$-G$^{e2p}$-C$^{e2p}$-T$^{e2p}$-G$^{e2p}$-A$^{e2p}$-T$^{e2p}$-C$^{e2p}$-T$^{e2p}$-G$^{e2p}$-C$^{e2p}$-T$^{e2p}$-G$^{e2p}$-G$^{e2p}$-C$^{e2p}$-A$^{e2p}$-T$^{e2p}$-C$^{e2p}$-T$^{e2p}$-CH$_2$CH$_2$CH$_2$OH, (SEQ ID NO: 4)

(J-32)  HO-A$^{ms}$-G$^{e2s}$-C$^{e2s}$-T$^{e2s}$-G$^{e2s}$-A$^{ms}$-T$^{e2s}$-C$^{ms}$-U$^{ms}$-G$^{ms}$-C$^{ms}$-U$^{ms}$-G$^{ms}$-G$^{e2s}$-C$^{e2s}$-A$^{ms}$-T$^{e2s}$-C$^{e2s}$-T$^{e2s}$-CH$_2$CH$_2$CH$_2$OH, (SEQ ID NO: 200)

(J-33)  HO-A$^{ms}$-G$^{e2p}$-C$^{e2p}$-T$^{e2p}$-G$^{e2p}$-A$^{ms}$-T$^{e2p}$-C$^{ms}$-U$^{ms}$-G$^{ms}$-C$^{ms}$-U$^{ms}$-G$^{ms}$-G$^{e2p}$-C$^{e2p}$-A$^{ms}$-T$^{e2p}$-C$^{e2p}$-T$^{e2p}$-CH$_2$CH$_2$CH$_2$OH, (SEQ ID NO: 200)

(J-34)  HO-A$^{mp}$-G$^{mp}$-C$^{e2p}$-T$^{e2p}$-G$^{mp}$-A$^{mp}$-T$^{e2p}$-C$^{e2p}$-T$^{e2p}$-G$^{mp}$-C$^{e2p}$-T$^{e2p}$-G$^{mp}$-G$^{mp}$-C$^{e2p}$-A$^{mp}$-T$^{e2p}$-C$^{e2p}$-T$^{e2p}$-CH$_2$CH$_2$CH$_2$OH, (SEQ ID NO: 4)

(J-35)  HO-A$^{ms}$-G$^{ms}$-C$^{e2s}$-T$^{e2s}$-G$^{ms}$-A$^{ms}$-T$^{e2s}$-C$^{e2s}$-T$^{e2s}$-G$^{ms}$-C$^{e2s}$-T$^{e2s}$-G$^{ms}$-G$^{ms}$-C$^{e2s}$-A$^{ms}$-T$^{e2s}$-C$^{e2s}$-T$^{e2s}$-CH$_2$CH$_2$CH$_2$OH, (SEQ ID NO: 4)

(J-36)  HO-A$^{ms}$-G$^{ms}$-C$^{e2p}$-T$^{e2p}$-G$^{ms}$-A$^{ms}$-T$^{e2p}$-C$^{e2p}$-T$^{e2p}$-G$^{ms}$-C$^{e2p}$-T$^{e2p}$-G$^{ms}$-G$^{ms}$-C$^{e2p}$-A$^{ms}$-T$^{e2p}$-C$^{e2p}$-T$^{e2p}$-CH$_2$CH$_2$CH$_2$OH, (SEQ ID NO: 4)

(J-37) HO-A$^{mp}$-G$^{e1p}$-C$^{e2p}$-T$^{e2p}$-G$^{e1p}$-A$^{mp}$-T$^{e2p}$-C$^{mp}$-U$^{mp}$-G$^{mp}$-C$^{mp}$-U$^{mp}$-G$^{mp}$-G$^{e1p}$-C$^{e2p}$-A$^{mp}$-T$^{e2p}$-C$^{e2p}$-T$^{e2p}$-CH$_2$CH$_2$OH, (SEQ ID NO: 200)

(J-38) HO-A$^{ms}$-G$^{e1s}$-C$^{e2s}$-T$^{e2s}$-G$^{e1s}$-A$^{ms}$-T$^{e2s}$-C$^{ms}$-U$^{ms}$-G$^{ms}$-C$^{ms}$-U$^{ms}$-G$^{ms}$-G$^{e1s}$-C$^{e2s}$-A$^{ms}$-T$^{e2s}$-C$^{e2s}$-T$^{e2s}$-CH$_2$CH$_2$OH, (SEQ ID NO: 200)

(J-39) HO-A$^{ms}$-G$^{e1p}$-C$^{e2p}$-T$^{e2p}$-G$^{e1p}$-A$^{ms}$-T$^{e2p}$-C$^{ms}$-U$^{ms}$-G$^{ns}$-C$^{ms}$-U$^{ms}$-G$^{ns}$-G$^{e1p}$-C$^{e2p}$-A$^{ms}$-T$^{e2p}$-C$^{e2p}$-T$^{e2p}$-CH$_2$CH$_2$OH, (SEQ ID NO: 200)

(J-40) HO-A$^{mp}$-G$^{mp}$-C$^{e1p}$-T$^{e2p}$-G$^{mp}$-A$^{mp}$-T$^{e2p}$-C$^{e1p}$-T$^{e2p}$-G$^{mp}$-C$^{e1p}$-T$^{e2p}$-G$^{mp}$-G$^{mp}$-C$^{e2p}$-A$^{mp}$-T$^{e2p}$-C$^{e1p}$-T$^{e2p}$-CH$_2$CH$_2$OH, (SEQ ID NO: 4)

(J-41) HO-A$^{ms}$-G$^{ms}$-C$^{e1s}$-T$^{e2s}$-G$^{ms}$-A$^{ms}$-T$^{e2s}$-C$^{e1s}$-T$^{e2s}$-G$^{ms}$-C$^{e1s}$-T$^{e2s}$-G$^{ms}$-G$^{ms}$-C$^{e2s}$-A$^{ms}$-T$^{e2s}$-C$^{e1s}$-T$^{e2s}$-CH$_2$CH$_2$OH, (SEQ ID NO: 4)

(J-42) HO-A$^{ms}$-G$^{ms}$-C$^{e1p}$-T$^{e2p}$-G$^{ms}$-A$^{ms}$-T$^{e2p}$-C$^{e1p}$-T$^{e2p}$-G$^{ns}$-C$^{e1p}$-T$^{e2p}$-G$^{ms}$-G$^{ms}$-C$^{e1p}$-A$^{ms}$-T$^{e2p}$-C$^{e1p}$-T$^{e2p}$-CH$_2$CH$_2$OH, (SEQ ID NO: 4)

(J-43) HO-A$^{mp}$-G$^{mp}$-C$^{mp}$-T$^{e2p}$-G$^{mp}$-A$^{mp}$-T$^{e2p}$-C$^{mp}$-T$^{e2p}$-G$^{mp}$-C$^{mp}$-T$^{e2p}$-G$^{mp}$-G$^{mp}$-C$^{mp}$-A$^{mp}$-T$^{e2p}$-C$^{mp}$-T$^{e2p}$-CH$_2$CH$_2$OH, (SEQ ID NO: 4)

(J-44) HO-A$^{ms}$-G$^{ms}$-C$^{ms}$-T$^{e2s}$-G$^{ms}$-A$^{ms}$-T$^{e2s}$-C$^{ms}$-T$^{e2s}$-G$^{ms}$-C$^{ms}$-T$^{e2s}$-G$^{ms}$-G$^{ms}$-C$^{ms}$-A$^{ms}$-T$^{e2s}$-C$^{ms}$-T$^{e2s}$-CH$_2$CH$_2$OH, (SEQ ID NO: 4)

(J-45) HO-A$^{ms}$-G$^{ms}$-C$^{ms}$-T$^{e2p}$-G$^{ms}$-A$^{ms}$-T$^{e2p}$-C$^{ms}$-T$^{e2p}$-G$^{ms}$-C$^{ms}$-T$^{e2p}$-G$^{ms}$-G$^{ms}$-C$^{ms}$-A$^{ms}$-T$^{e2p}$-C$^{ms}$-T$^{e2p}$-CH$_2$CH$_2$OH (SEQ ID NO: 4)

(J-46) HO-G$^{e2p}$-A$^{e2p}$-T$^{e2p}$-C$^{e2p}$-T$^{e2p}$-G$^{mp}$-C$^{mp}$-U$^{mp}$-G$^{mp}$-G$^{mp}$-C$^{mp}$-A$^{mp}$-U$^{mp}$-C$^{e2p}$-T$^{e2p}$-T$^{e2p}$-G$^{e2p}$-C$^{e2p}$-CH$_2$CH$_2$OH (SEQ ID NO: 202)

(J-47) HO-G$^{e2p}$-A$^{e2p}$-T$^{e2p}$-C$^{e2p}$-T$^{e2p}$-G$^{e2p}$-C$^{e2p}$-U$^{e2p}$-G$^{e2p}$-G$^{e2p}$-C$^{e2p}$-A$^{e2p}$-T$^{e2p}$-C$^{e2p}$-T$^{e2p}$-CH$_2$CH$_2$OH (SEQ ID NO: 197)

(J-48) HO-G$^{e1p}$-A$^{e1p}$-T$^{e1p}$-C$^{e1p}$-T$^{e1p}$-G$^{mp}$-C$^{mp}$-U$^{mp}$-G$^{mp}$-G$^{mp}$-C$^{mp}$-A$^{mp}$-U$^{mp}$-C$^{e1p}$-T$^{e1p}$-T$^{e1p}$-G$^{e1p}$-C$^{e1p}$-CH$_2$CH$_2$OH (SEQ ID NO: 202)

(J-49) HO-G$^{e1p}$-A$^{e1p}$-T$^{e1p}$-C$^{e1p}$-T$^{e1p}$-G$^{e1p}$-C$^{e1p}$-U$^{e1p}$-G$^{e1p}$-G$^{e1p}$-C$^{e1p}$-A$^{e1p}$-T$^{e1p}$-C$^{e1p}$-T$^{e1p}$-CH$_2$CH$_2$OH (SEQ ID NO: 197)

(J-50) HO-G$^{e2p}$-A$^{e2p}$-T$^{e2p}$-C$^{e2p}$-T$^{e2p}$-G$^{ms}$-C$^{ms}$-U$^{ms}$-G$^{ms}$-G$^{ms}$-C$^{ms}$-A$^{ms}$-U$^{ms}$-C$^{e2p}$-T$^{e2p}$-T$^{e2p}$-G$^{e2p}$-C$^{e2p}$-CH$_2$CH$_2$OH (SEQ ID NO: 202)

(J-51) HO-G$^{e2s}$-A$^{e2s}$-T$^{e2s}$-C$^{e2s}$-T$^{e2s}$-G$^{e2s}$-C$^{e2s}$-U$^{e2s}$-G$^{e2s}$-G$^{e2s}$-C$^{e2s}$-A$^{e2s}$-T$^{e2s}$-C$^{e2s}$-T$^{e2s}$-CH$_2$CH$_2$OH (SEQ ID NO: 197)

(J-52) HO-G$^{e1p}$-A$^{e1p}$-T$^{e1p}$-C$^{e1p}$-T$^{e1p}$-G$^{ms}$-C$^{ms}$-U$^{ms}$-G$^{ms}$-G$^{ms}$-C$^{ms}$-A$^{ms}$-U$^{ms}$-C$^{e1p}$-T$^{e1p}$-T$^{e1p}$-G$^{e1p}$-C$^{e1p}$-CH$_2$CH$_2$OH (SEQ ID NO: 202)

-continued (J-53)  HO-$G^{els}$-$A^{els}$-$T^{els}$-$C^{els}$-$T^{els}$-$G^{els}$-$C^{els}$-$U^{els}$-$G^{els}$-$G^{els}$-$C^{els}$-$A^{els}$-$T^{els}$-$C^{els}$-$T^{els}$-$CH_2CH_2OH$  (SEQ ID NO: 197)

(J-54)  HO-$G^{e2s}$-$A^{e2s}$-$T^{e2s}$-$C^{e2s}$-$T^{e2s}$-$G^{ms}$-$C^{ms}$-$U^{ms}$-$G^{ms}$-$G^{ms}$-$C^{ms}$-$A^{ms}$-$U^{ms}$-$C^{e2s}$-$T^{e2s}$-$T^{e2s}$-$G^{e2s}$-$C^{e2s}$-$CH_2CH_2OH$  (SEQ ID NO: 202)

Especially preferable are (J-1) to (J-24) and (J-46) to (J-47).

Preferable examples of the compound represented by general formula (I') include the following compounds.

(J-1)  HO-$A^{e2p}$-$G^{e2p}$-$T^{e2p}$-$T^{e2p}$-$G^{e2p}$-$A^{mp}$-$G^{mp}$-$U^{mp}$-$C^{mp}$-$U^{mp}$-$U^{mp}$-$C^{mp}$-$G^{mp}$-$A^{mp}$-$A^{mp}$-$A^{mp}$-$C^{mp}$-$U^{mp}$-$G^{e2p}$-$A^{e2p}$-$G^{e2p}$-$C^{e2p}$-$A^{e2p}$-$CH_2CH_2OH$  (SEQ ID NO: 203)

(J-2)  HO-$A^{e2p}$-$G^{e2p}$-$T^{e2p}$-$T^{e2p}$-$G^{e2p}$-$A^{e2p}$-$G^{e2p}$-$T^{e2p}$-$C^{mp}$-$U^{mp}$-$U^{mp}$-$C^{mp}$-$G^{mp}$-$A^{mp}$-$A^{mp}$-$A^{e2p}$-$C^{e2p}$-$T^{e2p}$-$G^{e2p}$-$A^{e2p}$-$G^{e2p}$-$C^{e2p}$-$A^{e2p}$-$CH_2CH_2OH$  (SEQ ID NO: 204)

(J-3)  HO-$A^{e2p}$-$A^{e2p}$-$A^{e2p}$-$C^{e2p}$-$T^{e2p}$-$G^{mp}$-$A^{mp}$-$G^{mp}$-$C^{mp}$-$A^{mp}$-$A^{mp}$-$A^{mp}$-$U^{mp}$-$T^{e2p}$-$T^{e2p}$-$G^{e2p}$-$C^{e2p}$-$T^{e2p}$-$CH_2CH_2OH$  (SEQ ID NO: 205)

(J-4)  HO-$A^{e2p}$-$G^{e2p}$-$T^{e2p}$-$T^{e2p}$-$G^{e2p}$-$A^{ms}$-$G^{ms}$-$U^{ms}$-$C^{ms}$-$U^{ms}$-$U^{ms}$-$C^{ms}$-$G^{ms}$-$A^{ms}$-$A^{ms}$-$A^{ms}$-$C^{ms}$-$U^{ms}$-$G^{e2p}$-$A^{e2p}$-$G^{e2p}$-$C^{e2p}$-$A^{e2p}$-$CH_2CH_2OH$  (SEQ ID NO: 203)

(J-5)  HO-$A^{e2p}$-$G^{e2p}$-$T^{e2p}$-$T^{e2p}$-$G^{e2p}$-$A^{e2p}$-$G^{e2p}$-$T^{e2p}$-$C^{ms}$-$U^{ms}$-$U^{ms}$-$C^{ms}$-$G^{ms}$-$A^{ms}$-$A^{ms}$-$A^{e2p}$-$C^{e2p}$-$T^{e2p}$-$G^{e2p}$-$A^{e2p}$-$G^{e2p}$-$C^{e2p}$-$A^{e2p}$-$CH_2CH_2OH$  (SEQ ID NO: 204)

(J-6)  HO-$A^{e2p}$-$A^{e2p}$-$A^{e2p}$-$C^{e2p}$-$T^{e2p}$-$G^{ms}$-$A^{ms}$-$G^{ms}$-$C^{ms}$-$A^{ms}$-$A^{ms}$-$A^{ms}$-$U^{ms}$-$T^{e2p}$-$T^{e2p}$-$G^{e2p}$-$C^{e2p}$-$T^{e2p}$-$CH_2CH_2OH$  (SEQ ID NO: 205)

(J-7)  HO-$A^{e2s}$-$G^{e2s}$-$T^{e2s}$-$T^{e2s}$-$G^{e2s}$-$A^{ms}$-$G^{ms}$-$U^{ms}$-$C^{ms}$-$U^{ms}$-$U^{ms}$-$C^{ms}$-$G^{ms}$-$A^{ms}$-$A^{ms}$-$A^{ms}$-$C^{ms}$-$U^{ms}$-$G^{e2s}$-$A^{e2s}$-$G^{e2s}$-$C^{e2s}$-$A^{e2s}$-$CH_2CH_2OH$  (SEQ ID NO: 203)

(J-8)  HO-$A^{e2s}$-$G^{e2s}$-$T^{e2s}$-$T^{e2s}$-$G^{e2s}$-$A^{e2s}$-$G^{e2s}$-$T^{e2s}$-$C^{ms}$-$U^{ms}$-$U^{ms}$-$C^{ms}$-$G^{ms}$-$A^{ms}$-$A^{ms}$-$A^{e2s}$-$C^{e2s}$-$T^{e2s}$-$G^{e2s}$-$A^{e2s}$-$G^{e2s}$-$C^{e2s}$-$A^{e2s}$-$CH_2CH_2OH$  (SEQ ID NO: 204)

(J-9)  HO-$A^{e2s}$-$A^{e2s}$-$A^{e2s}$-$C^{e2s}$-$T^{e2s}$-$G^{ms}$-$A^{ms}$-$G^{ms}$-$C^{ms}$-$A^{ms}$-$A^{ms}$-$A^{ms}$-$U^{ms}$-$T^{e2s}$-$T^{e2s}$-$G^{e2s}$-$C^{e2s}$-$T^{e2s}$-$CH_2CH_2OH$  (SEQ ID NO: 205)

(J-10)  HO-$A^{elp}$-$G^{elp}$-$T^{elp}$-$T^{elp}$-$G^{elp}$-$A^{mp}$-$G^{mp}$-$U^{mp}$-$C^{mp}$-$U^{mp}$-$U^{mp}$-$C^{mp}$-$G^{mp}$-$A^{mp}$-$A^{mp}$-$A^{mp}$-$C^{mp}$-$U^{mp}$-$G^{elp}$-$A^{elp}$-$G^{elp}$-$C^{elp}$-$A^{elp}$-$CH_2CH_2OH$  (SEQ ID NO: 203)

(J-11)  HO-$A^{elp}$-$G^{elp}$-$T^{elp}$-$T^{elp}$-$G^{elp}$-$A^{elp}$-$G^{elp}$-$T^{elp}$-$C^{mp}$-$U^{mp}$-$U^{mp}$-$C^{mp}$-$G^{mp}$-$A^{mp}$-$A^{mp}$-$A^{elp}$-$C^{elp}$-$T^{elp}$-$G^{elp}$-$A^{elp}$-$G^{elp}$-$C^{elp}$-$A^{elp}$-$CH_2CH_2OH$  (SEQ ID NO: 204)

(J-12)  HO-$A^{elp}$-$A^{elp}$-$A^{elp}$-$C^{elp}$-$T^{elp}$-$G^{mp}$-$A^{mp}$-$G^{mp}$-$C^{mp}$-$A^{mp}$-$A^{mp}$-$A^{mp}$-$U^{mp}$-$T^{elp}$-$T^{elp}$-$G^{elp}$-$C^{elp}$-$T^{elp}$-$CH_2CH_2OH$  (SEQ ID NO: 205)

(J-13)  HO-$A^{elp}$-$G^{elp}$-$T^{elp}$-$T^{elp}$-$G^{elp}$-$A^{ms}$-$G^{ms}$-$U^{ms}$-$C^{ms}$-$U^{ms}$-$U^{ms}$-$C^{ms}$-$G^{ms}$-$A^{ms}$-$A^{ms}$-$A^{ms}$-$C^{ms}$-$U^{ms}$-$G^{elp}$-$A^{elp}$-$G^{elp}$-$C^{elp}$-$A^{elp}$-$CH_2CH_2OH$  (SEQ ID NO: 203)

(J-14) HO-$A^{elp}$-$G^{elp}$-$T^{elp}$-$T^{elp}$-$G^{elp}$-$A^{elp}$-$G^{elp}$-$T^{elp}$-$C^{ms}$-$U^{ms}$-$U^{ms}$-$C^{ms}$-$G^{ms}$-$A^{ms}$-$A^{ms}$-$A^{elp}$-$C^{elp}$-$T^{elp}$-$G^{elp}$-$A^{elp}$-$G^{elp}$-$C^{elp}$-$A^{elp}$-$CH_2CH_2OH$ (SEQ ID NO: 204)

(J-15) HO-$A^{elp}$-$A^{elp}$-$A^{elp}$-$C^{elp}$-$T^{elp}$-$G^{ms}$-$A^{ms}$-$G^{ms}$-$C^{ms}$-$A^{ms}$-$A^{ms}$-$A^{ms}$-$U^{ms}$-$T^{elp}$-$T^{elp}$-$G^{elp}$-$C^{elp}$-$T^{elp}$-$CH_2CH_2OH$ (SEQ ID NO: 205)

(J-16) HO-$A^{els}$-$G^{els}$-$T^{els}$-$T^{els}$-$G^{els}$-$A^{ms}$-$G^{ms}$-$U^{ms}$-$C^{ms}$-$U^{ms}$-$U^{ms}$-$C^{ms}$-$G^{ms}$-$A^{ms}$-$A^{ms}$-$A^{ms}$-$C^{ms}$-$U^{ms}$-$G^{els}$-$A^{els}$-$G^{els}$-$C^{els}$-$A^{els}$-$CH_2CH_2OH$ (SEQ ID NO: 203)

(J-17) HO-$A^{els}$-$G^{els}$-$T^{els}$-$T^{els}$-$G^{els}$-$A^{els}$-$G^{els}$-$T^{els}$-$C^{ms}$-$U^{ms}$-$U^{ms}$-$C^{ms}$-$G^{ms}$-$A^{ms}$-$A^{els}$-$C^{els}$-$T^{els}$-$G^{els}$-$A^{els}$-$G^{els}$-$C^{els}$-$A^{els}$-$CH_2CH_2OH$ (SEQ ID NO: 204)

(J-18) HO-$A^{els}$-$A^{els}$-$A^{els}$-$C^{els}$-$T^{els}$-$G^{ms}$-$A^{ms}$-$G^{ms}$-$C^{ms}$-$A^{ms}$-$A^{ms}$-$A^{ms}$-$U^{ms}$-$T^{els}$-$T^{els}$-$G^{els}$-$C^{els}$-$T^{els}$-$CH_2CH_2OH$ (SEQ ID NO: 205)

Especially preferable are (J-1) to (J-9).

Preferable examples of the compound represented by general formula (II') include the following compounds.

(k-1) HO-$T^{e2p}$-$T^{e2p}$-$G^{e2p}$-$A^{e2p}$-$G^{e2p}$-$U^{mp}$-$C^{mp}$-$U^{mp}$-$U^{mp}$-$C^{mp}$-$A^{mp}$-$A^{mp}$-$A^{mp}$-$A^{e2p}$-$C^{e2p}$-$T^{e2p}$-$G^{e2p}$-$A^{e2p}$-$CH_2CH_2OH$ (SEQ ID NO: 206)

(k-2) HO-$T^{e2p}$-$T^{e2p}$-$G^{e2p}$-$A^{e2p}$-$G^{e2p}$-$U^{ms}$-$C^{ms}$-$U^{ms}$-$U^{ms}$-$C^{ms}$-$A^{ms}$-$A^{ms}$-$A^{ms}$-$A^{e2p}$-$C^{e2p}$-$T^{e2p}$-$G^{e2p}$-$A^{e2s}$-$CH_2CH_2OH$ (SEQ ID NO: 206)

(k-3) HO-$T^{e2s}$-$T^{e2s}$-$G^{e2s}$-$A^{e2s}$-$G^{e2s}$-$U^{ms}$-$C^{ms}$-$U^{ms}$-$U^{ms}$-$C^{ms}$-$A^{ms}$-$A^{ms}$-$A^{ms}$-$A^{e2s}$-$C^{e2s}$-$T^{e2s}$-$G^{e2s}$-$A^{e2s}$-$CH_2CH_2OH$ (SEQ ID NO: 206)

(k-4) HO-$T^{e2p}$-$T^{e2p}$-$G^{mp}$-$A^{mp}$-$G^{mp}$-$T^{e2p}$-$C^{e2p}$-$T^{e2p}$-$T^{e2p}$-$C^{e2p}$-$A^{mp}$-$A^{mp}$-$A^{mp}$-$A^{mp}$-$C^{e2p}$-$T^{e2p}$-$G^{mp}$-$A^{mp}$-$CH_2CH_2OH$ (SEQ ID NO: 12)

(k-5) HO-$T^{e2p}$-$T^{e2p}$-$G^{ms}$-$A^{ms}$-$G^{ms}$-$T^{e2p}$-$C^{e2p}$-$T^{e2p}$-$T^{e2p}$-$C^{e2p}$-$A^{ms}$-$A^{ms}$-$A^{ms}$-$A^{ms}$-$C^{e2p}$-$T^{e2p}$-$G^{ms}$-$A^{ms}$-$CH_2CH_2OH$ (SEQ ID NO: 12)

(k-6) HO-$T^{e2s}$-$T^{e2s}$-$G^{ms}$-$A^{ms}$-$G^{ms}$-$T^{e2s}$-$C^{e2s}$-$T^{e2s}$-$T^{e2s}$-$C^{e2s}$-$A^{ms}$-$A^{ms}$-$A^{ms}$-$A^{ms}$-$C^{e2s}$-$T^{e2s}$-$G^{ms}$-$A^{ms}$-$CH_2CH_2OH$ (SEQ ID NO: 12)

(k-7) HO-$G^{e2p}$-$T^{e2p}$-$G^{e2p}$-$C^{e2p}$-$A^{e2p}$-$A^{mp}$-$A^{mp}$-$G^{mp}$-$U^{mp}$-$U^{mp}$-$G^{mp}$-$A^{mp}$-$G^{mp}$-$T^{e2p}$-$C^{e2p}$-$T^{e2p}$-$T^{e2p}$-$C^{e2p}$-$CH_2CH_2OH$ (SEQ ID NO: 207)

(k-8) HO-$G^{e2p}$-$T^{e2p}$-$G^{e2p}$-$C^{e2p}$-$A^{e2p}$-$A^{ms}$-$A^{ms}$-$G^{ms}$-$U^{ms}$-$U^{ms}$-$G^{ms}$-$A^{ms}$-$G^{ms}$-$T^{e2p}$-$C^{e2p}$-$T^{e2p}$-$T^{e2p}$-$C^{e2p}$-$CH_2CH_2OH$ (SEQ ID NO: 207)

-continued (k-9) HO-G$^{e2s}$-T$^{e2s}$-G$^{e2s}$-C$^{e2s}$-A$^{e2s}$-A$^{ms}$-A$^{ms}$-G$^{ms}$-U$^{ms}$-U$^{ms}$-G$^{ms}$-A$^{ms}$-G$^{ms}$-T$^{e2s}$-C$^{e2s}$-T$^{e2s}$-
(SEQ ID NO: 207)

C$^{e2s}$-CH$_2$CH$_2$OH (k-10) HO-G$^{mp}$-T$^{e2p}$-G$^{mp}$-C$^{e2p}$-A$^{mp}$-A$^{mp}$-A$^{mp}$-G$^{mp}$-T$^{e2p}$-T$^{e2p}$-G$^{mp}$-A$^{mp}$-G$^{mp}$-T$^{e2p}$-C$^{e2p}$-T$^{e2p}$-
(SEQ ID NO: 13)

T$^{e2p}$-C$^{e2p}$-CH$_2$CH$_2$OH (k-11) HO-G$^{ms}$-T$^{e2p}$-G$^{ms}$-C$^{e2p}$-A$^{ms}$-A$^{ms}$-A$^{ms}$-G$^{mp}$-T$^{e2p}$-T$^{e2p}$-G$^{ms}$-A$^{ms}$-G$^{ms}$-T$^{e2p}$-C$^{e2p}$-T$^{e2p}$-
(SEQ ID NO: 13)

C$^{e2p}$-CH$_2$CH$_2$OH (k-12) HO-G$^{ms}$-T$^{e2s}$-G$^{ms}$-C$^{e2s}$-A$^{ms}$-A$^{ms}$-A$^{ms}$-G$^{ms}$-T$^{e2s}$-T$^{e2s}$-G$^{ms}$-A$^{ms}$-G$^{ms}$-T$^{e2s}$-C$^{e2s}$-T$^{e2s}$-
(SEQ ID NO: 13)

C$^{e2s}$-CH$_2$CH$_2$OH (k-13) HO-T$^{e1p}$-T$^{e1p}$-G$^{e1p}$-A$^{e1p}$-G$^{e1p}$-U$^{mp}$-C$^{mp}$-U$^{mp}$-U$^{mp}$-C$^{mp}$-A$^{mp}$-A$^{mp}$-A$^{mp}$-A$^{e1p}$-C$^{e1p}$-T$^{e1p}$-
(SEQ ID NO: 206)

G$^{e1p}$-A$^{e1p}$-CH$_2$CH$_2$OH (k-14) HO-T$^{e1p}$-T$^{e1p}$-G$^{e1p}$-A$^{e1p}$-G$^{e1p}$-U$^{ms}$-C$^{ms}$-U$^{ms}$-U$^{ms}$-C$^{ms}$-A$^{ms}$-A$^{ms}$-A$^{ms}$-A$^{e1p}$-C$^{e1p}$-T$^{e1p}$-
(SEQ ID NO: 206)

G$^{e1p}$-A$^{e1s}$-CH$_2$CH$_2$OH (k-15) HO-T$^{e1s}$-T$^{e1s}$-G$^{e1s}$-A$^{e1s}$-G$^{e1s}$-U$^{ms}$-C$^{ms}$-U$^{ms}$-U$^{ms}$-C$^{ms}$-A$^{ms}$-A$^{ms}$-A$^{ms}$-A$^{e1s}$-C$^{e1s}$-T$^{e1s}$-
(SEQ ID NO: 206)

G$^{e1s}$-

A$^{e1s}$-CH$_2$CH$_2$OH (k-16) HO-T$^{e1p}$-T$^{e1p}$-G$^{mp}$-A$^{mp}$-G$^{mp}$-T$^{e1p}$-C$^{e1p}$-T$^{e1p}$-T$^{e1p}$-C$^{e1p}$-A$^{mp}$-A$^{mp}$-A$^{mp}$-A$^{mp}$-C$^{e1p}$-T$^{e1p}$-
(SEQ ID NO: 12)

G$^{mp}$-A$^{mp}$-CH$_2$CH$_2$OH (k-17) HO-T$^{e1p}$-T$^{e1p}$-G$^{ms}$-A$^{ms}$-G$^{ms}$-T$^{e1p}$-C$^{e1p}$-T$^{e1p}$-T$^{e1p}$-C$^{e1p}$-A$^{ms}$-A$^{ms}$-A$^{ms}$-A$^{ms}$-C$^{e1p}$-T$^{e1p}$-
(SEQ ID NO: 12)

G$^{ms}$-

A$^{ms}$-CH$_2$CH$_2$OH (k-18) HO-T$^{e1s}$-T$^{e1s}$-G$^{ms}$-A$^{ms}$-G$^{ms}$-T$^{e1s}$-C$^{e1s}$-T$^{e1s}$-T$^{e1s}$-C$^{e1s}$-A$^{ms}$-A$^{ms}$-A$^{ms}$-A$^{ms}$-C$^{e1s}$-T$^{e1s}$-
(SEQ ID NO: 12)

G$^{ms}$-

A$^{ms}$-CH$_2$CH$_2$OH (k-19) HO-G$^{e1p}$-T$^{e1p}$-G$^{e1p}$-C$^{e1p}$-A$^{e1p}$-A$^{mp}$-A$^{mp}$-G$^{mp}$-U$^{mp}$-U$^{mp}$-G$^{mp}$-A$^{mp}$-G$^{mp}$-T$^{e1p}$-C$^{e1p}$-T$^{e1p}$-
(SEQ ID NO: 207)

T$^{e1p}$-C$^{e1p}$-CH$_2$CH$_2$OH (k-20) HO-G$^{e1p}$-T$^{e1p}$-G$^{e1p}$-C$^{e1p}$-A$^{e1p}$-A$^{ms}$-A$^{ms}$-G$^{ms}$-U$^{ms}$-U$^{ms}$-G$^{ms}$-A$^{ms}$-G$^{ms}$-T$^{e1p}$-C$^{e1p}$-T$^{e1p}$-
(SEQ ID NO: 207)

T$^{e1p}$-C$^{e1p}$-CH$_2$CH$_2$OH (k-21) HO-G$^{e1s}$-T$^{e1s}$-G$^{e1s}$-C$^{e1s}$-A$^{e1s}$-A$^{ms}$-A$^{ms}$-G$^{ms}$-U$^{ms}$-U$^{ms}$-G$^{ms}$-A$^{ms}$-G$^{ms}$-T$^{e1s}$-C$^{e1s}$-T$^{e1s}$-
(SEQ ID NO: 207)

T$^{e1s}$-

C$^{e1s}$-CH$_2$CH$_2$OH (k-22) HO-G$^{mp}$-T$^{e1p}$-G$^{mp}$-C$^{e1p}$-A$^{mp}$-A$^{mp}$-A$^{mp}$-G$^{mp}$-T$^{e1p}$-T$^{e1p}$-G$^{mp}$-A$^{mp}$-G$^{mp}$-T$^{e1p}$-C$^{e1p}$-T$^{e1p}$-
(SEQ ID NO: 13)

T$^{e1p}$-C$^{e1p}$-CH$_2$CH$_2$OH

-continued (k-23) HO-$G^{ms}$-$T^{elp}$-$G^{ms}$-$C^{elp}$-$A^{ms}$-$A^{ms}$-$A^{ms}$-$G^{m}$-$T^{elp}$-$T^{elp}$-$G^{ms}$-$A^{ms}$-$G^{ms}$-$T^{elp}$-$C^{elp}$-$T^{elp}$-$T^{elp}$-$C^{elp}$-CH$_2$CH$_2$OH (SEQ ID NO: 13)

(k-24) HO-$G^{ms}$-$T^{els}$-$G^{ms}$-$C^{els}$-$A^{ms}$-$A^{ms}$-$A^{ms}$-$G^{m}$-$T^{els}$-$T^{els}$-$G^{ms}$-$A^{ms}$-$G^{ms}$-$T^{els}$-$C^{els}$-$T^{els}$-$T^{els}$-$C^{els}$-CH$_2$CH$_2$OH (SEQ ID NO: 13)

Especially preferable are (k-1) to (k-12).

Preferable examples of the compound represented by general formula (III') include the following compounds.

(m-1) HO-$G^{e2p}$-$C^{e2p}$-$C^{e2p}$-$G^{e2p}$-$C^{e2p}$-$U^{mp}$-$G^{mp}$-$C^{mp}$-$C^{mp}$-$C^{mp}$-$A^{e2p}$-$A^{e2p}$-$T^{e2p}$-$G^{e2p}$-$C^{e2p}$-CH$_2$CH$_2$OH (SEQ ID NO: 208)

(m-2) HO-$G^{e2p}$-$C^{e2p}$-$C^{e2p}$-$G^{e2p}$-$C^{e2p}$-$U^{ms}$-$G^{ms}$-$C^{ms}$-$C^{ms}$-$C^{ms}$-$A^{e2p}$-$A^{e2p}$-$T^{e2p}$-$G^{e2p}$-$C^{e2p}$-CH$_2$CH$_2$OH (SEQ ID NO: 208)

(m-3) HO-$G^{e2s}$-$C^{e2s}$-$C^{e2s}$-$G^{e2s}$-$C^{e2s}$-$U^{ms}$-$G^{ms}$-$C^{ms}$-$C^{ms}$-$C^{ms}$-$A^{e2s}$-$A^{e2s}$-$T^{e2s}$-$G^{e2s}$-$C^{e2s}$-CH$_2$CH$_2$OH (SEQ ID NO: 208)

(m-4) HO-$C^{e2p}$-$G^{mp}$-$C^{e2p}$-$T^{e2p}$-$G^{mp}$-$C^{mp}$-$C^{e2p}$-$C^{e2p}$-$A^{mp}$-$A^{mp}$-$T^{e2p}$-$G^{mp}$-$C^{e2p}$-$C^{e2p}$-$A^{mp}$-$U^{mp}$-$C^{e2p}$-$C^{e2p}$-CH$_2$CH$_2$OH (SEQ ID NO: 209)

(m-5) HO-$C^{e2p}$-$G^{ms}$-$C^{e2p}$-$T^{e2p}$-$G^{ms}$-$C^{ms}$-$C^{e2p}$-$C^{e2p}$-$A^{ms}$-$A^{ms}$-$T^{e2p}$-$G^{ms}$-$C^{e2p}$-$C^{e2p}$-$A^{ms}$-$U^{ms}$-$C^{e2p}$-$C^{e2p}$-CH$_2$CH$_2$OH (SEQ ID NO: 209)

(m-6) HO-$C^{e2s}$-$G^{ms}$-$C^{e2s}$-$T^{e2s}$-$G^{ms}$-$C^{ms}$-$C^{e2s}$-$C^{e2s}$-$A^{ms}$-$A^{ms}$-$T^{e2s}$-$G^{ms}$-$C^{e2s}$-$C^{e2s}$-$A^{ms}$-$U^{ms}$-$C^{e2s}$-$C^{e2s}$-CH$_2$CH$_2$OH (SEQ ID NO: 209)

(m-7) HO-$G^{elp}$-$C^{elp}$-$C^{elp}$-$G^{elp}$-$C^{elp}$-$U^{mp}$-$G^{mp}$-$C^{mp}$-$C^{mp}$-$C^{mp}$-$A^{elp}$-$A^{elp}$-$T^{elp}$-$G^{elp}$-$C^{elp}$-CH$_2$CH$_2$OH (SEQ ID NO: 208)

(m-8) HO-$G^{elp}$-$C^{elp}$-$C^{elp}$-$G^{elp}$-$C^{elp}$-$U^{ms}$-$G^{ms}$-$C^{ms}$-$C^{ms}$-$C^{ms}$-$A^{elp}$-$A^{elp}$-$T^{elp}$-$G^{elp}$-$C^{elp}$-CH$_2$CH$_2$OH (SEQ ID NO: 208)

(m-9) HO-$G^{els}$-$C^{els}$-$C^{els}$-$G^{els}$-$C^{els}$-$U^{ms}$-$G^{ms}$-$C^{ms}$-$C^{ms}$-$C^{ms}$-$A^{els}$-$A^{els}$-$T^{els}$-$G^{els}$-$C^{els}$-CH$_2$CH$_2$OH (SEQ ID NO: 208)

(m-10) HO-$C^{elp}$-$G^{mp}$-$C^{elp}$-$T^{elp}$-$G^{mp}$-$C^{elp}$-$C^{elp}$-$C^{elp}$-$A^{mp}$-$A^{mp}$-$T^{elp}$-$G^{mp}$-$C^{elp}$-$C^{elp}$-$A^{mp}$-$U^{mp}$-$C^{elp}$-$C^{elp}$-CH$_2$CH$_2$OH (SEQ ID NO: 209)

(m-11) HO-$C^{elp}$-$G^{ms}$-$C^{elp}$-$T^{elp}$-$G^{ms}$-$C^{elp}$-$C^{elp}$-$C^{elp}$-$A^{ms}$-$A^{ms}$-$T^{elp}$-$G^{ms}$-$C^{elp}$-$C^{elp}$-$A^{ms}$-$U^{ms}$-$C^{elp}$-$C^{elp}$-CH$_2$CH$_2$OH (SEQ ID NO: 209)

(m-12) HO-$C^{els}$-$G^{ms}$-$C^{els}$-$T^{els}$-$G^{ms}$-$C^{els}$-$C^{els}$-$C^{els}$-$A^{ms}$-$A^{ms}$-$T^{els}$-$G^{ms}$-$C^{els}$-$C^{els}$-$A^{ms}$-$U^{ms}$-$C^{els}$-$C^{els}$-CH$_2$CH$_2$OH (SEQ ID NO: 209)

Especially preferable are (m-1) to (m-6).

Preferable examples of the compound represented by general formula (IV') include the following compounds.

(n-1) HO-$C^{e2p}$-$A^{mp}$-$G^{mp}$-$T^{e2p}$-$T^{e2p}$-$U^{mp}$-$G^{mp}$-$C^{e2p}$-$C^{e2p}$-$G^{mp}$-$C^{e2p}$-$T^{e2p}$-$G^{mp}$-$C^{e2p}$-$C^{e2p}$-$C^{e2p}$- (SEQ ID NO: 210)

$A^{mp}$-$A^{mp}$-$CH_2CH_2OH$ (n-2) HO-$T^{e2p}$-$G^{mp}$-$T^{e2p}$-$T^{e2p}$-$C^{e2p}$-$T^{e2p}$-$G^{mp}$-$A^{mp}$-$C^{e2p}$-$A^{mp}$-$A^{mp}$-$C^{e2p}$-$A^{mp}$-$G^{mp}$-$T^{e2p}$-$T^{e2p}$- (SEQ ID NO: 17)
$T^{e2p}$-

$G^{mp}$-$CH_2CH_2OH$ (n-3) HO-$C^{e2p}$-$A^{ms}$-$G^{ms}$-$T^{e2p}$-$T^{e2p}$-$U^{ms}$-$G^{ms}$-$C^{e2p}$-$C^{e2p}$-$G^{ms}$-$C^{e2p}$-$T^{e2p}$-$G^{ms}$-$C^{e2p}$-$C^{e2p}$-$C^{e2p}$- (SEQ ID NO: 210)
$A^{ms}$-

$A^{ms}$-$CH_2CH_2OH$ (n-4) HO-$T^{e2p}$-$G^{ms}$-$T^{e2p}$-$T^{e2p}$-$C^{e2p}$-$T^{e2p}$-$G^{ms}$-$A^{ms}$-$C^{e2p}$-$A^{ms}$-$A^{ms}$-$C^{e2p}$-$A^{ms}$-$G^{ms}$-$T^{e2p}$-$T^{e2p}$- (SEQ ID NO: 17)
$T^{e2p}$-

$G^{ms}$-$CH_2CH_2OH$ (n-5) HO-$C^{e2s}$-$A^{ms}$-$G^{ms}$-$T^{e2s}$-$T^{e2s}$-$U^{ms}$-$G^{ms}$-$C^{e2s}$-$C^{e2s}$-$G^{ms}$-$C^{e2s}$-$T^{e2s}$-$G^{ms}$-$C^{e2s}$-$C^{e2s}$-$C^{e2s}$-$A^{ms}$- (SEQ ID NO: 210)

$A^{ms}$-$CH_2CH_2OH$ (n-6) HO-$T^{e2s}$-$G^{ms}$-$T^{e2s}$-$T^{e2s}$-$C^{e2s}$-$T^{e2s}$-$G^{ms}$-$A^{ms}$-$C^{e2s}$-$A^{ms}$-$A^{ms}$-$C^{e2s}$-$A^{ms}$-$G^{ms}$-$T^{e2s}$-$T^{e2s}$-$T^{e2s}$- (SEQ ID NO: 17)

$G^{ms}$-$CH_2CH_2OH$ (n-7) HO-$C^{e1p}$-$A^{mp}$-$G^{mp}$-$T^{e1p}$-$T^{e1p}$-$U^{mp}$-$G^{mp}$-$C^{e1p}$-$C^{e1p}$-$G^{mp}$-$C^{e1p}$-$T^{e1p}$-$G^{mp}$-$C^{e1p}$-$C^{e1p}$-$C^{e1p}$- (SEQ ID NO: 210)

$A^{mp}$-$A^{mp}$-$CH_2CH_2OH$ (n-8) HO-$T^{e1p}$-$G^{mp}$-$T^{e1p}$-$T^{e1p}$-$C^{e1p}$-$T^{e1p}$-$G^{mp}$-$A^{mp}$-$C^{e1p}$-$A^{mp}$-$A^{mp}$-$C^{e1p}$-$A^{mp}$-$G^{mp}$-$T^{e1p}$-$T^{e1p}$- (SEQ ID NO: 17)
$T^{e1p}$-

$G^{mp}$-$CH_2CH_2OH$ (n-9) HO-$C^{e1p}$-$A^{ms}$-$G^{ms}$-$T^{e1p}$-$T^{e1p}$-$U^{ms}$-$G^{ms}$-$C^{e1p}$-$C^{e1p}$-$G^{ms}$-$C^{e1p}$-$T^{e1p}$-$G^{ms}$-$C^{e1p}$-$C^{e1p}$-$C^{e1p}$- (SEQ ID NO: 210)
$A^{ms}$-

$A^{ms}$-$CH_2CH_2OH$ (n-10) HO-$T^{e1p}$-$G^{ms}$-$T^{e1p}$-$T^{e1p}$-$C^{e1p}$-$T^{e1p}$-$G^{ms}$-$A^{ms}$-$C^{e1p}$-$A^{ms}$-$A^{ms}$-$C^{e1p}$-$A^{ms}$-$G^{ms}$-$T^{e1p}$-$T^{e1p}$- (SEQ ID NO: 17)
$T^{e1p}$-

$G^{ms}$-$CH_2CH_2OH$ (n-11) HO-$C^{e1s}$-$A^{ms}$-$G^{ms}$-$T^{e1s}$-$T^{e1s}$-$U^{ms}$-$G^{ms}$-$C^{e1s}$-$C^{e1s}$-$G^{ms}$-$C^{e1s}$-$T^{e1s}$-$G^{ms}$-$C^{e1s}$-$C^{e1s}$-$C^{e1s}$-$A^{ms}$- (SEQ ID NO: 210)

$A^{ms}$-$CH_2CH_2OH$ (n-12) HO-$T^{e1s}$-$G^{ms}$-$T^{e1s}$-$T^{e1s}$-$C^{e1s}$-$T^{e1s}$-$G^{ms}$-$A^{ms}$-$C^{e1s}$-$A^{ms}$-$A^{ms}$-$C^{e1s}$-$A^{ms}$-$G^{ms}$-$T^{e1s}$-$T^{e1s}$-$T^{e1s}$- (SEQ ID NO: 17)

$G^{ms}$-$CH_2CH_2OH$

Especially preferable are (m-1), (m-3) and (m-5).

Preferable examples of the compound represented by general formula (V') include the following compounds.

(o-1) HO-$G^{e2p}$-$C^{e2p}$-$T^{e2p}$-$C^{e2p}$-$T^{e2p}$-$T^{e2p}$-$U^{mp}$-$C^{mp}$-$U^{mp}$-$U^{mp}$-$U^{mp}$-$A^{mp}$-$G^{mp}$-$U^{mp}$-$U^{mp}$-$G^{e2p}$- (SEQ ID NO: 211)
$C^{e2p}$-

$T^{e2p}$-$G^{e2p}$-$C^{e2p}$-$CH_2CH_2OH$

-continued (o-2) HO-G$^{e2p}$-C$^{e2p}$-T$^{e2p}$-T$^{e2p}$-T$^{e2p}$-U$^{ms}$-C$^{ms}$-U$^{ms}$-U$^{ms}$-U$^{ms}$-U$^{ms}$-A$^{ms}$-G$^{ms}$-U$^{ms}$-U$^{ms}$-G$^{e2p}$-C$^{e2p}$-T$^{e2p}$-G$^{e2p}$-C$^{e2p}$-CH$_2$CH$_2$OH (SEQ ID NO: 211)

(o-3) HO-G$^{e2s}$-C$^{e2s}$-T$^{e2s}$-T$^{e2s}$-T$^{e2s}$-U$^{ms}$-C$^{ms}$-U$^{ms}$-U$^{ms}$-U$^{ms}$-U$^{ms}$-A$^{ms}$-G$^{ms}$-U$^{ms}$-U$^{ms}$-G$^{e2s}$-C$^{e2s}$-T$^{e2s}$-G$^{e2s}$-C$^{e2s}$-CH$_2$CH$_2$OH (SEQ ID NO: 211)

(o-4) HO-C$^{mp}$-U$^{mp}$-U$^{mp}$-U$^{mp}$-U$^{mp}$-A$^{e2p}$-G$^{e2p}$-T$^{e2p}$-T$^{e2p}$-G$^{e2p}$-C$^{e2p}$-T$^{e2p}$-G$^{e2p}$-C$^{e2p}$-T$^{e2p}$-C$^{e2p}$-T$^{e2p}$-U$^{mp}$-U$^{mp}$-U$^{mp}$-C$^{mp}$-C$^{mp}$-CH$_2$CH$_2$OH (SEQ ID NO: 212)

(o-5) HO-C$^{ms}$-U$^{ms}$-U$^{ms}$-U$^{ms}$-U$^{ms}$-A$^{e2p}$-G$^{e2p}$-T$^{e2p}$-T$^{e2p}$-G$^{e2p}$-C$^{e2p}$-T$^{e2p}$-G$^{e2p}$-C$^{e2p}$-T$^{e2p}$-C$^{e2p}$-T$^{e2p}$-U$^{ms}$-U$^{ms}$-U$^{ms}$-C$^{ms}$-C$^{ms}$-CH$_2$CH$_2$OH (SEQ ID NO: 212)

(o-6) HO-C$^{ms}$-U$^{ms}$-U$^{ms}$-U$^{ms}$-U$^{ms}$-A$^{e2s}$-G$^{e2s}$-T$^{e2s}$-T$^{e2s}$-G$^{e2s}$-C$^{e2s}$-T$^{e2s}$-G$^{e2s}$-C$^{e2s}$-T$^{e2s}$-C$^{e2s}$-T$^{e2s}$-U$^{ms}$-U$^{ms}$-U$^{ms}$-C$^{ms}$-C$^{ms}$-CH$_2$CH$_2$OH (SEQ ID NO: 212)

(o-7) HO-G$^{e1p}$-C$^{e1p}$-T$^{e1p}$-T$^{e1p}$-T$^{e1p}$-U$^{mp}$-C$^{mp}$-U$^{mp}$-U$^{mp}$-U$^{mp}$-U$^{mp}$-A$^{mp}$-G$^{mp}$-U$^{mp}$-U$^{mp}$-G$^{e1p}$-C$^{e1p}$-T$^{e1p}$-G$^{e1p}$-C$^{e1p}$-CH$_2$CH$_2$OH (SEQ ID NO: 211)

(o-8) HO-G$^{e1p}$-C$^{e1p}$-T$^{e1p}$-T$^{e1p}$-T$^{e1p}$-U$^{ms}$-C$^{ms}$-U$^{ms}$-U$^{ms}$-U$^{ms}$-U$^{ms}$-A$^{ms}$-G$^{ms}$-U$^{ms}$-U$^{ms}$-G$^{e1p}$-C$^{e1p}$-T$^{e1p}$-G$^{e1p}$-C$^{e1p}$-CH$_2$CH$_2$OH (SEQ ID NO: 211)

(o-9) HO-G$^{e1s}$-C$^{e1s}$-T$^{e1s}$-T$^{e1s}$-T$^{e1s}$-U$^{ms}$-C$^{ms}$-U$^{ms}$-U$^{ms}$-U$^{ms}$-U$^{ms}$-A$^{ms}$-G$^{ms}$-U$^{ms}$-U$^{ms}$-G$^{e1s}$-C$^{e1s}$-T$^{e1s}$-G$^{e1s}$-C$^{e1s}$-CH$_2$CH$_2$OH (SEQ ID NO: 211)

(o-10) HO-C$^{mp}$-U$^{mp}$-U$^{mp}$-U$^{mp}$-U$^{mp}$-A$^{e1p}$-G$^{e1p}$-T$^{e1p}$-T$^{e1p}$-G$^{e1p}$-C$^{e1p}$-T$^{e1p}$-G$^{e1p}$-C$^{e1p}$-T$^{e1p}$-C$^{e1p}$-T$^{e1p}$-U$^{mp}$-U$^{mp}$-U$^{mp}$-C$^{mp}$-C$^{mp}$-CH$_2$CH$_2$OH (SEQ ID NO: 212)

(o-11) HO-C$^{ms}$-U$^{ms}$-U$^{ms}$-U$^{ms}$-U$^{ms}$-A$^{e1p}$-G$^{e1p}$-T$^{e1p}$-T$^{e1p}$-G$^{e1p}$-C$^{e1p}$-T$^{e1p}$-G$^{e1p}$-C$^{e1p}$-T$^{e1p}$-C$^{e1p}$-T$^{e1p}$-U$^{ms}$-U$^{ms}$-U$^{ms}$-C$^{ms}$-C$^{ms}$-CH$_2$CH$_2$OH (SEQ ID NO: 212)

(o-12) HO-C$^{ms}$-U$^{ms}$-U$^{ms}$-U$^{ms}$-U$^{ms}$-A$^{e1s}$-G$^{e1s}$-T$^{e1s}$-T$^{e1s}$-G$^{e1s}$-C$^{e1s}$-T$^{e1s}$-G$^{e1s}$-C$^{e1s}$-T$^{e1s}$-C$^{e1s}$-T$^{e1s}$-U$^{ms}$-U$^{ms}$-U$^{ms}$-C$^{ms}$-C$^{ms}$-CH$_2$CH$_2$OH (SEQ ID NO: 212)

Especially preferable are (o-1) to (o-6).

Preferable examples of the compound represented by general formula (VI') include the following compounds.

(p-1) HO-T$^{e2p}$-T$^{e2p}$-T$^{e2p}$-T$^{e2p}$-C$^{e2p}$-C$^{mp}$-A$^{mp}$-G$^{mp}$-G$^{mp}$-U$^{mp}$-U$^{mp}$-C$^{mp}$-A$^{mp}$-A$^{e2p}$-G$^{e2p}$-T$^{e2p}$-G$^{e2p}$-G$^{e2p}$-CH$_2$CH$_2$OH (SEQ ID NO: 213)

(p-2) HO-T$^{e2p}$-T$^{e2p}$-T$^{e2p}$-T$^{e2p}$-C$^{e2p}$-C$^{ms}$-A$^{ms}$-G$^{ms}$-G$^{ms}$-U$^{ms}$-U$^{ms}$-C$^{ms}$-A$^{ms}$-A$^{e2p}$-G$^{e2p}$-T$^{e2p}$-G$^{e2p}$-G$^{e2p}$-CH$_2$CH$_2$OH (SEQ ID NO: 213)

(p-3) HO-T$^{e2s}$-T$^{e2s}$-T$^{e2s}$-T$^{e2s}$-C$^{e2s}$-C$^{ms}$-A$^{ms}$-G$^{ms}$-G$^{ms}$-U$^{ms}$-U$^{ms}$-C$^{ms}$-A$^{ms}$-A$^{e2s}$-G$^{e2s}$-T$^{e2s}$-G$^{e2s}$-G$^{e2s}$-CH$_2$CH$_2$OH (SEQ ID NO: 213)

(p-4) HO-T$^{elp}$-T$^{elp}$-T$^{elp}$-T$^{elp}$-C$^{elp}$-C$^{mp}$-A$^{mp}$-G$^{mp}$-G$^{mp}$-U$^{mp}$-U$^{mp}$-C$^{mp}$-A$^{mp}$-A$^{elp}$-G$^{elp}$-T$^{elp}$-G$^{elp}$-G$^{elp}$-CH$_2$CH$_2$OH (SEQ ID NO: 213)

(p-5) HO-T$^{elp}$-T$^{elp}$-T$^{elp}$-T$^{elp}$-C$^{elp}$-C$^{ms}$-A$^{ms}$-G$^{ms}$-G$^{ms}$-U$^{ms}$-U$^{ms}$-C$^{ms}$-A$^{ms}$-A$^{elp}$-G$^{elp}$-T$^{elp}$-G$^{elp}$-G$^{elp}$-CH$_2$CH$_2$OH (SEQ ID NO: 213)

(p-6) HO-T$^{els}$-T$^{els}$-T$^{els}$-T$^{els}$-C$^{els}$-C$^{ms}$-A$^{ms}$-G$^{ms}$-G$^{ms}$-U$^{ms}$-U$^{ms}$-C$^{ms}$-A$^{ms}$-A$^{els}$-G$^{els}$-T$^{els}$-G$^{els}$-G$^{els}$-CH$_2$CH$_2$OH (SEQ ID NO: 213)

Especially preferable are (p-1) to (p-3).

Preferable examples of the compound represented by general formula (Vii') include the following compounds.

(q-1) HO-C$^{e2p}$-T$^{e2p}$-G$^{e2p}$-C$^{e2p}$-T$^{e2p}$-U$^{mp}$-C$^{mp}$-C$^{mp}$-U$^{mp}$-C$^{mp}$-C$^{e2p}$-A$^{e2p}$-A$^{e2p}$-C$^{e2p}$-C$^{e2p}$-CH$_2$CH$_2$OH (SEQ ID NO: 214)

(q-2) HO-G$^{e2p}$-T$^{e2p}$-T$^{e2p}$-A$^{e2p}$-T$^{e2p}$-C$^{mp}$-U$^{mp}$-G$^{mp}$-C$^{mp}$-U$^{mp}$-U$^{mp}$-C$^{mp}$-C$^{mp}$-U$^{mp}$-C$^{mp}$-C$^{e2p}$-A$^{e2p}$-A$^{e2p}$-C$^{e2p}$-C$^{e2p}$-CH$_2$CH$_2$OH (SEQ ID NO: 215)

(q-3) HO-C$^{e2p}$-U$^{mp}$-G$^{mp}$-C$^{e2p}$-U$^{mp}$-U$^{mp}$-C$^{e2p}$-C$^{e2p}$-U$^{mp}$-C$^{e2p}$-C$^{e2p}$-A$^{mp}$-A$^{mp}$-C$^{e2p}$-C$^{e2p}$-CH$_2$CH$_2$OH (SEQ ID NO: 23)

(q-4) HO-C$^{e2p}$-T$^{e2p}$-G$^{mp}$-C$^{e2p}$-T$^{e2p}$-U$^{mp}$-C$^{mp}$-C$^{e2p}$-U$^{mp}$-C$^{mp}$-C$^{e2p}$-A$^{mp}$-A$^{mp}$-C$^{e2p}$-C$^{e2p}$-CH$_2$CH$_2$OH (SEQ ID NO: 214)

(q-5) HO-C$^{e2p}$-T$^{e2p}$-G$^{e2p}$-C$^{e2p}$-T$^{e2p}$-U$^{ms}$-C$^{ms}$-C$^{ms}$-U$^{ms}$-C$^{ms}$-C$^{e2p}$-A$^{e2p}$-A$^{e2p}$-C$^{e2p}$-C$^{e2p}$-CH$_2$CH$_2$OH (SEQ ID NO: 214)

(q-6) HO-G$^{e2p}$-T$^{e2p}$-T$^{e2p}$-A$^{e2p}$-T$^{e2p}$-C$^{ms}$-U$^{ms}$-G$^{ms}$-C$^{ms}$-U$^{ms}$-U$^{ms}$-C$^{ms}$-C$^{ms}$-U$^{ms}$-C$^{ms}$-C$^{e2p}$-A$^{e2p}$-A$^{e2p}$-C$^{e2p}$-C$^{e2p}$-CH$_2$CH$_2$OH (SEQ ID NO: 215)

(q-7) HO-C$^{e2s}$-U$^{ms}$-G$^{ms}$-C$^{e2s}$-U$^{ms}$-U$^{ms}$-C$^{e2s}$-C$^{e2s}$-U$^{ms}$-C$^{e2s}$-C$^{e2s}$-A$^{ms}$-A$^{ms}$-C$^{e2s}$-C$^{e2s}$-CH$_2$CH$_2$OH (SEQ ID NO: 23)

(q-8) HO-C$^{e2s}$-T$^{e2s}$-G$^{ms}$-C$^{e2s}$-T$^{e2s}$-U$^{ms}$-C$^{ms}$-C$^{e2s}$-U$^{ms}$-C$^{ms}$-C$^{e2s}$-A$^{ms}$-A$^{ms}$-C$^{e2s}$-C$^{e2s}$-CH$_2$CH$_2$OH (SEQ ID NO: 214)

(q-9) HO-C$^{e2s}$-T$^{e2s}$-G$^{e2s}$-C$^{e2s}$-T$^{e2s}$-U$^{ms}$-C$^{ms}$-C$^{ms}$-U$^{ms}$-C$^{ms}$-C$^{e2s}$-A$^{e2s}$-A$^{e2s}$-C$^{e2s}$-C$^{e2s}$-CH$_2$CH$_2$OH (SEQ ID NO: 214)

(q-10) HO-G$^{e2s}$-T$^{e2s}$-T$^{e2s}$-A$^{e2s}$-T$^{e2s}$-C$^{ms}$-U$^{ms}$-G$^{ms}$-C$^{ms}$-U$^{ms}$-U$^{ms}$-C$^{ms}$-C$^{ms}$-U$^{ms}$-C$^{ms}$-C$^{e2s}$-A$^{e2s}$-A$^{e2s}$-C$^{e2s}$-C$^{e2s}$-CH$_2$CH$_2$OH (SEQ ID NO: 215)

(q-11) HO-C$^{e2s}$-U$^{ms}$-G$^{ms}$-C$^{e2s}$-U$^{ms}$-U$^{ms}$-C$^{e2s}$-C$^{e2s}$-U$^{ms}$-C$^{e2s}$-C$^{e2s}$-A$^{ms}$-A$^{ms}$-C$^{e2s}$-C$^{e2s}$-CH$_2$CH$_2$OH (SEQ ID NO: 23)

(q-12) HO-C$^{e2s}$-T$^{e2s}$-G$^{ms}$-C$^{e2s}$-T$^{e2s}$-U$^{ms}$-C$^{ms}$-C$^{e2s}$-U$^{ms}$-C$^{ms}$-C$^{e2s}$-A$^{ms}$-A$^{ms}$-C$^{e2s}$-C$^{e2s}$-CH$_2$CH$_2$OH (SEQ ID NO: 214)

(q-13) HO-C$^{e2p}$-T$^{e2p}$-G$^{e2p}$-C$^{e2p}$-T$^{e2p}$-U$^{mp}$-C$^{mp}$-C$^{mp}$-U$^{mp}$-C$^{mp}$-C$^{e2p}$-A$^{e2p}$-A$^{e2p}$-C$^{e2p}$-C$^{e2p}$-CH$_2$CH$_2$OH (SEQ ID NO: 214)

(q-14) HO-G$^{e2p}$-T$^{e2p}$-T$^{e2p}$-A$^{e2p}$-T$^{e2p}$-C$^{mp}$-U$^{mp}$-G$^{mp}$-C$^{mp}$-U$^{mp}$-U$^{mp}$-C$^{mp}$-C$^{mp}$-U$^{mp}$-C$^{mp}$-C$^{e2p}$-A$^{e2p}$-A$^{e2p}$-C$^{e2p}$-C$^{e2p}$-CH$_2$CH$_2$OH (SEQ ID NO: 215)

(q-15) HO-C$^{e2p}$-U$^{mp}$-G$^{mp}$-C$^{e2p}$-U$^{mp}$-U$^{mp}$-C$^{e2p}$-C$^{e2p}$-U$^{mp}$-C$^{e2p}$-C$^{e2p}$-A$^{mp}$-A$^{mp}$-C$^{e2p}$-C$^{e2p}$-CH$_2$CH$_2$OH (SEQ ID NO: 23)

(q-16) HO-C$^{e2p}$-T$^{e2p}$-G$^{mp}$-C$^{e2p}$-T$^{e2p}$-U$^{mp}$-C$^{mp}$-C$^{e2p}$-U$^{mp}$-C$^{mp}$-C$^{e2p}$-A$^{mp}$-A$^{mp}$-C$^{e2p}$-C$^{e2p}$-CH$_2$CH$_2$OH (SEQ ID NO: 214)

(q-17) HO-C$^{e2p}$-T$^{e2p}$-G$^{e2p}$-C$^{e2p}$-T$^{e2p}$-U$^{ms}$-C$^{ms}$-C$^{ms}$-U$^{ms}$-C$^{ms}$-C$^{e2p}$-A$^{e2p}$-A$^{e2p}$-C$^{e2p}$-C$^{e2p}$-CH$_2$CH$_2$OH (SEQ ID NO: 214)

(q-18) HO-G$^{e2p}$-T$^{e2p}$-T$^{e2p}$-A$^{e2p}$-T$^{e2p}$-C$^{ms}$-U$^{ms}$-G$^{ms}$-C$^{ms}$-U$^{ms}$-U$^{ms}$-C$^{ms}$-C$^{ms}$-U$^{ms}$-C$^{ms}$-C$^{e2p}$-A$^{e2p}$-A$^{e2p}$-C$^{e2p}$-C$^{e2p}$-CH$_2$CH$_2$OH (SEQ ID NO: 215)

(q-19) HO-C$^{e2s}$-U$^{ms}$-G$^{ms}$-C$^{e2s}$-U$^{ms}$-U$^{ms}$-C$^{e2s}$-C$^{e2s}$-U$^{ms}$-C$^{e2s}$-C$^{e2s}$-A$^{ms}$-A$^{ms}$-C$^{e2s}$-C$^{e2s}$-CH$_2$CH$_2$OH (SEQ ID NO: 23)

(q-20) HO-C$^{e2s}$-T$^{e2s}$-G$^{ms}$-C$^{e2s}$-T$^{e2s}$-U$^{ns}$-C$^{ms}$-C$^{ms}$-U$^{ns}$-C$^{ms}$-C$^{e2s}$-A$^{ms}$-A$^{ms}$-C$^{e2s}$-C$^{e2s}$-CH$_2$CH$_2$OH (SEQ ID NO: 214)

(q-21) HO-C$^{e2s}$-T$^{e2s}$-G$^{e2s}$-C$^{e2s}$-T$^{e2s}$-U$^{ms}$-C$^{ms}$-C$^{ms}$-U$^{ms}$-C$^{ms}$-C$^{e2s}$-A$^{e2s}$-A$^{e2s}$-C$^{e2s}$-C$^{e2s}$-CH$_2$CH$_2$OH (SEQ ID NO: 214)

(q-22) HO-G$^{e2s}$-T$^{e2s}$-T$^{e2s}$-A$^{e2s}$-T$^{e2s}$-C$^{ms}$-U$^{ms}$-G$^{ms}$-C$^{ms}$-U$^{ms}$-U$^{ms}$-C$^{ms}$-C$^{ms}$-U$^{ms}$-C$^{ms}$-C$^{e2s}$-A$^{e2s}$-A$^{e2s}$-C$^{e2s}$-C$^{e2s}$-CH$_2$CH$_2$OH (SEQ ID NO: 215)

(q-23) HO-C$^{e2s}$-U$^{ms}$-G$^{ms}$-C$^{e2s}$-U$^{ms}$-U$^{ms}$-C$^{e2s}$-C$^{e2s}$-U$^{ms}$-C$^{e2s}$-C$^{e2s}$-A$^{ms}$-A$^{ms}$-C$^{e2s}$-C$^{e2s}$-CH$_2$CH$_2$OH (SEQ ID NO: 23)

(q-24) HO-C$^{e2s}$-T$^{e2s}$-G$^{ms}$-C$^{e2s}$-T$^{e2s}$-U$^{ms}$-C$^{ms}$-C$^{e2s}$-U$^{ms}$-C$^{ms}$-C$^{e2s}$-A$^{ms}$-A$^{ms}$-C$^{e2s}$-C$^{e2s}$-CH$_2$CH$_2$OH (SEQ ID NO: 214)

Especially preferable are (q-1) to (q-12).

Preferable examples of the compound represented by general formula (I') include the following compounds.

(I"-1) HO-G$^{mp}$-T$^{e2p}$-A$^{mp}$-U$^{mp}$-T$^{e2p}$-T$^{e2p}$-A$^{mp}$-G$^{mp}$-C$^{e2p}$-A$^{mp}$-T$^{e2p}$-G$^{mp}$-U$^{mp}$-T$^{e2p}$-C$^{mp}$-C$^{e2p}$-C$^{e2p}$-A$^{mp}$-CH$_2$CH$_2$OH (SEQ ID NO:)

(I"-2) HO-$C^{e2p}$-$C^{e2p}$-$A^{mp}$-$U^{mp}$-$T^{e2p}$-$U^{mp}$-$G^{mp}$-$T^{e2p}$-$A^{mp}$-$U^{mp}$-$T^{e2p}$-$T^{e2p}$-$A^{mp}$-$G^{mp}$-$C^{e2p}$-$A^{mp}$-$T^{e2p}$- (SEQ ID NO:)

$G^{mp}$-$CH_2CH_2OH$ (I"-3) HO-$G^{mp}$-$T^{e1p}$-$A^{mp}$-$U^{mp}$-$T^{e1p}$-$T^{e1p}$-$A^{mp}$-$G^{mp}$-$C^{e1p}$-$A^{mp}$-$T^{e1p}$-$G^{mp}$-$U^{mp}$-$T^{e1p}$-$C^{mp}$-$C^{e1p}$-$C^{e1p}$- (SEQ ID NO: 34)

$A^{mp}$-$CH_2CH_2OH$ (I"-4) HO-$C^{e1p}$-$C^{e1p}$-$A^{mp}$-$U^{mp}$-$T^{e1p}$-$U^{mp}$-$G^{mp}$-$T^{e1p}$-$A^{mp}$-$U^{mp}$-$T^{e1p}$-$T^{e1p}$-$A^{mp}$-$G^{mp}$-$C^{e1p}$-$A^{mp}$-$T^{e1p}$- (SEQ ID NO: 39)

$G^{mp}$-$CH_2CH_2OH$ (I"-5) HO-$G^{ms}$-$T^{e2p}$-$A^{ms}$-$U^{ms}$-$T^{e2p}$-$T^{e2p}$-$A^{ms}$-$G^{ms}$-$C^{e2p}$-$A^{ms}$-$T^{e2p}$-$G^{ms}$-$U^{ms}$-$T^{e2p}$-$C^{ms}$-$C^{e2p}$-$C^{e2p}$- (SEQ ID NO: 34)

$A^{ms}$-$CH_2CH_2OH$ (I"-6) HO-$C^{e2p}$-$C^{e2p}$-$A^{ms}$-$U^{ms}$-$T^{e2p}$-$U^{ms}$-$G^{ms}$-$T^{e2p}$-$A^{ms}$-$U^{ms}$-$T^{e2p}$-$T^{e2p}$-$A^{ms}$-$G^{ms}$-$C^{e2p}$-$A^{ms}$-$T^{e2p}$- (SEQ ID NO: 39)

$G^{ms}$-$CH_2CH_2OH$ (I"-7) HO-$G^{ms}$-$T^{e1p}$-$A^{ms}$-$U^{ms}$-$T^{e1p}$-$T^{e1p}$-$A^{ms}$-$G^{ms}$-$C^{e1p}$-$A^{ms}$-$T^{e1p}$-$G^{ms}$-$U^{ms}$-$T^{e1p}$-$C^{ms}$-$C^{e1p}$-$C^{e1p}$- (SEQ ID NO: 34)

$A^{ms}$-$CH_2CH_2OH$ (I"-8) HO-$C^{e1p}$-$C^{e1p}$-$A^{ms}$-$U^{ms}$-$T^{e1p}$-$U^{ms}$-$G^{ms}$-$T^{e1p}$-$A^{ms}$-$U^{ms}$-$T^{e1p}$-$T^{e1p}$-$A^{ms}$-$G^{ms}$-$C^{e1p}$-$A^{ms}$-$T^{e1p}$- (SEQ ID NO: 39)

$G^{ms}$-$CH_2CH_2OH$ (I"-9) HO-$G^{ms}$-$T^{e2s}$-$A^{ms}$-$U^{ms}$-$T^{e2s}$-$T^{e2s}$-$A^{ms}$-$G^{ms}$-$C^{e2s}$-$A^{ms}$-$T^{e2s}$-$G^{ms}$-$U^{ms}$-$T^{e2s}$-$C^{ms}$-$C^{e2s}$-$C^{e2s}$- (SEQ ID NO: 34)

$A^{ms}$-$CH_2CH_2OH$ (I"-10) HO-$C^{e2s}$-$C^{e2s}$-$A^{ms}$-$U^{ms}$-$T^{e2s}$-$U^{ms}$-$G^{ms}$-$T^{e2s}$-$A^{ms}$-$U^{ms}$-$T^{e2s}$-$T^{e2s}$-$A^{ms}$-$G^{ms}$-$C^{e2s}$-$A^{ms}$-$T^{e2s}$- (SEQ ID NO: 39)

$G^{ms}$-$CH_2CH_2OH$ (I"-11) HO-$G^{ms}$-$T^{e1s}$-$A^{ms}$-$U^{ms}$-$T^{e1s}$-$T^{e1s}$-$A^{ms}$-$G^{ms}$-$C^{e1s}$-$A^{ms}$-$T^{e1s}$-$G^{ms}$-$U^{ms}$-$T^{e1s}$-$C^{ms}$-$C^{e1s}$-$C^{e1s}$- (SEQ ID NO: 34)

$A^{ms}$-$CH_2CH_2OH$ (I"-12) HO-$C^{e1s}$-$C^{e1s}$-$A^{ms}$-$U^{ms}$-$T^{e1s}$-$U^{ms}$-$G^{ms}$-$T^{e1s}$-$A^{ms}$-$U^{ms}$-$T^{e1s}$-$T^{e1s}$-$A^{ms}$-$G^{ms}$-$C^{e1s}$-$A^{ms}$-$T^{e1s}$- (SEQ ID NO: 39)

$G^{ms}$-$CH_2CH_2OH$

Especially preferable are (I"-1), (I"-2), (I"-9) and (I"-10).

Preferable examples of the compound represented by general formula (II") include the following compounds.

(II"-1) HO-$A^{mp}$-$G^{mp}$-$C^{e2p}$-$A^{mp}$-$T^{e2p}$-$G^{mp}$-$T^{e2p}$-$T^{e2p}$-$C^{mp}$-$C^{mp}$-$C^{e2p}$-$A^{mp}$-$A^{mp}$-$T^{e2p}$-$U^{mp}$-$C^{mp}$-$T^{e2p}$- (SEQ ID NO: 35)

$C^{e2p}$-$CH_2CH_2OH$ (II"-2) HO-$T^{e2p}$-$U^{mp}$-$C^{e2p}$-$C^{mp}$-$C^{e2p}$-$A^{mp}$-$A^{mp}$-$T^{e2p}$-$U^{mp}$-$C^{mp}$-$T^{e2p}$-$C^{e2p}$-$A^{mp}$-$G^{mp}$-$G^{mp}$-$A^{e2p}$- (SEQ ID NO: 38)

$A^{mp}$-$T^{e2p}$-$CH_2CH_2OH$ (II"-3) HO-$A^{mp}$-$G^{mp}$-$C^{e1p}$-$A^{mp}$-$T^{e1p}$-$G^{mp}$-$T^{e1p}$-$T^{e1p}$-$C^{mp}$-$C^{mp}$-$C^{e1p}$-$A^{mp}$-$A^{mp}$-$T^{e1p}$-$U^{mp}$-$C^{mp}$- (SEQ ID NO: 35)
$T^{e1p}$-

$C^{e1p}$-$CH_2CH_2OH$ (II"-4) HO-$T^{e1p}$-$U^{mp}$-$C^{e1p}$-$C^{mp}$-$C^{e1p}$-$A^{mp}$-$A^{mp}$-$T^{e1p}$-$U^{mp}$-$C^{mp}$-$T^{e1p}$-$C^{e1p}$-$A^{mp}$-$G^{mp}$-$G^{mp}$-$A^{e1p}$- (SEQ ID NO: 38)

$A^{mp}$-$T^{e1p}$-$CH_2CH_2OH$ (II"-5) HO-$A^{ms}$-$G^{ms}$-$C^{e2p}$-$A^{ms}$-$T^{e2p}$-$G^{ms}$-$T^{e2p}$-$T^{e2p}$-$C^{ms}$-$C^{ms}$-$C^{e2p}$-$A^{ms}$-$A^{ms}$-$T^{e2p}$-$U^{ms}$-$C^{ms}$- (SEQ ID NO: 35)
$T^{e2p}$-

$C^{e2p}$-$CH_2CH_2OH$ (II"-6) HO-$T^{e2p}$-$U^{ms}$-$C^{e2p}$-$C^{ms}$-$C^{e2p}$-$A^{ms}$-$A^{ms}$-$T^{e2p}$-$U^{ms}$-$C^{ms}$-$T^{e2p}$-$C^{e2p}$-$A^{ms}$-$G^{ms}$-$G^{ms}$-$A^{e2p}$- (SEQ ID NO: 38)
$A^{ms}$-

$T^{e2p}$-$CH_2CH_2OH$ (II"-7) HO-$A^{ms}$-$G^{ms}$-$C^{e1p}$-$A^{ms}$-$T^{e1p}$-$G^{ms}$-$T^{e1p}$-$T^{e1p}$-$C^{ms}$-$C^{ms}$-$C^{e1p}$-$A^{ms}$-$A^{ms}$-$T^{e1p}$-$U^{ms}$-$C^{ms}$- (SEQ ID NO: 35)
$T^{e1p}$-

$C^{e1p}$-$CH_2CH_2OH$ (II"-8) HO-$T^{e1p}$-$U^{ms}$-$C^{e1p}$-$C^{ms}$-$C^{e1p}$-$A^{ms}$-$A^{ms}$-$T^{e1p}$-$U^{ms}$-$C^{ms}$-$T^{e1p}$-$C^{e1p}$-$A^{ms}$-$G^{ms}$-$G^{ms}$-$A^{e1p}$- (SEQ ID NO: 38)
$A^{ms}$-

$T^{e1p}$-$CH_2CH_2OH$ (II"-9) HO-$A^{ms}$-$G^{ms}$-$C^{e2s}$-$A^{ms}$-$T^{e2s}$-$G^{ms}$-$T^{e2s}$-$T^{e2s}$-$C^{ms}$-$C^{ms}$-$C^{e2s}$-$A^{ms}$-$A^{ms}$-$T^{e2s}$-$U^{ms}$-$C^{ms}$- (SEQ ID NO: 35)
$T^{e2s}$-

$C^{e2s}$-$CH_2CH_2OH$ (II"-10) HO-$T^{e2s}$-$U^{ms}$-$C^{e2s}$-$C^{ms}$-$C^{e2s}$-$A^{ms}$-$A^{ms}$-$T^{e2s}$-$U^{ms}$-$C^{ms}$-$T^{e2s}$-$C^{e2s}$-$A^{ms}$-$G^{ms}$-$G^{ms}$-$A^{e2s}$- (SEQ ID NO: 38)
$A^{ms}$-

$T^{e2s}$-$CH_2CH_2OH$ (II"-11) HO-$A^{ms}$-$G^{ms}$-$C^{e1s}$-$A^{ms}$-$T^{e1s}$-$G^{ms}$-$T^{e1s}$-$T^{e1s}$-$C^{ms}$-$C^{ms}$-$C^{e1s}$-$A^{ms}$-$A^{ms}$-$T^{e1s}$-$U^{ms}$-$C^{ms}$- (SEQ ID NO: 35)
$T^{e1s}$-

$C^{e1s}$-$CH_2CH_2OH$ (II"-12) HO-$T^{e1s}$-$U^{ms}$-$C^{e1s}$-$C^{ms}$-$C^{e1s}$-$A^{ms}$-$A^{ms}$-$T^{e1s}$-$U^{ms}$-$C^{ms}$-$T^{e1s}$-$C^{e1s}$-$A^{ms}$-$G^{ms}$-$G^{ms}$-$A^{e1s}$- (SEQ ID NO: 38)
$A^{ms}$-

$T^{e1s}$-$CH_2CH_2OH$

Especially preferable are (II"-1), (II"-2), (II"-9) and (II"-10)
Preferable examples of the compound represented by general formula (III") include the following compounds.

(III"-1) HO-$G^{mp}$-$A^{e2p}$-$A^{mp}$-$A^{mp}$-$A^{mp}$-$C^{e2p}$-$G^{mp}$-$C^{e2p}$-$C^{e2p}$-$G^{mp}$-$C^{mp}$-$C^{e2p}$-$A^{mp}$-$T^{e2p}$-$U^{mp}$-$U^{mp}$- (SEQ ID NO: 30)

$C^{e2p}$-$T^{e2p}$-$CH_2CH_2OH$ (III"-2) HO-$G^{mp}$-$C^{e2p}$-$C^{e2p}$-$G^{mp}$-$C^{e2p}$-$C^{mp}$-$A^{mp}$-$T^{e2p}$-$U^{mp}$-$U^{mp}$-$C^{e2p}$-$U^{mp}$-$C^{e2p}$-$A^{mp}$-$A^{mp}$-$C^{e2p}$- (SEQ ID NO: 36)

$A^{e2p}$-$G^{mp}$-$CH_2CH_2OH$

-continued (III''-3) HO-$C^{e2p}$-$A^{mp}$-$T^{e2p}$-$A^{mp}$-$A^{mp}$-$T^{e2p}$-$G^{mp}$-$A^{mp}$-$A^{e2p}$-$A^{mp}$-$A^{mp}$-$C^{e2p}$-$G^{mp}$-$C^{mp}$-$C^{e2p}$-$G^{mp}$-$C^{e2p}$-$C^{e2p}$-$CH_2CH_2OH$ (SEQ ID NO: 37)

(III''-4) HO-$G^{mp}$-$A^{e1p}$-$A^{mp}$-$A^{mp}$-$A^{mp}$-$C^{e1p}$-$G^{mp}$-$C^{e1p}$-$C^{e1p}$-$G^{mp}$-$C^{mp}$-$C^{e1p}$-$A^{mp}$-$T^{e1p}$-$U^{mp}$-$U^{mp}$-$C^{e1p}$-$T^{e1p}$-$CH_2CH_2OH$ (SEQ ID NO: 30)

(III''-5) HO-$G^{mp}$-$C^{e1p}$-$C^{e1p}$-$G^{mp}$-$C^{e1p}$-$C^{mp}$-$A^{mp}$-$T^{e1p}$-$U^{mp}$-$U^{mp}$-$C^{e1p}$-$U^{mp}$-$C^{e1p}$-$A^{mp}$-$A^{mp}$-$C^{e1p}$-$A^{e1p}$-$G^{mp}$-$CH_2CH_2OH$ (SEQ ID NO: 36)

(III''-6) HO-$C^{e1p}$-$A^{mp}$-$T^{e1p}$-$A^{mp}$-$A^{mp}$-$T^{e1p}$-$G^{mp}$-$A^{mp}$-$A^{e1p}$-$A^{mp}$-$A^{mp}$-$C^{e1p}$-$G^{mp}$-$C^{mp}$-$C^{e1p}$-$G^{mp}$-$C^{e1p}$-$C^{e1p}$-$CH_2CH_2OH$ (SEQ ID NO: 37)

(III''-7) HO-$G^{ms}$-$A^{e2p}$-$A^{ms}$-$A^{ms}$-$A^{ms}$-$C^{e2p}$-$G^{ms}$-$C^{e2p}$-$C^{e2p}$-$G^{ms}$-$C^{ms}$-$C^{e2p}$-$A^{ms}$-$T^{e2p}$-$U^{ms}$-$U^{ms}$-$C^{e2p}$-$T^{e2p}$-$CH_2CH_2OH$ (SEQ ID NO: 30)

(III''-8) HO-$G^{ms}$-$C^{e2p}$-$C^{e2p}$-$G^{ms}$-$C^{e2p}$-$C^{ms}$-$A^{ms}$-$T^{e2p}$-$U^{ms}$-$U^{ms}$-$C^{e2p}$-$U^{ms}$-$C^{e2p}$-$A^{ms}$-$A^{ms}$-$C^{e2p}$-$A^{e2p}$-$G^{ms}$-$CH_2CH_2OH$ (SEQ ID NO: 36)

(III''-9) HO-$C^{e2p}$-$A^{ms}$-$T^{e2p}$-$A^{ms}$-$A^{ms}$-$T^{e2p}$-$G^{ms}$-$A^{ms}$-$A^{e2p}$-$A^{ms}$-$A^{ms}$-$C^{e2p}$-$G^{ms}$-$C^{ms}$-$C^{e2p}$-$G^{ms}$-$C^{e2p}$-$C^{e2p}$-$CH_2CH_2OH$ (SEQ ID NO: 37)

(III''-10) HO-$G^{ms}$-$A^{e1p}$-$A^{ms}$-$A^{ms}$-$A^{ms}$-$C^{e1p}$-$G^{ms}$-$C^{e1p}$-$C^{e1p}$-$G^{ms}$-$C^{ms}$-$C^{e1p}$-$A^{ms}$-$T^{e1p}$-$U^{ms}$-$U^{ms}$-$C^{e1p}$-$T^{e1p}$-$CH_2CH_2OH$ (SEQ ID NO: 30)

(III''-11) HO-$G^{ms}$-$C^{e1p}$-$C^{e1p}$-$G^{ms}$-$C^{e1p}$-$C^{ms}$-$A^{ms}$-$T^{e1p}$-$U^{ms}$-$U^{ms}$-$C^{e1p}$-$U^{ms}$-$C^{e1p}$-$A^{ms}$-$A^{ms}$-$C^{e1p}$-$A^{e1p}$-$G^{ms}$-$CH_2CH_2OH$ (SEQ ID NO: 36)

(III''-12) HO-$C^{e1p}$-$A^{ms}$-$T^{e1p}$-$A^{ms}$-$A^{ms}$-$T^{e1p}$-$G^{ms}$-$A^{ms}$-$A^{e1p}$-$A^{ms}$-$A^{ms}$-$C^{e1p}$-$G^{ms}$-$C^{ms}$-$C^{e1p}$-$G^{ms}$-$C^{e1p}$-$C^{e1p}$-$CH_2CH_2OH$ (SEQ ID NO: 37)

(III''-13) HO-$G^{ms}$-$A^{e2s}$-$A^{ms}$-$A^{ms}$-$A^{ms}$-$C^{e2s}$-$G^{ms}$-$C^{e2s}$-$C^{e2s}$-$G^{ms}$-$C^{ms}$-$C^{e2s}$-$A^{ms}$-$T^{e2s}$-$U^{ms}$-$U^{ms}$-$C^{e2s}$-$T^{e2s}$-$CH_2CH_2OH$ (SEQ ID NO: 30)

(III''-14) HO-$G^{ms}$-$C^{e2s}$-$C^{e2s}$-$G^{ms}$-$C^{e2s}$-$C^{ms}$-$A^{ms}$-$T^{e2s}$-$U^{ms}$-$U^{ms}$-$C^{e2s}$-$U^{ms}$-$C^{e2s}$-$A^{ms}$-$A^{ms}$-$C^{e2s}$-$A^{e2s}$-$G^{ms}$-$CH_2CH_2OH$ (SEQ ID NO: 36)

(III''-15) HO-$C^{e2s}$-$A^{ms}$-$T^{e2s}$-$A^{ms}$-$A^{ms}$-$T^{e2s}$-$G^{ms}$-$A^{ms}$-$A^{e2s}$-$A^{ms}$-$A^{ms}$-$C^{e2s}$-$G^{ms}$-$C^{ms}$-$C^{e2s}$-$G^{ms}$-$C^{e2s}$-$C^{e2s}$-$CH_2CH_2OH$ (SEQ ID NO: 37)

(III''-16) HO-$G^{ms}$-$A^{e1s}$-$A^{ms}$-$A^{ms}$-$A^{ms}$-$C^{e1s}$-$G^{ms}$-$C^{e1s}$-$C^{e1s}$-$G^{ms}$-$C^{ms}$-$C^{e1s}$-$A^{ms}$-$T^{e1s}$-$U^{ms}$-$U^{ms}$-$C^{e1s}$-$T^{e1s}$-$CH_2CH_2OH$ (SEQ ID NO: 30)

(III''-17) HO-$G^{ms}$-$C^{e1s}$-$C^{e1s}$-$G^{ms}$-$C^{e1s}$-$C^{ms}$-$A^{ms}$-$T^{e1s}$-$U^{ms}$-$U^{ms}$-$C^{e1s}$-$U^{ms}$-$C^{e1s}$-$A^{ms}$-$A^{ms}$-$C^{e1s}$-$A^{e1s}$-$G^{ms}$-$CH_2CH_2OH$ (SEQ ID NO: 36)

-continued (III"-18) HO-$C^{els}$-$A^{ms}$-$T^{els}$-$A^{ms}$-$A^{ms}$-$T^{els}$-$G^{ms}$-$A^{ms}$-$A^{els}$-$A^{ms}$-$A^{ms}$-$C^{els}$-$G^{ms}$-$C^{ms}$-$C^{els}$-$G^{ms}$- (SEQ ID NO: 37)

$C^{els}$-

$C^{els}$-CH$_2$CH$_2$OH

Especially preferable are (III"-1), (III"-2), (III"-3), (III"-13), (III"-14) and (III"-15).

Preferable examples of the compound represented by general formula (IV") include the following compounds.

(IV"-1) HO-$G^{mp}$-$G^{mp}$-$C^{e2p}$-$T^{e2p}$-$G^{mp}$-$C^{mp}$-$T^{e2p}$-$T^{e2p}$-$U^{mp}$-$G^{mp}$-$C^{e2p}$-$C^{mp}$-$C^{mp}$-$T^{e2p}$-$C^{e2p}$-$A^{mp}$- (SEQ ID NO: 43)

$G^{mp}$-$C^{e2p}$-CH$_2$CH$_2$OH (IV"-2) HO-$G^{mp}$-$C^{e2p}$-$T^{e2p}$-$A^{mp}$-$G^{mp}$-$G^{mp}$-$T^{e2p}$-$C^{e2p}$-$A^{mp}$-$G^{mp}$-$G^{mp}$-$C^{e2p}$-$T^{e2p}$-$G^{mp}$-$C^{mp}$-$T^{e2p}$- (SEQ ID NO: 46)

$T^{e2p}$-$U^{mp}$-CH$_2$CH$_2$OH (IV"-3) HO-$G^{mp}$-$G^{mp}$-$C^{e1p}$-$T^{e1p}$-$G^{mp}$-$C^{mp}$-$T^{e1p}$-$T^{e1p}$-$U^{mp}$-$G^{mp}$-$C^{e1p}$-$C^{mp}$-$C^{mp}$-$T^{e1p}$-$C^{e1p}$-$A^{mp}$- (SEQ ID NO: 43)

$G^{mp}$-$C^{e1p}$-CH$_2$CH$_2$OH (IV"-4) HO-$G^{mp}$-$C^{e1p}$-$T^{e1p}$-$A^{mp}$-$G^{mp}$-$G^{mp}$-$T^{e1p}$-$C^{e1p}$-$A^{mp}$-$G^{mp}$-$G^{mp}$-$C^{e1p}$-$T^{e1p}$-$G^{mp}$-$C^{mp}$-$T^{e1p}$- (SEQ ID NO: 46)

$T^{e1p}$-$U^{mp}$-CH$_2$CH$_2$OH (IV"-5) HO-$G^{ms}$-$G^{ms}$-$C^{e2p}$-$T^{e2p}$-$G^{ms}$-$C^{ms}$-$T^{e2p}$-$T^{e2p}$-$U^{ms}$-$G^{ms}$-$C^{e2p}$-$C^{ms}$-$C^{ms}$-$T^{e2p}$-$C^{e2p}$-$A^{ms}$- (SEQ ID NO: 43)

$G^{ms}$-

$C^{e2p}$-CH$_2$CH$_2$OH (IV"-6) HO-$G^{ms}$-$C^{e2p}$-$T^{e2p}$-$A^{ms}$-$G^{ms}$-$G^{ms}$-$T^{e2p}$-$C^{e2p}$-$A^{ms}$-$G^{ms}$-$G^{ms}$-$C^{e2p}$-$T^{e2p}$-$G^{ms}$-$C^{ms}$-$T^{e2p}$- (SEQ ID NO: 46)

$T^{e2p}$-

$U^{ms}$-CH$_2$CH$_2$OH (IV"-7) HO-$G^{ms}$-$G^{ms}$-$C^{e1p}$-$T^{e1p}$-$G^{ms}$-$C^{ms}$-$T^{e1p}$-$T^{e1p}$-$U^{ms}$-$G^{ms}$-$C^{e1p}$-$C^{ms}$-$C^{ms}$-$T^{e1p}$-$C^{e1p}$-$A^{ms}$- (SEQ ID NO: 43)

$G^{ms}$-

$C^{e1p}$-CH$_2$CH$_2$OH (IV"-8) HO-$G^{ms}$-$C^{e1p}$-$T^{e1p}$-$A^{ms}$-$G^{ms}$-$G^{ms}$-$T^{e1p}$-$C^{e1p}$-$A^{ms}$-$G^{ms}$-$G^{ms}$-$C^{e1p}$-$T^{e1p}$-$G^{ms}$-$C^{ms}$-$T^{e1p}$- (SEQ ID NO: 46)

$T^{e1p}$-

$U^{ms}$-CH$_2$CH$_2$OH (IV"-9) HO-$G^{ms}$-$G^{ms}$-$C^{e2s}$-$T^{e2s}$-$G^{ms}$-$C^{ms}$-$T^{e2s}$-$T^{e2s}$-$U^{ms}$-$G^{ms}$-$C^{e2s}$-$C^{ms}$-$C^{ms}$-$T^{e2s}$-$C^{e2s}$-$A^{ms}$- (SEQ ID NO: 43)

$G^{ms}$-

$C^{e2s}$-CH$_2$CH$_2$OH (IV"-10) HO-$G^{ms}$-$C^{e2s}$-$T^{e2s}$-$A^{ms}$-$G^{ms}$-$G^{ms}$-$T^{e2s}$-$C^{e2s}$-$A^{ms}$-$G^{ms}$-$G^{ms}$-$C^{e2s}$-$T^{e2s}$-$G^{ms}$-$C^{ms}$-$T^{e2s}$- (SEQ ID NO: 46)

$T^{e2s}$-

$U^{ms}$-CH$_2$CH$_2$OH (IV"-11) HO-$G^{ms}$-$G^{ms}$-$C^{els}$-$T^{els}$-$G^{ms}$-$C^{ms}$-$T^{els}$-$T^{els}$-$U^{ms}$-$G^{ms}$-$C^{els}$-$C^{ms}$-$C^{ms}$-$T^{els}$-$C^{els}$-$A^{ms}$- (SEQ ID NO: 43)

$G^{ms}$-

$C^{els}$-CH$_2$CH$_2$OH (IV"-12) HO-$G^{ms}$-$C^{els}$-$T^{els}$-$A^{ms}$-$G^{ms}$-$G^{ms}$-$T^{els}$-$C^{els}$-$A^{ms}$-$G^{ms}$-$G^{ms}$-$C^{els}$-$T^{els}$-$G^{ms}$-$C^{ms}$-$T^{els}$- (SEQ ID NO: 46)

$T^{els}$-

$U^{ms}$-CH$_2$CH$_2$OH

Especially preferable are (IV"-1), (IV"-2), (IV"-9) and (IV"-10).

Preferable examples of the compound represented by general formula (V") include the following compounds.

(SEQ ID NO: 44)
(V"-1) HO-$A^{mp}$-$G^{mp}$-$T^{e2p}$-$C^{e2p}$-$C^{e2p}$-$A^{mp}$-$G^{mp}$-$G^{mp}$-$A^{e2p}$-$G^{mp}$-$C^{e2p}$-$T^{e2p}$-$A^{mp}$-$G^{mp}$-$G^{mp}$-$T^{e2p}$-

$C^{e2p}$-$A^{mp}$-$CH_2CH_2OH$ (SEQ ID NO: 44)
(V"-2) HO-$A^{mp}$-$G^{mp}$-$T^{e1p}$-$C^{e1p}$-$C^{e1p}$-$A^{mp}$-$G^{mp}$-$G^{mp}$-$A^{e1p}$-$G^{mp}$-$C^{e1p}$-$T^{e1p}$-$A^{mp}$-$G^{mp}$-$G^{mp}$-$T^{e1p}$-

$C^{e1p}$-$A^{mp}$-$CH_2CH_2OH$ (SEQ ID NO: 44)
(V"-3) HO-$A^{ms}$-$G^{ms}$-$T^{e2p}$-$C^{e2p}$-$C^{e2p}$-$A^{ms}$-$G^{ms}$-$G^{ms}$-$A^{e2p}$-$G^{ms}$-$C^{e2p}$-$T^{e2p}$-$A^{ms}$-$G^{ms}$-$G^{ms}$-$T^{e2p}$-

$C^{e2p}$-$A^{ms}$-$CH_2CH_2OH$ (SEQ ID NO: 44)
(V"-4) HO-$A^{ms}$-$G^{ms}$-$T^{e1p}$-$C^{e1p}$-$C^{e1p}$-$A^{ms}$-$G^{ms}$-$G^{ms}$-$A^{e1p}$-$G^{ms}$-$C^{e1p}$-$T^{e1p}$-$A^{ms}$-$G^{ms}$-$G^{ms}$-$T^{e1p}$-

$C^{e1p}$-$A^{ms}$-$CH_2CH_2OH$ (SEQ ID NO: 44)
(V"-5) HO-$A^{ms}$-$G^{ms}$-$T^{e2s}$-$C^{e2s}$-$C^{e2s}$-$A^{ms}$-$G^{ms}$-$G^{ms}$-$A^{e2s}$-$G^{ms}$-$C^{e2s}$-$T^{e2s}$-$A^{ms}$-$G^{ms}$-$G^{ms}$-$T^{e2s}$-

$C^{e2s}$-$A^{ms}$-$CH_2CH_2OH$ (SEQ ID NO: 44)
(V"-6) HO-$A^{ms}$-$G^{ms}$-$T^{e1s}$-$C^{e1s}$-$C^{e1s}$-$A^{ms}$-$G^{ms}$-$G^{ms}$-$A^{e1s}$-$G^{ms}$-$C^{e1s}$-$T^{e1s}$-$A^{ms}$-$G^{ms}$-$G^{ms}$-$T^{e1s}$-

$C^{e1s}$-$A^{ms}$-$CH_2CH_2OH$

Especially preferable are (V"-1) and (V"-5)

Preferable examples of the compound represented by general formula (VI") include the following compounds.

(SEQ ID NO: 47)
(VI"-1) HO-$G^{mp}$-$C^{e2p}$-$A^{mp}$-$G^{mp}$-$C^{e2p}$-$C^{e2p}$-$U^{mp}$-$C^{mp}$-$T^{e2p}$-$C^{mp}$-$G^{mp}$-$C^{e2p}$-$T^{e2p}$-$C^{mp}$-$A^{mp}$-$C^{e2p}$-

$T^{e2p}$-$C^{mp}$-$CH_2CH_2OH$ (SEQ ID NO: 48)
(VI"-2) HO-$T^{e2p}$-$C^{e2p}$-$U^{mp}$-$U^{mp}$-$C^{e2p}$-$C^{e2p}$-$A^{mp}$-$A^{mp}$-$A^{mp}$-$G^{mp}$-$C^{e2p}$-$A^{mp}$-$G^{mp}$-$C^{e2p}$-$C^{mp}$-$U^{mp}$-

$C^{e2p}$-$T^{e2p}$-$CH_2CH_2OH$ (SEQ ID NO: 47)
(VI"-3) HO-$G^{mp}$-$C^{e1p}$-$A^{mp}$-$G^{mp}$-$C^{e1p}$-$C^{e1p}$-$U^{mp}$-$C^{mp}$-$T^{e1p}$-$C^{mp}$-$G^{mp}$-$C^{e1p}$-$T^{e1p}$-$C^{mp}$-$A^{mp}$-$C^{e1p}$-

$T^{e1p}$-$C^{mp}$-$CH_2CH_2OH$ (SEQ ID NO: 48)
(VI"-4) HO-$T^{e1p}$-$C^{e1p}$-$U^{mp}$-$U^{mp}$-$C^{e1p}$-$C^{e1p}$-$A^{mp}$-$A^{mp}$-$A^{mp}$-$G^{mp}$-$C^{e1p}$-$A^{mp}$-$G^{mp}$-$C^{e1p}$-$C^{mp}$-$U^{mp}$-

$C^{e1p}$-$T^{e1p}$-$CH_2CH_2OH$ (SEQ ID NO: 47)
(VI"-5) HO-$G^{ms}$-$C^{e2p}$-$A^{ms}$-$G^{ms}$-$C^{e2p}$-$C^{e2p}$-$U^{ms}$-$C^{ms}$-$T^{e2p}$-$C^{ms}$-$G^{ms}$-$C^{e2p}$-$T^{e2p}$-$C^{ms}$-$A^{ms}$-$C^{e2p}$-

$T^{e2p}$-

$C^{ms}$-$CH_2CH_2OH$ (SEQ ID NO: 48)
(VI"-6) HO-$T^{e2p}$-$C^{e2p}$-$U^{ms}$-$U^{ms}$-$C^{e2p}$-$C^{e2p}$-$A^{ms}$-$A^{ms}$-$A^{ms}$-$G^{ms}$-$C^{e2p}$-$A^{ms}$-$G^{ms}$-$C^{e2p}$-$C^{ms}$-$U^{ms}$-

$C^{e2p}$-

$T^{e2p}$-$CH_2CH_2OH$

-continued (SEQ ID NO: 47)
(VI"-7) HO-$G^{ms}$-$C^{e1p}$-$A^{ms}$-$G^{ms}$-$C^{e1p}$-$C^{e1p}$-$U^{ms}$-$C^{ms}$-$T^{e1p}$-$C^{ms}$-$G^{ms}$-$C^{e1p}$-$T^{e1p}$-$C^{ms}$-$A^{ms}$-$C^{e1p}$-$T^{e1p}$-

$C^{ms}$-$CH_2CH_2OH$ (SEQ ID NO: 48)
(VI"-8) HO-$T^{e1p}$-$C^{e1p}$-$U^{ms}$-$U^{ms}$-$C^{e1p}$-$C^{e1p}$-$A^{ms}$-$A^{ms}$-$A^{ms}$-$G^{ms}$-$C^{e1p}$-$A^{ms}$-$G^{ms}$-$C^{e1p}$-$C^{ms}$-$U^{ms}$-$C^{e1p}$-

$T^{e1p}$-$CH_2CH_2OH$ (SEQ ID NO: 47)
(VI"-9) HO-$G^{ms}$-$C^{e2s}$-$A^{ms}$-$G^{ms}$-$C^{e2s}$-$C^{e2s}$-$U^{ms}$-$C^{ms}$-$T^{e2s}$-$C^{ms}$-$G^{ms}$-$C^{e2s}$-$T^{e2s}$-$C^{ms}$-$A^{ms}$-$C^{e2s}$-$T^{e2s}$-

$C^{ms}$-$CH_2CH_2OH$ (SEQ ID NO: 48)
(VI"-10) HO-$T^{e2s}$-$C^{e2s}$-$U^{ms}$-$U^{ms}$-$C^{e2s}$-$C^{e2s}$-$A^{ms}$-$A^{ms}$-$A^{ms}$-$G^{ms}$-$C^{e2s}$-$A^{ms}$-$G^{ms}$-$C^{e2s}$-$C^{ms}$-$U^{ms}$-$C^{e2s}$-

$T^{e2s}$-$CH_2CH_2OH$ (SEQ ID NO: 47)
(VI"-11) HO-$G^{ms}$-$C^{e1s}$-$A^{ms}$-$G^{ms}$-$C^{e1s}$-$C^{e1s}$-$U^{ms}$-$C^{ms}$-$T^{e1s}$-$C^{ms}$-$G^{ms}$-$C^{e1s}$-$T^{e1s}$-$C^{ms}$-$A^{ms}$-$C^{e1s}$-$T^{e1s}$-

$C^{ms}$-$CH_2CH_2OH$ (SEQ ID NO: 48)
(VI"-12) HO-$T^{e1s}$-$C^{e1s}$-$U^{ms}$-$U^{ms}$-$C^{e1s}$-$C^{e1s}$-$A^{ms}$-$A^{ms}$-$A^{ms}$-$G^{ms}$-$C^{e1s}$-$A^{ms}$-$G^{ms}$-$C^{e1s}$-$C^{ms}$-$U^{ms}$-$C^{e1s}$-

$T^{e1s}$-$CH_2CH_2OH$

Especially preferable are (VI"-1), (VI"-2), (VI"-9) and (VI"-10).

Preferable examples of the compound represented by general formula (VII") include the following compounds.

(SEQ ID NO: 55)
(VII"-1) HO-$C^{mp}$-$T^{e2p}$-$A^{mp}$-$T^{e2p}$-$G^{mp}$-$A^{mp}$-$G^{mp}$-$T^{e2p}$-$T^{e2p}$-$T^{e2p}$-$C^{mp}$-$T^{e2p}$-$T^{e2p}$-$C^{mp}$-$C^{mp}$-$A^{mp}$-

$A^{e2p}$-$A^{mp}$-$CH_2CH_2OH$ (SEQ ID NO: 55)
(VII"-2) HO-$C^{mp}$-$T^{e1p}$-$A^{mp}$-$T^{e1p}$-$G^{mp}$-$A^{mp}$-$G^{mp}$-$T^{e1p}$-$T^{e1p}$-$T^{e1p}$-$C^{mp}$-$T^{e1p}$-$T^{e1p}$-$C^{mp}$-$C^{mp}$-$A^{mp}$-

$A^{e1p}$-$A^{mp}$-$CH_2CH_2OH$ (SEQ ID NO: 55)
(VII"-3) HO-$C^{ms}$-$T^{e2p}$-$A^{ms}$-$T^{e2p}$-$G^{ms}$-$A^{ms}$-$G^{ms}$-$T^{e2p}$-$T^{e2p}$-$T^{e2p}$-$C^{ms}$-$T^{e2p}$-$T^{e2p}$-$C^{ms}$-$C^{ms}$-$A^{ms}$-

$A^{e2p}$-$A^{ms}$-$CH_2CH_2OH$ (SEQ ID NO: 55)
(VII"-4) HO-$C^{ms}$-$T^{e1p}$-$A^{ms}$-$T^{e1p}$-$G^{ms}$-$A^{ms}$-$G^{ms}$-$T^{e1p}$-$T^{e1p}$-$T^{e1p}$-$C^{ms}$-$T^{e1p}$-$T^{e1p}$-$C^{ms}$-$C^{ms}$-$A^{ms}$-

$A^{e1p}$-$A^{ms}$-$CH_2CH_2OH$ (SEQ ID NO: 55)
(VII"-5) HO-$C^{ms}$-$T^{e2s}$-$A^{ms}$-$T^{e2s}$-$G^{ms}$-$A^{ms}$-$G^{ms}$-$T^{e2s}$-$T^{e2s}$-$T^{e2s}$-$C^{ms}$-$T^{e2s}$-$T^{e2s}$-$C^{ms}$-$C^{ms}$-$A^{ms}$-

$A^{e2s}$-$A^{ms}$-$CH_2CH_2OH$ (SEQ ID NO: 55)
(VII"-6) HO-$C^{ms}$-$T^{e1s}$-$A^{ms}$-$T^{e1s}$-$G^{ms}$-$A^{ms}$-$G^{ms}$-$T^{e1s}$-$T^{e1s}$-$T^{e1s}$-$C^{ms}$-$T^{e1s}$-$T^{e1s}$-$C^{ms}$-$C^{ms}$-$A^{ms}$-

$A^{e1s}$-$A^{ms}$-$CH_2CH_2OH$

Especially preferable are (VII"-1) and (VII"-5).

Preferable examples of the compound represented by general formula (VIII") include the following compounds.

(SEQ ID NO: 53)
(VIII"-1) HO-$A^{mp}$-$G^{mp}$-$C^{e2p}$-$T^{e2p}$-$C^{mp}$-$U^{mp}$-$T^{e2p}$-$U^{mp}$-$T^{e2p}$-$A^{mp}$-$C^{mp}$-$T^{e2p}$-$C^{e2p}$-$C^{mp}$-$C^{mp}$-$T^{e2p}$-$T^{e2p}$-$G^{mp}$-$CH_2CH_2OH$ (SEQ ID NO: 54)
(VIII"-2) HO-$C^{e2p}$-$C^{e2p}$-$A^{mp}$-$U^{mp}$-$T^{e2p}$-$G^{mp}$-$U^{mp}$-$T^{e2p}$-$U^{mp}$-$C^{e2p}$-$A^{mp}$-$U^{mp}$-$C^{e2p}$-$A^{mp}$-$G^{mp}$-$C^{mp}$-$T^{e2p}$-$C^{e2p}$-$CH_2CH_2OH$ (SEQ ID NO: 53)
(VIII"-3) HO-$A^{mp}$-$G^{mp}$-$C^{e1p}$-$T^{e1p}$-$C^{mp}$-$U^{mp}$-$T^{e1p}$-$U^{mp}$-$T^{e1p}$-$A^{mp}$-$C^{mp}$-$T^{e1p}$-$C^{e1p}$-$C^{mp}$-$C^{mp}$-$T^{e1p}$-$T^{e1p}$-$G^{mp}$-$CH_2CH_2OH$ (SEQ ID NO: 54)
(VIII"-4) HO-$C^{e1p}$-$C^{e1p}$-$A^{mp}$-$U^{mp}$-$T^{e1p}$-$G^{mp}$-$U^{mp}$-$T^{e1p}$-$U^{mp}$-$C^{e1p}$-$A^{mp}$-$U^{mp}$-$C^{e1p}$-$A^{mp}$-$G^{mp}$-$C^{mp}$-$T^{e1p}$-$C^{e1p}$-$CH_2CH_2OH$ (SEQ ID NO: 53)
(VIII"-5) HO-$A^{ms}$-$G^{ms}$-$C^{e2p}$-$T^{e2p}$-$C^{ms}$-$U^{ms}$-$T^{e2p}$-$U^{ms}$-$T^{e2p}$-$A^{ms}$-$C^{ms}$-$T^{e2p}$-$C^{e2p}$-$C^{ms}$-$C^{ms}$-$T^{e2p}$-$T^{e2p}$-$G^{ms}$-$CH_2CH_2OH$ (SEQ ID NO: 54)
(VIII"-6) HO-$C^{e2p}$-$C^{e2p}$-$A^{ms}$-$U^{ms}$-$T^{e2p}$-$G^{ms}$-$U^{ms}$-$T^{e2p}$-$U^{ms}$-$C^{e2p}$-$A^{ms}$-$U^{ms}$-$C^{e2p}$-$A^{ms}$-$G^{ms}$-$C^{ms}$-$T^{e2p}$-$C^{e2p}$-$CH_2CH_2OH$ (SEQ ID NO: 53)
(VIII"-7) HO-$A^{ms}$-$G^{ms}$-$C^{e1p}$-$T^{e1p}$-$C^{ms}$-$U^{ms}$-$T^{e1p}$-$U^{ms}$-$T^{e1p}$-$A^{ms}$-$C^{ms}$-$T^{e1p}$-$C^{e1p}$-$C^{ms}$-$C^{ms}$-$T^{e1p}$-$T^{e1p}$-$G^{ms}$-$CH_2CH_2OH$ (SEQ ID NO: 54)
(VIII"-8) HO-$C^{e1p}$-$C^{e1p}$-$A^{ms}$-$U^{ms}$-$T^{e1p}$-$G^{ms}$-$U^{ms}$-$T^{e1p}$-$U^{ms}$-$C^{e1p}$-$A^{ms}$-$U^{ms}$-$C^{e1p}$-$A^{ms}$-$G^{ms}$-$C^{ms}$-$T^{e1p}$-$C^{e1p}$-$CH_2CH_2OH$ (SEQ ID NO: 53)
(VIII"-9) HO-$A^{ms}$-$G^{ms}$-$C^{e2s}$-$T^{e2s}$-$C^{ms}$-$U^{ms}$-$T^{e2s}$-$U^{ms}$-$T^{e2s}$-$A^{ms}$-$C^{ms}$-$T^{e2s}$-$C^{e2s}$-$C^{ms}$-$C^{ms}$-$T^{e2s}$-$T^{e2s}$-$G^{ms}$-$CH_2CH_2OH$ (SEQ ID NO: 54)
(VIII"-10) HO-$C^{e2s}$-$C^{e2s}$-$A^{ms}$-$U^{ms}$-$T^{e2s}$-$G^{ms}$-$U^{ms}$-$T^{e2s}$-$U^{ms}$-$C^{e2s}$-$A^{ms}$-$U^{ms}$-$C^{e2s}$-$A^{ms}$-$G^{ms}$-$C^{ms}$-$T^{e2s}$-$C^{e2s}$-$CH_2CH_2OH$ (SEQ ID NO: 53)
(VIII"-11) HO-$A^{ms}$-$G^{ms}$-$C^{e1s}$-$T^{e1s}$-$C^{ms}$-$U^{ms}$-$T^{e1s}$-$U^{ms}$-$T^{e1s}$-$A^{ms}$-$C^{ms}$-$T^{e1s}$-$C^{e1s}$-$C^{ms}$-$C^{ms}$-$T^{e1s}$-$T^{e1s}$-$G^{ms}$-$CH_2CH_2OH$ (SEQ ID NO: 54)
(VIII"-12) HO-$C^{e1s}$-$C^{e1s}$-$A^{ms}$-$U^{ms}$-$T^{e1s}$-$G^{ms}$-$U^{ms}$-$T^{e1s}$-$U^{ms}$-$C^{e1s}$-$A^{ms}$-$U^{ms}$-$C^{e1s}$-$A^{ms}$-$G^{ms}$-$C^{ms}$-$T^{e1s}$-$C^{e1s}$-$CH_2CH_2OH$

Especially preferable are (VIII'-1), (VIII'-2), (VIII'-9) and (VIII'-10).

Preferable examples of the compound represented by general formula (IX") include the following compounds.

(SEQ ID NO: 63)
(IX"-1) HO-$T^{e2p}$-$A^{e2p}$-$A^{e2p}$-$C^{e2p}$-$A^{e2p}$-$G^{mp}$-$U^{mp}$-$C^{mp}$-$U^{mp}$-$G^{mp}$-$A^{mp}$-$G^{mp}$-$U^{mp}$-$A^{e2p}$-$G^{e2p}$-$G^{e2p}$-$A^{e2p}$-$G^{e2p}$-$CH_2CH_2OH$ (SEQ ID NO: 56)
(IX"-2) Ph-$T^{e2p}$-$G^{e2p}$-$T^{e2p}$-$G^{e2p}$-$T^{e2p}$-$C^{mp}$-$A^{mp}$-$C^{mp}$-$C^{mp}$-$A^{mp}$-$G^{mp}$-$A^{mp}$-$G^{mp}$-$U^{mp}$-$A^{mp}$-$A^{e2p}$-$C^{e2p}$-$A^{e2p}$-$G^{e2p}$-$T^{e2p}$-$CH_2CH_2OH$

-continued (SEQ ID NO: 56)
(IX"-3) HO-T$^{e2p}$-G$^{e2p}$-T$^{e2p}$-G$^{e2p}$-T$^{e2p}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e2p}$-C$^{e2p}$-A$^{e2p}$-G$^{e2p}$-T$^{e2p}$-CH$_2$CH$_2$OH (SEQ ID NO: 63)
(IX"-4) HO-T$^{e1p}$-A$^{e1p}$-A$^{e1p}$-C$^{e1p}$-A$^{e1p}$-G$^{mp}$-U$^{mp}$-C$^{mp}$-U$^{mp}$-G$^{mp}$-A$^{mp}$-G$^{mp}$-U$^{mp}$-A$^{e1p}$-G$^{e1p}$-G$^{e1p}$-A$^{e1p}$-G$^{e1p}$-CH$_2$CH$_2$OH (SEQ ID NO: 56)
(IX"-5) Ph-T$^{e1p}$-G$^{e1p}$-T$^{e1p}$-G$^{e1p}$-T$^{e1p}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e1p}$-C$^{e1p}$-A$^{e1p}$-G$^{e1p}$-T$^{e1p}$-CH$_2$CH$_2$OH (SEQ ID NO: 56)
(IX"-6) HO-T$^{e1p}$-G$^{e1p}$-T$^{e1p}$-G$^{e1p}$-T$^{e1p}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e1p}$-C$^{e1p}$-A$^{e1p}$-G$^{e1p}$-T$^{e1p}$-CH$_2$CH$_2$OH (SEQ ID NO: 63)
(IX"-7) HO-T$^{e2p}$-A$^{e2p}$-A$^{e2p}$-C$^{e2p}$-A$^{e2p}$-G$^{ms}$-U$^{ms}$-C$^{ms}$-U$^{ms}$-G$^{ms}$-A$^{ms}$-G$^{ms}$-U$^{ms}$-A$^{e2p}$-G$^{e2p}$-G$^{e2p}$-A$^{e2p}$-G$^{e2p}$-CH$_2$CH$_2$OH (SEQ ID NO: 56)
(IX"-8) Ph-T$^{e2p}$-G$^{e2p}$-T$^{e2p}$-G$^{e2p}$-T$^{e2p}$-C$^{ms}$-A$^{ms}$-C$^{ms}$-C$^{ms}$-A$^{ms}$-G$^{ms}$-A$^{ms}$-G$^{ms}$-U$^{ms}$-A$^{ms}$-A$^{e2p}$-C$^{e2p}$-A$^{e2p}$-G$^{e2p}$-T$^{e2p}$-CH$_2$CH$_2$OH (SEQ ID NO: 56)
(IX"-9) HO-T$^{e2p}$-G$^{e2p}$-T$^{e2p}$-G$^{e2p}$-T$^{e2p}$-C$^{ms}$-A$^{ms}$-C$^{ms}$-C$^{ms}$-A$^{ms}$-G$^{ms}$-A$^{ms}$-G$^{ms}$-U$^{ms}$-A$^{ms}$-A$^{e2p}$-C$^{e2p}$-A$^{e2p}$-G$^{e2p}$-T$^{e2p}$-CH$_2$CH$_2$OH (SEQ ID NO: 63)
(IX"-10) HO-T$^{e1p}$-A$^{e1p}$-A$^{e1p}$-C$^{e1p}$-A$^{e1p}$-G$^{ms}$-U$^{ms}$-C$^{ms}$-U$^{ms}$-G$^{ms}$-A$^{ms}$-G$^{ms}$-U$^{ms}$-A$^{e1p}$-G$^{e1p}$-G$^{e1p}$-A$^{e1p}$-G$^{e1p}$-CH$_2$CH$_2$OH (SEQ ID NO: 56)
(IX"-11) Ph-T$^{e1p}$-G$^{e1p}$-T$^{e1p}$-G$^{e1p}$-T$^{e1p}$-C$^{ms}$-A$^{ms}$-C$^{ms}$-C$^{ms}$-A$^{ms}$-G$^{ms}$-A$^{ms}$-G$^{ms}$-U$^{ms}$-A$^{ms}$-A$^{e1p}$-C$^{e1p}$-A$^{e1p}$-G$^{e1p}$-T$^{e1p}$-CH$_2$CH$_2$OH (SEQ ID NO: 56)
(IX"-12) HO-T$^{e1p}$-G$^{e1p}$-T$^{e1p}$-G$^{e1p}$-T$^{e1p}$-C$^{ms}$-A$^{ms}$-C$^{ms}$-C$^{ms}$-A$^{ms}$-G$^{ms}$-A$^{ms}$-G$^{ms}$-U$^{ms}$-A$^{ms}$-A$^{e1p}$-C$^{e1p}$-A$^{e1p}$-G$^{e1p}$-T$^{e1p}$-CH$_2$CH$_2$OH (SEQ ID NO: 63)
(IX"-13) HO-T$^{e2s}$-A$^{e2s}$-A$^{e2s}$-C$^{e2s}$-A$^{e2s}$-G$^{mp}$-U$^{mp}$-C$^{mp}$-U$^{mp}$-G$^{mp}$-A$^{mp}$-G$^{mp}$-U$^{mp}$-A$^{e2s}$-G$^{e2s}$-G$^{e2s}$-A$^{e2s}$-G$^{e2s}$-CH$_2$CH$_2$OH (SEQ ID NO: 56)
(IX"-14) Ph-T$^{e2s}$-G$^{e2s}$-T$^{e2s}$-G$^{e2s}$-T$^{e2s}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e2s}$-C$^{e2s}$-A$^{e2s}$-G$^{e2s}$-T$^{e2s}$-CH$_2$CH$_2$OH (SEQ ID NO: 56)
(IX"-15) HO-T$^{e2s}$-G$^{e2s}$-T$^{e2s}$-G$^{e2s}$-T$^{e2s}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e2s}$-C$^{e2s}$-A$^{e2s}$-G$^{e2s}$-T$^{e2s}$-CH$_2$CH$_2$OH (SEQ ID NO: 63)
(IX"-16) HO-T$^{e1s}$-A$^{e1s}$-A$^{e1s}$-C$^{e1s}$-A$^{e1s}$-G$^{mp}$-U$^{mp}$-C$^{mp}$-U$^{mp}$-G$^{mp}$-A$^{mp}$-G$^{mp}$-U$^{mp}$-A$^{e1s}$-G$^{e1s}$-G$^{e1s}$-A$^{e1s}$-G$^{e1s}$-CH$_2$CH$_2$OH (SEQ ID NO: 56)
(IX"-17) Ph-T$^{e1s}$-G$^{e1s}$-T$^{e1s}$-G$^{e1s}$-T$^{e1s}$-C$^{mp}$-A$^{mp}$-C$^{mp}$-C$^{mp}$-A$^{mp}$-G$^{mp}$-A$^{mp}$-G$^{mp}$-U$^{mp}$-A$^{mp}$-A$^{e1s}$-C$^{e1s}$-A$^{e1s}$-G$^{e1s}$-T$^{e1s}$-CH$_2$CH$_2$OH -continued (IX"-18) HO-$T^{els}$-$G^{els}$-$T^{els}$-$G^{els}$-$T^{els}$-$C^{mp}$-$A^{mp}$-$C^{mp}$-$C^{mp}$-$A^{mp}$-$G^{mp}$-$A^{mp}$-$G^{mp}$-$U^{mp}$-$A^{mp}$-$A^{els}$-$C^{els}$-$A^{els}$-$G^{els}$-$T^{els}$-$CH_2CH_2OH$ (SEQ ID NO: 56)

Especially preferable are (IX"-1), (IX"-2), (IX"-3), (IX"-13), (IX"-14) and (IX"-15).

Preferable examples of the compound represented by general formula (X") include the following compounds.

(X"-1) Ph-$A^{e2p}$-$G^{e2p}$-$G^{e2p}$-$T^{e2p}$-$T^{e2p}$-$G^{mp}$-$U^{mp}$-$G^{mp}$-$U^{mp}$-$C^{mp}$-$A^{mp}$-$C^{mp}$-$C^{mp}$-$A^{mp}$-$G^{mp}$-$A^{e2p}$-$G^{e2p}$-$T^{e2p}$-$A^{e2p}$-$A^{e2p}$-$CH_2CH_2OH$ (SEQ ID NO: 57)

(X"-2) HO-$A^{e2p}$-$G^{e2p}$-$G^{e2p}$-$T^{e2p}$-$T^{e2p}$-$G^{mp}$-$U^{mp}$-$G^{mp}$-$U^{mp}$-$C^{mp}$-$A^{mp}$-$C^{mp}$-$C^{mp}$-$A^{mp}$-$G^{mp}$-$A^{e2p}$-$G^{e2p}$-$T^{e2p}$-$A^{e2p}$-$A^{e2p}$-$CH_2CH_2OH$ (SEQ ID NO: 57)

(X"-3) Ph-$A^{e1p}$-$G^{e1p}$-$G^{e1p}$-$T^{e1p}$-$T^{e1p}$-$G^{mp}$-$U^{mp}$-$G^{mp}$-$U^{mp}$-$C^{mp}$-$A^{mp}$-$C^{mp}$-$C^{mp}$-$A^{mp}$-$G^{mp}$-$A^{e1p}$-$G^{e1p}$-$T^{e1p}$-$A^{e1p}$-$A^{e1p}$-$CH_2CH_2OH$ (SEQ ID NO: 57)

(X"-4) HO-$A^{e1p}$-$G^{e1p}$-$G^{e1p}$-$T^{e1p}$-$T^{e1p}$-$G^{mp}$-$U^{mp}$-$G^{mp}$-$U^{mp}$-$C^{mp}$-$A^{mp}$-$C^{mp}$-$C^{mp}$-$A^{mp}$-$G^{mp}$-$A^{e1p}$-$G^{e1p}$-$T^{e1p}$-$A^{e1p}$-$A^{e1p}$-$CH_2CH_2OH$ (SEQ ID NO: 57)

(X"-5) Ph-$A^{e2p}$-$G^{e2p}$-$G^{e2p}$-$T^{e2p}$-$T^{e2p}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e2p}$-$G^{e2p}$-$T^{e2p}$-$A^{e2p}$-$A^{e2p}$-$CH_2CH_2OH$ (SEQ ID NO: 57)

(X"-6) HO-$A^{e2p}$-$G^{e2p}$-$G^{e2p}$-$T^{e2p}$-$T^{e2p}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e2p}$-$G^{e2p}$-$T^{e2p}$-$A^{e2p}$-$A^{e2p}$-$CH_2CH_2OH$ (SEQ ID NO: 57)

(X"-7) Ph-$A^{e1p}$-$G^{e1p}$-$G^{e1p}$-$T^{e1p}$-$T^{e1p}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e1p}$-$G^{e1p}$-$T^{e1p}$-$A^{e1p}$-$A^{e1p}$-$CH_2CH_2OH$ (SEQ ID NO: 57)

(X"-8) HO-$A^{e1p}$-$G^{e1p}$-$G^{e1p}$-$T^{e1p}$-$T^{e1p}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e1p}$-$G^{e1p}$-$T^{e1p}$-$A^{e1p}$-$A^{e1p}$-$CH_2CH_2OH$ (SEQ ID NO: 57)

(X"-9) Ph-$A^{e2s}$-$G^{e2s}$-$G^{e2s}$-$T^{e2s}$-$T^{e2s}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e2s}$-$G^{e2s}$-$T^{e2s}$-$A^{e2s}$-$A^{e2s}$-$CH_2CH_2OH$ (SEQ ID NO: 57)

(X"-10) HO-$A^{e2s}$-$G^{e2s}$-$G^{e2s}$-$T^{e2s}$-$T^{e2s}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{e2s}$-$G^{e2s}$-$T^{e2s}$-$A^{e2s}$-$A^{e2s}$-$CH_2CH_2OH$ (SEQ ID NO: 57)

(X"-11) Ph-$A^{els}$-$G^{els}$-$G^{els}$-$T^{els}$-$T^{els}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{els}$-$G^{els}$-$T^{els}$-$A^{els}$-$A^{els}$-$CH_2CH_2OH$ (SEQ ID NO: 57)

(X"-12) HO-$A^{els}$-$G^{els}$-$G^{els}$-$T^{els}$-$T^{els}$-$G^{ms}$-$U^{ms}$-$G^{ms}$-$U^{ms}$-$C^{ms}$-$A^{ms}$-$C^{ms}$-$C^{ms}$-$A^{ms}$-$G^{ms}$-$A^{els}$-$G^{els}$-$T^{els}$-$A^{els}$-$A^{els}$-$CH_2CH_2OH$ (SEQ ID NO: 57)

Especially preferable are (X"-1), (X"-2), (X"-9) and (X'-10).

Preferable examples of the compound represented by general formula (XI") include the following compounds.

(XI"-1) Ph-$A^{e2p}$-$G^{e2p}$-$T^{e2p}$-$A^{e2p}$-$A^{e2p}$-$C^{mp}$-$C^{mp}$-$A^{mp}$-$C^{mp}$-$A^{mp}$-$G^{mp}$-$G^{mp}$-$U^{mp}$-$U^{mp}$-$G^{mp}$-$T^{e2p}$-$G^{e2p}$-$T^{e2p}$-$C^{e2p}$-$A^{e2p}$-$CH_2CH_2OH$ (SEQ ID NO: 58)

(XI"-2) HO-$A^{e2p}$-$G^{e2p}$-$T^{e2p}$-$A^{e2p}$-$A^{e2p}$-$C^{mp}$-$C^{mp}$-$A^{mp}$-$C^{mp}$-$A^{mp}$-$G^{mp}$-$G^{mp}$-$U^{mp}$-$U^{mp}$-$G^{mp}$-$T^{e2p}$-$G^{e2p}$-$T^{e2p}$-$C^{e2p}$-$A^{e2p}$-$CH_2CH_2OH$ (SEQ ID NO: 58)

(XI"-3) Ph-$A^{e1p}$-$G^{e1p}$-$T^{e1p}$-$A^{e1p}$-$A^{e1p}$-$C^{mp}$-$C^{mp}$-$A^{mp}$-$C^{mp}$-$A^{mp}$-$G^{mp}$-$G^{mp}$-$U^{mp}$-$U^{mp}$-$G^{mp}$-$T^{e1p}$-$G^{e1p}$-$T^{e1p}$-$C^{e1p}$-$A^{e1p}$-$CH_2CH_2OH$ (SEQ ID NO: 58)

(XI"-4) HO-$A^{e1p}$-$G^{e1p}$-$T^{e1p}$-$A^{e1p}$-$A^{e1p}$-$C^{mp}$-$C^{mp}$-$A^{mp}$-$C^{mp}$-$A^{mp}$-$G^{mp}$-$G^{mp}$-$U^{mp}$-$U^{mp}$-$G^{mp}$-$T^{e1p}$-$G^{e1p}$-$T^{e1p}$-$C^{e1p}$-$A^{e1p}$-$CH_2CH_2OH$ (SEQ ID NO: 58)

(XI"-5) Ph-$A^{e2p}$-$G^{e2p}$-$T^{e2p}$-$A^{e2p}$-$A^{e2p}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e2p}$-$G^{e2p}$-$T^{e2p}$-$C^{e2p}$-$A^{e2p}$-$CH_2CH_2OH$ (SEQ ID NO: 58)

(XI"-6) HO-$A^{e2p}$-$G^{e2p}$-$T^{e2p}$-$A^{e2p}$-$A^{e2p}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e2p}$-$G^{e2p}$-$T^{e2p}$-$C^{e2p}$-$A^{e2p}$-$CH_2CH_2OH$ (SEQ ID NO: 58)

(XI"-7) Ph-$A^{e1p}$-$G^{e1p}$-$T^{e1p}$-$A^{e1p}$-$A^{e1p}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e1p}$-$G^{e1p}$-$T^{e1p}$-$C^{e1p}$-$A^{e1p}$-$CH_2CH_2OH$ (SEQ ID NO: 58)

(XI"-8) HO-$A^{e1p}$-$G^{e1p}$-$T^{e1p}$-$A^{e1p}$-$A^{e1p}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e1p}$-$G^{e1p}$-$T^{e1p}$-$C^{e1p}$-$A^{e1p}$-$CH_2CH_2OH$ (SEQ ID NO: 58)

(XI"-9) Ph-$A^{e2s}$-$G^{e2s}$-$T^{e2s}$-$A^{e2s}$-$A^{e2s}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e2s}$-$G^{e2s}$-$T^{e2s}$-$C^{e2s}$-$A^{e2s}$-$CH_2CH_2OH$ (SEQ ID NO: 58)

(XI"-10) HO-$A^{e2s}$-$G^{e2s}$-$T^{e2s}$-$A^{e2s}$-$A^{e2s}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e2s}$-$G^{e2s}$-$T^{e2s}$-$C^{e2s}$-$A^{e2s}$-$CH_2CH_2OH$ (SEQ ID NO: 58)

(XI"-11) Ph-$A^{e1s}$-$G^{e1s}$-$T^{e1s}$-$A^{e1s}$-$A^{e1s}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e1s}$-$G^{e1s}$-$T^{e1s}$-$C^{e1s}$-$A^{e1s}$-$CH_2CH_2OH$ (SEQ ID NO: 58)

(XI"-12) HO-$A^{e1s}$-$G^{e1s}$-$T^{e1s}$-$A^{e1s}$-$A^{e1s}$-$C^{ms}$-$C^{ms}$-$A^{ms}$-$C^{ms}$-$A^{ms}$-$G^{ms}$-$G^{ms}$-$U^{ms}$-$U^{ms}$-$G^{ms}$-$T^{e1s}$-$G^{e1s}$-$T^{e1s}$-$C^{e1s}$-$A^{e1s}$-$CH_2CH_2OH$ (SEQ ID NO: 58)

Especially preferable are (XI"-1), (XI"-2), (XI"-9) and (XF-10).

Preferable examples of the compound represented by general formula (XII") include the following compounds.

(XII"-1) Ph-$C^{e2p}$-$A^{e2p}$-$C^{e2p}$-$C^{e2p}$-$C^{e2p}$-$U^{mp}$-$C^{mp}$-$U^{mp}$-$G^{mp}$-$U^{mp}$-$G^{mp}$-$A^{mp}$-$U^{mp}$-$U^{mp}$-$U^{mp}$-$T^{e2p}$-$A^{e2p}$-$T^{e2p}$-$A^{e2p}$-$A^{e2p}$-$CH_2CH_2OH$ (SEQ ID NO: 60)

(XII"-2) Ph-$A^{e2p}$-$C^{e2p}$-$C^{e2p}$-$C^{e2p}$-$A^{e2p}$-$C^{mp}$-$C^{mp}$-$A^{mp}$-$U^{mp}$-$C^{mp}$-$A^{mp}$-$C^{mp}$-$C^{mp}$-$U^{mp}$-$C^{e2p}$-$T^{e2p}$-$G^{e2p}$-$T^{e2p}$-$G^{e2p}$-$CH_2CH_2OH$ (SEQ ID NO: 61)

-continued (XII''-3) HO-$C^{e2p}$-$A^{e2p}$-$C^{e2p}$-$C^{e2p}$-$C^{e2p}$-$U^{mp}$-$C^{mp}$-$U^{mp}$-$G^{mp}$-$U^{mp}$-$G^{mp}$-$A^{mp}$-$U^{mp}$-$U^{mp}$-$U^{mp}$-$T^{e2p}$-$A^{e2p}$-$T^{e2p}$-$A^{e2p}$-$A^{e2p}$-$CH_2CH_2OH$ (SEQ ID NO: 60)

(XII''-4) HO-$A^{e2p}$-$C^{e2p}$-$C^{e2p}$-$C^{e2p}$-$A^{e2p}$-$C^{mp}$-$C^{mp}$-$A^{mp}$-$U^{mp}$-$C^{mp}$-$A^{mp}$-$C^{mp}$-$C^{mp}$-$C^{mp}$-$U^{mp}$-$C^{e2p}$-$T^{e2p}$-$G^{e2p}$-$T^{e2p}$-$G^{e2p}$-$CH_2CH_2OH$ (SEQ ID NO: 61)

(XII''-5) Ph-$C^{e1p}$-$A^{e1p}$-$C^{e1p}$-$C^{e1p}$-$C^{e1p}$-$U^{mp}$-$C^{mp}$-$U^{mp}$-$G^{mp}$-$U^{mp}$-$G^{mp}$-$A^{mp}$-$U^{mp}$-$U^{mp}$-$U^{mp}$-$T^{e1p}$-$A^{e1p}$-$T^{e1p}$-$A^{e1p}$-$A^{e1p}$-$CH_2CH_2OH$ (SEQ ID NO: 60)

(XII''-6) Ph-$A^{e1p}$-$C^{e1p}$-$C^{e1p}$-$C^{e1p}$-$A^{e1p}$-$C^{mp}$-$C^{mp}$-$A^{mp}$-$U^{mp}$-$C^{mp}$-$A^{mp}$-$C^{mp}$-$C^{mp}$-$C^{mp}$-$U^{mp}$-$C^{e1p}$-$T^{e1p}$-$G^{e1p}$-$T^{e1p}$-$G^{e1p}$-$CH_2CH_2OH$ (SEQ ID NO: 61)

(XII''-7) HO-$C^{e1p}$-$A^{e1p}$-$C^{e1p}$-$C^{e1p}$-$C^{e1p}$-$U^{mp}$-$C^{mp}$-$U^{mp}$-$G^{mp}$-$U^{mp}$-$G^{mp}$-$A^{mp}$-$U^{mp}$-$U^{mp}$-$U^{mp}$-$T^{e1p}$-$A^{e1p}$-$T^{e1p}$-$A^{e1p}$-$A^{e1p}$-$CH_2CH_2OH$ (SEQ ID NO: 60)

(XII''-8) HO-$A^{e1p}$-$C^{e1p}$-$C^{e1p}$-$C^{e1p}$-$A^{e1p}$-$C^{mp}$-$C^{mp}$-$A^{mp}$-$U^{mp}$-$C^{mp}$-$A^{mp}$-$C^{mp}$-$C^{mp}$-$C^{mp}$-$U^{mp}$-$C^{e1p}$-$T^{e1p}$-$G^{e1p}$-$T^{e1p}$-$G^{e1p}$-$CH_2CH_2OH$ (SEQ ID NO: 61)

(XII''-9) Ph-$C^{e2p}$-$A^{e2p}$-$C^{e2p}$-$C^{e2p}$-$C^{e2p}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e2p}$-$A^{e2p}$-$T^{e2p}$-$A^{e2p}$-$A^{e2p}$-$CH_2CH_2OH$ (SEQ ID NO: 60)

(XII''-10) Ph-$A^{e2p}$-$C^{e2p}$-$C^{e2p}$-$C^{e2p}$-$A^{e2p}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e2p}$-$T^{e2p}$-$G^{e2p}$-$T^{e2p}$-$G^{e2p}$-$CH_2CH_2OH$ (SEQ ID NO: 61)

(XII''-11) HO-$C^{e2p}$-$A^{e2p}$-$C^{e2p}$-$C^{e2p}$-$C^{e2p}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e2p}$-$A^{e2p}$-$T^{e2p}$-$A^{e2p}$-$A^{e2p}$-$CH_2CH_2OH$ (SEQ ID NO: 60)

(XII''-12) HO-$A^{e2p}$-$C^{e2p}$-$C^{e2p}$-$C^{e2p}$-$A^{e2p}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e2p}$-$T^{e2p}$-$G^{e2p}$-$T^{e2p}$-$G^{e2p}$-$CH_2CH_2OH$ (SEQ ID NO: 61)

(XII''-13) Ph-$C^{e1p}$-$A^{e1p}$-$C^{e1p}$-$C^{e1p}$-$C^{e1p}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e1p}$-$A^{e1p}$-$T^{e1p}$-$A^{e1p}$-$A^{e1p}$-$CH_2CH_2OH$ (SEQ ID NO: 60)

(XII''-14) Ph-$A^{e1p}$-$C^{e1p}$-$C^{e1p}$-$C^{e1p}$-$A^{e1p}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e1p}$-$T^{e1p}$-$G^{e1p}$-$T^{e1p}$-$G^{e1p}$-$CH_2CH_2OH$ (SEQ ID NO: 61)

(XII''-15) HO-$C^{e1p}$-$A^{e1p}$-$C^{e1p}$-$C^{e1p}$-$C^{e1p}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e1p}$-$A^{e1p}$-$T^{e1p}$-$A^{e1p}$-$A^{e1p}$-$CH_2CH_2OH$ (SEQ ID NO: 60)

(XII''-16) HO-$A^{e1p}$-$C^{e1p}$-$C^{e1p}$-$C^{e1p}$-$A^{e1p}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e1p}$-$T^{e1p}$-$G^{e1p}$-$T^{e1p}$-$G^{e1p}$-$CH_2CH_2OH$ (SEQ ID NO: 61)

(XII''-17) Ph-$C^{e2s}$-$A^{e2s}$-$C^{e2s}$-$C^{e2s}$-$C^{e2s}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e2s}$-$A^{e2s}$-$T^{e2s}$-$A^{e2s}$-$A^{e2s}$-$CH_2CH_2OH$ (SEQ ID NO: 60)

(XII''-18) Ph-$A^{e2s}$-$C^{e2s}$-$C^{e2s}$-$C^{e2s}$-$A^{e2s}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e2s}$-$T^{e2s}$-$G^{e2s}$-$T^{e2s}$-$G^{e2s}$-$CH_2CH_2OH$ (SEQ ID NO: 61)

-continued (XII"-19) HO-$C^{e2s}$-$A^{e2s}$-$C^{e2s}$-$C^{e2s}$-$C^{e2s}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e2s}$-$A^{e2s}$-$T^{e2s}$-$A^{e2s}$-$A^{e2s}$-$CH_2CH_2OH$ (SEQ ID NO: 60)

(XII"-20) HO-$A^{e2s}$-$C^{e2s}$-$C^{e2s}$-$C^{e2s}$-$A^{e2s}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e2s}$-$T^{e2s}$-$G^{e2s}$-$T^{e2s}$-$G^{e2s}$-$CH_2CH_2OH$ (SEQ ID NO: 61)

(XII"-21) Ph-$C^{e1s}$-$A^{e1s}$-$C^{e1s}$-$C^{e1s}$-$C^{e1s}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e1s}$-$A^{e1s}$-$T^{e1s}$-$A^{e1s}$-$A^{e1s}$-$CH_2CH_2OH$ (SEQ ID NO: 60)

(XII"-22) Ph-$A^{e1s}$-$C^{e1s}$-$C^{e1s}$-$C^{e1s}$-$A^{e1s}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e1s}$-$T^{e1s}$-$G^{e1s}$-$T^{e1s}$-$G^{e1s}$-$CH_2CH_2OH$ (SEQ ID NO: 61)

(XII"-23) HO-$C^{e1s}$-$A^{e1s}$-$C^{e1s}$-$C^{e1s}$-$C^{e1s}$-$U^{ms}$-$C^{ms}$-$U^{ms}$-$G^{ms}$-$U^{ms}$-$G^{ms}$-$A^{ms}$-$U^{ms}$-$U^{ms}$-$U^{ms}$-$T^{e1s}$-$A^{e1s}$-$T^{e1s}$-$A^{e1s}$-$A^{e1s}$-$CH_2CH_2OH$ (SEQ ID NO: 60)

(XII"-24) HO-$A^{e1s}$-$C^{e1s}$-$C^{e1s}$-$C^{e1s}$-$A^{e1s}$-$C^{ms}$-$C^{ms}$-$A^{ms}$-$U^{ms}$-$C^{ms}$-$A^{ms}$-$C^{ms}$-$C^{ms}$-$C^{ms}$-$U^{ms}$-$C^{e1s}$-$T^{e1s}$-$G^{e1s}$-$T^{e1s}$-$G^{e1s}$-$CH_2CH_2OH$ (SEQ ID NO: 61)

Especially preferable are (XII"-1), (XII"-2), (XIP'-3), (XII"-4), (XII"-17), (XIP'-18), (XII"-19) and (XII"-20).

Preferable examples of the compound represented by general formula (XIII") include the following compounds.

(XIII"-1) Ph-$C^{e2p}$-$C^{e2p}$-$T^{e2p}$-$C^{e2p}$-$A^{e2p}$-$A^{mp}$-$G^{mp}$-$G^{mp}$-$U^{mp}$-$C^{mp}$-$A^{mp}$-$C^{mp}$-$C^{mp}$-$C^{mp}$-$A^{mp}$-$C^{e2p}$-$C^{e2p}$-$A^{e2p}$-$T^{e2p}$-$C^{e2p}$-$CH_2CH_2OH$ (SEQ ID NO: 62)

(XIII"-2) HO-$C^{e2p}$-$C^{e2p}$-$T^{e2p}$-$C^{e2p}$-$A^{e2p}$-$A^{mp}$-$G^{mp}$-$G^{mp}$-$U^{mp}$-$C^{mp}$-$A^{mp}$-$C^{mp}$-$C^{mp}$-$C^{mp}$-$A^{mp}$-$C^{e2p}$-$C^{e2p}$-$A^{e2p}$-$T^{e2p}$-$C^{e2p}$-$CH_2CH_2OH$ (SEQ ID NO: 62)

(XIII"-3) Ph-$C^{e1p}$-$C^{e1p}$-$T^{e1p}$-$C^{e1p}$-$A^{e1p}$-$A^{mp}$-$G^{mp}$-$G^{mp}$-$U^{mp}$-$C^{mp}$-$A^{mp}$-$C^{mp}$-$C^{mp}$-$C^{mp}$-$A^{mp}$-$C^{e1p}$-$C^{e1p}$-$A^{e1p}$-$T^{e1p}$-$C^{e1p}$-$CH_2CH_2OH$ (SEQ ID NO: 62)

(XIII"-4) HO-$C^{e1p}$-$C^{e1p}$-$T^{e1p}$-$C^{e1p}$-$A^{e1p}$-$A^{mp}$-$G^{mp}$-$G^{mp}$-$U^{mp}$-$C^{mp}$-$A^{mp}$-$C^{mp}$-$C^{mp}$-$C^{mp}$-$A^{mp}$-$C^{e1p}$-$C^{e1p}$-$A^{e1p}$-$T^{e1p}$-$C^{e1p}$-$CH_2CH_2OH$ (SEQ ID NO: 62)

(XIII"-5) Ph-$C^{e2p}$-$C^{e2p}$-$T^{e2p}$-$C^{e2p}$-$A^{e2p}$-$A^{ms}$-$G^{ns}$-$G^{ms}$-$U^{ns}$-$C^{ms}$-$A^{ms}$-$C^{ms}$-$C^{ns}$-$C^{ms}$-$A^{ms}$-$C^{e2p}$-$C^{e2p}$-$A^{e2p}$-$T^{e2p}$-$C^{e2p}$-$CH_2CH_2OH$ (SEQ ID NO: 62)

(XIII"-6) HO-$C^{e2p}$-$C^{e2p}$-$T^{e2p}$-$C^{e2p}$-$A^{e2p}$-$A^{ms}$-$G^{ns}$-$G^{ms}$-$U^{ns}$-$C^{ms}$-$A^{ms}$-$C^{ms}$-$C^{ns}$-$C^{ms}$-$A^{ms}$-$C^{e2p}$-$C^{e2p}$-$A^{e2p}$-$T^{e2p}$-$C^{e2p}$-$CH_2CH_2OH$ (SEQ ID NO: 62)

(XIII"-7) Ph-$C^{e1p}$-$C^{e1p}$-$T^{e1p}$-$C^{e1p}$-$A^{e1p}$-$A^{ms}$-$G^{ns}$-$G^{ms}$-$U^{ns}$-$C^{ms}$-$A^{ms}$-$C^{ms}$-$C^{ns}$-$C^{ms}$-$A^{ms}$-$C^{e1p}$-$C^{e1p}$-$A^{e1p}$-$T^{e1p}$-$C^{e1p}$-$CH_2CH_2OH$ (SEQ ID NO: 62)

(XIII"-8) HO-$C^{e1p}$-$C^{e1p}$-$T^{e1p}$-$C^{e1p}$-$A^{e1p}$-$A^{ms}$-$G^{ns}$-$G^{ms}$-$U^{ns}$-$C^{ms}$-$A^{ms}$-$C^{ms}$-$C^{ns}$-$C^{ms}$-$A^{ms}$-$C^{e1p}$-$C^{e1p}$-$A^{e1p}$-$T^{e1p}$-$C^{e1p}$-$CH_2CH_2OH$ (SEQ ID NO: 62)

(XIII"-9) Ph-$C^{e2s}$-$C^{e2s}$-$T^{e2s}$-$C^{e2s}$-$A^{e2s}$-$A^{ms}$-$G^{ms}$-$G^{ms}$-$U^{ns}$-$C^{ms}$-$A^{ms}$-$C^{ms}$-$C^{ms}$-$C^{ms}$-$A^{ms}$-$C^{e2s}$-$C^{e2s}$-$A^{e2s}$-$T^{e2s}$-$C^{e2s}$-$CH_2CH_2OH$ (SEQ ID NO: 62)

-continued (XIII"-10) HO-$C^{e2s}$-$C^{e2s}$-$T^{e2s}$-$C^{e2s}$-$A^{e2s}$-$A^{ms}$-$G^{ms}$-$G^{ms}$-$U^{ms}$-$C^{ms}$-$A^{ms}$-$C^{ms}$-$C^{ms}$-$C^{ms}$-$A^{ms}$-$C^{e2s}$-$C^{e2s}$-$A^{e2s}$-$T^{e2s}$-$C^{e2s}$-$CH_2CH_2OH$ (SEQ ID NO: 62)

(XIII"-11) Ph-$C^{els}$-$C^{els}$-$T^{els}$-$C^{els}$-$A^{els}$-$A^{ms}$-$G^{ms}$-$G^{ms}$-$U^{ms}$-$C^{ms}$-$A^{ms}$-$C^{ms}$-$C^{ms}$-$C^{ms}$-$A^{ms}$-$C^{els}$-$C^{els}$-$A^{els}$-$T^{els}$-$C^{els}$-$CH_2CH_2OH$ (SEQ ID NO: 62)

(XIII"-12) HO-$C^{els}$-$C^{els}$-$T^{els}$-$C^{els}$-$A^{els}$-$A^{ms}$-$G^{ms}$-$G^{ms}$-$U^{ms}$-$C^{ms}$-$A^{ms}$-$C^{ms}$-$C^{ms}$-$C^{ms}$-$A^{ms}$-$C^{els}$-$C^{els}$-$A^{els}$-$T^{els}$-$C^{els}$-$CH_2CH_2OH$ (SEQ ID NO: 62)

Especially preferable are (XIII"-1), (XIII"-2), (XIII"-9) and (XIII"-10).

Preferable examples of the compound represented by general formula (XIV") include the following compounds.

(XIV"-1) Ph-$T^{e2p}$-$T^{e2p}$-$G^{e2p}$-$A^{e2p}$-$T^{e2p}$-$C^{mp}$-$A^{mp}$-$A^{mp}$-$G^{mp}$-$C^{mp}$-$A^{mp}$-$G^{mp}$-$A^{mp}$-$G^{mp}$-$A^{mp}$-$A^{e2p}$-$A^{e2p}$-$G^{e2p}$-$C^{e2p}$-$C^{e2p}$-$CH_2CH_2OH$ (SEQ ID NO: 59)

(XIV"-2) HO-$T^{e2p}$-$T^{e2p}$-$G^{e2p}$-$A^{e2p}$-$T^{e2p}$-$C^{mp}$-$A^{mp}$-$A^{mp}$-$G^{mp}$-$C^{mp}$-$A^{mp}$-$G^{mp}$-$A^{mp}$-$G^{mp}$-$A^{mp}$-$A^{e2p}$-$A^{e2p}$-$G^{e2p}$-$C^{e2p}$-$C^{e2p}$-$CH_2CH_2OH$ (SEQ ID NO: 59)

(XIV"-3) HO-$A^{e2p}$-$G^{e2p}$-$C^{e2p}$-$C^{e2p}$-$A^{e2p}$-$G^{mp}$-$U^{mp}$-$C^{mp}$-$G^{mp}$-$G^{mp}$-$U^{mp}$-$A^{mp}$-$A^{mp}$-$G^{e2p}$-$T^{e2p}$-$T^{e2p}$-$C^{e2p}$-$T^{e2p}$-$CH_2CH_2OH$ (SEQ ID NO: 65)

(XIV"-4) Ph-$T^{e1p}$-$T^{e1p}$-$G^{e1p}$-$A^{e1p}$-$T^{e1p}$-$C^{mp}$-$A^{mp}$-$A^{mp}$-$G^{mp}$-$C^{mp}$-$A^{mp}$-$G^{mp}$-$A^{mp}$-$G^{mp}$-$A^{mp}$-$A^{e1p}$-$A^{e1p}$-$G^{e1p}$-$C^{e1p}$-$C^{e1p}$-$CH_2CH_2OH$ (SEQ ID NO: 59)

(XIV"-5) HO-$T^{e1p}$-$T^{e1p}$-$G^{e1p}$-$A^{e1p}$-$T^{e1p}$-$C^{mp}$-$A^{mp}$-$A^{mp}$-$G^{mp}$-$C^{mp}$-$A^{mp}$-$G^{mp}$-$A^{mp}$-$G^{mp}$-$A^{mp}$-$A^{e1p}$-$A^{e1p}$-$G^{e1p}$-$C^{e1p}$-$C^{e1p}$-$CH_2CH_2OH$ (SEQ ID NO: 59)

(XIV"-6) HO-$A^{e1p}$-$G^{e1p}$-$C^{e1p}$-$C^{e1p}$-$A^{e1p}$-$G^{mp}$-$U^{mp}$-$C^{mp}$-$G^{mp}$-$G^{mp}$-$U^{mp}$-$A^{mp}$-$A^{mp}$-$G^{e1p}$-$T^{e1p}$-$T^{e1p}$-$C^{e1p}$-$T^{e1p}$-$CH_2CH_2OH$ (SEQ ID NO: 65)

(XIV"-7) Ph-$T^{e2p}$-$T^{e2p}$-$G^{e2p}$-$A^{e2p}$-$T^{e2p}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e2p}$-$A^{e2p}$-$G^{e2p}$-$C^{e2p}$-$C^{e2p}$-$CH_2CH_2OH$ (SEQ ID NO: 59)

(XIV"-8) HO-$T^{e2p}$-$T^{e2p}$-$G^{e2p}$-$A^{e2p}$-$T^{e2p}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e2p}$-$A^{e2p}$-$G^{e2p}$-$C^{e2p}$-$C^{e2p}$-$CH_2CH_2OH$ (SEQ ID NO: 59)

(XIV"-9) HO-$A^{e2p}$-$G^{e2p}$-$C^{e2p}$-$C^{e2p}$-$A^{e2p}$-$G^{ms}$-$U^{ms}$-$C^{ms}$-$G^{ms}$-$G^{ms}$-$U^{ms}$-$A^{ms}$-$A^{ms}$-$G^{e2p}$-$T^{e2p}$-$T^{e2p}$-$C^{e2p}$-$T^{e2p}$-$CH_2CH_2OH$ (SEQ ID NO: 65)

(XIV"-10) Ph-$T^{e1p}$-$T^{e1p}$-$G^{e1p}$-$A^{e1p}$-$T^{e1p}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e1p}$-$A^{e1p}$-$G^{e1p}$-$C^{e1p}$-$C^{e1p}$-$CH_2CH_2OH$ (SEQ ID NO: 59)

(XIV"-11) HO-$T^{e1p}$-$T^{e1p}$-$G^{e1p}$-$A^{e1p}$-$T^{e1p}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e1p}$-$A^{e1p}$-$G^{e1p}$-$C^{e1p}$-$C^{e1p}$-$CH_2CH_2OH$ (SEQ ID NO: 59)

(XIV"-12) HO-$A^{e1p}$-$G^{e1p}$-$C^{e1p}$-$C^{e1p}$-$A^{e1p}$-$G^{ms}$-$U^{ms}$-$C^{ms}$-$G^{ms}$-$G^{ms}$-$U^{ms}$-$A^{ms}$-$A^{ms}$-$G^{e1p}$-$T^{e1p}$-$T^{e1p}$-$C^{e1p}$-$T^{e1p}$-$CH_2CH_2OH$ (SEQ ID NO: 65)

(XIV"-13) Ph-$T^{e2s}$-$T^{e2s}$-$G^{e2s}$-$A^{e2s}$-$T^{e2s}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e2s}$-$A^{e2s}$-$G^{e2s}$-$C^{e2s}$-$C^{e2s}$-$CH_2CH_2OH$ (SEQ ID NO: 59)

(XIV"-14) HO-$T^{e2s}$-$T^{e2s}$-$G^{e2s}$-$A^{e2s}$-$T^{e2s}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e2s}$-$A^{e2s}$-$G^{e2s}$-$C^{e2s}$-$C^{e2s}$-$CH_2CH_2OH$ (SEQ ID NO: 59)

(XIV"-15) HO-$A^{e2s}$-$G^{e2s}$-$C^{e2s}$-$C^{e2s}$-$A^{e2s}$-$G^{ms}$-$U^{ms}$-$C^{ms}$-$G^{ms}$-$G^{ms}$-$U^{ms}$-$A^{ms}$-$A^{ms}$-$G^{e2s}$-$T^{e2s}$-$T^{e2s}$-$C^{e2s}$-$T^{e2s}$-$CH_2CH_2OH$ (SEQ ID NO: 65)

(XIV"-16) Ph-$T^{e1s}$-$T^{e1s}$-$G^{e1s}$-$A^{e1s}$-$T^{e1s}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e1s}$-$A^{e1s}$-$G^{e1s}$-$C^{e1s}$-$C^{e1s}$-$CH_2CH_2OH$ (SEQ ID NO: 59)

(XIV"-17) HO-$T^{e1s}$-$T^{e1s}$-$G^{e1s}$-$A^{e1s}$-$T^{e1s}$-$C^{ms}$-$A^{ms}$-$A^{ms}$-$G^{ms}$-$C^{ms}$-$A^{ms}$-$G^{ms}$-$A^{ms}$-$G^{ms}$-$A^{ms}$-$A^{e1s}$-$A^{e1s}$-$G^{e1s}$-$C^{e1s}$-$C^{e1s}$-$CH_2CH_2OH$ (SEQ ID NO: 59)

(XIV"-18) HO-$A^{e1s}$-$G^{e1s}$-$C^{e1s}$-$C^{e1s}$-$A^{e1s}$-$G^{ms}$-$U^{ms}$-$C^{ms}$-$G^{ms}$-$G^{ms}$-$U^{ms}$-$A^{ms}$-$A^{ms}$-$G^{e1s}$-$T^{e1s}$-$T^{e1s}$-$C^{e1s}$-$T^{e1s}$-$CH_2CH_2OH$ (SEQ ID NO: 65)

Especially preferable are (XIV"-1), (XIV"-2), (XIV"-3), (XIV"-13), (XIV"-14) and (XIV"-15).

Preferable examples of the compound represented by general formula (XV") include the following compounds.

(XV"-1) HO-$G^{e2p}$-$G^{e2p}$-$C^{e2p}$-$A^{e2p}$-$T^{e2p}$-$U^{mp}$-$U^{mp}$-$C^{mp}$-$U^{mp}$-$A^{mp}$-$G^{mp}$-$U^{mp}$-$U^{mp}$-$T^{e2p}$-$G^{e2p}$-$G^{e2p}$-$A^{e2p}$-$G^{e2p}$-$CH_2CH_2OH$ (SEQ ID NO: 64)

(XV"-2) HO-$A^{e2p}$-$G^{e2p}$-$T^{e2p}$-$T^{e2p}$-$T^{e2p}$-$G^{mp}$-$G^{mp}$-$A^{mp}$-$G^{mp}$-$A^{mp}$-$U^{mp}$-$G^{mp}$-$G^{mp}$-$C^{e2p}$-$A^{e2p}$-$G^{e2p}$-$T^{e2p}$-$T^{e2p}$-$CH_2CH_2OH$ (SEQ ID NO: 66)

(XV"-3) HO-$G^{mp}$-$G^{mp}$-$C^{e2p}$-$A^{mp}$-$T^{e2p}$-$T^{e2p}$-$U^{mp}$-$C^{e2p}$-$T^{e2p}$-$A^{mp}$-$G^{mp}$-$U^{mp}$-$T^{e2p}$-$T^{e2p}$-$G^{mp}$-$G^{mp}$-$A^{e2p}$-$G^{mp}$-$CH_2CH_2OH$ (SEQ ID NO: 87)

(XV"-4) HO-$A^{e2p}$-$G^{mp}$-$T^{e2p}$-$U^{mp}$-$T^{e2p}$-$G^{mp}$-$G^{mp}$-$A^{e2p}$-$G^{mp}$-$A^{mp}$-$T^{e2p}$-$G^{mp}$-$G^{mp}$-$C^{e2p}$-$A^{e2p}$-$G^{mp}$-$T^{e2p}$-$T^{e2p}$-$CH_2CH_2OH$ (SEQ ID NO: 88)

(XV"-5) HO-$G^{e1p}$-$G^{e1p}$-$C^{e1p}$-$A^{e1p}$-$T^{e1p}$-$U^{mp}$-$U^{mp}$-$C^{mp}$-$U^{mp}$-$A^{mp}$-$G^{mp}$-$U^{mp}$-$U^{mp}$-$T^{e1p}$-$G^{e1p}$-$G^{e1p}$-$A^{e1p}$-$G^{e1p}$-$CH_2CH_2OH$ (SEQ ID NO: 64)

(XV"-6) HO-$A^{e1p}$-$G^{e1p}$-$T^{e1p}$-$T^{e1p}$-$T^{e1p}$-$G^{mp}$-$G^{mp}$-$A^{mp}$-$G^{mp}$-$A^{mp}$-$U^{mp}$-$G^{mp}$-$G^{mp}$-$C^{e1p}$-$A^{e1p}$-$G^{e1p}$-$T^{e1p}$-$T^{e1p}$-$CH_2CH_2OH$ (SEQ ID NO: 66)

(XV"-7) HO-$G^{mp}$-$G^{mp}$-$C^{e1p}$-$A^{mp}$-$T^{e1p}$-$T^{e1p}$-$U^{mp}$-$C^{e1p}$-$T^{e1p}$-$A^{mp}$-$G^{mp}$-$U^{mp}$-$T^{e1p}$-$T^{e1p}$-$G^{mp}$-$G^{mp}$-$A^{e1p}$-$G^{mp}$-$CH_2CH_2OH$ (SEQ ID NO: 87)

(XV"-8) HO-$A^{e1p}$-$G^{mp}$-$T^{e1p}$-$U^{mp}$-$T^{e1p}$-$G^{mp}$-$G^{mp}$-$A^{e1p}$-$G^{mp}$-$A^{mp}$-$T^{e1p}$-$G^{mp}$-$G^{mp}$-$C^{e1p}$-$A^{e1p}$-$G^{mp}$-$T^{e1p}$-$T^{e1p}$-$CH_2CH_2OH$ (SEQ ID NO: 88)

(XV"-9) HO-$G^{e2p}$-$G^{e2p}$-$C^{e2p}$-$A^{e2p}$-$T^{e2p}$-$U^{ms}$-$U^{ms}$-$C^{ms}$-$U^{ms}$-$A^{ms}$-$G^{ms}$-$U^{ms}$-$U^{ms}$-$T^{e2p}$-$G^{e2p}$-$G^{e2p}$-$A^{e2p}$-$G^{e2p}$-$CH_2CH_2OH$ (SEQ ID NO: 64)

-continued (SEQ ID NO: 66)
(XV"-10) HO-$A^{e2p}$-$G^{e2p}$-$T^{e2p}$-$T^{e2p}$-$T^{e2p}$-$G^{ms}$-$G^{ms}$-$A^{ms}$-$G^{ms}$-$A^{ms}$-$U^{ms}$-$G^{ms}$-$G^{ms}$-$C^{e2p}$-$A^{e2p}$-$G^{e2p}$-$T^{e2p}$-$T^{e2p}$-$CH_2CH_2OH$ (SEQ ID NO: 87)
(XV"-11) HO-$G^{ms}$-$G^{ms}$-$C^{e2p}$-$A^{ms}$-$T^{e2p}$-$T^{e2p}$-$U^{ms}$-$C^{e2p}$-$T^{e2p}$-$A^{ms}$-$G^{ms}$-$U^{ms}$-$T^{e2p}$-$T^{e2p}$-$G^{ms}$-$G^{ms}$-$A^{e2p}$-$G^{ms}$-$CH_2CH_2OH$ (SEQ ID NO: 88)
(XV"-12) HO-$A^{e2p}$-$G^{ms}$-$T^{e2p}$-$U^{ms}$-$T^{e2p}$-$G^{ms}$-$G^{ms}$-$A^{e2p}$-$G^{ms}$-$A^{ms}$-$T^{e2p}$-$G^{ms}$-$G^{ms}$-$C^{e2p}$-$A^{e2p}$-$G^{ms}$-$T^{e2p}$-$T^{e2p}$-$CH_2CH_2OH$ (SEQ ID NO: 64)
(XV"-13) HO-$G^{e1p}$-$G^{e1p}$-$C^{e1p}$-$A^{e1p}$-$T^{e1p}$-$U^{ms}$-$U^{ms}$-$C^{ms}$-$U^{ms}$-$A^{ms}$-$G^{ms}$-$U^{ms}$-$U^{ms}$-$T^{e1p}$-$G^{e1p}$-$G^{e1p}$-$A^{e1p}$-$G^{e1p}$-$CH_2CH_2OH$ (SEQ ID NO: 66)
(XV"-14) HO-$A^{e1p}$-$G^{e1p}$-$T^{e1p}$-$T^{e1p}$-$T^{e1p}$-$G^{ms}$-$G^{ms}$-$A^{ms}$-$G^{ms}$-$A^{ms}$-$U^{ms}$-$G^{ms}$-$G^{ms}$-$C^{e1p}$-$A^{e1p}$-$G^{e1p}$-$T^{e1p}$-$T^{e1p}$-$CH_2CH_2OH$ (SEQ ID NO: 87)
(XV"-15) HO-$G^{ms}$-$G^{ms}$-$C^{e1p}$-$A^{ms}$-$T^{e1p}$-$T^{e1p}$-$U^{ms}$-$C^{e1p}$-$T^{e1p}$-$A^{ms}$-$G^{ms}$-$U^{ms}$-$T^{e1p}$-$T^{e1p}$-$G^{ms}$-$G^{ms}$-$A^{e1p}$-$G^{ms}$-$CH_2CH_2OH$ (SEQ ID NO: 88)
(XV"-16) HO-$A^{e1p}$-$G^{ms}$-$T^{e1p}$-$U^{ms}$-$T^{e1p}$-$G^{ms}$-$G^{ms}$-$A^{e1p}$-$G^{ms}$-$A^{ms}$-$T^{e1p}$-$G^{ms}$-$G^{ms}$-$C^{e1p}$-$A^{e1p}$-$G^{ms}$-$T^{e1p}$-$T^{e1p}$-$CH_2CH_2OH$ (SEQ ID NO: 64)
(XV"-17) HO-$G^{e2s}$-$G^{e2s}$-$C^{e2s}$-$A^{e2s}$-$T^{e2s}$-$U^{ms}$-$U^{ms}$-$C^{ms}$-$U^{ms}$-$A^{ms}$-$G^{ms}$-$U^{ms}$-$U^{ms}$-$T^{e2s}$-$G^{e2s}$-$G^{e2s}$-$A^{e2s}$-$G^{e2s}$-$CH_2CH_2OH$ (SEQ ID NO: 66)
(XV"-18) HO-$A^{e2s}$-$G^{e2s}$-$T^{e2s}$-$T^{e2s}$-$T^{e2s}$-$G^{ms}$-$G^{ms}$-$A^{ms}$-$G^{ms}$-$A^{ms}$-$U^{ms}$-$G^{ms}$-$G^{ms}$-$C^{e2s}$-$A^{e2s}$-$G^{e2s}$-$T^{e2s}$-$T^{e2s}$-$CH_2CH_2OH$ (SEQ ID NO: 87)
(XV"-19) HO-$G^{ms}$-$G^{ms}$-$C^{e2s}$-$A^{ms}$-$T^{e2s}$-$T^{e2s}$-$U^{ms}$-$C^{e2s}$-$T^{e2s}$-$A^{ms}$-$G^{ms}$-$U^{ms}$-$T^{e2s}$-$T^{e2s}$-$G^{ms}$-$G^{ms}$-$A^{e2s}$-$G^{ms}$-$CH_2CH_2OH$ (SEQ ID NO: 88)
(XV"-20) HO-$A^{e2s}$-$G^{ms}$-$T^{e2s}$-$U^{ms}$-$T^{e2s}$-$G^{ms}$-$G^{ms}$-$A^{e2s}$-$G^{ms}$-$A^{ms}$-$T^{e2s}$-$G^{ms}$-$G^{ms}$-$C^{e2s}$-$A^{e2s}$-$G^{ms}$-$T^{e2s}$-$T^{e2s}$-$CH_2CH_2OH$ (SEQ ID NO: 64)
(XV"-21) HO-$G^{e1s}$-$G^{e1s}$-$C^{e1s}$-$A^{e1s}$-$T^{e1s}$-$U^{ms}$-$U^{ms}$-$C^{ms}$-$U^{ms}$-$A^{ms}$-$G^{ms}$-$U^{ms}$-$U^{ms}$-$T^{e1s}$-$G^{e1s}$-$G^{e1s}$-$A^{e1s}$-$G^{e1s}$-$CH_2CH_2OH$ (SEQ ID NO: 66)
(XV"-22) HO-$A^{e1s}$-$G^{e1s}$-$T^{e1s}$-$T^{e1s}$-$T^{e1s}$-$G^{ms}$-$G^{ms}$-$A^{ms}$-$G^{ms}$-$A^{ms}$-$U^{ms}$-$G^{ms}$-$G^{ms}$-$C^{e1s}$-$A^{e1s}$-$G^{e1s}$-$T^{e1s}$-$T^{e1s}$-$CH_2CH_2OH$ (SEQ ID NO: 87)
(XV"-23) HO-$G^{ms}$-$G^{ms}$-$C^{e1s}$-$A^{ms}$-$T^{e1s}$-$T^{e1s}$-$U^{ms}$-$C^{e1s}$-$T^{e1s}$-$A^{ms}$-$G^{ms}$-$U^{ms}$-$T^{e1s}$-$T^{e1s}$-$G^{ms}$-$G^{ms}$-$A^{e1s}$-$G^{ms}$-$CH_2CH_2OH$ (SEQ ID NO: 88)
(XV"-24) HO-$A^{e1s}$-$G^{ms}$-$T^{e1s}$-$U^{ms}$-$T^{e1s}$-$G^{ms}$-$G^{ms}$-$A^{e1s}$-$G^{ms}$-$A^{ms}$-$T^{e1s}$-$G^{ms}$-$G^{ms}$-$C^{e1s}$-$A^{e1s}$-$G^{ms}$-$T^{e1s}$-$T^{e1s}$-$CH_2CH_2OH$ Especially preferable are (XV"-1), (XV"-2), (XV"-3) (XV"-4), (XV"-17) (XV"-18), (XV"-19) and (XV"-20).

Preferable examples of the compound represented by general formula (XVI") include the following compounds.

(XVI"-1) HO-T$^{e2p}$-T$^{e2p}$-C$^{mp}$-T$^{e2p}$-T$^{e2p}$-G$^{mp}$-T$^{e2p}$-A$^{mp}$-C$^{mp}$-T$^{e2p}$-T$^{e2p}$-C$^{mp}$-A$^{mp}$-T$^{e2p}$-C$^{mp}$-C$^{e2p}$-C$^{e2p}$-A$^{mp}$-CH$_2$CH$_2$OH  (SEQ ID NO: 68)

(XVI"-2) HO-C$^{e2p}$-T$^{e2p}$-G$^{mp}$-A$^{mp}$-A$^{mp}$-G$^{mp}$-G$^{mp}$-T$^{e2p}$-G$^{mp}$-T$^{e2p}$-T$^{e2p}$-C$^{e2p}$-T$^{e2p}$-T$^{e2p}$-G$^{mp}$-T$^{e2p}$-A$^{mp}$-C$^{e2p}$-CH$_2$CH$_2$OH  (SEQ ID NO: 75)

(XVI"-3) HO-T$^{e1p}$-T$^{e1p}$-C$^{mp}$-T$^{e1p}$-T$^{e1p}$-G$^{mp}$-T$^{e1p}$-A$^{mp}$-C$^{mp}$-T$^{e1p}$-T$^{e1p}$-C$^{mp}$-A$^{mp}$-T$^{e1p}$-C$^{mp}$-C$^{e1p}$-C$^{e1p}$-A$^{mp}$-CH$_2$CH$_2$OH  (SEQ ID NO: 68)

(XVI"-4) HO-C$^{e1p}$-T$^{e1p}$-G$^{mp}$-A$^{mp}$-A$^{mp}$-G$^{mp}$-G$^{mp}$-T$^{e1p}$-G$^{mp}$-T$^{e1p}$-T$^{e1p}$-C$^{e1p}$-T$^{e1p}$-T$^{e1p}$-G$^{mp}$-T$^{e1p}$-A$^{mp}$-C$^{e1p}$-CH$_2$CH$_2$OH  (SEQ ID NO: 75)

(XVI"-5) HO-T$^{e2p}$-T$^{e2p}$-C$^{ms}$-T$^{e2p}$-T$^{e2p}$-G$^{ms}$-T$^{e2p}$-A$^{ms}$-C$^{ms}$-T$^{e2p}$-T$^{e2p}$-C$^{ms}$-A$^{ms}$-T$^{e2p}$-C$^{ms}$-C$^{e2p}$-C$^{e2p}$-A$^{ms}$-CH$_2$CH$_2$OH  (SEQ ID NO: 68)

(XVI"-6) HO-C$^{e2p}$-T$^{e2p}$-G$^{ms}$-A$^{ms}$-A$^{ms}$-G$^{ms}$-G$^{ms}$-T$^{e2p}$-G$^{ms}$-T$^{e2p}$-T$^{e2p}$-C$^{e2p}$-T$^{e2p}$-T$^{e2p}$-G$^{ms}$-T$^{e2p}$-A$^{ms}$-C$^{e2p}$-CH$_2$CH$_2$OH  (SEQ ID NO: 75)

(XVI"-7) HO-T$^{e1p}$-T$^{e1p}$-C$^{ms}$-T$^{e1p}$-T$^{e1p}$-G$^{ms}$-T$^{e1p}$-A$^{ms}$-C$^{ms}$-T$^{e1p}$-T$^{e1p}$-C$^{ms}$-A$^{ms}$-T$^{e1p}$-C$^{ms}$-C$^{e1p}$-C$^{e1p}$-A$^{ms}$-CH$_2$CH$_2$OH  (SEQ ID NO: 68)

(XVI"-8) HO-C$^{e1p}$-T$^{e1p}$-G$^{ms}$-A$^{ms}$-A$^{ms}$-G$^{ms}$-G$^{ms}$-T$^{e1p}$-G$^{ms}$-T$^{e1p}$-T$^{e1p}$-C$^{e1p}$-T$^{e1p}$-T$^{e1p}$-G$^{ms}$-T$^{e1p}$-A$^{ms}$-C$^{e1p}$-CH$_2$CH$_2$OH  (SEQ ID NO: 75)

(XVI"-9) HO-T$^{e2s}$-T$^{e2s}$-C$^{ms}$-T$^{e2s}$-T$^{e2s}$-G$^{ms}$-T$^{e2s}$-A$^{ms}$-C$^{ms}$-T$^{e2s}$-T$^{e2s}$-C$^{ms}$-A$^{ms}$-T$^{e2s}$-C$^{ms}$-C$^{e2s}$-C$^{e2s}$-A$^{ms}$-CH$_2$CH$_2$OH  (SEQ ID NO: 68)

(XVI"-10) HO-C$^{e2s}$-T$^{e2s}$-G$^{ms}$-A$^{ms}$-A$^{ms}$-G$^{ms}$-G$^{ms}$-T$^{e2s}$-G$^{ms}$-T$^{e2s}$-T$^{e2s}$-C$^{e2s}$-T$^{e2s}$-T$^{e2s}$-G$^{ms}$-T$^{e2s}$-A$^{ms}$-C$^{e2s}$-CH$_2$CH$_2$OH  (SEQ ID NO: 75)

(XVI"-11) HO-T$^{e1s}$-T$^{e1s}$-C$^{ms}$-T$^{e1s}$-T$^{e1s}$-G$^{ms}$-T$^{e1s}$-A$^{ms}$-C$^{ms}$-T$^{e1s}$-T$^{e1s}$-C$^{ms}$-A$^{ms}$-T$^{e1s}$-C$^{ms}$-C$^{e1s}$-C$^{e1s}$-A$^{ms}$-CH$_2$CH$_2$OH  (SEQ ID NO: 68)

(XVI"-12) HO-C$^{e1s}$-T$^{e1s}$-G$^{ms}$-A$^{ms}$-A$^{ms}$-G$^{ms}$-G$^{ms}$-T$^{e1s}$-G$^{ms}$-T$^{e1s}$-T$^{e1s}$-C$^{e1s}$-T$^{e1s}$-T$^{e1s}$-G$^{ms}$-T$^{e1s}$-A$^{ms}$-C$^{e1s}$-CH$_2$CH$_2$OH  (SEQ ID NO: 75)

Especially preferable are (XVI"-1), (XVI"-2), (XVI"-9) and (XVI"-10)

Preferable examples of the compound represented by general formula (XVII") include the following compounds.

(XVII"-1) HO-C$^{e2p}$-C$^{e2p}$-U$^{mp}$-C$^{e2p}$-C$^{e2p}$-G$^{mp}$-G$^{mp}$-T$^{e2p}$-T$^{e2p}$-C$^{e2p}$-T$^{e2p}$-G$^{mp}$-A$^{mp}$-A$^{mp}$-G$^{mp}$-G$^{mp}$-T$^{e2p}$-G$^{mp}$-CH$_2$CH$_2$OH  (SEQ ID NO: 69)

(XVII"-2) HO-C$^{e1p}$-C$^{e1p}$-U$^{mp}$-C$^{e1p}$-C$^{e1p}$-G$^{mp}$-G$^{mp}$-T$^{e1p}$-T$^{e1p}$-C$^{e1p}$-T$^{e1p}$-G$^{mp}$-A$^{mp}$-A$^{mp}$-G$^{mp}$-G$^{mp}$-T$^{e1p}$-G$^{mp}$-CH$_2$CH$_2$OH  (SEQ ID NO: 69)

-continued (XVII"-3) HO-$C^{e2p}$-$C^{e2p}$-$U^{ms}$-$C^{e2p}$-$C^{e2p}$-$G^{ms}$-$G^{ms}$-$T^{e2p}$-$T^{e2p}$-$C^{e2p}$-$T^{e2p}$-$G^{ms}$-$A^{ms}$-$A^{ms}$-$G^{ms}$-$G^{ms}$-$T^{e2p}$-$G^{ms}$-$CH_2CH_2OH$  (SEQ ID NO: 69)

(XVII"-4) HO-$C^{e1p}$-$C^{e1p}$-$U^{ms}$-$C^{e1p}$-$C^{e1p}$-$G^{ms}$-$G^{ms}$-$T^{e1p}$-$T^{e1p}$-$C^{e1p}$-$T^{e1p}$-$G^{ms}$-$A^{ms}$-$A^{ms}$-$G^{ms}$-$G^{ms}$-$T^{e1p}$-$G^{ms}$-$CH_2CH_2OH$  (SEQ ID NO: 69)

(XVII"-5) HO-$C^{e2s}$-$C^{e2s}$-$U^{ms}$-$C^{e2s}$-$C^{e2s}$-$G^{ms}$-$G^{ms}$-$T^{e2s}$-$T^{e2s}$-$C^{e2s}$-$T^{e2s}$-$G^{ms}$-$A^{ms}$-$A^{ms}$-$G^{ms}$-$G^{ms}$-$T^{e2s}$-$G^{ms}$-$CH_2CH_2OH$  (SEQ ID NO: 69)

(XVII"-6) HO-$C^{e1s}$-$C^{e1s}$-$U^{ms}$-$C^{e1s}$-$C^{e1s}$-$G^{ms}$-$G^{ms}$-$T^{e1s}$-$T^{e1s}$-$C^{e1s}$-$T^{e1s}$-$G^{ms}$-$A^{ms}$-$A^{ms}$-$G^{ms}$-$G^{ms}$-$T^{e1s}$-$G^{ms}$-$CH_2CH_2OH$  (SEQ ID NO: 69)

Especially preferable are (XVII"-1) and (XVII"-5)

Preferable examples of the compound represented by general formula (XVIII") include the following compounds.

(XVIII"-1) HO-$T^{e2p}$-$A^{mp}$-$A^{mp}$-$G^{mp}$-$A^{mp}$-$C^{e2p}$-$C^{e2p}$-$T^{e2p}$-$G^{mp}$-$C^{e2p}$-$T^{e2p}$-$C^{e2p}$-$A^{mp}$-$G^{mp}$-$C^{e2p}$-$U^{mp}$-$T^{e2p}$-$C^{e2p}$-$CH_2CH_2OH$  (SEQ ID NO: 72)

(XVIII"-2) HO-$C^{e2p}$-$T^{e2p}$-$C^{e2p}$-$A^{mp}$-$G^{mp}$-$C^{e2p}$-$T^{e2p}$-$U^{mp}$-$C^{mp}$-$T^{e2p}$-$T^{e2p}$-$C^{mp}$-$C^{mp}$-$T^{e2p}$-$T^{e2p}$-$A^{mp}$-$G^{mp}$-$C^{e2p}$-$CH_2CH_2OH$  (SEQ ID NO: 77)

(XVIII"-3) HO-$T^{e1p}$-$A^{mp}$-$A^{mp}$-$G^{mp}$-$A^{mp}$-$C^{e1p}$-$C^{e1p}$-$T^{e1p}$-$G^{mp}$-$C^{e1p}$-$T^{e1p}$-$C^{e1p}$-$A^{mp}$-$G^{mp}$-$C^{e1p}$-$U^{mp}$-$T^{e1p}$-$C^{e1p}$-$CH_2CH_2OH$  (SEQ ID NO: 72)

(XVIII"-4) HO-$C^{e1p}$-$T^{e1p}$-$C^{e1p}$-$A^{mp}$-$G^{mp}$-$C^{e1p}$-$T^{e1p}$-$U^{mp}$-$C^{mp}$-$T^{e1p}$-$T^{e1p}$-$C^{mp}$-$C^{mp}$-$T^{e1p}$-$T^{e1p}$-$A^{mp}$-$G^{mp}$-$C^{e1p}$-$CH_2CH_2OH$  (SEQ ID NO: 77)

(XVIII"-5) HO-$T^{e2p}$-$A^{ms}$-$A^{ms}$-$G^{ms}$-$A^{ms}$-$C^{e2p}$-$C^{e2p}$-$T^{e2p}$-$G^{ms}$-$C^{e2p}$-$T^{e2p}$-$C^{e2p}$-$A^{ms}$-$G^{ms}$-$C^{e2p}$-$U^{ms}$-$T^{e2p}$-$C^{e2p}$-$CH_2CH_2OH$  (SEQ ID NO: 72)

(XVIII"-6) HO-$C^{e2p}$-$T^{e2p}$-$C^{e2p}$-$A^{ms}$-$G^{ms}$-$C^{e2p}$-$T^{e2p}$-$U^{ms}$-$C^{ms}$-$T^{e2p}$-$T^{e2p}$-$C^{ms}$-$C^{ms}$-$T^{e2p}$-$T^{e2p}$-$A^{ms}$-$G^{ms}$-$C^{e2p}$-$CH_2CH_2OH$  (SEQ ID NO: 77)

(XVIII"-7) HO-$T^{e1p}$-$A^{ms}$-$A^{ms}$-$G^{ms}$-$A^{ms}$-$C^{e1p}$-$C^{e1p}$-$T^{e1p}$-$G^{ms}$-$C^{e1p}$-$T^{e1p}$-$C^{e1p}$-$A^{ms}$-$G^{ms}$-$C^{e1p}$-$U^{ms}$-$T^{e1p}$-$C^{e1p}$-$CH_2CH_2OH$  (SEQ ID NO: 72)

(XVIII"-8) HO-$C^{e1p}$-$T^{e1p}$-$C^{e1p}$-$A^{ms}$-$G^{ms}$-$C^{e1p}$-$T^{e1p}$-$U^{ms}$-$C^{ms}$-$T^{e1p}$-$T^{e1p}$-$C^{ms}$-$C^{ms}$-$T^{e1p}$-$T^{e1p}$-$A^{ms}$-$G^{ms}$-$C^{e1p}$-$CH_2CH_2OH$  (SEQ ID NO: 77)

(XVIII"-9) HO-$T^{e2s}$-$A^{ms}$-$A^{ms}$-$G^{ms}$-$A^{ms}$-$C^{e2s}$-$C^{e2s}$-$T^{e2s}$-$G^{ms}$-$C^{e2s}$-$T^{e2s}$-$C^{e2s}$-$A^{ms}$-$G^{ms}$-$C^{e2s}$-$U^{ms}$-$T^{e2s}$-$C^{e2s}$-$CH_2CH_2OH$  (SEQ ID NO: 72)

(XVIII"-10) HO-$C^{e2s}$-$T^{e2s}$-$C^{e2s}$-$A^{ms}$-$G^{ms}$-$C^{e2s}$-$T^{e2s}$-$U^{ms}$-$C^{ms}$-$T^{e2s}$-$T^{e2s}$-$C^{ms}$-$C^{ms}$-$T^{e2s}$-$T^{e2s}$-$A^{ms}$-$G^{ms}$-$C^{e2s}$-$CH_2CH_2OH$  (SEQ ID NO: 77)

(XVIII"-11) HO-$T^{e1s}$-$A^{ms}$-$A^{ms}$-$G^{ms}$-$A^{ms}$-$C^{e1s}$-$C^{e1s}$-$T^{e1s}$-$G^{ms}$-$C^{e1s}$-$T^{e1s}$-$C^{e1s}$-$A^{ms}$-$G^{ms}$-$C^{e1s}$-$U^{ms}$-$T^{e1s}$-$C^{e1s}$-$CH_2CH_2OH$  (SEQ ID NO: 72)

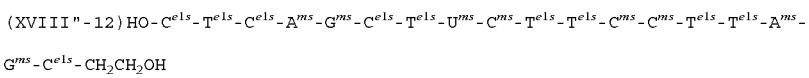
(SEQ ID NO: 77)

Especially preferable are (XVIII"-1), (XVIII"-2), (XVIII"-9) and (XVIII"-10).

Preferable examples of the compound represented by general formula (XIX") include the following compounds.

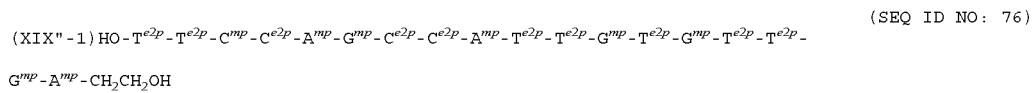
(SEQ ID NO: 76)

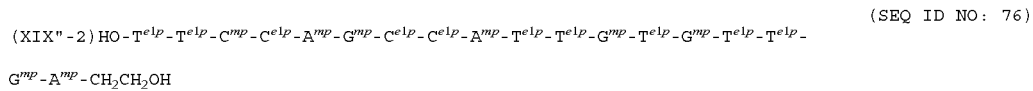
(SEQ ID NO: 76)

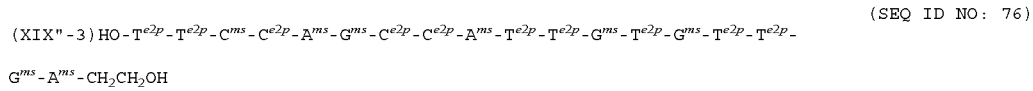
(SEQ ID NO: 76)

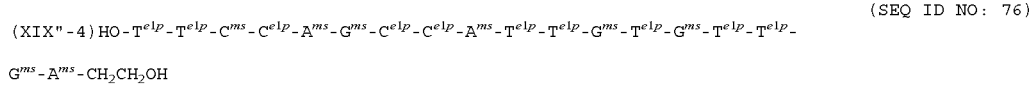
(SEQ ID NO: 76)

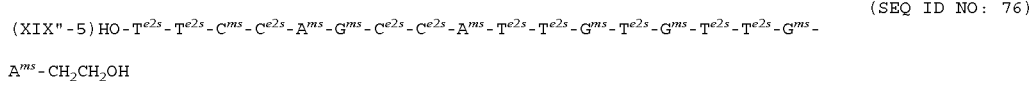
(SEQ ID NO: 76)

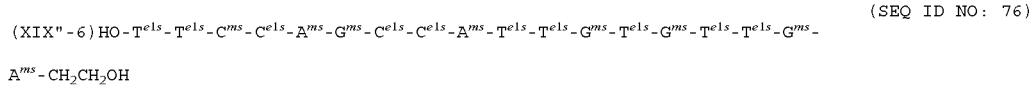
(SEQ ID NO: 76)

Especially preferable are (XIX"-1) and (XIX"-5).

Preferable examples of the compound represented by general formula (XX") include the following compounds.

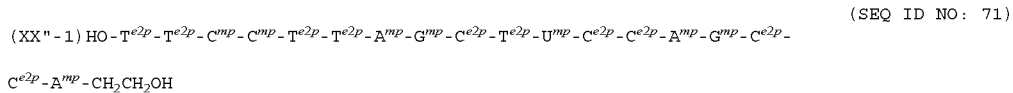
(SEQ ID NO: 71)

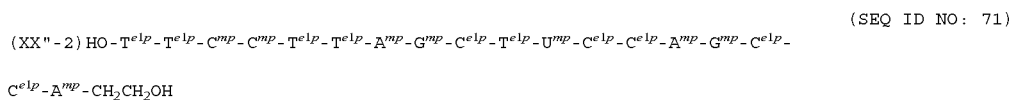
(SEQ ID NO: 71)

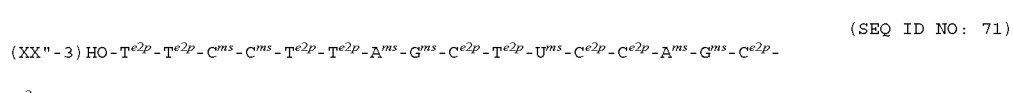
(SEQ ID NO: 71)

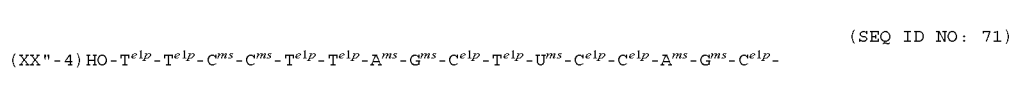
(SEQ ID NO: 71)

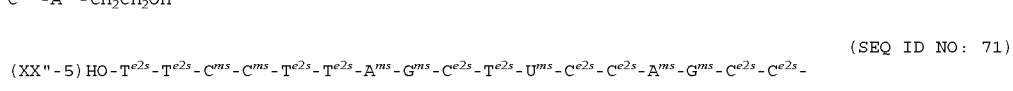
(SEQ ID NO: 71)

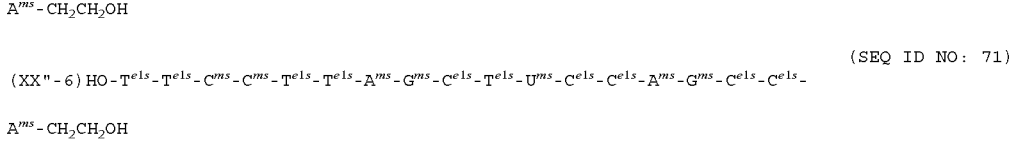
(SEQ ID NO: 71)

Especially preferable are (XX"-1) and (XX"-5).

Preferable examples of the compound represented by general formula (XXI") include the following compounds.

(XXI"-1) HO-G$^{mp}$-C$^{e2p}$-T$^{e2p}$-T$^{e2p}$-C$^{mp}$-U$^{mp}$-T$^{e2p}$-C$^{e2p}$-C$^{mp}$-U$^{mp}$-T$^{e2p}$-A$^{mp}$-G$^{mp}$-C$^{e2p}$-U$^{mp}$-T$^{e2p}$-C$^{e2p}$-C$^{e2p}$-CH$_2$CH$_2$OH (SEQ ID NO: 78)

(XXI"-2) HO-G$^{mp}$-C$^{e1p}$-T$^{e1p}$-T$^{e1p}$-C$^{mp}$-U$^{mp}$-T$^{e1p}$-C$^{e1p}$-C$^{mp}$-U$^{mp}$-T$^{e1p}$-A$^{mp}$-G$^{mp}$-C$^{e1p}$-U$^{mp}$-T$^{e1p}$-C$^{e1p}$-C$^{e1p}$-CH$_2$CH$_2$OH (SEQ ID NO: 78)

(XXI"-3) HO-G$^{ms}$-C$^{e2p}$-T$^{e2p}$-T$^{e2p}$-C$^{ms}$-U$^{ms}$-T$^{e2p}$-C$^{e2p}$-C$^{ms}$-U$^{ms}$-T$^{e2p}$-A$^{ms}$-G$^{ms}$-C$^{e2p}$-U$^{ms}$-T$^{e2p}$-C$^{e2p}$-C$^{e2p}$-CH$_2$CH$_2$OH (SEQ ID NO: 78)

(XXI"-4) HO-G$^{ms}$-C$^{e1p}$-T$^{e1p}$-T$^{e1p}$-C$^{ms}$-U$^{ms}$-T$^{e1p}$-C$^{e1p}$-C$^{ms}$-U$^{ms}$-T$^{e1p}$-A$^{ms}$-G$^{ms}$-C$^{e1p}$-U$^{ms}$-T$^{e1p}$-C$^{e1p}$-C$^{e1p}$-CH$_2$CH$_2$OH (SEQ ID NO: 78)

(XXI"-5) HO-G$^{ms}$-C$^{e2s}$-T$^{e2s}$-T$^{e2s}$-C$^{ms}$-U$^{ms}$-T$^{e2s}$-C$^{e2s}$-C$^{ms}$-U$^{ms}$-T$^{e2s}$-A$^{ms}$-G$^{ms}$-C$^{e2s}$-U$^{ms}$-T$^{e2s}$-C$^{e2s}$-C$^{e2s}$-CH$_2$CH$_2$OH (SEQ ID NO: 78)

(XXI"-6) HO-G$^{ms}$-C$^{e1s}$-T$^{e1s}$-T$^{e1s}$-C$^{ms}$-U$^{ms}$-T$^{e1s}$-C$^{e1s}$-C$^{ms}$-U$^{ms}$-T$^{e1s}$-A$^{ms}$-G$^{ms}$-C$^{e1s}$-U$^{ms}$-T$^{e1s}$-C$^{e1s}$-C$^{e1s}$-CH$_2$CH$_2$OH (SEQ ID NO: 78)

Especially preferable are (XXI"-1) and (XXI"-5).

In the present specification, A$^{e1p}$, G$^{e1p}$, C$^{e1p}$, T$^{e1p}$, A$^{e2p}$, G$^{e2p}$, C$^{e2p}$, T$^{e2p}$, A$^{mp}$, G$^{mp}$, C$^{mp}$, U$^{mp}$, A$^{e1s}$, G$^{e1s}$, C$^{e1s}$, T$^{e1s}$, A$^{e2s}$, G$^{e2s}$, C$^{e2s}$, T$^{e2s}$, A$^{ms}$, G$^{ms}$, C$^{ms}$, U$^{ms}$ and Ph are groups having the following structures, respectively.

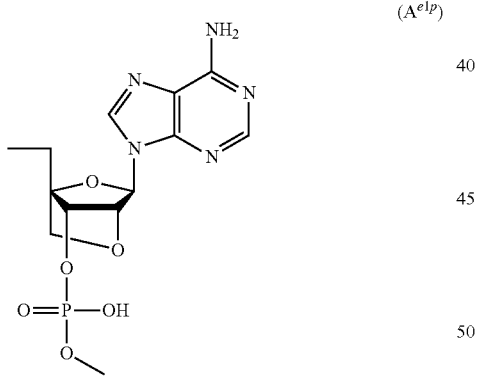

(A$^{e1p}$)

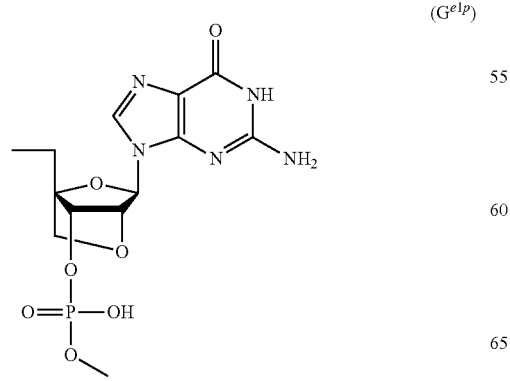

(G$^{e1p}$)

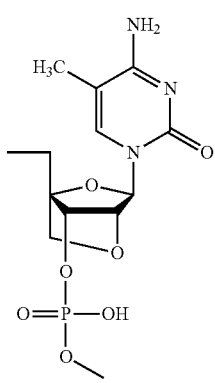

(C$^{e1p}$)

-continued

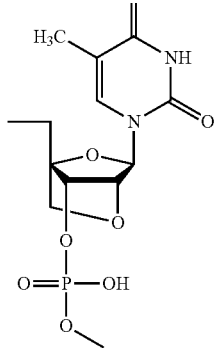

(T$^{e1p}$)

195
-continued
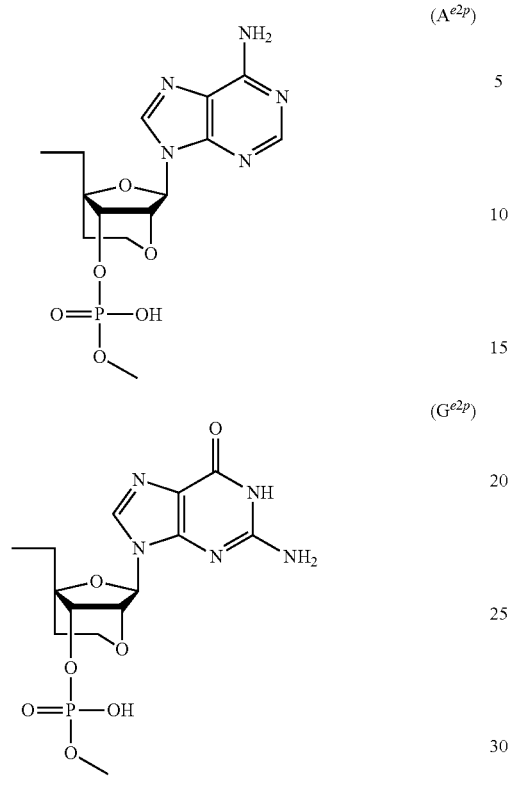
(A^{e2p})
(G^{e2p})
(C^{e2p})
(T^{e2p})
196
-continued
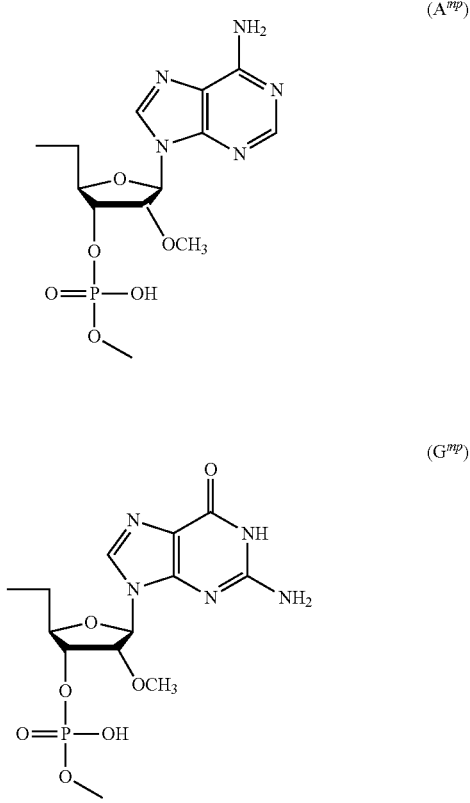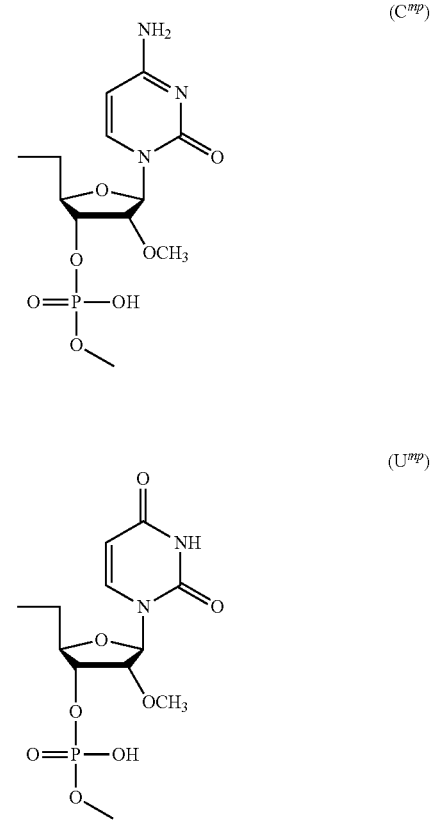
(A^{mp})
(G^{mp})
(C^{mp})
(U^{mp})

197
-continued
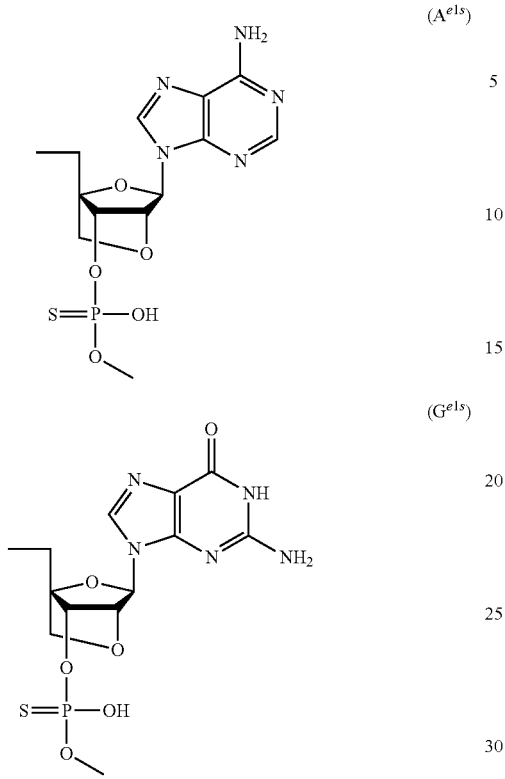
(A^els)
(G^els)
(C^els)
(T^els)
198
-continued
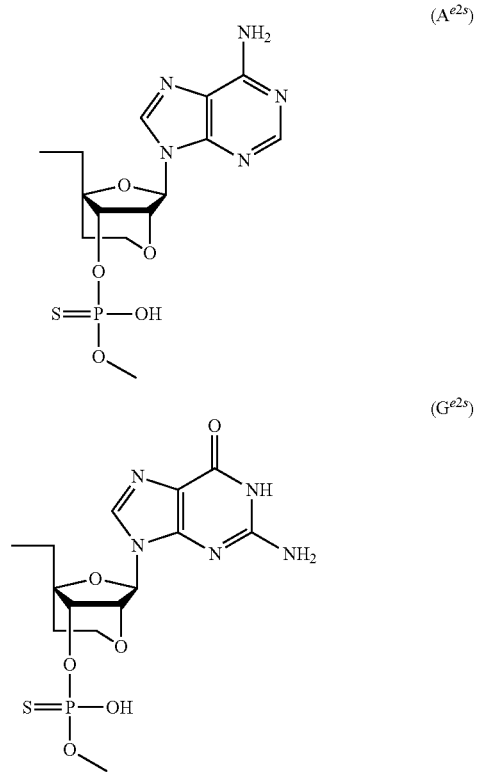
(A^e2s)
(G^e2s)
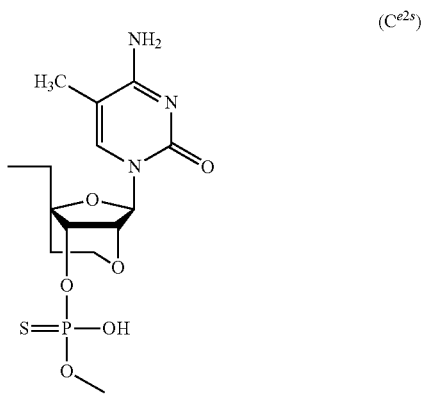
(C^e2s)
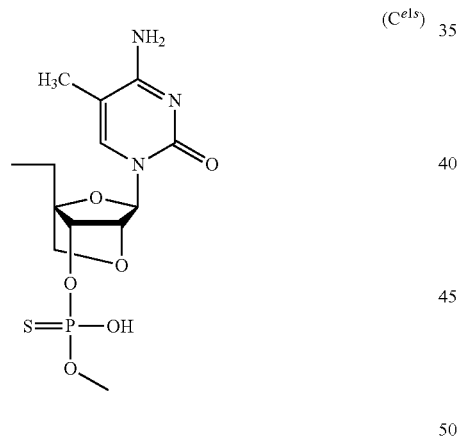
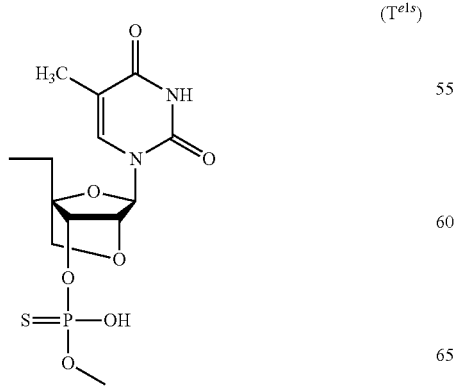
(T^e2s)

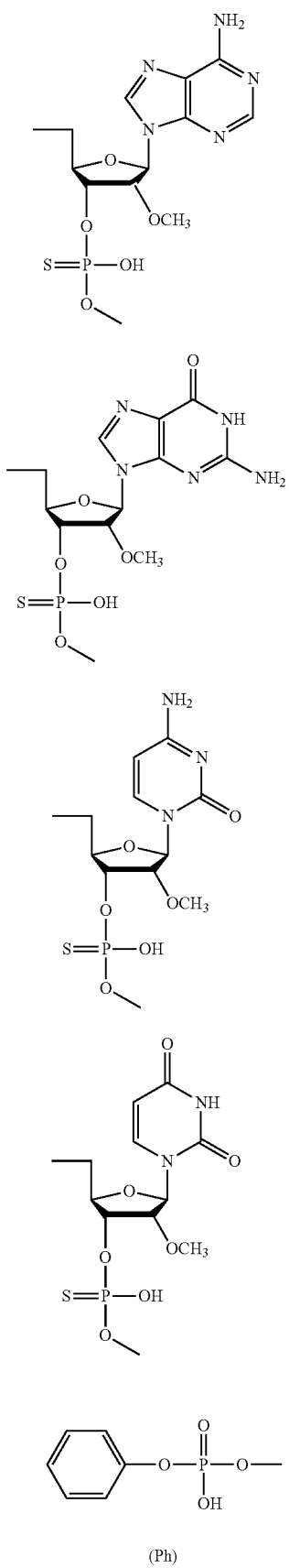

The term "pharmacologically acceptable salt thereof" used in the present specification refers to salts of the oligonucleotide of the invention (e.g. oligonucleotide having the nucleotide sequence as shown in any one of SEQ ID NOS: 1-6, 10-22, 30-78, 87 or 88) or salts of those compounds represented by general formulas (I), (I') to (VII') and (I") to (XXI"). Examples of such salts include metal salts such as alkali metal salts (e.g. sodium salts, potassium salts, lithium salts), alkaline earth metal salts (e.g. calcium salts, magnesium salts), aluminium salts, iron salts, zinc salts, copper salts, nickel salts, cobalt salts and the like; amine salts such as inorganic salts (e.g. ammonium salts), organic salts [e.g. t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts; N',N'-dibenzylethylenediamine salts, chloroprocaine salts, procaine salts, diethanolamine salts, N-benzyl-phenetylamine salts, piperazine salts, tetramethylammonium salts, tris(hydroxymethyl)aminomethane salts] and the like; inorganic acid salts such as halogenated hydroacid salts (e.g. hydrofluorates, hydrochlorides, hydrobromates, hydriodates), nitrates, perchlorates, sulfates, phosphates and the like; organic acid salts such as lower alkane sulfonates (e.g. methanesulfonates, trifluoromethanesulfonates, ethanesulfonates), aryl sulfonates (e.g. benzensulfonates, p-toluenesulfonates), acetates, malates, fumarates, succinates, citrates, tartrates, oxalates, maleates and the like; and amino acid salts (e.g. glycine salts, lysine salts, arginine salts, ornithine salts, glutamates, aspartates). These salts may be prepared according to known methods.

It should be noted that compounds represented by general formulas (I), (I') to (VII') and (I") to (XXI") may occur as hydrates and that such hydrates are also included in the present invention.

The oligonucleotide of the invention, the compounds represented by general formulas (I), (I') to (VII') and (I") to (XXI") (hereinafter, referred to as the "compound of the invention") and pharmacologically acceptable salts thereof are effective as pharmaceuticals for treating muscular dystrophy.

The compound of the invention may be synthesized based on the method described in the literature (Nucleic Acids Research, 12: 4539 (1984)) using a commercial synthesizer (e.g. PerkinElmer Model 392 employing the phosphoroamidite method). As to the phosphoroamidite reagents used in the synthesis, commercial reagents are available for natural nucleosides and 2'-O-methylnucleosides (i.e. 2'-O-methylguanosine, 2'-O-methyladenosine, 2'-O-methylcytosine and 2'-O-methyluridine). As to 2'-O-alkyl-guanosine, -adenosine, -cytosine and -uridine where the alkyl group has 2-6 carbon atoms, they may be synthesized or purchased as described below.

2'-O-aminoethyl-guanosine, -adenosine, -cytosine and -uridine may be synthesized according to Blommers et al., Biochemistry (1998), 37: 17714-17725.

2'-O-propyl-guanosine, -adenosine, -cytosine and -uridine may be synthesized according to Lesnik, E. A. et al., Biochemistry (1993), 32: 7832-7838.

2'-O-allyl-guanosine, -adenosine, -cytosine and -uridine are commercially available.

2'-O-methoxyethyl-guanosine, -adenosine, -cytosine and -uridine may be synthesized according to U.S. Pat. No. 6,261,840 or Martin, P., Helv. Chim. Acta. (1995) 78: 486-504.

2'-O-butyl-guanosine, -adenosine, -cytosine and -uridine may be synthesized according to Lesnik, E. A. et al., Biochemistry (1993), 32: 7832-7838.

2'-O-pentyl-guanosine, -adenosine, -cytosine and -uridine may be synthesized according to Lesnik, E. A. et al., Biochemistry (1993), 32: 7832-7838.

2'-O-propargyl-guanosine, -adenosine, -cytosine and -uridine are commercially available.

2'-O,4'-C-methylene-guanosine, -adenosine, 5-methyl-cytosine and -thymidine may be synthesized according to the method described in WO99/14226.

2'-O,4'-C-alkylene-guanosine and -adenosine where the alkylene group has 2-5 carbon atoms, 5-methyl-cytosine and -thymidine may be synthesized according to the method described in WO00/47599.

In the thioation of phosphate groups, thioate derivatives may be obtained based on the methods described in Tetrahedron Letters, 32, 3005 (1991) and J. Am. Chem. Soc., 112, 1253 (1990), using sulfur and a reagent such as tetraethylthiuram disulfide (TETD; Applied Biosystems) or Beaucage reagent (Glen Research) which reacts with a trivalent phosphate to form a thioate.

With respect to the controlled pore glass (DPG) used in the synthesizer, use of a modified CPG (described in Example 12b of Japanese Unexamined Patent Publication No. H7-87982) allows synthesis of oligonucleotides to which 2-hydroxyethylphosphate group is attached at the 3' end. Further, use of 3'-amino-Modifier C3 CPG 3'-amino-Modifier C7 CPG Glyceryl CPG (Glen Research), 3'-specer C3 SynBase CPG 1000 or 3'-specer C9 SynBase CPG 1000 (Link Technologies) allows synthesis of oligonucleotides to which a hydroxyalkylphosphate group or aminoalkylphosphate group is attached at the 3' end.

The compounds of the present invention and pharmacologically acceptable salts thereof have an effect of inducing skipping of exon 19, 41, 45, 46, 44, 50, 55, 51 or 53 of the dystrophin gene. The compounds of the invention represented by general formulas (I), (I') to (VII') and (I'') to (XXI'') and pharmacologically acceptable salts thereof have high binding strength to RNA and high resistance to nuclease. Therefore, the compounds of the invention and pharmacologically acceptable salts thereof are useful as pharmaceuticals for treating muscular dystrophy.

When the compound of the invention or a pharmacologically acceptable salt thereof is used as a therapeutic for muscular dystrophy, the compound or a pharmacologically acceptable salt or ester thereof may be administered by itself. Alternatively, the compound or a pharmacologically acceptable salt or ester thereof may be mixed with appropriate pharmacologically acceptable excipients or diluents, prepared into tablets, capsules, granules, powders, syrups, etc. and administered orally; or prepared into injections, suppositories, patches, external medicines, etc. and administered parenterally.

These formulations may be prepared by well-known methods using additives such as excipients [organic excipients e.g. sugar derivatives (such as lactose, white sugar, glucose, mannitol and sorbitol), starch derivatives (such as corn starch, potato starch, a starch and dextrin), cellulose derivatives (such as crystalline cellulose), gum arabic, dextran, pullulan and the like; and inorganic excipients e.g. silicate derivatives (such as light silicic acid anhydride, synthetic aluminium silicate, calcium silicate and magnesium aluminate metasilicate), phosphates (such as calcium hydrogenphosphate), carbonates (such as calcium carbonate), sulfates (such as calcium sulfate) and the like], lubricants (e.g. metal salts of stearic acid such as stearic acid, calcium stearate, and magnesium stearate; talc; colloidal silica; waxes such as bees wax and spermaceti; boric acid; adipic acid; sulfates such as sodium sulfate; glycol; fumaric acid; sodium benzoate; DL leucine; lauryl sulfates such as sodium lauryl sulfate and magnesium lauryl sulfate; silicic acid materials such as silicic acid anhydride and silicic acid hydrate; above-mentioned starch derivatives), binders (e.g. hydroxypropylcellulose, hydroxypropylmethylcellulose, polyvinylpyrrolidone, macrogol, compounds enumerated above as excipients), disintegrants (e.g. cellulose derivatives such as low-substituted hydroxypropylcellulose, carboxymethylcellulose, calcium carboxymethylcellulose, internally crosslinked sodium carboxymethylcellulose; chemically modifies starches/celluloses such as carboxymethyl starch, sodium carboxymethyl starch, crosslinked polyvinylpyrrolidone), emulsifiers (e.g. colloidal clay such as bentonite, Veegum; metal hydroxides such as magnesium hydroxide, aluminium hydroxide; anionic surfactants such as sodium lauryl sulfate, calcium stearate; cation surfactants such as benzalkonium chloride; nonionic surfactants such as polyoxyethylene alkyl ethers, polyoxyethylene sorbitan fatty acid esters, sucrose fatty acid ester), stabilizers (e.g. paraoxybenzoic acid esters such as methyl paraben, propyl paraben; alcohols such as chlorobutanol, benzyl alcohol, phenylethyl alcohol; benzalkonium chloride; phenols such as phenol, cresol; thimerosal; dehydroacetic acid; sorbic acid), flavoring/aromatic agents (e.g. conventionally used sweeteners, acidifiers, aromatics, etc.) or diluents.

The therapeutic agent of the present invention comprises preferably 0.05-5 µmoles/ml of the compound of the invention or a pharmacologically acceptable salt thereof, 0.02-10% w/v of carbohydrates or polyhydric alcohols, and 0.01-0.4% w/v of pharmacologically acceptable surfactants. More preferable range for the content of the compound of the invention or a pharmacologically acceptable salt thereof is 0.1-1 µmoles/ml.

For the above carbohydrates, monosaccharides and/or disaccharides are especially preferable. Examples of these carbohydrates and polyhydric alcohols include, but are not limited to, glucose, galactose, mannose, lactose, maltose, mannitol and sorbitol. These may be used alone or in combination.

Preferable examples of surfactants include, but are not limited to, polyoxyethylene sorbitan mono- to tri-esters, alkyl phenyl polyoxyethylene, sodium taurocholate, sodium cholate and polyhydric alcohol esters. Especially preferable are polyoxyethylene sorbitan mono- to tri-esters, where especially preferable esters are oleates, laurates, stearates and palmitates. These surfactants may be used alone or in combination.

More preferably, the therapeutic agent of the invention comprises 0.03-0.09 M of pharmacologically acceptable neutral salt, e.g. sodium chloride, potassium chloride and/or calcium chloride.

Still more preferably, the therapeutic agent of the invention may comprise 0.002-0.05 M of pharmacologically acceptable buffer. Examples of preferable buffers include sodium citrate, sodium glycinate, sodium phosphate and tris(hydroxymethyl)aminomethane. These buffers may be used alone or in combination.

The above-described therapeutic agent of the invention may be supplied in the state of solution. However, considering the storing of the therapeutic agent for some period of time, usually, it is preferable to lyophilize the therapeutic agent for the purpose of stabilizing the antisense oligonucleotide and thereby preventing the lowering of its therapeutic effect. The lyophilized therapeutic agent may be reconstructed with a dissolving liquid (e.g. distilled water for injection) at the time of use, and used in the state of solution. Thus, the therapeutic agent of the invention encompasses such a lyophilized therapeutic agent to be reconstructed with a dissolving liquid at the time of use so that individual components fall under specific concentration ranges. In order to enhance the solubility of the lyophilized product, the therapeutic agent may further contain albumin or amino acids such as glycine.

When the compound of the invention or a pharmacologically acceptable salt thereof is administered to humans, for example, the compound or salt may be administered orally or intravenously at a dose of about 0.1-100 mg/kg body weight per day, preferably 1-50 mg/kg body weight per day for adult patients once a day or divided into several portions. The dose and the number of times of administration may be appropriately changed depending on the type of disease, conditions, the age of the patient, the route of administration, etc.

Administration of the compound of the invention or a pharmacologically acceptable salt thereof to DMD patients may be performed, for example, as described below. Briefly, the compound of the invention or a pharmacologically acceptable salt thereof may be prepared by methods well-known to those skilled in the art, sterilized by conventional methods and then formulated into, for example, an injection solution with a concentration of 1200 μg/ml. This solution is, for example, drip-fed to the patient intravenously in the form of infusion so that the antisense oligonucleotide is administered to the patient at a dose of, for example, 20 mg/kg body weight. Such administration may be repeated, for example, 4 times at intervals of 2 weeks. Then, while confirming the therapeutic effect using indicators such as expression of dystrophin protein in muscle biopsy tissues, serum creatine kinase levels and clinical symptoms, this treatment is repeated appropriately. If therapeutic effect is recognized and yet no definite side effect is observed, this treatment is continued; in principle, the administration is continued throughout life time.

The present specification includes the contents disclosed in the specifications and/or drawings of the Japanese Patent Applications No. 2002-340857 and No. 2003-204381 based on which the present application claims priority.

BEST MODES FOR CARRYING OUT THE INVENTION

Figure 1:
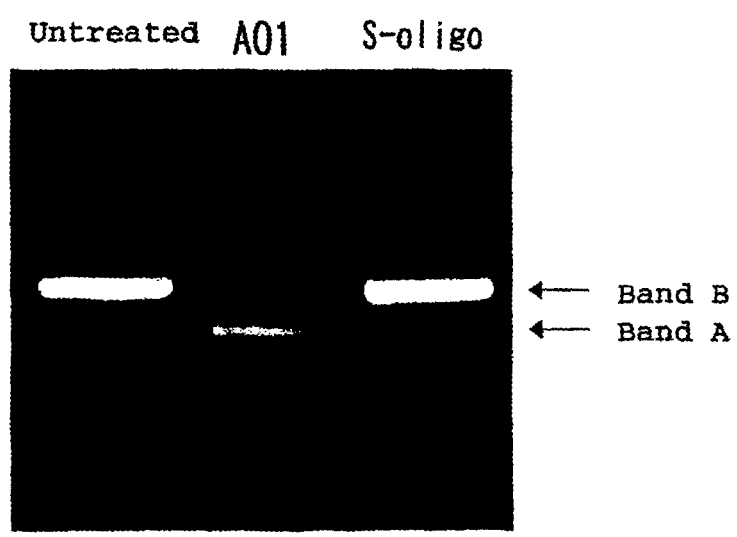
FIG. 1 is a photograph of electrophoresis showing the results of amplification of exons 17-20 by RT-PCR using RNAs extracted from muscular cells transfected with the compound of Example 1 (AO1) and from untreated muscular cells.

Hereinbelow, the present invention will be described specifically with reference to the following Examples. These Examples are provided only for the purpose of illustration, and they are not intended to limit the present invention.

Example 1

Synthesis of HO-$G^{c2P}$-$C^{c2P}$-$C^{c2P}$-$T^{c2P}$-$G^{c2P}$-$A^{mp}$-$G^{mp}$-$C^{mp}$-$U^{mp}$-$G^{mp}$-$A^{mp}$-$U^{mp}$-$C^{mp}$-$U^{mp}$-$G^{mp}$-$C^{mp}$-$U^{mp}$-$G^{mp}$-$G^{mp}$-$C^{mp}$-$A^{mp}$-$U^{mp}$-$C^{mp}$-$U^{mp}$-$U^{mp}$-$G^{mp}$-$C^{e2p}$-$A^{e2p}$-$G^{e2p}$-$T^{e2p}$-$T^{e2p}$-$CH_2CH_2OH$ (AO1) (SEQ ID NO: 196)

The subject compound was synthesized with an automated nucleic acid synthesizer (PerkinElmer ABI model 394 DNA/RNA synthesizer) at a 40 nmol scale. The concentrations of solvents, reagents and phosphoroamidites at individual synthesis cycles were the same as used in the synthesis of natural oligonucleotides. The solvents, reagents and phosphoroamidites of 2'-O-methylnucleoside (adenosine form: product No. 27-1822-41; guanosine form: product No. 27-1826-41; citydine form: product No. 27-1823-02; uridine form: product No. 27-1825-42) were products from Amersham Pharmacia. As non-natural phosphoroamidites, those compounds disclosed in Example 14 (5'-O-dimethoxytrityl-2'-O,4'-C-ethylene-6-N-benzoyladenosine-3'-O-(2-cyanoethyl N,N-diisopropyl)phosphoroamidite), Example 27 (5'-O-dimethoxytrityl-2'-O,4'-C-ethylene-2-N-isobutylylguanosine-3'-O-(2-cyanoethyl N,N-diisopropyl) phosphoroamidite), Example 22 (5'-O-dimethoxytrityl-2'-O, 4'-C-ethyl ene-4-N-benzoyl-5-methylcitydine-3'-O-(2-cyanoethyl N,N-diisopropyl)phosphoroamidite), and Example 9 (5'-O-dimethoxytrityl-2'-O,4'-C-ethylene-5-methyluridine-3'-O-(2-cyanoethyl N,N-diisopropyl)phosphoroamidite) of Japanese Unexamined Patent Publication No. 2000-297097 were used. The subject compound was synthesized on a modified control pore glass (CPG) (disclosed in Example 12b of Japanese Unexamined Patent Publication No. H7-87982) as a solid support. However, the time period for condensation of amidites was 15 min.

The protected oligonucleotide analogue having the sequence of interest was treated with concentrated aqueous ammonia to thereby cut out the oligomer from the support and, at the same time, remove the protective cyanoethyl groups on phosphorus atoms and the protective groups on nucleic acid bases. The solvent was distilled off under reduced pressure, and the resultant residue was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.06 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 9.61 min. (0.393 $A_{260}$ units) (λmax ($H_2O$)=260 nm)

The compound was identified by negative ion ESI mass spectrometric analysis (calculated value: 10628.04; measured value: 10626.86).

The nucleotide sequence of the subject compound is complementary to the nucleotides Nos. 2571-2607 of dystrophin cDNA (Gene Bank accession No. NM_004006.1).

Example 2

Synthesis of HO-$G^{e2p}$-$A^{e2p}$-$T^{e2p}$-$C^{e2p}$-$T^{e2p}$-$G^{mp}$-$C^{mp}$-$U^{mp}$-$G^{mp}$-$G^{mp}$-$C^{e2p}$-$A^{e2p}$-$T^{e2p}$-$C^{e2p}$-$T^{e2p}$-$CH_2CH_2OH$ (AO14) (SEQ ID NO: 197)

The compound of Example 2 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.64 min was collected. When analyzed by reversed phase HPLC [column: Merck, Chromolith Performance RP-18e (4.6×100 mm)); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 4.58 min. (0.806 $A_{260}$ units) (λmax ($H_2O$)=261 nm)

The compound was identified by negative ion ESI mass spectrometric analysis (calculated value: 5281.60; measured value: 5281.40).

The nucleotide sequence of the subject compound is complementary to the nucleotides Nos. 2578-2592 of dystrophin cDNA (Gene Bank accession No. NM_004006.1).

Example 3

Synthesis of HO-$G^{e2p}$-$A^{e2p}$-$T^{e2p}$-$C^{e2p}$-$T^{e2p}$-$G^{mp}$-$C^{mp}$-$U^{mp}$-$G^{mp}$-$G^{mp}$-$C^{mp}$-$A^{mp}$-$U^{mp}$-$C^{mp}$-$U^{mp}$-$U^{mp}$-$G^{mp}$-$C^{e2p}$-$A^{e2p}$-$G^{e2p}$-$T^{e2p}$-$T^{e2p}$-$CH_2CH_2OH$ (AO15) (SEQ ID NO: 198)

The compound of Example 3 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.47 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 7.38 min. (15.05 $A_{260}$ units) (λmax ($H_2O$)=259 nm)

The compound was identified by negative ion EST mass spectrometric analysis (calculated value: 7609.08; measured value: 7609.43).

The nucleotide sequence of the subject compound is complementary to the nucleotides Nos. 2571-2592 of dystrophin cDNA (Gene Bank accession No. NM_004006.1).

Example 4

Synthesis of HO-$G^{e2p}$-$A^{mp}$-$T^{e2p}$-$C^{e2p}$-$T^{e2p}$-$G^{e2p}$-$C^{mp}$-$U^{mp}$-$G^{mp}$-$G^{mp}$-$C^{mp}$-$A^{mp}$-$U^{mp}$-$C^{mp}$-$T^{e2p}$-$T^{e2p}$-$G^{e2p}$-$C^{e2p}$-$A^{mp}$-$G^{e2P}$-$CH_2CH_2OH$ (AO16) (SEQ ID NO: 199)

The compound of Example 4 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→55% (10 min, linear gradient); 60° C.; 2 ml/min; 254 nm]. The fraction eluted at 6.23 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 6.34 min. (6.13 $A_{260}$ units) ($\lambda$max (H$_2$O)=259.4 nm)

The compound was identified by negative ion EST mass spectrometric analysis (calculated value: 6968.69; measured value: 6969.14).

The nucleotide sequence of the subject compound is complementary to the nucleotides Nos. 2573-2592 of dystrophin cDNA (Gene Bank accession No. NM_004006.1).

Example 5

Synthesis of HO-A$^{mp}$-G$^{e2p}$-C$^{e2p}$-T$^{e2p}$-G$^{e2p}$-A$^{mp}$-T$^{e2p}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$OH (AO18) (SEQ ID NO: 200)

The compound of Example 5 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.39 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 5.22 min. (6.88 $A_{260}$ units) ($\lambda$max (H$_2$O)=261 nm)

The compound was identified by negative ion ESI mass spectrometric analysis (calculated value: 6623.48; measured value: 6623.68).

The nucleotide sequence of the subject compound is complementary to the nucleotides Nos. 2578-2596 of dystrophin cDNA (Gene Bank accession No. NM_004006.1).

Example 6

Synthesis of HO-G$^{e2p}$-C$^{e2p}$-C$^{e2p}$-T$^{e2p}$-G$^{e2P}$-A$^{mp}$-G$^{mp}$-C$^{mp}$-U$^{mp}$-G$^{mp}$-A$^{mp}$-U$^{mp}$-C$^{mp}$-U$^{mp}$-G$^{mp}$-C$^{mp}$-U$^{mp}$-G$^{mp}$-G$^{e2p}$-C$^{e2p}$-A$^{mp}$-T$^{e2p}$-C$^{e2p}$-T$^{e2p}$-CH$_2$CH$_2$OH (AO19) (SEQ ID NO: 201)

The compound of Example 6 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.10 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 7.07 min. (6.98 $A_{260}$ units) ($\lambda$max (H$_2$O)=259 nm)

The compound was identified by negative ion ESI mass spectrometric analysis (calculated value: 8300.57; measured value: 8300.14).

The nucleotide sequence of the subject compound is complementary to the nucleotides Nos. 2578-2601 of dystrophin cDNA (Gene Bank accession No. NM_004006.1).

Example 7

Synthesis of HO-A$^{e2p}$-G$^{e2p}$-C$^{e2p}$-T$^{e2p}$-G$^{e2p}$-A$^{e2p}$-T$^{e2p}$-C$^{e2p}$-T$^{e2p}$-G$^{e2p}$-C$^{e2p}$-T$^{e2p}$-G$^{e2p}$-G$^{e2p}$-C$^{e2p}$-A$^{e2p}$-T$^{e2p}$-C$^{e2p}$-T$^{e2p}$-CH$_2$CH$_2$OH (AO25) (SEQ ID NO: 4)

The compound of Example 7 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 4.71 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 8.75 min. (5.26 $A_{260}$ units) ($\lambda$max (H$_2$O)=261 nm)

The compound was identified by negative ion ESI mass spectrometric analysis (calculated value: 6787.68; measured value: 6786.90).

The nucleotide sequence of the subject compound is complementary to the nucleotides Nos. 2578-2596 of dystrophin cDNA (Gene Bank accession No. NM_004006.1).

Example 8

Synthesis of HO-A$^{ms}$-G$^{e2s}$-C$^{e2s}$-T$^{e2s}$-G$^{e2s}$-A$^{ms}$-T$^{e2s}$-C$^{ms}$-U$^{ms}$-G$^{ms}$-C$^{ms}$-U$^{ms}$-G$^{ms}$-G$^{e2s}$-C$^{e2s}$-A$^{ms}$-T$^{e2s}$-C$^{e2s}$-T$^{e2s}$-CH$_2$CH$_2$OH (AO50) (SEQ ID NO: 200)

The compound of Example 5 having a sequence of interest was synthesized in the same manner as in Example 1 except for using a program for 1 μmol scale [installed in the automated nucleic acid synthesizer (PerkinElmer ABI model 394 DNA/RNA synthesizer)]. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→55% (10 min, linear gradient); 60° C.; 2 ml/min; 254 nm]. The fraction eluted at 10.57 min was collected. When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 7.38 min. (49.06 $A_{260}$ units) ($\lambda$max (H$_2$O)=261 nm)

The compound was identified by negative ion ESI mass spectrometric analysis (calculated value: 6928.74; measured value: 6928.73).

The nucleotide sequence of the subject compound is complementary to the nucleotides Nos. 2578-2596 of dystrophin cDNA (Gene Bank accession No. NM_004006.1).

Example 9

Synthesis of HO-$A^{ms}$-$G^{e2p}$-$C^{e2p}$-$T^{e2p}$-$G^{e2p}$-$A^{ms}$-$T^{e2p}$-$C^{ms}$-$U^{ms}$-$G^{ms}$-$C^{ms}$-$U^{ms}$-$G^{ms}$-$G^{e2p}$-$C^{e2p}$-$A^{ms}$-$T^{e2p}$-$C^{e2p}$-$T^{e2p}$-$CH_2CH_2OH$ (AO51) (SEQ ID NO: 200)

The compound of Example 5 having a sequence of interest was synthesized in the same manner as in Example 8 using a program for 1 μmol scale. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→60% (10 min, linear gradient); 60° C.; 2 ml/min; 254 nm]. The fraction eluted at 5.20 min was collected. When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 4.48 min. (30.78 $A_{260}$ units) (λmax ($H_2O$)=260 nm)

The compound was identified by negative ion EST mass spectrometric analysis (calculated value: 6768.08; measured value: 6768.06).

The nucleotide sequence of the subject compound is complementary to the nucleotides Nos. 2578-2596 of dystrophin cDNA (Gene Bank accession No. NM_004006.1)

Example 10

Synthesis of HO-$A^{mp}$-$G^{mp}$-$C^{e2p}$-$T^{e2p}$-$G^{mp}$-$A^{mp}$-$T^{e2p}$-$C^{e2p}$-$T^{e2p}$-$G^{mp}$-$C^{e2p}$-$T^{e2p}$-$G^{mp}$-$G^{mp}$-$C^{e2p}$-$A^{mp}$-$T^{e2p}$-$C^{e2p}$-$T^{e2p}$-$CH_2CH_2OH$ (AO52) (SEQ ID NO: 4)

The compound of Example 5 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→60% (10 min, linear gradient); 60° C.; 2 ml/min; 254 nm]. The fraction eluted at 5.32 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 25%→100% (10 min, linear gradient); 60° C.; 2 ml/min; 254 nm], the subject compound was eluted at 8.51 min. (1.67 $A_{260}$ units) (λmax ($H_2O$)=261 nm)

The compound was identified by negative ion ESI mass spectrometric analysis (calculated value: 6691.60; measured value: 6691.37).

The nucleotide sequence of the subject compound is complementary to the nucleotides Nos. 2578-2596 of dystrophin cDNA (Gene Bank accession No. NM_004006.1).

Example 11

Synthesis of HO-$A^{ms}$-$G^{ms}$-$C^{e2s}$-$T^{e2s}$-$G^{ms}$-$A^{ms}$-$T^{e2s}$-$C^{e2s}$-$T^{e2s}$-$G^{ms}$-$C^{e2s}$-$T^{e2s}$-$G^{ms}$-$G^{ms}$-$C^{e2s}$-$A^{ms}$-$T^{e2s}$-$C^{e2s}$-$T^{e2s}$-$CH_2CH_2OH$ (AO53) (SEQ ID NO: 4)

The compound of Example 5 having a sequence of interest was synthesized in the same manner as in Example 8 using a program for 1 μmol scale. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→50% (10 min, linear gradient); 60° C.; 2 ml/min; 254 nm]. The fraction eluted at 10.59 min was collected. When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.61 min. (36.63 $A_{260}$ units) (λmax ($H_2O$)=263 nm)

The compound was identified by negative ion ESI mass spectrometric analysis (calculated value: 6996.86; measured value: 6996.80).

The nucleotide sequence of the subject compound is complementary to the nucleotides Nos. 2578-2596 of dystrophin cDNA (Gene Bank accession No. NM_004006.1).

Example 12

Synthesis of HO-$A^{ms}$-$G^{ms}$-$C^{e2p}$-$T^{e2p}$-$G^{ms}$-$A^{ms}$-$T^{e2p}$-$C^{e2p}$-$T^{e2p}$-$G^{ms}$-$C^{e2p}$-$T^{e2p}$-$G^{ms}$-$G^{ms}$-$C^{e2p}$-$A^{ms}$-$T^{e2p}$-$C^{e2p}$-$T^{e2p}$-$CH_2CH_2OH$ (AO54) (SEQ ID NO: 4)

The compound of Example 5 having a sequence of interest was synthesized in the same manner as in Example 8 using a program for 1 μmol scale. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→60% (10 min, linear gradient); 60° C.; 2 ml/min; 254 nm]. The fraction eluted at 5.02 min was collected. When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 4.51 min. (44.20 $A_{260}$ units) (λmax ($H_2O$)=260 nm)

The compound was identified by negative ion ESI mass spectrometric analysis (calculated value: 6820.13; measured value: 6820.12).

The nucleotide sequence of the subject compound is complementary to the nucleotides Nos. 2578-2596 of dystrophin cDNA (Gene Bank accession No. NM_004006.1).

Example 13

Synthesis of HO-$G^{e2p}$-$A^{e2p}$-$T^{e2p}$-$C^{e2p}$-$T^{e2p}$-$G^{mp}$-$C^{mp}$-$U^{mp}$-$G^{mp}$-$G^{mp}$-$C^{mp}$-$A^{mp}$-$U^{mp}$-$C^{e2p}$-$T^{e2p}$-$T^{e2p}$-$G^{e2p}$-$C^{e2p}$-$CH_2CH_2OH$ (AO17) (SEQ ID NO: 202)

The compound of Example 13 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 8.32 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 7.14 min. (5.91 $A_{260}$ units) ($\lambda$max ($H_2O$)=260 nm)

The compound was identified by negative ion ESI mass spectrometric analysis (calculated value: 6280.24; measured value: 6279.98).

The nucleotide sequence of the subject compound is complementary to the nucleotides Nos. 2575-2592 of dystrophin cDNA (Gene Bank accession No. NM_004006.1).

Example 14

Synthesis of HO-$G^{e2p}$-$A^{e2p}$-$T^{e2p}$-$C^{e2p}$-$T^{e2p}$-$G^{e2p}$-$C^{e2p}$-$U^{e2p}$-$G^{e2p}$-$G^{e2p}$-$C^{e2p}$-$A^{e2p}$-$T^{e2p}$-$C^{e2p}$-$T^{e2p}$-$CH_2CH_2OH$ (AO24) (SEQ ID NO: 197)

The compound of Example 14 having a sequence of interest was synthesized in the same manner as in Example 1. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→55% (10 min, linear gradient); 60° C.; 2 ml/min; 254 nm]. The fraction eluted at 7.80 min was collected. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 8.89 min. (11.30 $A_{260}$ units) ($\lambda$max ($H_2O$)=261 nm)

The compound was identified by negative ion ESI mass spectrometric analysis (calculated value: 5369.71; measured value: 5369.20).

The nucleotide sequence of the subject compound is complementary to the nucleotides Nos. 2578-2592 of dystrophin cDNA (Gene Bank accession No. NM_004006.1).

Example 15

Synthesis of HO-$A^{e2P}$-$G^{e2p}$-$T^{e2p}$-$T^{e2p}$-$G^{e2p}$-$A^{mp}$-$G^{mp}$-$U^{mp}$-$C^{mp}$-$U^{mp}$-$C^{mp}$-$G^{mp}$-$A^{mp}$-$A^{mp}$-$A^{mp}$-$C^{mp}$-$U^{mp}$-$G^{e2p}$-$A^{e2p}$-$G^{e2p}$-$C^{e2p}$-$A^{e2p}$-$CH_2CH_2OH$ (AO20) (SEQ ID NO: 203)

The subject compound was synthesized with an automated nucleic acid synthesizer (PerkinElmer ABI model 394 DNA/RNA synthesizer) using a 40 nmol DNA program. The concentrations of solvents, reagents and phosphoroamidites at individual synthesis cycles were the same as used in the synthesis of natural oligonucleotides. The solvents, reagents and phosphoroamidites of 2'-O-methylnucleoside (adenosine form: product No. 27-1822-41; guanosine form: product No. 27-1826-41; citydine form: product No. 27-1823-02; uridine form: product No. 27-1825-42) were products from Amersham Pharmacia. As non-natural phosphoroamidites, those compounds disclosed in Example 28 (5'-O-dimethoxytrityl-2'-C-ethylene-6-N-benzoyladenosine-3'-O-(2-cyanoethyl N,N-diisopropyl)phosphoroamidite), Example 41 (5'-O-dimethoxytrityl-2'-O,4'-C-ethylene-N-isobutylyl-guanosine-3'-O-(2-cyanoethyl N,N-diisopropyl)phosphoroamidite), Example 36 (5'-O-dimethoxytrityl-2'-O,4'-C-ethylene-4-N-benzoyl-5-methylcitydine-3'-O-(2-cyanoethyl N,N-diisopropyl)phosphoroamidite), and Example 23 (5'-O-dimethoxytrityl-2'-O,4'-C-ethylene-5-methyluridine-3'-O-(2-cyanoethyl N,N-diisopropyl)phosphoroamidite) of Japanese Unexamined Patent Publication No. 2000-297097 were used. The subject compound was synthesized using approx. 0.25 µmol of a modified control pore glass (CPG) (disclosed in Example 12b of Japanese Unexamined Patent Publication No. H7-87982) as a solid support. However, the time period for condensation of amidites was 15 min.

The protected oligonucleotide analogue having the sequence of interest was treated with concentrated aqueous ammonia to thereby cut out the oligomer from the support and, at the same time, remove the protective cyanoethyl groups on phosphorus atoms and the protective groups on nucleic acid bases. The solvent was distilled off under reduced pressure, and the resultant residue was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→55% (10 min, linear gradient); 60° C.; 2 ml/min; 254 nm]. The fraction eluted at 6.29 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (0.473 $A_{260}$ units) ($\lambda$max ($H_2O$)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 10%→65% (10 min, linear gradient); 60° C.; 2 ml/min; 254 nm], the subject compound was eluted at 7.62 min. The compound was identified by negative ion ESI mass spectrometric analysis (calculated value: 7980.34).

The nucleotide sequence of the subject compound is complementary to the nucleotides Nos. 6133-6155 of dystrophin cDNA (Gene Bank accession No. NM_004006.1).

Example 16

Synthesis of HO-$A^{e2P}$-$G^{e2p}$-$T^{e2p}$-$T^{e2p}$-$G^{e2p}$-$A^{e2p}$-$G^{e2p}$-$T^{e2p}$-$C^{mp}$-$U^{mp}$-$U^{mp}$-$C^{mp}$-$G^{mp}$-$A^{mp}$-$A^{mp}$-$A^{e2p}$-$C^{e2p}$-$T^{e2p}$-$G^{e2p}$-$A^{e2p}$-$G^{e2p}$-$C^{e2p}$-$A^{e2p}$-$CH_2CH_2OH$ (AO26) (SEQ ID NO: 204)

The compound of Example 16 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→60% (10 min, linear gradient); 60° C.; 2 ml/min; 254 nm]. The fraction eluted at 9.76 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (7.93 $A_{260}$ units) (λmax ($H_2O$)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→70% (10 min, linear gradient); 60° C.; 2 ml/min; 254 nm], the subject compound was eluted at 7.03 min. The compound was identified by negative ion ESI mass spectrometric analysis (calculated value: 8094.48; measured value: 8093.74).

The nucleotide sequence of the subject compound is complementary to the nucleotides Nos. 6133-6155 of dystrophin cDNA (Gene Bank accession No. NM_004006.1).

Example 17

Synthesis of HO-$A^{e2p}$-$A^{e2p}$-$A^{e2p}$-$C^{e2p}$-$T^{e2p}$-$G^{mp}$-$A^{mp}$-$G^{mp}$-$C^{mp}$-$A^{mp}$-$A^{mp}$-$A^{mp}$-$U^{mp}$-$T^{e2p}$-$T^{e2p}$-$G^{e2p}$-$C^{e2p}$-$T^{e2p}$-$CH_2CH_2OH$ (AO55) (SEQ ID NO: 205)

The compound of Example 17 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 9.00 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.50 $A_{260}$ units) (λmax ($H_2O$)=259 nm). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr; gradient: solution B 10→40% (10 min, linear gradient); 60° C.; 2 ml/min], the subject compound was eluted at 6.14 min. The compound was identified by negative ion ESI mass spectrometric analysis (calculated value: 6350.31; measured value: 6350.07).

The nucleotide sequence of the subject compound is complementary to the nucleotides Nos. 6125-6142 of dystrophin cDNA (Gene Bank accession No. NM_004006.1).

Example 18

Synthesis of HO-$T^{e2p}$-$T^{e2p}$-$G^{e2p}$-$A^{e2p}$-$G^{e2p}$-$U^{mp}$-$C^{mp}$-$U^{mp}$-$U^{mp}$-$C^{mp}$-$A^{mp}$-$A^{mp}$-$A^{mp}$-$A^{e2p}$-$C^{e2p}$-$T^{e2p}$-$G^{e2p}$-$A^{e2p}$-$CH_2CH_2OH$ (AO56) (SEQ ID NO: 206)

The compound of Example 18 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 6.44 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.15 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 6.38 min. The compound was identified by negative ion ESI mass spectrometric analysis (calculated value: 6254.21; measured value: 6254.15).

The nucleotide sequence of the subject compound is complementary to the nucleotides Nos. 6136-6153 of dystrophin cDNA (Gene Bank accession No. NM_004006.1).

Example 19

Synthesis of HO-$G^{e2p}$-$T^{e2p}$-$G^{e2p}$-$C^{e2p}$-$A^{e2p}$-$A^{mp}$-$A^{mp}$-$G^{mp}$-$U^{mp}$-$U^{mp}$-$G^{mp}$-$A^{mp}$-$G^{mp}$-$T^{e2p}$-$C^{e2p}$-$T^{e2p}$-$T^{e2p}$-$C^{e2p}$-$CH_2CH_2OH$ (AO57) (SEQ ID NO: 207)

The compound of Example 19 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 8.06 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.60 $A_{260}$ units) (λmax ($H_2O$)=258 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 5.73 min. The compound was identified by negative ion ESI mass spectrometric analysis (calculated value: 6328.29; measured value: 6327.91).

The nucleotide sequence of the subject compound is complementary to the nucleotides Nos. 6144-6161 of dystrophin cDNA (Gene Bank accession No. NM_004006.1).

Example 20

Synthesis of HO-$T^{e2p}$-$T^{e2p}$-$G^{mp}$-$A^{mp}$-$G^{mp}$-$T^{e2p}$-$C^{e2p}$-$T^{e2p}$-$T^{e2p}$-$C^{e2p}$-$A^{mp}$-$A^{mp}$-$A^{mp}$-$A^{mp}$-$C^{e2p}$-$T^{e2p}$-$G^{mp}$-$A^{mp}$-$CH_2CH_2OH$ (AO76) (SEQ ID NO: 12)

The compound of Example 20 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.30 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (13.64 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 8.67 min. The compound was identified by negative ion ESI mass spectrometric analysis (calculated value: 6312.34; measured value: 6312.06).

The nucleotide sequence of the subject compound is complementary to the nucleotides Nos. 6136-6153 of dystrophin cDNA (Gene Bank accession No. NM_004006.1).

Example 21

Synthesis of HO-T$^{e2p}$-T$^{e2p}$-G$^{ms}$-As-G$^{ms}$-T$^{e2p}$-C$^{e2p}$-T$^{e2p}$-T$^{e2p}$-C$_{e2p}$-A$^{ms}$-A$^{ms}$-A$^{ms}$-A$^{ms}$-C$^{e2p}$-T$^{e2p}$-G$^{ms}$-A$^{ms}$-CH$_2$CH$_2$OH (AO77) (SEQ ID NO: 12)

The compound of Example 21 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.81 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (5.26 $A_{260}$ units) (λmax ($H_2O$)=262 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 10.0 min. The compound was identified by negative ion ESI mass spectrometric analysis (calculated value: 6456.94; measured value: 6456.59).

The nucleotide sequence of the subject compound is complementary to the nucleotides Nos. 6136-6153 of dystrophin cDNA (Gene Bank accession No. NM_004006.1).

Example 22

Synthesis of HO-T$^{e2s}$-T$^{e2s}$-G$^{ms}$-A$^{ms}$-G$^{ms}$-T$^{e2s}$-C$^{e2s}$-T$^{e2s}$-T$^{e2s}$-C$^{e2s}$-A$^{ms}$-A$^{ms}$-A$^{ms}$-A$^{ms}$-C$^{e2s}$-T$^{e2s}$-G$^{ms}$-A$^{ms}$-CH$_2$CH$_2$OH (AO78) (SEQ ID NO: 12)

The compound of Example 22 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.75 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (15.04 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 10.2 min. The compound was identified by negative ion ESI mass spectrometric analysis (calculated value: 6601.53; measured value: 6601.11).

The nucleotide sequence of the subject compound is complementary to the nucleotides Nos. 6136-6153 of dystrophin cDNA (Gene Bank accession No. NM_004006.1).

Example 23

Synthesis of HO-G$^{mp}$-T$^{e2p}$-G$^{mp}$-C$^{e2p}$-A$^{mp}$-A$^{mp}$-A$^{mp}$-G$^{mp}$-T$^{e2p}$-T$^{e2p}$-G$^{mp}$-A$^{mp}$-G$^{mp}$-T$^{e2p}$-C$^{e2p}$-T$^{e2p}$-T$^{e2p}$-C$^{e2p}$-CH$_2$CH$_2$OH (AO79) (SEQ ID NO: 13)

The compound of Example 23 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.95 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.73 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 6.52 min. The compound was identified by negative ion ESI mass spectrometric analysis (calculated value: 6344.33; measured value: 6344.28).

The nucleotide sequence of the subject compound is complementary to the nucleotides Nos. 6144-6161 of dystrophin cDNA (Gene Bank accession No. NM_004006.1).

Example 24

Synthesis of HO-$G^{ms}$-$T^{e2p}$-$G^{ms}$-$C^{e2p}$-$A^{ms}$-$A^{ms}$-$A^{ms}$-$G^{ms}$-$T^{e2p}$-$T^{e2p}$-$G^{ms}$-$A^{ms}$-$G^{ms}$-$T^{e2p}$-$C^{e2p}$-$T^{e2p}$-$T^{e2p}$-$C^{e2p}$-$CH_2CH_2OH$ (AO80) (SEQ ID NO: 13)

The compound of Example 24 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.55 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (15.27 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 8.71 min. The compound was identified by negative ion ESI mass spectrometric analysis (calculated value: 6488.93; measured value: 6489.03).

The nucleotide sequence of the subject compound is complementary to the nucleotides Nos. 6144-6161 of dystrophin cDNA (Gene Bank accession No. NM_004006.1).

Example 25

Synthesis of HO-$G^{ms}$-$T^{e2s}$-$G^{ms}$-$C^{e2s}$-$A^{ms}$-$A^{ms}$-$A^{ms}$-$G^{ms}$-$T^{e2s}$-$T^{e2s}$-$G^{ms}$-$A^{ms}$-$G^{ms}$-$T^{e2s}$-$C^{e2s}$-$T^{e2s}$-$T^{e2s}$-$C^{e2s}$-$CH_2CH_2OH$ (AO81) (SEQ ID NO: 13)

The compound of Example 25 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.10 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (17.01 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 9.12 min. The compound was identified by negative ion ESI mass spectrometric analysis (calculated value: 6633.53; measured value: 6633.51).

The nucleotide sequence of the subject compound is complementary to the nucleotides Nos. 6144-6161 of dystrophin cDNA (Gene Bank accession No. NM_004006.1).

Example 26

Synthesis of HO-$G^{e2p}$-$C^{e2p}$-$C^{e2p}$-$G^{e2p}$-$C^{e2p}$-$U^{mp}$-$G^{mp}$-$C^{mp}$-$C^{mp}$-$C^{mp}$-$A^{e2P}$-$A^{e2P}$-$T^{e2p}$-$G^{e2p}$-$C^{e2p}$-$CH_2CH_2OH$ (AO33) (SEQ ID NO: 208)

The compound of Example 26 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 7.36 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (12.70 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→60% (10 min, linear gradient); 60° C.; 2 ml/min; 254 nm], the subject compound was eluted at 7.92 min. The compound was identified by negative ion ESI mass spectrometric analysis (calculated value: 5250.59; measured value: 5250.61).

The nucleotide sequence of the subject compound is complementary to the nucleotides Nos. 6696-6710 of dystrophin cDNA (Gene Bank accession No. NM_004006.1).

Example 27

Synthesis of HO-$C^{e2p}$-$G^{mp}$-$C^{e2p}$-$T^{e2p}$-$G^{mp}$-$C^{mp}$-$C^{e2p}$-$C^{e2p}$-$A^{mp}$-$A^{mp}$-$T^{e2p}$-$G^{mp}$-$C^{e2p}$-$C^{e2p}$-$A^{mp}$-$U^{mp}$-$C^{e2p}$-$C^{e2p}$-$CH_2CH_2OH$ (AO85) (SEQ ID NO: 209)

The compound of Example 27 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.32 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (7.93 $A_{260}$ units) ($\lambda$max ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 5.63 min. The compound was identified by negative ion ESI mass spectrometric analysis (calculated value: 6263.34; measured value: 6263.40).

The nucleotide sequence of the subject compound is complementary to the nucleotides Nos. 6691-6708 of dystrophin cDNA (Gene Bank accession No. NM_004006.1).

Example 28

Synthesis of HO-$C^{e2p}$-$A^{mp}$-$G^{mp}$-$T^{e2p}$-$T^{e2p}$-$U^{mp}$-$G^{mp}$-$C^{e2p}$-$C^{e2p}$-$G^{mp}$-$C^{e2p}$-$T^{e2p}$-$G^{mp}$-$C^{e2p}$-$C^{e2p}$-$C^{e2p}$-$A^{mp}$-$A^{mp}$-$CH_2CH_2OH$ (AO86) (SEQ ID NO: 210)

The compound of Example 28 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.10 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.01 $A_{260}$ units) ($\lambda$max ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 6.27 min. The compound was identified by negative ion ESI mass spectrometric analysis (calculated value: 6304.35; measured value: 6304.47).

The nucleotide sequence of the subject compound is complementary to the nucleotides Nos. 6699-6716 of dystrophin cDNA (Gene Bank accession No. NM_004006.1).

Example 29

Synthesis of HO-$T^{e2p}$-$G^{mp}$-$T^{e2p}$-$T^{e2p}$-$C^{e2p}$-$T^{e2p}$-$G^{mp}$-$A^{mp}$-$C^{e2p}$-$A^{mp}$-$A^{mp}$-$C^{e2p}$-$A^{mp}$-$G^{mp}$-$T^{e2p}$-$T^{e2p}$-$T^{e2p}$-$G^{mp}$-$CH_2CH_2OH$ (AO87) (SEQ ID NO: 17)

The compound of Example 29 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.63 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (8.65 $A_{260}$ units) ($\lambda$max ($H_2O$)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 6.06 min. The compound was identified by negative ion ESI mass spectrometric analysis (calculated value: 6331.33; measured value: 6331.14).

The nucleotide sequence of the subject compound is complementary to the nucleotides Nos. 6710-6727 of dystrophin cDNA (Gene Bank accession No. NM_004006.1).

Example 30

Synthesis of HO-$C^{e2s}$-$G^{ms}$-$C^{e2s}$-$T^{e2s}$-$G^{ms}$-$C^{ms}$-$C^{e2s}$-$C^{e2s}$-$A^{ms}$-$A^{ms}$-$T^{e2s}$-$G^{ms}$-$C^{e2s}$-$C^{e2s}$-$A^{ms}$-$U^{ms}$-$C^{e2s}$-$C^{e2s}$-$CH_2CH_2OH$ (AO88) (SEQ ID NO: 209)

The compound of Example 30 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.57 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (12.02 $A_{260}$ units) ($\lambda$max ($H_2O$)=262 nm). When analyzed by ion exchange [column: Tosoh TSK-gel DEAE-5PW (7.5×75 mm); solution A: 20% acetonitrile; solution B: 20% acetonitrile, 67 mM phosphate buffer (pH 6.8), 1.5 M KBr; gradient: solution B 20→60%

(10 min, linear gradient); 40° C.; 2 ml/min], the subject compound was eluted at 7.11 min. The compound was identified by negative ion ESI mass spectrometric analysis (calculated value: 6552.54; measured value: 6553.12).

The nucleotide sequence of the subject compound is complementary to the nucleotides Nos. 6691-6708 of dystrophin cDNA (Gene Bank accession No. NM_004006.1).

Example 31

Synthesis of HO-$G^{e2p}$-$C^{e2p}$-$T^{e2p}$-$T^{e2p}$-$T^{e2p}$-$U^{mp}$-$C^{mp}$-$U^{mp}$-$U^{mp}$-$U^{mp}$-$U^{mp}$-$A^{mp}$-$G^{mp}$-$U^{mp}$-$U^{mp}$-$G^{e2p}$-$C^{e2p}$-$T^{e2p}$-$G^{e2p}$-$C^{e2p}$-$CH_2CH_2OH$ (AO2) (SEQ ID NO: 211)

The compound of Example 31 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.13 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.91 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 10%→50% (10 min, linear gradient); 60° C.; 2 ml/min; 254 nm], the subject compound was eluted at 9.95 min. The compound was identified by negative ion ESI mass spectrometric analysis (calculated value: 6859.54; measured value: 6858.95).

The nucleotide sequence of the subject compound is complementary to the nucleotides Nos. 6973-6992 of dystrophin cDNA (Gene Bank accession No. NM_004006.1).

Example 32

Synthesis of HO-$C^{mp}$-$U^{mp}$-$U^{mp}$-$U^{mp}$-$U^{mp}$-$A^{e2p}$-$G^{e2p}$-$T^{e2p}$-$T^{e2p}$-$G^{e2p}$-$C^{e2p}$-$T^{e2p}$-$G^{e2p}$-$C^{e2p}$-$T^{e2p}$-$C^{e2p}$-$T^{e2p}$-$U^{mp}$-$CH_2CH_2OH$ (AO23) (SEQ ID NO: 212)

The compound of Example 32 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.60 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.56 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 9.31 min. The compound was identified by negative ion ESI mass spectrometric analysis (calculated value: 7496.97; measured value: 7496.53).

The nucleotide sequence of the subject compound is complementary to the nucleotides Nos. 6965-6986 of dystrophin cDNA (Gene Bank accession No. NM_004006.1).

Example 33

Synthesis of HO-$C^{e2p}$-$T^{e2p}$-$G^{e2p}$-$C^{e2p}$-$T^{e2p}$-$U^{mp}$-$C^{mp}$-$C^{mp}$-$U^{mp}$-$C^{mp}$-$C^{e2p}$-$A^{e2p}$-$A^{e2p}$-$C^{e2p}$-$C^{e2p}$-$CH_2CH_2OH$ (AO27) (SEQ ID NO: 214)

The compound of Example 33 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→55% (10 min, linear gradient); 60° C.; 2 ml/min; 254 nm]. The fraction eluted at 6.76 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (6.29 $A_{260}$ units) (λmax ($H_2O$)=265 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 6.27 min. The compound was identified by negative ion ESI mass spectrometric analysis (calculated value: 5160.54; measured value: 5159.90).

The nucleotide sequence of the subject compound is complementary to the nucleotides Nos. 6921-6935 of dystrophin cDNA (Gene Bank accession No. NM_004006.1).

Example 34

Synthesis of HO-$G^{e2p}$-$T^{e2p}$-$T^{e2p}$-$A^{e2p}$-$T^{e2p}$-$C^{mp}$-$U^{mp}$-$G^{mp}$-$C^{mp}$-$U^{mp}$-$U^{mp}$-$C^{mp}$-$C^{mp}$-$U^{mp}$-$C^{mp}$-$C^{e2p}$-$A^{e2p}$-$A^{e2p}$-$C^{e2p}$-$C^{e2p}$-$CH_2CH_2OH$ (AO28) (SEQ ID NO: 215)

The compound of Example 34 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.04 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (5.83 $A_{260}$ units) (λmax ($H_2O$)=263 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 7.16 min. The compound was identified by negative ion ESI mass spectrometric analysis (calculated value: 6808.57; measured value: 6809.21).

The nucleotide sequence of the subject compound is complementary to the nucleotides Nos. 6921-6940 of dystrophin cDNA (Gene Bank accession No. NM_004006.1).

Example 35

Synthesis of HO-$C^{e2p}$-$T^{e2p}$-$T^{e2p}$-$T^{e2p}$-$T^{e2p}$-$A^{mp}$-$G^{mp}$-$U^{mp}$-$U^{mp}$-$G^{mp}$-$C^{mp}$-$U^{mp}$-$G^{mp}$-$C^{mp}$-$U^{mp}$-$C^{mp}$-$U^{mp}$-$T^{e2p}$-$T^{e2p}$-$T^{e2p}$-$C^{e2p}$-$C^{e2p}$-$CH_2CH_2OH$ (AO29) (SEQ ID NO: 216)

The compound of Example 35 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.34 min was collected. (1.83 $A_{260}$ units) (λmax ($H_2O$)=261 nm)
After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→65% (10 min, linear gradient); 60° C.; 2 ml/min; 254 nm], the subject compound was eluted at 7.45 min. The compound was identified by negative ion ESI mass spectrometric analysis (calculated value: 7501.00; measured value: 7500.93).

The nucleotide sequence of the subject compound is complementary to the nucleotides Nos. 6965-6986 of dystrophin cDNA (Gene Bank accession No. NM_004006.1).

Example 36

Synthesis of HO-$T^{e2p}$-$T^{e2p}$-$T^{e2p}$-$T^{e2p}$-$C^{e2p}$-$C^{mp}$-$A^{mp}$-$G^{mp}$-$G^{mp}$-$U^{mp}$-$U^{mp}$-$C^{mp}$-$A^{mp}$-$A^{e2p}$-$G^{e2p}$-$T^{e2p}$-$G^{e2p}$-$G^{e2p}$-$CH_2CH_2OH$ (AO48) (SEQ ID NO: 213)

The compound of Example 36 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 7.55 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (19.88 $A_{260}$ units) (λmax ($H_2O$)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→60% (10 min, linear gradient); 60° C.; 2 ml/min; 254 nm], the subject compound was eluted at 8.72 min. The compound was identified by negative ion ESI mass spectrometric analysis (calculated value: 6291.22; measured value: 6290.99).

The nucleotide sequence of the subject compound is complementary to the nucleotides Nos. 6953-6970 of dystrophin cDNA (Gene Bank accession No. NM_004006.1).

Example 37

Synthesis of HO-$C^{e2s}$-$T^{e2s}$-$G^{e2s}$-$C^{e2s}$-$T^{e2s}$-$U^{ms}$-$C^{ms}$-$C^{ms}$-$U^{ms}$-$C^{ms}$-$C^{e2s}$-$A^{e2s}$-$A^{e2s}$-$C^{e2s}$-$C^{e2s}$-$CH_2CH_2OH$ (AO89) (SEQ ID NO: 214)

The compound of Example 37 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.56 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (5.42 $A_{260}$ units) (λmax ($H_2O$)=267 nm). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→60% (10 min, linear gradient); 40° C.; 2 ml/min], the subject compound was eluted at 6.10 min. The compound was identified by negative ion ESI mass spectrometric analysis (calculated value: 5401.54; measured value: 5401.12).

The nucleotide sequence of the subject compound is complementary to the nucleotides Nos. 6921-6935 of dystrophin cDNA (Gene Bank accession No. NM_004006.1).

Example 38

Synthesis of HO-C$^{e2p}$-U$^{mp}$-G$^{mp}$-C$^{e2p}$-U$^{mp}$-U$^{mp}$-C$^{e2p}$-C$^{e2p}$-U$^{mp}$-C$^{e2p}$-C$^{e2p}$-A$^{mp}$-A$^{mp}$-C$^{e2p}$-C$^{e2p}$-CH$_2$CH$_2$OH (AO90) (SEQ ID NO: 23)

The compound of Example 38 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 7.05 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.86 A$_{260}$ units) (λmax (H$_2$O)=266 nm). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 5→25% (10 min, linear gradient); 40° C.; 2 ml/min], the subject compound was eluted at 8.50 min. The compound was identified by negative ion ESI mass spectrometric analysis (calculated value: 5150.55; measured value: 5150.69).

The nucleotide sequence of the subject compound is complementary to the nucleotides Nos. 6921-6935 of dystrophin cDNA (Gene Bank accession No. NM_004006.1).

Example 39

Synthesis of HO-C$^{e2s}$-U$^{ms}$-G$^{ms}$-C$^{e2s}$-U$^{ms}$-U$^{ms}$-C$^{e2s}$-C$^{e2s}$-U$^{ms}$-C$^{e2s}$-C$^{e2s}$-A$^{ms}$-A$^{ms}$-C$^{e2s}$-C$^{e2s}$-CH$_2$CH$_2$OH (AO91) (SEQ ID NO: 23)

The compound of Example 39 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (10 min, linear gradient); 60° C.; 2 ml/min; 254 nm]. The fraction eluted at 7.21 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.77 A$_{260}$ units) (λmax (H$_2$O)=266 nm). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→60% (10 min, linear gradient); 40° C.; 2 ml/min], the subject compound was eluted at 6.12 min. The compound was identified by negative ion ESI mass spectrometric analysis (calculated value: 5391.55; measured value: 5391.76).

The nucleotide sequence of the subject compound is complementary to the nucleotides Nos. 6921-6935 of dystrophin cDNA (Gene Bank accession No. NM_004006.1).

Example 40

Synthesis of HO-C$^{e2p}$-T$^{c2p}$-G$^{mp}$-C$^{c2p}$-T$^{c2p}$-U$^{mp}$-C$^{mp}$-C$^{c2p}$-U$^{mp}$-C$^{mp}$-C$^{c2p}$-A$^{mp}$-A$^{mp}$-C$^{c2p}$-C$^{c2p}$-CH$_2$CH$_2$OH (AO92) (SEQ ID NO: 214)

The compound of Example 40 having a sequence of interest was synthesized in the same manner as the compound of Example 15 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 7.48 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.64 A$_{260}$ units) (λmax (H$_2$O)=266 nm). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 5→25% (10 min, linear gradient); 40° C.; 2 ml/min], the subject compound was eluted at 5.71 min. The compound was identified by negative ion ESI mass spectrometric analysis (calculated value: 5150.55; measured value: 5150.62).

The nucleotide sequence of the subject compound is complementary to the nucleotides Nos. 6921-6935 of dystrophin cDNA (Gene Bank accession No. NM_004006.1).

Example 41

Synthesis of HO-C$^{e2s}$-T$^{e2s}$-G$^{ms}$-C$^{e2s}$-T$^{e2s}$-U$^{ms}$-C$^{ms}$-C$^{e2s}$-U$^{ms}$-C$^{ms}$-C$^{e2s}$-A$^{ms}$-A$^{ms}$-C$^{e2s}$-C$^{e2s}$-CH$_2$CH$_2$OH (AO93) (SEQ ID NO: 214)

The compound of Example 41 having a sequence of interest was synthesized in the same manner as the compound of Example 15 was synthesized. However, the portion with a phosphorothioate bond was sulfurized by treating with a mixed solution of 0.02 M xanthane hydride/acetonitrile-pyridine (9:1 v/v mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.22 min was collected. (12.77 A$_{260}$ units) (λmax (H$_2$O)=267 nm)

After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest. When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→60% (10 min, linear gradient); 40° C.; 2 ml/min], the subject compound was eluted at 6.42 min. The compound was identified by negative ion ESI mass spectrometric analysis (calculated value: 5391.55; measured value: 5391.64).

The nucleotide sequence of the subject compound is complementary to the nucleotides Nos. 6921-6935 of dystrophin cDNA (Gene Bank accession No. NM_004006.1).

Reference Example 1

Synthesis of hAON4 hAON4 [FAM-CUG CUU CCU CCA ACC (SEQ ID NO: 23); all the nucleotides are 2'-O-methylnucleotide and linked with each other by a phosphorothioate bond] which is disclosed in a document (van Deutekom, J. C. T. et al. (2001) Hum. Mol. Genet. 10, 1547-1554) and known as an oligonucleotide that induces exon 46 skipping was synthesized according to the above document.

FAM is a fluorescence group with the following structure.

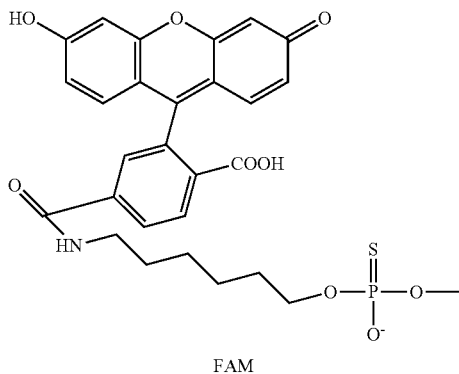

FAM

Reference Example 2

Synthesis of hAON6 hAON6 [FAM-GUU AUC UGC UUC CUC CAA CC (SEQ ID NO: 24); all the nucleotides are 2'-O-methylnucleotide and linked with each other by a phosphorothioate bond] which is disclosed in a document (van Deutekom, J. C. T. et al. (2001) Hum. Mol. Genet. 10, 1547-1554) and known as an oligonucleotide that induces exon 46 skipping was synthesized according to the above document.

Reference Example 3 hAON8 [FAM-GCU UUU CUU UUA GUU GCU GC (SEQ ID NO: 25); all the nucleotides are 2'-O-methylnucleotide and linked with each other by a phosphorothioate bond] which is disclosed in a document (van Deutekom, J. C. T. et al. (2001) Hum. Mol. Genet. 10, 1547-1554) and known as an oligonucleotide that induces exon 46 skipping was synthesized according to the above document.

Example 42

Synthesis of HO-$G^{mp}$-$A^{e2p}$-$A^{mp}$-$A^{mp}$-$A^{mp}$-$C^{e2p}$-$G^{mp}$-$C^{e2p}$-$C^{e2p}$-$G^{mp}$-$C^{mp}$-$C^{e2p}$-$A^{mp}$-$T^{e2p}$-$U^{mp}$-$U^{mp}$-$C^{e2p}$-$T^{e2p}$-$CH_2CH_2OH$ (AO100) (SEQ ID NO: 30)

The subject compound was synthesized with an automated nucleic acid synthesizer (PerkinElmer ABI model 394 DNA/RNA synthesizer) at a 40 nmol scale. The concentrations of solvents, reagents and phosphoroamidites at individual synthesis cycles were the same as used in the synthesis of natural oligonucleotides. The solvents, reagents and phosphoroamidites of 2'-O-methylnucleoside (adenosine form: product No. 27-1822-41; guanosine form: product No. 27-1826-41; citydine form: product No. 27-1823-02; uridine form: product No. 27-1825-42) were products from Amersham Pharmacia. As non-natural phosphoroamidites, those compounds disclosed in Example 55 (5'-O-dimethoxytrityl-2'-O,4'-C-ethylene-6-N-b enzoyladenosine-3'-O-(2-cyanoethyl N,N-diisopropyl)phosphoroamidite), Example 68 (5'-O-dimethoxytrityl-2'-O,4'-C-ethylene-N-isobutylylguanosine-3'-O-(2-cyanoethyl N,N-diisopropyl) phosphoroamidite), Example 63 (5'-O-dimethoxytrityl-2'-O,4'-C-ethylene-4-N-benzoyl-5-methylcitydine-3'-O-(2-cyanoethyl N,N-diisopropyl)phosphoroamidite), and Example 50 (5'-O-dimethoxytrityl-2'-O,4'-C-ethylene-5-methyluridine-3'-O-(2-cyanoethyl N,N-diisopropyl)phosphoroamidite) of Japanese Unexamined Patent Publication No. 2000-297097 were used. The subject compound was synthesized on a modified control pore glass (CPG) (disclosed in Example 12b of Japanese Unexamined Patent Publication No. H7-87982) as a solid support. However, the time period for condensation of amidites was 15 min.

The protected oligonucleotide analogue having the sequence of interest was treated with concentrated aqueous ammonia to thereby cut out the oligomer from the support and, at the same time, remove the protective cyanoethyl groups on phosphorus atoms and the protective groups on nucleic acid bases. The solvent was distilled off under reduced pressure, and the resultant residue was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.55 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (1.40 $A_{260}$ units) (λmax ($H_2O$)=264 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.40 min. The compound was identified by negative ion ESI mass spectrometric analysis (calculated value: 6246.28; measured value: 6245.68).

Example 43

Synthesis of HO-C$^{e2p}$-T$^{e2p}$-G$^{mp}$-U$^{mp}$-T$^{e2p}$-A$^{mp}$-G$^{mp}$-C$^{e2p}$-C$^{mp}$-A$^{mp}$-C$^{e2p}$-T$^{e2p}$-G$^{mp}$-A$^{mp}$-T$^{e2p}$-T$^{e2p}$-A$^{mp}$-A$^{mp}$-CH$_2$CH$_2$OH (AO102) (SEQ ID NO: 31)

The compound of Example 43 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.76 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (14.2 A$_{260}$ units) (λmax (H$_2$O)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 6.42 min. The compound was identified by negative ion ESI mass spectrometric analysis (calculated value: 6262.27; measured value: 6261.87).

The nucleotide sequence of the subject compound is complementary to the nucleotides Nos. 6591-6608 of dystrophin cDNA (Gene Bank accession No. NM_004006.1).

Example 44

Synthesis of HO-T$^{e2p}$-G$^{mp}$-A$^{mp}$-G$^{mp}$-A$^{e2p}$-A$^{mp}$-A$^{mp}$-C$^{e2p}$-T$^{e2p}$-G$^{mp}$-T$^{e2p}$-U$^{mp}$-C$^{e2p}$-A$^{mp}$-G$^{mp}$-C$^{e2p}$-U$^{mp}$-T$^{e2p}$-CH$_2$CH$_2$OH (AO103) (SEQ ID NO: 32)

The compound of Example 44 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 8.12 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (0.204 A$_{260}$ units) (λmax (H$_2$O)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.84 min. The compound was identified by negative ion ESI mass spectrometric analysis (calculated value: 6288.27; measured value: 6288.16).

The nucleotide sequence of the subject compound is complementary to the nucleotides Nos. 6609-6626 of dystrophin cDNA (Gene Bank accession No. NM_004006.1).

Example 45

Synthesis of HO-C$^{e2p}$-A$^{mp}$-G$^{mp}$-G$^{mp}$-A$^{e2p}$-A$^{mp}$-T$^{e2p}$-T$^{e2p}$-U$^{mp}$-G$^{mp}$-T$^{e2p}$-G$^{mp}$-U$^{mp}$-C$^{e2p}$-U$^{mp}$-U$^{mp}$-T$^{e2p}$-C$^{e2p}$-CH$_2$CH$_2$OH (AO104) (SEQ ID NO: 33)

The compound of Example 45 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.46 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.73 A$_{260}$ units) (λmax (H$_2$O)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 6.20 min. The compound was identified by negative ion ESI mass spectrometric analysis (calculated value: 6242.19; measured value: 6241.47).

The nucleotide sequence of the subject compound is complementary to the nucleotides Nos. 6627-6644 of dystrophin cDNA (Gene Bank accession No. NM_004006.1).

Example 45

Synthesis of HO-G$^{mp}$-T$^{e2p}$-A$^{mp}$-U$^{mp}$-T$^{e2p}$-T$^{e2p}$-A$^{mp}$-G$^{mp}$-C$^{e2p}$-A$^{mp}$-T$^{e2p}$-G$^{mp}$-U$^{mp}$-T$^{e2p}$-C$^{mp}$-C$^{e2p}$-C$^{e2p}$-A$^{mp}$-CH$_2$CH$_2$OH (AO105) (SEQ ID NO: 34)

The compound of Example 46 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.11 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (14.8 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 6.04 min. The compound was identified by negative ion ESI mass spectrometric analysis (calculated value: 6239.23; measured value: 6238.90).

The nucleotide sequence of the subject compound is complementary to the nucleotides Nos. 6650-6667 of dystrophin cDNA (Gene Bank accession No. NM_004006.1).

Example 47

Synthesis of HO-$A^{mp}$-$G^{mp}$-$C^{c2p}$-$A^{mp}$-$T^{c2p}$-$G^{mp}$-$T^{c2p}$-$T^{c2p}$-$C^{mp}$-$U^{mp}$-$C^{c2p}$-$A^{mp}$-$A^{mp}$-$T^{c2p}$-$U^{mp}$-$C^{mp}$-$T^{c2p}$-$C^{c2p}$-$CH_2CH_2OH$ (AO106) (SEQ ID NO: 35)

The compound of Example 47 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.51 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (6.97 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 6.22 min. The compound was identified by negative ion ESI mass spectrometric analysis (calculated value: 6198.22; measured value: 6197.87).

The nucleotide sequence of the subject compound is complementary to the nucleotides Nos. 6644-6661 of dystrophin cDNA (Gene Bank accession No. NM_004006.1).

Example 48

Synthesis of HO-$C^{mp}$-$T^{e2p}$-$C^{e2p}$-$A^{mp}$-$G^{mp}$-$A^{mp}$-$T^{e2p}$-$C^{e2p}$-$U^{mp}$-$U^{mp}$-$C^{e2p}$-$T^{e2p}$-$A^{mp}$-$A^{mp}$-$C^{e2p}$-$U^{mp}$-$U^{mp}$-$C^{e2p}$-$CH_2CH_2OH$ (AO108) (SEQ ID NO: 40)

The compound of Example 48 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.74 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (4.91 $A_{260}$ units) (λmax ($H_2O$)=263 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.94 min. The compound was identified by negative ion ESI mass spectrometric analysis (calculated value: 6159.18; measured value: 6159.35).

The nucleotide sequence of the subject compound is complementary to the nucleotides Nos. 7447-7464 of dystrophin cDNA (Gene Bank accession No. NM_004006.1).

Example 49

Synthesis of HO-$A^{mp}$-$C^{e2p}$-$C^{e2p}$-$G^{mp}$-$C^{mp}$-$C^{e2p}$-$T^{e2p}$-$U^{mp}$-$C^{mp}$-$C^{e2p}$-$A^{mp}$-$C^{mp}$-$T^{e2p}$-$C^{e2p}$-$A^{mp}$-$G^{mp}$-$A^{e2p}$-$G^{mp}$-$CH_2CH_2OH$ (AO109) (SEQ ID NO: 41)

The compound of Example 49 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.72 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.30 $A_{260}$ units) (λmax ($H_2O$)=261 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.53 min. The compound was identified by negative ion ESI mass spectrometric analysis (calculated value: 6221.27; measured value: 6220.43).

The nucleotide sequence of the subject compound is complementary to the nucleotides Nos. 7465-7482 of dystrophin cDNA (Gene Bank accession No. NM_004006.1).

Example 50

Synthesis of HO-$T^{e2p}$-$C^{mp}$-$T^{e2p}$-$T^{e2p}$-$G^{mp}$-$A^{mp}$-$A^{mp}$-$G^{mp}$-$T^{e2p}$-$A^{mp}$-$A^{e2p}$-$A^{mp}$-$C^{e2p}$-$G^{mp}$-$G^{mp}$-$T^{e2p}$-$U^{mp}$-$T^{e2p}$-$CH_2CH_2OH$ (AO110) (SEQ ID NO: 42)

The compound of Example 50 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 7.18 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.92 $A_{260}$ units) (λmax ($H_2O$)=258 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.66 min. The compound was identified by negative ion ESI mass spectrometric analysis (calculated value: 6289.26; measured value: 6288.99).

The nucleotide sequence of the subject compound is complementary to the nucleotides Nos. 7483-7500 of dystrophin cDNA (Gene Bank accession No. NM_004006.1).

Example 51

Synthesis of HO-$G^{mp}$-$G^{mp}$-$C^{e2p}$-$T^{e2p}$-$G^{mp}$-$C^{mp}$-$T^{e2p}$-$T^{e2p}$-$U^{mp}$-$G^{mp}$-$C^{e2p}$-$C^{mp}$-$C^{mp}$-$T^{e2p}$-$C^{e2p}$-$A^{mp}$-$G^{mp}$-$C^{e2p}$-$CH_2CH_2OH$ (AO111) (SEQ ID NO: 43)

The compound of Example 51 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 5.91 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.48 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 4.81 min. The compound was identified by negative ion ESI mass spectrometric analysis (calculated value: 6245.24; measured value: 6244.86).

The nucleotide sequence of the subject compound is complementary to the nucleotides Nos. 7501-7518 of dystrophin cDNA (Gene Bank accession No. NM_004006.1).

Example 52

Synthesis of HO-$A^{mp}$-$G^{mp}$-$T^{e2p}$-$C^{e2p}$-$C^{e2p}$-$A^{mp}$-$G^{mp}$-$G^{mp}$-$A^{e2p}$-$G^{mp}$-$C^{e2p}$-$T^{e2p}$-$A^{mp}$-$G^{mp}$-$G^{mp}$-$T^{e2p}$-$C^{e2p}$-$A^{mp}$-$CH_2CH_2OH$ (AO112) (SEQ ID NO: 44)

The compound of Example 52 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.00 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (0.200 $A_{260}$ units) (λmax ($H_2O$)=253 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 4.33 min. The compound was identified by negative ion ESI mass spectrometric analysis (calculated value: 6365.37; measured value: 6365.99).

The nucleotide sequence of the subject compound is complementary to the nucleotides Nos. 7519-7536 of dystrophin cDNA (Gene Bank accession No. NM_004006.1).

Example 53

Synthesis of HO-$G^{mp}$-$C^{e2p}$-$T^{e2p}$-$C^{mp}$-$C^{e2p}$-$A^{mp}$-$A^{mp}$-$T^{e2p}$-$A^{mp}$-$G^{mp}$-$T^{e2p}$-$G^{mp}$-$G^{mp}$-$T^{e2p}$-$C^{e2p}$-$A^{mp}$-$G^{mp}$-$T^{e2p}$-$CH_2CH_2OH$ (AO113) (SEQ ID NO: 45)

The compound of Example 53 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 5.22 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (4.96 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 4.96 min. The compound was identified by negative ion ESI mass spectrometric analysis (calculated value: 6317.31; measured value: 6317.06).

The nucleotide sequence of the subject compound is complementary to the nucleotides Nos. 7534-7551 of dystrophin cDNA (Gene Bank accession No. NM_004006.1).

Example 54

Synthesis of HO-G$^{mp}$-C$^{e2p}$-A$^{mp}$-G$^{mp}$-C$^{e2p}$-C$^{e2p}$-U$^{mp}$-C$^{mp}$-T$^{e2p}$-C$^{mp}$-G$^{mp}$-C$^{e2p}$-T$^{e2p}$-C$^{mp}$-A$^{mp}$-C$^{e2p}$-T$^{e2p}$-C$^{mp}$-CH$_2$CH$_2$OH (AO114) (SEQ ID NO: 47)

The compound of Example 54 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 5.13 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.02 A$_{260}$ units) (λmax (H$_2$O)=267 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.89 min. The compound was identified by negative ion ESI mass spectrometric analysis (calculated value: 6188.23; measured value: 6187.79).

The nucleotide sequence of the subject compound is complementary to the nucleotides Nos. 8275-8292 of dystrophin cDNA (Gene Bank accession No. NM_004006.1).

Example 55

Synthesis of HO-T$^{e2p}$-C$^{e2p}$-U$^{mp}$-U$^{mp}$-C$^{e2p}$-C$^{e2p}$-A$^{mp}$-A$^{mp}$-A$^{mp}$-G$^{mp}$-C$^{e2p}$-A$^{mp}$-G$^{mp}$-C$^{e2p}$-C$^{mp}$-U$^{mp}$-C$^{e2p}$-T$^{e2p}$-CH$_2$CH$_2$OH (AO115) (SEQ ID NO: 48)

The compound of Example 55 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.08 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.68 A$_{260}$ units) (λmax (H$_2$O)=262 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.85 min. The compound was identified by negative ion ESI mass spectrometric analysis (calculated value: 6197.24; measured value: 6196.74).

The nucleotide sequence of the subject compound is complementary to the nucleotides Nos. 8284-8301 of dystrophin cDNA (Gene Bank accession No. NM_004006.1).

Example 56

Synthesis of HO-T$^{e2p}$-G$^{mp}$-C$^{e2p}$-A$^{mp}$-G$^{mp}$-T$^{e2p}$-A$^{mp}$-A$^{mp}$-T$^{e2p}$-C$^{e2p}$-U$^{mp}$-A$^{mp}$-T$^{e2p}$-G$^{mp}$-A$^{mp}$-G$^{mp}$-T$^{e2p}$-T$^{e2p}$-CH$_2$CH$_2$OH (AO116) (SEQ ID NO: 49)

The compound of Example 56 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.02 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (13.40 A$_{260}$ units) (λmax (H$_2$O)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 6.55 min. The compound was identified by negative ion ESI mass spectrometric analysis (calculated value: 6303.28; measured value: 6302.90).

The nucleotide sequence of the subject compound is complementary to the nucleotides Nos. 8302-8319 of dystrophin cDNA (Gene Bank accession No. NM_004006.1).

Example 57

Synthesis of HO-G$^{mp}$-T$^{e2p}$-T$^{e2p}$-U$^{mp}$-C$^{e2p}$-A$^{mp}$-G$^{mp}$-C$^{e2p}$-U$^{mp}$-T$^{e2p}$-C$^{mp}$-T$^{e2p}$-G$^{mp}$-T$^{e2p}$-A$^{mp}$-A$^{mp}$-G$^{mp}$-C$^{e2p}$-CH$_2$CH$_2$OH (AO118) (SEQ ID NO: 50)

The compound of Example 57 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.69 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (8.16 A$_{260}$ units) (λmax (H$_2$O)=261 nm). When analyzed by reversed phase HPLC

[column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.69 min. The compound was identified by negative ion ESI mass spectrometric analysis (calculated value: 6255.23; measured value: 6254.64).

The nucleotide sequence of the subject compound is complementary to the nucleotides Nos. 8356-8373 of dystrophin cDNA (Gene Bank accession No. NM_004006.1).

Example 58

Synthesis of HO-$T^{e2p}$-$G^{mp}$-$T^{e2p}$-$A^{mp}$-$G^{mp}$-$G^{mp}$-$A^{mp}$-$C^{e2p}$-$A^{mp}$-$T^{e2p}$-$T^{e2p}$-$G^{mp}$-$G^{mp}$-$C^{e2p}$-$A^{mp}$-$G^{mp}$-$T^{e2p}$-$T^{e2p}$-$CH_2CH_2OH$ (AO119) (SEQ ID NO: 51)

The compound of Example 58 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.62 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (8.06 $A_{260}$ units) (λmax ($H_2O$)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.72 min. The compound was identified by negative ion ESI mass spectrometric analysis (calculated value: 6358.32; measured value: 6357.91).

The nucleotide sequence of the subject compound is complementary to the nucleotides Nos. 8374-8391 of dystrophin cDNA (Gene Bank accession No. NM_004006.1).

Example 59

Synthesis of HO-$T^{e2p}$-$C^{mp}$-$C^{mp}$-$T^{e2p}$-$T^{e2p}$-$A^{mp}$-$C^{e2p}$-$G^{mp}$-$G^{mp}$-$G^{mp}$-$T^{e2p}$-$A^{mp}$-$G^{mp}$-$C^{e2p}$-$A^{mp}$-$U^{mp}$-$C^{e2p}$-$C^{e2p}$-$CH_2CH_2OH$ (AO120) (SEQ ID NO: 52)

The compound of Example 59 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.14 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (0.459 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.09 min. The compound was identified by negative ion ESI mass spectrometric analysis (calculated value: 6253.26; measured value: 6253.06).

The nucleotide sequence of the subject compound is complementary to the nucleotides Nos. 8392-8409 of dystrophin cDNA (Gene Bank accession No. NM_004006.1).

Example 60

Synthesis of HO-$A^{mp}$-$G^{mp}$-$C^{e2p}$-$T^{e2p}$-$C^{mp}$-$U^{mp}$-$T^{e2p}$-$U^{mp}$-$T^{e2p}$-$A^{mp}$-$C^{mp}$-$T^{e2p}$-$C^{e2p}$-$C^{mp}$-$C^{mp}$-$T^{e2p}$-$T^{e2p}$-$G^{mp}$-$CH_2CH_2OH$ (AO122) (SEQ ID NO: 53)

The compound of Example 60 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.13 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (7.93 $A_{260}$ units) (λmax ($H_2O$)=263 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.55 min. The compound was identified by negative ion ESI mass spectrometric analysis (calculated value: 6152.14; measured value: 6151.48).

The nucleotide sequence of the subject compound is complementary to the nucleotides Nos. 8428-8445 of dystrophin cDNA (Gene Bank accession No. NM_004006.1).

Example 61

Synthesis of HO-$C^{e2p}$-$C^{e2p}$-$A^{mp}$-$U^{mp}$-$T^{e2p}$-$G^{mp}$-$U^{mp}$-$T^{e2p}$-$U^{mp}$-$C^{e2p}$-$A^{mp}$-$U^{mp}$-$C^{e2p}$-$A^{mp}$-$G^{mp}$-$C^{mp}$-$T^{e2p}$-$C^{e2p}$-$CH_2CH_2OH$ (AO123) (SEQ ID NO: 54)

The compound of Example 61 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.71 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.66 $A_{260}$ units) (λmax ($H_2O$)=263 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→100% (10 min, linear gradient); 60° C.; 2 ml/min; 254 nm], the subject compound was eluted at 5.69 min. The compound was identified by negative ion ESI mass spectrometric analysis (calculated value: 6175.18; measured value: 6174.65).

The nucleotide sequence of the subject compound is complementary to the nucleotides Nos. 8441-8458 of dystrophin cDNA (Gene Bank accession No. NM_004006.1).

Example 62

Synthesis of HO-$G^{mp}$-$C^{e2p}$-$C^{e2p}$-$G^{mp}$-$C^{e2p}$-$C^{mp}$-$A^{mp}$-$T^{e2p}$-$U^{mp}$-$U^{mp}$-$C^{e2p}$-$U^{mp}$-$C^{e2p}$-$A^{mp}$-$A^{mp}$-$C^{e2p}$-$A^{e2p}$-$G^{mp}$-$CH_2CH_2OH$ (AO124) (SEQ ID NO: 36)

The compound of Example 62 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.59 min was collected. (12.70 $A_{260}$ units).

After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest. When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 6.13 min. The compound was identified by negative ion ESI mass spectrometric analysis (calculated value: 6222.25; measured value: 6222.24).

The nucleotide sequence of the subject compound is complementary to the nucleotides Nos. 6549-6566 of dystrophin cDNA (Gene Bank accession No. NM_004006.1).

Example 63

Synthesis of HO-$C^{e2p}$-$A^{mp}$-$T^{e2p}$-$A^{mp}$-$A^{mp}$-$T^{e2p}$-$G^{mp}$-$A^{mp}$-$A^{e2p}$-$A^{mp}$-$A^{mp}$-$C^{e2p}$-$G^{mp}$-$C^{mp}$-$C^{e2p}$-$G^{mp}$-$C^{e2p}$-$C^{e2p}$-$CH_2CH_2OH$ (AO125) (SEQ ID NO: 37)

The compound of Example 63 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.68 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.74 $A_{260}$ units). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 7.41 min. The compound was identified by negative ion ESI mass spectrometric analysis (calculated value: 6292.36; measured value: 6292.55).

The nucleotide sequence of the subject compound is complementary to the nucleotides Nos. 6561-6578 of dystrophin cDNA (Gene Bank accession No. NM_004006.1).

Example 64

Synthesis of HO-$T^{e2p}$-$U^{mp}$-$C^{e2p}$-$C^{mp}$-$C^{e2p}$-$A^{mp}$-$A^{mp}$-$T^{e2p}$-$U^{mp}$-$C^{mp}$-$T^{e2p}$-$C^{e2p}$-$A^{mp}$-$G^{mp}$-$G^{mp}$-$A^{e2p}$-$A^{mp}$-$T^{e2p}$-$CH_2CH_2OH$ (AO126) (SEQ ID NO: 38)

The compound of Example 64 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.91 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (13.31 $A_{260}$ units). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 6.25 min. The compound was identified by negative ion ESI mass spectrometric analysis (calculated value: 6208.22; measured value: 6208.15).

The nucleotide sequence of the subject compound is complementary to the nucleotides Nos. 6638-6655 of dystrophin cDNA (Gene Bank accession No. NM_004006.1).

Example 65

Synthesis of HO-$C^{e2p}$-$C^{e2p}$-$A^{mp}$-$U^{mp}$-$T^{e2p}$-$U^{mp}$-$G^{mp}$-$T^{e2p}$-$A^{mp}$-$U^{mp}$-$T^{e2p}$-$T^{e2p}$-$A^{mp}$-$G^{mp}$-$C^{e2p}$-$A^{mp}$-$T^{e2p}$-$G^{mp}$-$CH_2CH_2OH$ (AO127) (SEQ ID NO: 39)

The compound of Example 65 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.49 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.38 $A_{260}$ units). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 6.24 min. The compound was identified by negative ion EST mass spectrometric analysis (calculated value: 6240.22; measured value: 6239.82).

The nucleotide sequence of the subject compound is complementary to the nucleotides Nos. 6656-6673 of dystrophin cDNA (Gene Bank accession No. NM_004006.1).

Example 66

Synthesis of HO-$G^{mp}$-$C^{e2p}$-$T^{e2p}$-$A^{mp}$-$G^{mp}$-$G^{mp}$-$T^{e2p}$-$C^{e2p}$-$A^{mp}$-$G^{mp}$-$G^{mp}$-$C^{e2p}$-$T^{e2p}$-$G^{mp}$-$C^{mp}$-$T^{e2p}$-$T^{e2p}$-$U^{mp}$-CH$_2$CH$_2$OH (AO128) (SEQ ID NO: 46)

The compound of Example 66 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 5.61 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (1.11 $A_{260}$ units). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 5.59 min. The compound was identified by negative ion ESI mass spectrometric analysis (calculated value: 6310.27; measured value: 6310.33).

The nucleotide sequence of the subject compound is complementary to the nucleotides Nos. 7510-7527 of dystrophin cDNA (Gene Bank accession No. NM_004006.1).

Example 67

Synthesis of HO-$C^{mp}$-$T^{e2p}$-$A^{mp}$-$T^{e2p}$-$G^{mp}$-$A^{mp}$-$G^{mp}$-$T^{e2p}$-$T^{e2p}$-$T^{e2p}$-$C^{mp}$-$T^{e2p}$-$T^{e2p}$-$C^{mp}$-$C^{mp}$-$A^{mp}$-$A^{e2p}$-$A^{mp}$-CH$_2$CH$_2$OH (AO129) (SEQ ID NO: 55)

The compound of Example 67 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.83 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.21 $A_{260}$ units). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (8 min, linear gradient); 60° C.; 2 ml/min; 254 nm], the subject compound was eluted at 6.70 min. The compound was identified by negative ion ESI mass spectrometric analysis (calculated value: 6209.21; measured value: 6209.06).

The nucleotide sequence of the subject compound is complementary to the nucleotides Nos. 8293-8310 of dystrophin cDNA (Gene Bank accession No. NM_004006.1).

Exon 51

Example 68

Synthesis of Ph-$T^{e2p}$-$G^{e2p}$-$T^{e2p}$-$G^{e2p}$-$T^{e2p}$-$C^{mp}$-Arnp-$C^{mp}$-$C^{mp}$-$A^{mp}$-$G^{mp}$-$A^{mp}$-$U^{mp}$-$A^{mp}$-$A^{e2p}$-$C^{e2p}$-$A^{e2p}$-$G^{e2p}$-$T^{e2p}$-CH$_2$CH$_2$OH (AO3) (SEQ ID NO: 56)

The compound of Example 68 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 5.24 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (1.21 $A_{260}$ units) (λmax (H$_2$O)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 5.79 min. The compound was identified by negative ion ESI mass spectrometric analysis (calculated value: 6240.22; measured value: 6239.82).

The nucleotide sequence of the subject compound is complementary to the nucleotides Nos. 7565-7584 of dystrophin cDNA (Gene Bank accession No. NM_004006.1).

Example 69

Synthesis of Ph-A$^{e2p}$-G$^{e2p}$-G$^{e2p}$-T$^{e2p}$-T$^{e2p}$-G$^{mp}$-U$^{mp}$-G$^{mp}$-U$^{mp}$-C$^{mp}$-A$^{mp}$-C$^{mp}$-C$^{mp}$-A$^{mp}$-G$^{mp}$-A$^{e2p}$-G$^{e2p}$-T$^{e2p}$-A$^{e2p}$-A$^{e2p}$-CH$_2$CH$_2$OH (AO4) (SEQ ID NO: 57)

The compound of Example 69 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 6.23 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.67 A$_{260}$ units) (λmax (H$_2$O)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 6.45 min. The compound was identified by negative ion ESI mass spectrometric analysis (calculated value: 7153.77; measured value: 7152.95).

The nucleotide sequence of the subject compound is complementary to the nucleotides Nos. 7569-7588 of dystrophin cDNA (Gene Bank accession No. NM_004006.1).

Example 70

Synthesis of Ph-A$^{e2p}$-G$^{e2p}$-T$^{e2p}$-A$^{e2p}$-A$^{e2p}$-C$^{mp}$-C$^{mp}$-A$^{mp}$-C$^{mp}$-A$^{mp}$-G$^{mp}$-G$^{mp}$-U$^{mp}$-U$^{mp}$-G$^{mp}$-T$^{e2p}$-G$^{e2p}$-T$^{e2p}$-C$^{e2p}$-A$^{e2P}$-CH$_2$CH$_2$OH (AO5) (SEQ ID NO: 58)

The compound of Example 70 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 4.71 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (0.836 A$_{260}$ units) (λmax (H$_2$O)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 5.56 min. The compound was identified by negative ion ESI mass spectrometric analysis (calculated value: 7127.78; measured value: 7127.27).

The nucleotide sequence of the subject compound is complementary to the nucleotides Nos. 7578-7597 of dystrophin cDNA (Gene Bank accession No. NM_004006.1).

Example 71

Synthesis of Ph-T$^{e2p}$-T$^{e2p}$-G$^{e2p}$-A$^{e2p}$-T$^{e2p}$-C$^{mp}$-A$^{mp}$-A$^{mp}$-G$^{mp}$-C$^{mp}$-A$^{mp}$-G$^{mp}$-A$^{mp}$-U$^{mp}$-A$^{mp}$-A$^{e2p}$-A$^{e2p}$-G$^{e2p}$-C$^{e2p}$-C$^{e2p}$-CH$_2$CH$_2$OH (AO6) (SEQ ID NO: 59)

The compound of Example 71 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 7.79 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.04 A$_{260}$ units) (λmax (H$_2$O)=258 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 7.81 min. The compound was identified by negative ion ESI mass spectrometric analysis (calculated value: 7187.88; measured value: 7187.41).

The nucleotide sequence of the subject compound is complementary to the nucleotides Nos. 7698-7717 of dystrophin cDNA (Gene Bank accession No. NM_004006.1).

Example 72

Synthesis of Ph-C$^{e2p}$-A$^{e2p}$-C$^{e2p}$-C$^{e2p}$-C$^{e2p}$-U$^{mp}$-C$^{mp}$-U$^{mp}$-G$^{mp}$-U$^{mp}$-G$^{mp}$-A$^{mp}$-U$^{mp}$-U$^{mp}$-U$^{mp}$-T$^{e2p}$-A$^{e2p}$-T$^{e2p}$-A$^{e2p}$-A$^{e2p}$-CH$_2$CH$_2$OH (AO8) (SEQ ID NO: 60)

The compound of Example 72 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→13% (8 min, linear gradient); 60° C.; 2 ml/min; 254 nm]. The fraction eluted at 7.20 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (2.64 $A_{260}$ units) (λmax ($H_2O$)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 7.07 min. The compound was identified by negative ion ESI mass spectrometric analysis (calculated value: 7014.69; measured value: 7014.45).

The nucleotide sequence of the subject compound is complementary to the nucleotides Nos. 7719-7738 of dystrophin cDNA (Gene Bank accession No. NM_004006.1).

Example 73

Synthesis of Ph-$A^{e2P}$-$C^{e2p}$-$C^{e2p}$-$C^{e2p}$-$A^{e2p}$-$C^{mp}$-$C^{mp}$-$A^{mp}$-$U^{mp}$-$C^{mp}$-$A^{mp}$-$C^{mp}$-$C^{mp}$-$C^{mp}$-$U^{mp}$-$C^{e2p}$-$T^{e2p}$-$G^{e2p}$-$T^{e2p}$-$G^{e2p}$-$CH_2CH_2OH$ (AO9) (SEQ ID NO: 61)

The compound of Example 73 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 6.74 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.08 $A_{260}$ units) (λmax ($H_2O$)=265 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 7.20 min. The compound was identified by negative ion ESI mass spectrometric analysis (calculated value: 6986.72; measured value: 6986.81).

The nucleotide sequence of the subject compound is complementary to the nucleotides Nos. 7728-7747 of dystrophin cDNA (Gene Bank accession No. NM_004006.1).

Example 74

Synthesis of Ph-$C^{e2p}$-$C^{e2p}$-$T^{e2p}$-$C^{e2p}$-$A^{e2p}$-$A^{mp}$-$G^{mp}$-$G^{mp}$-$U^{mp}$-$C^{mp}$-$A^{mp}$-$C^{mp}$-$C^{mp}$-$C^{mp}$-$A^{mp}$-$C^{e2p}$-$C^{e2p}$-$A^{e2p}$-$T^{e2p}$-$C^{e2p}$-$CH_2CH_2OH$ (AO10) (SEQ ID NO: 62)

The compound of Example 74 having a sequence of interest was synthesized in the same manner as in Example 42, except that phenyl 2-cyanoethyl N,N-diisopropylphosphoramidite (Hotoda, H. et al. Nucleosides & Nucleotides 15, 531-538, (1996)) was used in the final condensation to introduce phenylphosphate on the 5' terminal side. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm]. The fraction eluted at 6.62 min was collected. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.31 $A_{260}$ units) (λmax ($H_2O$)=266 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: acetonitrile B %: 5%→15% (10 min, linear gradient); 60° C.; 2 ml/min; 254 nm], the subject compound was eluted at 6.46 min. The compound was identified by negative ion ESI mass spectrometric analysis (calculated value: 7037.82; measured value: 7036.73).

The nucleotide sequence of the subject compound is complementary to the nucleotides Nos. 7738-7757 of dystrophin cDNA (Gene Bank accession No. NM_004006.1).

Example 75

Synthesis of HO-$T^{e2p}$-$A^{e2p}$-$A^{e2p}$-$C^{e2p}$-$A^{e2p}$-$G^{mp}$-$U^{mp}$-$C^{mp}$-$U^{mp}$-$G^{mp}$-$A^{mp}$-$G^{mp}$-$U^{mp}$-$A^{e2p}$-$G^{e2p}$-$G^{e2p}$-$A^{e2p}$-$G^{e2p}$-$CH_2CH_2OH$ (AO37) (SEQ ID NO: 63)

The compound of Example 75 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 7.64 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (17.9 $A_{260}$ units) (λmax ($H_2O$)=257 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→60% (10 min, linear gradient); 60° C.; 2 ml/min; 254 nm], the subject compound was eluted at 9.03 min. The compound was identified by negative ion ESI mass spectrometric analysis (calculated value: 6344.26; measured value: 6343.66).

The nucleotide sequence of the subject compound is complementary to the nucleotides Nos. 7554-7571 of dystrophin cDNA (Gene Bank accession No. NM_004006.1).

Example 76

Synthesis of HO-G$^{e2p}$-G$^{e2p}$-C$^{e2p}$-A$^{e2p}$-T$^{e2p}$-U$^{mp}$-U$^{mp}$-C$^{mp}$-U$^{mp}$-A$^{mp}$-G$^{mp}$-U$^{mp}$-U$^{mp}$-T$^{e2p}$-G$^{e2p}$-G$^{e2p}$-A$^{e2p}$-G$^{e2p}$-CH$_2$CH$_2$OH (AO39) (SEQ ID NO: 64)

The compound of Example 76 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.82 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (17.5 A$_{260}$ units) (λmax (H$_2$O)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→60% (10 min, linear gradient); 60° C.; 2 ml/min; 254 nm], the subject compound was eluted at 7.51 min. The compound was identified by negative ion ESI mass spectrometric analysis (calculated value: 6289.17; measured value: 6289.10).

The nucleotide sequence of the subject compound is complementary to the nucleotides Nos. 7612-7629 of dystrophin cDNA (Gene Bank accession No. NM_004006.1).

Example 77

Synthesis of HO-A$^{e2p}$-G$^{e2p}$-C$^{e2p}$-C$^{e2p}$-A$^{e2p}$-G$^{mp}$-U$^{mp}$-C$^{mp}$-G$^{mp}$-G$^{mp}$-U$^{mp}$-A$^{mp}$-A$^{mp}$-G$^{e2p}$-T$^{e2p}$-T$^{e2p}$-C$^{e2p}$-T$^{e2p}$-CH$_2$CH$_2$OH (AO43) (SEQ ID NO: 65)

The compound of Example 77 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (10 min, linear gradient); 60° C.; 2 ml/min; 254 nm]. The fraction eluted at 6.76 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (6.57 A$_{260}$ units) (λmax (H$_2$O)=258 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→60% (10 min, linear gradient); 60° C.; 2 ml/min; 254 nm], the subject compound was eluted at 8.90 min. The compound was identified by negative ion ESI mass spectrometric analysis (calculated value: 6313.28; measured value: 6313.15).

The nucleotide sequence of the subject compound is complementary to the nucleotides Nos. 7684-7701 of dystrophin cDNA (Gene Bank accession No. NM_004006.1).

Example 78

Synthesis of HO-A$^{e2P}$-G$^{e2p}$-T$^{e2p}$-T$^{e2p}$-T$^{e2p}$-G$^{mp}$-G$^{mp}$-A$^{mp}$-G$^{mp}$-A$^{mp}$-U$^{mp}$-G$^{mp}$-G$^{mp}$-C$^{e2p}$-A$^{e2p}$-G$^{e2p}$-T$^{e2p}$-T$^{e2p}$-CH$_2$CH$_2$OH (AO58) (SEQ ID NO: 66)

The compound of Example 78 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→38% (8 min, linear gradient); 60° C.; 2 ml/min; 254 nm]. The fraction eluted at 6.62 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.7 A$_{260}$ units) (λmax (H$_2$O)=258 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 4.80 min. The compound was identified by negative ion ESI mass spectrometric analysis (calculated value: 6313.28; measured value: 6313.15).

The nucleotide sequence of the subject compound is complementary to the nucleotides Nos. 7603-7620 of dystrophin cDNA (Gene Bank accession No. NM_004006.1).

Exon 53

Example 79

Synthesis of HO-C$^{e2p}$-T$^{e2p}$-G$^{mp}$-A$^{mp}$-T$^{e2p}$-T$^{e2p}$-C$^{mp}$-T$^{e2p}$-G$^{mp}$-A$^{mp}$-A$^{mp}$-T$^{e2p}$-T$^{e2p}$-C$^{e2p}$-U$^{mp}$-U$^{mp}$-T$^{e2p}$-C$^{e2p}$-CH$_2$CH$_2$OH (AO64) (SEQ ID NO: 67)

The compound of Example 79 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.06 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.08 A$_{260}$ units) (λmax (H$_2$O)=263 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 7.62 min. The compound was identified by negative ion ESI mass spectrometric analysis (calculated value: 6229.23; measured value: 6229.27).

The nucleotide sequence of the subject compound is complementary to the nucleotides Nos. 7907-7924 of dystrophin cDNA (Gene Bank accession No. NM_004006.1).

Example 80

Synthesis of HO-T$^{e2p}$-T$^{e2p}$-C$^{mp}$-T$^{e2p}$-T$^{e2p}$-G$^{mp}$-T$^{e2p}$-A$^{mp}$-C$^{mp}$-T$^{e2p}$-T$^{e2p}$-C$^{mp}$-A$^{mp}$-T$^{e2p}$-C$^{mp}$-C$^{e2p}$-C$^{e2p}$-A$^{mp}$-CH$_2$CH$_2$OH (AO65) (SEQ ID NO: 68)

The compound of Example 80 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.16 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (7.19 A$_{260}$ units) (λmax (H$_2$O)=264 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 7.98 min. The compound was identified by negative ion ESI mass spectrometric analysis (calculated value: 6188.22; measured value: 6288.69).

The nucleotide sequence of the subject compound is complementary to the nucleotides Nos. 7925-7942 of dystrophin cDNA (Gene Bank accession No. NM_004006.1).

Example 81

Synthesis of HO-C$^{e2p}$-C$^{e2p}$-U$^{mp}$-C$^{e2p}$-C$^{e2p}$-G$^{mp}$-G$^{mp}$-T$^{e2p}$-T$^{e2p}$-C$^{e2p}$-T$^{e2p}$-G$^{mp}$-A$^{mp}$-A$^{mp}$-G$^{mp}$-G$^{mp}$-T$^{e2p}$-G$^{mp}$-CH$_2$CH$_2$OH (AO66) (SEQ ID NO: 69)

The compound of Example 81 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.01 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.7 A$_{260}$ units) (λmax (H$_2$O)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 7.80 min. The compound was identified by negative ion ESI mass spectrometric analysis (calculated value: 6335.32; measured value: 6334.97).

The nucleotide sequence of the subject compound is complementary to the nucleotides Nos. 7943-7960 of dystrophin cDNA (Gene Bank accession No. NM_004006.1).

Example 82

Synthesis of HO-C$^{e2p}$-A$^{mp}$-T$^{e2p}$-T$^{e2p}$-U$^{mp}$-C$^{e2p}$-A$^{mp}$-U$^{mp}$-T$^{e2p}$-C$^{e2p}$-A$^{mp}$-A$^{mp}$-C$^{e2p}$-T$^{e2p}$-G$^{mp}$-T$^{e2p}$-T$^{e2p}$-G$^{mp}$-CH$_2$CH$_2$OH (AO67) (SEQ ID NO: 70)

The compound of Example 82 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.36 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (13.8 A$_{260}$ units) (λmax (H$_2$O)=260 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 6.70 min. The compound was identified by negative ion ESI mass spectrometric analysis (calculated value: 6252.27; measured value: 6252.37).

The nucleotide sequence of the subject compound is complementary to the nucleotides Nos. 7961-7978 of dystrophin cDNA (Gene Bank accession No. NM_004006.1).

Example 83

Synthesis of HO-T$^{e2p}$-T$^{e2p}$-C$^{mp}$-C$^{mp}$-T$^{e2p}$-T$^{e2p}$-A$^{mp}$-G$^{mp}$-C$^{e2p}$-T$^{e2p}$-U$^{mp}$-C$^{e2p}$-C$^{e2p}$-A$^{mp}$-G$^{mp}$-C$^{e2p}$-C$^{e2p}$-A$^{mp}$-CH$_2$CH$_2$OH (AO69) (SEQ ID NO: 71)

The compound of Example 42 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.10 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (8.12 $A_{260}$ units) (λmax ($H_2O$)=264 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 7.02 min. The compound was identified by negative ion ESI mass spectrometric analysis (calculated value: 6226.27; measured value: 6226.10).

The nucleotide sequence of the subject compound is complementary to the nucleotides Nos. 7997-8014 of dystrophin cDNA (Gene Bank accession No. NM_004006.1).

Example 84

Synthesis of HO-$T^{e2p}$-$A^{mp}$-$A^{mp}$-$G^{mp}$-$A^{mp}$-$C^{e2p}$-$C^{e2p}$-$T^{e2p}$-$G^{mp}$-$C^{e2p}$-$T^{e2p}$-$C^{e2p}$-$A^{mp}$-$G^{mp}$-$C^{e2p}$-$U^{mp}$-$T^{e2p}$-$C^{e2p}$-$CH_2CH_2OH$ (AO70) (SEQ ID NO: 72)

The compound of Example 84 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 7.27 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (12.2 $A_{260}$ units) (λmax ($H_2O$)=262 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 8.57 min. The compound was identified by negative ion ESI mass spectrometric analysis (calculated value: 6289.29; measured value: 6289.34).

The nucleotide sequence of the subject compound is complementary to the nucleotides Nos. 8015-8032 of dystrophin cDNA (Gene Bank accession No. NM_004006.1).

Example 85

Synthesis of HO-$C^{e2p}$-$T^{e2p}$-$T^{e2p}$-$G^{mp}$-$G^{mp}$-$C^{e2p}$-$T^{e2p}$-$C^{mp}$-$T^{e2p}$-$G^{mp}$-$G^{mp}$-$C^{mp}$-$C^{e2p}$-$T^{e2p}$-$G^{mp}$-$U^{mp}$-$C^{e2p}$-$C^{e2p}$-$CH_2CH_2OH$ (AO71) (SEQ ID NO: 73)

The compound of Example 85 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 5.65 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.6 $A_{260}$ units) (λmax ($H_2O$)=262 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→80% (10 min, linear gradient); 60° C.; 2 ml/min; 254 nm], the subject compound was eluted at 5.68 min. The compound was identified by negative ion ESI mass spectrometric analysis (calculated value: 6274.27; measured value: 6274.42).

The nucleotide sequence of the subject compound is complementary to the nucleotides Nos. 8033-8050 of dystrophin cDNA (Gene Bank accession No. NM_004006.1).

Example 86

Synthesis of HO-$C^{e2p}$-$T^{e2p}$-$C^{mp}$-$C^{e2p}$-$T^{e2p}$-$U^{mp}$-$C^{e2p}$-$C^{e2p}$-$A^{mp}$-$T^{e2p}$-$G^{mp}$-$A^{mp}$-$C^{e2p}$-$T^{e2p}$-$C^{e2p}$-$A^{mp}$-$A^{mp}$-$G^{mp}$-$CH_2CH_2OH$ (AO72) (SEQ ID NO: 74)

The compound of Example 86 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→46% (8 min, linear gradient); 60° C.; 2 ml/min; 254 nm]. The fraction eluted at 6.09 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.1 $A_{260}$ units) (λmax ($H_2O$)=264 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 20%→60% (10 min, linear gradient); 60° C.; 2 ml/min; 254 nm], the subject compound was eluted at 8.33 min. The compound was identified by negative ion ESI mass spectrometric analysis (calculated value: 6249.31; measured value: 6249.21).

The nucleotide sequence of the subject compound is complementary to the nucleotides Nos. 8051-8068 of dystrophin cDNA (Gene Bank accession No. NM_004006.1).

Example 87

Synthesis of HO-C$^{e2P}$-T$^{e2p}$-G$^{mp}$-A$^{mp}$-A$^{mp}$-G$^{mp}$-G$^{mp}$-T$^{e2p}$-G$^{mp}$-T$^{e2p}$-T$^{e2p}$-C$^{e2p}$-T$^{e2p}$-T$^{e2p}$-G$^{mp}$-T$^{e2p}$-A$^{mp}$-C$^{e2p}$-CH$_2$CH$_2$OH (AO95) (SEQ ID NO: 75)

The compound of Example 87 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.22 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.6 A$_{260}$ units) (λmax (H$_2$O)=259 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 8.31 min. The compound was identified by negative ion ESI mass spectrometric analysis (calculated value: 6347.33; measured value: 6347.50).

The nucleotide sequence of the subject compound is complementary to the nucleotides Nos. 7934-7951 of dystrophin cDNA (Gene Bank accession No. NM_004006.1).

Example 88

Synthesis of HO-T$^{e2p}$-T$^{e2p}$-C$^{mp}$-C$^{e2p}$-A$^{mp}$-G$^{mp}$-C$^{e2p}$-C$^{e2p}$-A$^{mp}$-T$^{e2p}$-T$^{e2p}$-G$^{mp}$-T$^{e2p}$-G$^{mp}$-T$^{e2p}$-T$^{e2p}$-G$^{mp}$-A$^{mp}$-CH$_2$CH$_2$OH (AO96) (SEQ ID NO: 76)

The compound of Example 88 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.09 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (12.8 A$_{260}$ units) (λmax (H$_2$O)=262 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 8.60 min. The compound was identified by negative ion ESI mass spectrometric analysis (calculated value: 6307.31; measured value: 6307.34).

The nucleotide sequence of the subject compound is complementary to the nucleotides Nos. 7988-8005 of dystrophin cDNA (Gene Bank accession No. NM_004006.1).

Example 89

Synthesis of HO-C$^{e2p}$-T$^{e2p}$-C$^{e2p}$-A$^{mp}$-G$^{mp}$-C$^{e2p}$-T$^{e2p}$-U$^{mp}$-C$^{mp}$-T$^{e2p}$-T$^{e2p}$-C$^{mp}$-C$^{mp}$-T$^{e2p}$-T$^{e2p}$-A$^{mp}$-G$^{mp}$-C$^{e2p}$-CH$_2$CH$_2$OH (AO97) (SEQ ID NO: 77)

The compound of Example 89 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.74 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (10.7 A$_{260}$ units) (λmax (H$_2$O)=265 nm). When analyzed by reversed phase HPLC [column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 8.00 min. The compound was identified by negative ion ESI mass spectrometric analysis (calculated value: 6203.23; measured value: 6203.08).

The nucleotide sequence of the subject compound is complementary to the nucleotides Nos. 8006-8023 of dystrophin cDNA (Gene Bank accession No. NM_004006.1).

Example 90

Synthesis of HO-G$^{mp}$-C$^{c2p}$-T$^{c2p}$-T$^{e2p}$-C$^{mp}$-U$^{mp}$-T$^{c2p}$-C$^{c2p}$-C$^{mp}$-U$^{mp}$-T$^{e2p}$-A$^{mp}$-G$^{mp}$-C$^{e2p}$-U$^{mp}$-T$^{c2p}$-C$^{c2p}$-C$^{c2p}$-CH$_2$CH$_2$OH (AO98) (SEQ ID NO: 78)

The compound of Example 90 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 5.35 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.81 A$_{260}$ units) (λmax (H$_2$O)=265 nm). When analyzed by reversed phase HPLC

[column: Merck, Chromolith Performance RP-18e (4.6×100 mm); solution A: 5% acetonitrile, 0.1 M aqueous triethylamine acetate (TEAA), pH 7.0; solution B: 25% acetonitrile, 0.1 M TEAA B %: 15%→100% (10 min, linear gradient); 60° C.; 2 ml/min; 254 nm], the subject compound was eluted at 7.06 min. The compound was identified by negative ion ESI mass spectrometric analysis (calculated value: 6180.19; measured value: 6180.27).

The nucleotide sequence of the subject compound is complementary to the nucleotides Nos. 8002-8019 of dystrophin cDNA (Gene Bank accession No. NM_004006.1).

Example 91

Synthesis of HO-$G^{mp}$-$G^{mp}$-$C^{e2p}$-$A^{mp}$-$T^{e2p}$-$T^{e2p}$-$U^{mp}$-$C^{e2p}$-$T^{e2p}$-$A^{mp}$-$G^{mp}$-$U^{mp}$-$T^{e2p}$-$T^{e2p}$-$G^{mp}$-$G^{mp}$-$A^{e2p}$-$G^{mp}$-$CH_2CH_2OH$ (AO131) (SEQ ID NO: 87)

The compound of Example 91 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.27 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (1.80 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 15→60% (10 min, linear gradient); 40° C.; 2 ml/min], the subject compound was eluted at 4.89 min.

The nucleotide sequence of the subject compound is complementary to the nucleotides Nos. 7612-7629 of dystrophin cDNA (Gene Bank accession No. NM_004006.1).

Example 92

Synthesis of HO-$G^{ms}$-$G^{ms}$-$C^{e2s}$-$A^{ms}$-$T^{e2s}$-$T^{e2s}$-$U^{ms}$-$C^{e2s}$-$T^{e2s}$-$A^{ms}$-$G^{ms}$-$U^{ms}$-$T^{e2s}$-$T^{e2s}$-$G^{ms}$-$G^{ms}$-$A^{e2s}$-$G^{ms}$-$CH_2CH_2OH$ (AO132) (SEQ ID NO: 87)

The compound of Example 92 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.47 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (15.1 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 8.46 min.

The nucleotide sequence of the subject compound is complementary to the nucleotides Nos. 7612-7629 of dystrophin cDNA (Gene Bank accession No. NM_004006.1).

Example 93

Synthesis of HO-$G^{ms}$-$C^{e2s}$-$T^{e2s}$-$T^{e2s}$-$C^{ms}$-$U^{ms}$-$T^{e2s}$-$C^{e2s}$-$C^{ms}$-$U^{ms}$-$T^{e2s}$-$A^{ms}$-$G^{ms}$-$C^{e2s}$-$U^{ms}$-$T^{e2s}$-$C^{e2s}$-$C^{e2s}$-$CH_2CH_2OH$ (AO133) (SEQ ID NO: 78)

The compound of Example 93 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.65 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (15.1 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.47 min.

The nucleotide sequence of the subject compound is complementary to the nucleotides Nos. 8002-8019 of dystrophin cDNA (Gene Bank accession No. NM_004006.1).

Example 94

Synthesis of HO-$G^{ms}$-$A^{e2s}$-$A^{ms}$-$A^{ms}$-$A^{ms}$-$C^{e2s}$-$G^{ms}$-$C^{e2s}$-$C^{e2s}$-$G^{ms}$-$C^{ms}$-$C^{e2s}$-$A^{ms}$-$T^{e2s}$-$U^{ms}$-$U^{ms}$-$C^{e2s}$-$T^{e2s}$-$CH_2CH_2OH$ (AO134) (SEQ ID NO: 30)

The compound of Example 94 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-$H_2O$. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.51 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (6.65 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 7.46 min.

The nucleotide sequence of the subject compound is complementary to the nucleotides Nos. 6555-6572 of dystrophin cDNA (Gene Bank accession No. NM_004006.1).

Example 95

Synthesis of HO-$A^{ms}$-$C^{e2s}$-$C^{e2s}$-$G^{ms}$-$C^{ms}$-$C^{e2s}$-$T^{e2s}$-$U^{ms}$-$C^{ms}$-$C^{e2s}$-$A^{ms}$-$C^{ms}$-$T^{e2s}$-$C^{e2s}$-$A^{ms}$-$G^{ms}$-$A^{e2s}$-$G^{ms}$-CH$_2$CH$_2$OH (AO135) (SEQ ID NO: 41)

The compound of Example 95 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.87 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.06 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.92 min.

The nucleotide sequence of the subject compound is complementary to the nucleotides Nos. 7465-7482 of dystrophin cDNA (Gene Bank accession No. NM_004006.1).

Example 96

Synthesis of HO-$G^{ms}$-$C^{e2s}$-$A^{ms}$-$G^{ms}$-$C^{e2s}$-$C^{e2s}$-$U^{ms}$-$C^{ms}$-$T^{e2s}$-$C^{ms}$-$G^{ms}$-$C^{e2s}$-$T^{e2s}$-$C^{ms}$-$A^{ms}$-$C^{e2s}$-$T^{e2s}$-$C^{ms}$-CH$_2$CH$_2$OH (AO136) (SEQ ID NO: 47)

The compound of Example 96 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.24 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (11.2 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.66 min.

The nucleotide sequence of the subject compound is complementary to the nucleotides Nos. 8275-8292 of dystrophin cDNA (Gene Bank accession No. NM_004006.1).

Example 97

Synthesis of HO-$T^{e2s}$-$C^{e2s}$-$U^{ms}$-$U^{ms}$-$C^{e2s}$-$C^{e2s}$-$A^{ms}$-$A^{ms}$-$A^{ms}$-$G^{ms}$-$C^{e2s}$-$A^{ms}$-$G^{ms}$-$C^{e2s}$-$C^{ms}$-$U^{ms}$-$C^{e2s}$-$T^{e2s}$-CH$_2$CH$_2$OH (AO137) (SEQ ID NO: 48)

The compound of Example 97 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.40 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (9.46 $A_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.82 min.

The nucleotide sequence of the subject compound is complementary to the nucleotides Nos. 8284-8301 of dystrophin cDNA (Gene Bank accession No. NM_004006.1).

Example 98

Synthesis of HO-A$^{e2s}$-G$^{ms}$-T$^{e2s}$-U$^{ms}$-T$^{e2s}$-G$^{ms}$-G$^{ms}$-A$^{e2s}$-G$^{ms}$-A$^{ms}$-T$^{e2s}$-G$^{ms}$-G$^{ms}$-C$^{e2s}$-A$^{e2s}$-G$^{ms}$-T$^{e2s}$-T$^{e2s}$-CH$_2$CH$_2$OH (AO139) (SEQ ID NO: 88)

The compound of Example 98 having a sequence of interest was synthesized in the same manner as the compound of Example 42 was synthesized. However, the portion with a phosphorothioate bond was sulfurized by treating with a mixed solution of 0.02 M xanthane hydride/acetonitrile-pyridine (9:1 mixture) for 15 min, instead of the oxidation step with iodine-H$_2$O. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 7.08 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (12.9 A$_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 20→80% (10 min, linear gradient); 40° C.; 2 ml/min], the subject compound was eluted at 6.92 min.

The nucleotide sequence of the subject compound is complementary to the nucleotides Nos. 7603-7620 of dystrophin cDNA (Gene Bank accession No. NM_004006.1).

Example 99

Synthesis of HO-A$^{e2P}$-G$^{mp}$-T$^{e2p}$-U$^{mp}$-T$^{e2p}$-G$^{mp}$-G$^{mp}$-A$^{e2p}$-G$^{mp}$-A$^{mp}$-T$^{e2p}$-G$^{mp}$-G$^{mp}$-C$^{e2p}$-A$^{e2p}$-G$^{mp}$-T$^{e2p}$-T$^{e2p}$-CH$_2$CH$_2$OH (AO140) (SEQ ID NO: 88)

The compound of Example 99 having a sequence of interest was synthesized in the same manner as the compound of Example 42 was synthesized. After deprotection, the resultant product was purified by reversed phase HPLC [Shimadzu model LC-10VP; column: Merck, Chromolith Performance RP-18e (4.6×100 mm); solution A: 5% acetonitrile, 0.1 M aqueous triethylamine acetate (TEAA), pH 7.0; solution B: acetonitrile B %: 10%→45% (8 min, linear gradient); 60° C.; 2 ml/min; 254 nm]. The fraction eluted at 6.47 min was collected. After the solvent was distilled off under reduced pressure, 80% aqueous acetic acid solution was added to the residue, which was then left for 20 min to remove the DMTr group. After distilling off the solvent, the resultant residue was dissolved in 0.5 ml of water and filtered with Ultrafree-MC (Millipore: product No. UFC4 OHV 25). The solvent was distilled off to thereby obtain the compound of interest (3.54 A$_{260}$ units). When analyzed by ion exchange HPLC [column: Tosoh TSK-gel DEAE-5PW (7.5×75 mm); solution A: 20% acetonitrile; solution B: 20% acetonitrile, 67 mM phosphate buffer (pH 6.8), 1.5 M KBr, gradient: solution B 10→50% (10 min, linear gradient); 40° C.; 2 ml/min], the subject compound was eluted at 5.54 min.

The nucleotide sequence of the subject compound is complementary to the nucleotides Nos. 7603-7620 of dystrophin cDNA (Gene Bank accession No. NM_004006.1).

Test Example 1

Method of Analysis of the Exon Skipping Induction Ability by Antisense ENA

Preparation of Primary Culture of Myoblast Cells

A primary culture of myoblast cells was established as described below.

1. Muscle tissue samples taken from the rectus muscle of the thigh of Duchenne muscular dystrophy patients were cut into fine pieces and washed with PBS twice.
2. The muscle tissue from 1 above was treated with Difco Bacto™ tripton 250 at 37° C. for 30 min to thereby obtain free cells enzymatically.
3. The free cells from 2 above were washed with DMEM (containing 20% FBS) twice.
4. The cells from 3 above were suspended in DMEM (containing 20% FBS and 4% ultroser G).
5. The suspension cells from 4 were passed through a mesh (Becton Dickinson: cell strainer 35-2360) to recover only free cells.
6. The recovered cells from 5 above were seeded on gelatin-coated dishes.
7. The cells were cultured at 37° C. in an atmosphere of 5% CO$_2$ in air.

Induction of Differentiation

Differentiation of muscular cells was induced as described below.

1. Cultured cells obtained above were seeded on 6-well plates (gelatin coated). When cells became confluent, the medium was exchanged with DMEM (containing 2% horse serum (HS))
2. After a 4 day cultivation, the cells were transfected with the compounds prepared in Examples (ENAs) as described below.

ENA Transfection

Myoblast cells were transfected with the compounds prepared in Examples (ENAs) as described below.

1. 200 pmol of each of the compounds prepared in Examples (10 μg/20 μl milliQ) was dissolved in 100 μl of Opti-MEM (GIBCO-BRL).
2. 6 μl of Plus reagent (GIBCO-BRL) was added to the solution from 1 above, which was then left at room temperature for 15 min.
3. In another tube, 8 μl of Lipofectamine (GIBCO-BRL) was dissolved in 100 μl of Opti-MEM.
4. After completion of the treatment of 2 above, the solution from 3 above was added to the solution from 2 above. The resultant solution was left at room temperature for another 15 min.
5. Myoblast cells 4 days after the start of the induction of differentiation were washed with PBS once. Then, 800 μl of Opti-MEM was added thereto.
6. After completion of the treatment of 4 above, the treated solution was added to the cells from 5 above.
7. The cells from 6 above were cultured at 37° C. in an atmosphere of 5% CO$_2$ in air for 3 hr. Then, 500 μl of DMEM (containing 6% HS) was added to each well.
8. Cells were cultured further.

RNA Extraction

RNA was extracted as described below.
1. ENA-transfected cells were cultured for 2 days and then washed with PBS once. To these cells, 500 µl of ISOGEN (Nippon Gene) was added.
2. The cells were left at room temperature for 5 min, followed by recovery of ISOGEN in each well into tubes.
3. RNA was extracted according to the protocol of ISOGEN (Nippon Gene).
4. Finally, RNA was dissolved in 20 µl of DEPW.

Reverse Transcription

Reverse transcription was performed as described below.
1. To 2 µg of RNA, DEPW (sterilized water treated with diethylpyrocarbonate) was added to make a 6 µl solution.
2. To the solution from 1 above, 2 µl of random hexamer (Invitrogen: 3 µg/µl product was diluted to 20-fold before use) was added.
3. The resultant solution was heated at 65° for 10 min.
4. Then, the solution was cooled on ice for 2 min.
5. To the above reaction solution, the following was added:

| | |
|---|---|
| MMLV-reverse transcriptase (Invitrogen: 200 U/µl) | 1 µl |
| Human placenta ribonuclease inhibitor (Takara: 40 U/µl) | 1 µl |
| DTT (attached to MMLV-reverse transcriptase) | 1 µl |
| Buffer (attached to MMLV-reverse transcriptase) | 4 µl |
| dNTPs (attached to Takara Ex Taq) | 5 µl |

6. The resultant solution was kept at 37° C. for 1 hr, and then heated at 95° C. for 5 min.
7. After the reaction, the solution was stored at −80° C.

PCR Reaction

PCR reaction was performed as described below.
1. The following components were mixed and then heated at 94° C. for 4 min.

| | |
|---|---|
| Reverse transcription product | 3 µl |
| Forward primer (10 pmol/µl) | 1 µl |
| Reverse primer (10 pmol/µl) | 1 µl |
| dNTP (attached to TAKARA Ex Taq) | 2 µl |
| Buffer (attached to TAKARA Ex Taq) | 2 µl |
| Ex Taq (TAKARA) | 0.1 µl |
| Sterilized water | 11 µl |

2. After the above-mentioned treatment at 94° C. for 4 min, 35 cycles of 94° C. for 1 min/60° C. for 1 min/72° C. for 3 min were performed.
3. Then, the reaction solution was heated at 72° C. for 7 min.

The nucleotide sequences of the forward and reverse primers used in the PCR reaction are as described below.
Forward primer: GCA TGC TCA AGA GGA ACT TCC (exon 17) (SEQ ID NO: 8)
Reverse primer: TAG CAA CTG GCA GAA TTC GAT (exon 20) (SEQ ID NO: 9)
3. The PCR product was analyzed by 2% agarose gel electrophoresis.

The resultant gel was stained with ethidium bromide. The resultant band (A) (where exon 19 was skipped) and band (B) (where exon 19 was not skipped) were visualized with a gel photographing device (Printgraph Model AE-6911FXFD; ATTO) and quantitatively determined with ATTO Densitograph ver.4.1 for the Macintosh. The values obtained were put into the formula A/(A+B)×100 to obtain skipping efficiency (%).
5. The band where skipping had occurred was cut out, and the PCR product was subcloned into pT7 Blue-T vector (Novagen), followed by sequencing reaction with Thermo Sequenase™ II dye terminator cycle sequencing kit (Amersham Pharmacia Biotec) and confirmation of the nucleotide sequence with ABI PRISM 310 Genetic Analyzer (Applied Biosystems). The reaction procedures were according to the manual attached to the kit.

[Results]

Figure 2:
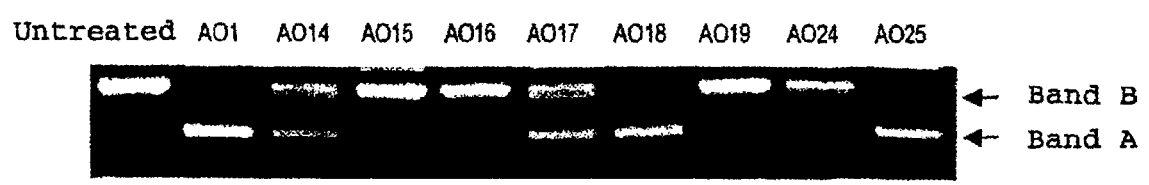
FIG. 2 a photograph of electrophoresis showing the results of amplification of exons 17-20 by RT-PCR using RNAs extracted from muscular cells transfected with any one of the compounds of Examples 1-7 (AO1, AO14, AO15, AO16, AO18, AO19 and AO25), 13 (AO17) and 14 (AO24) and from untreated muscular cells.
Figure 3:
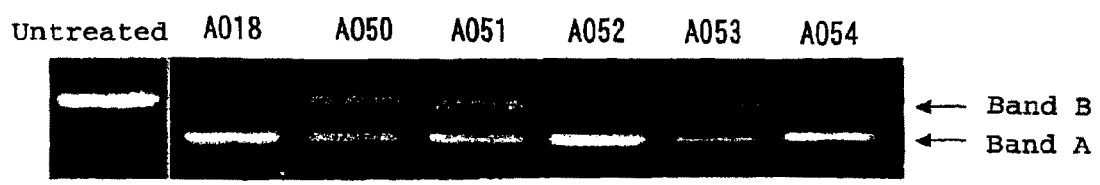
FIG. 3 a photograph of electrophoresis showing the results of amplification of exons 17-20 by RT-PCR using RNAs extracted from muscular cells transfected with any one of the compounds of Examples 5 (AO18) and 8-12 (AO50, AO51, AO52, AO53 and AO54) and from untreated muscular cells.

As shown in FIG. 1 and Table 1, the compound of Example 1 showed more efficient exon 19 skipping than 31mer-phosphorothioate oligonucleotide (S-oligo) disclosed in Y Takeshima et al., Brain & Development (2001) 23, 788-790, which has the same nucleotide sequence as that of the compound of Example 1. Further, as shown in FIGS. 2 and 3 and Tables 2 and 3, the compounds of Examples 2-14 also showed more efficient skipping than S-oligo.

TABLE 1

| Oligonucleotide | Skipping (%) |
|---|---|
| S-oligo | 2 |
| AO1 Example 1 | 80 |

TABLE 2

| Oligonucleotide | Skipping (%) |
|---|---|
| AO1 Example 1 | 88 |
| AO14 Example 2 | 29 |
| AO15 Example 3 | 3 |
| AO16 Example 4 | 4 |
| AO18 Example 5 | 92 |
| AO19 Example 6 | 5 |
| AO25 Example 7 | 83 |
| AO17 Example 13 | 39 |
| AO24 Example 14 | 14 |

TABLE 3

| Oligonucleotide | Skipping (%) |
|---|---|
| AO18 Example 5 | 90 |
| AO50 Example 8 | 53 |
| AO51 Example 9 | 55 |
| AO52 Example 10 | 97 |
| AO53 Example 11 | 55 |
| AO54 Example 12 | 91 |

Test Example 2

Method of Analysis of the Exon Skipping Induction Ability by Antisense ENA

Preparation of Primary Culture of Myoblast Cells

A primary culture of myoblast cells was established as described below.
1. Muscle tissue samples taken from the rectus muscle of the thigh of Duchenne muscular dystrophy patients were cut into fine pieces and washed with PBS twice.
2. The muscle tissue from 1 above was treated with Difco Bacto™ tripton 250 (5% solution in PBS) at 37° C. for 30 min to thereby obtain free cells enzymatically.
3. The free cells from 2 above were washed with DMEM (containing 20% FBS) twice.
4. The cells from 3 above were suspended in DMEM (containing 20% FBS and 4% ultroser G).
5. The suspension cells from 4 were passed through a mesh (Becton Dickinson: cell strainer 35-2360) to recover only free cells.

6. The recovered cells from 5 above were seeded on gelatin-coated dishes.
7. The cells were cultured at 37° C. in an atmosphere of 5% $CO_2$ in air.

Induction of Differentiation

Differentiation of muscular cells was induced as described below.

1. Cultured cells obtained above were seeded on 6-well plates (gelatin coated). When cells became confluent, the medium was exchanged with DMEM (containing 2% horse serum (HS)).
2. After a 4 day cultivation, the cells were transfected with the compounds prepared in Examples (ENAs) as described below.

ENA Transfection

Myoblast cells were transfected with the compounds prepared in Examples (ENAs) as described below.

1. 200 pmol of each of the compounds prepared in Examples (10 μg/20 μl milliQ) was dissolved in 100 μl of Opti-MEM (GIBCO-BRL).
2. 6 μl of Plus reagent (GIBCO-BRL) was added to the solution from 1 above, which was then left at room temperature for 15 min.
3. In another tube, 8 μl of Lipofectamine (GIBCO-BRL) was dissolved in 100 μl of Opti-MEM.
4. After completion of the treatment of 2 above, the solution from 3 above was added to the solution from 2 above. The resultant solution was left at room temperature for another 15 min.
5. Myoblast cells 4 days after the start of the induction of differentiation were washed with PBS once. Then, 800 μl of Opti-MEM was added thereto.
6. After completion of the treatment of 4 above, the treated solution was added to the cells from 5 above.
7. The cells from 6 above were cultured at 37° C. in an atmosphere of 5% $CO_2$ in air for 3 hr. Then, 500 μl of DMEM (containing 6% HS) was added to each well.
8. Cells were cultured further.

RNA Extraction

RNA was extracted as described below.

1. ENA-transfected cells were cultured for 2 days and then washed with PBS once. To these cells, 500 μl of ISOGEN (Nippon Gene) was added.
2. The cells were left at room temperature for 5 min, followed by recovery of ISOGEN in each well into tubes.
3. RNA was extracted according to the protocol of ISOGEN (Nippon Gene).
4. Finally, RNA was dissolved in 20 μl of DEPW.

Reverse Transcription

Reverse transcription was performed as described below.

1. To 2 μg of RNA, DEPW (sterilized water treated with diethylpyrocarbonate) was added to make a 6 μl solution.
2. To the solution from 1 above, 2 μl of random hexamer (Invitrogen: 3 μg/μl product was diluted to 20-fold before use) was added.
3. The resultant solution was heated at 65° for 10 min.
4. Then, the solution was cooled on ice for 2 min.
5. To the above reaction solution, the following was added:

| | |
|---|---|
| MMLV-reverse transcriptase (Invitrogen: 200 U/μl) | 1 μl |
| Human placenta ribonuclease inhibitor (Takara: 40 U/μl) | 1 μl |
| DTT (attached to MMLV-reverse transcriptase) | 1 μl |
| Buffer (attached to MMLV-reverse transcriptase) | 4 μl |
| dNTPs (attached to Takara Ex Taq) | 5 μl |

6. The resultant solution was kept at 37° C. for 1 hr, and then heated at 95° C. for 5 min.
7. After the reaction, the solution was stored at −80° C.

PCR Reaction

PCR reaction was performed as described below.

1. The following components were mixed and then heated at 94° C. for 4 min.

| | |
|---|---|
| Reverse transcription product | 3 μl |
| Forward primer (10 pmol/μl) | 1 μl |
| Reverse primer (10 pmol/μl) | 1 μl |
| dNTP (attached to TAKARA Ex Taq) | 2 μl |
| Buffer (attached to TAKARA Ex Taq) | 2 μl |
| Ex Taq (TAKARA) | 0.1 μl |
| Sterilized water | 11 μl |

2. After the above-mentioned treatment at 94° C. for 4 min, 35 cycles of 94° C. for 1 min/60° C. for 1 min/72° C. for 3 min were performed.
3. Then, the reaction solution was heated at 72° C. for 7 min.

The nucleotide sequences of the forward and reverse primers used in the PCR for detecting exon 41 skipping were as described below.

```
Forward primer:
                                (SEQ ID NO: 26)
5'-GGT ATC AGT ACA AGA GGC AGG CTG-3' (exon 40)

Reverse primer:
                                (SEQ ID NO: 27)
5'-CAC TTC TAA TAG GGC TTG TG-3' (exon 42)
```

The nucleotide sequences of the forward and reverse primers used in the PCR for detecting exon 45 and exon 46 skipping were as described below.

```
Forward primer:
                                (SEQ ID NO: 28)
5'-GCT GAA CAG TTT CTC AGA AAG ACA CAA-3'
(exon 44)

Reverse primer:
                                (SEQ ID NO: 29)
5'-TCC ACT GGA GAT TTG TCT GC-3' (exon 47)
```

4. The PCR product was analyzed by 2% agarose gel electrophoresis.

The resultant gel was stained with ethidium bromide. The resultant band (A) (where an exon was skipped) and band (B) (where an exon was not skipped) were visualized with a gel photographing device (Printgraph Model AE-6911FXFD; ATTO) and quantitatively determined with ATTO Densitograph ver.4.1 for the Macintosh. The values obtained were put into the formula A/(A+B)×100 to obtain skipping efficiency (%).

5. The band where skipping had occurred was cut out, and the PCR product was subcloned into pT7 Blue-T vector (Novagen), followed by sequencing reaction with Thermo Sequenase™ II dye terminator cycle sequencing kit (Amersham Pharmacia Biotec) and confirmation of the nucleotide sequence with ABI PRISM 310 Genetic Analyzer (Applied Biosystems). The reaction procedures were according to the manual attached to the kit.

[Results]

Figure 4:
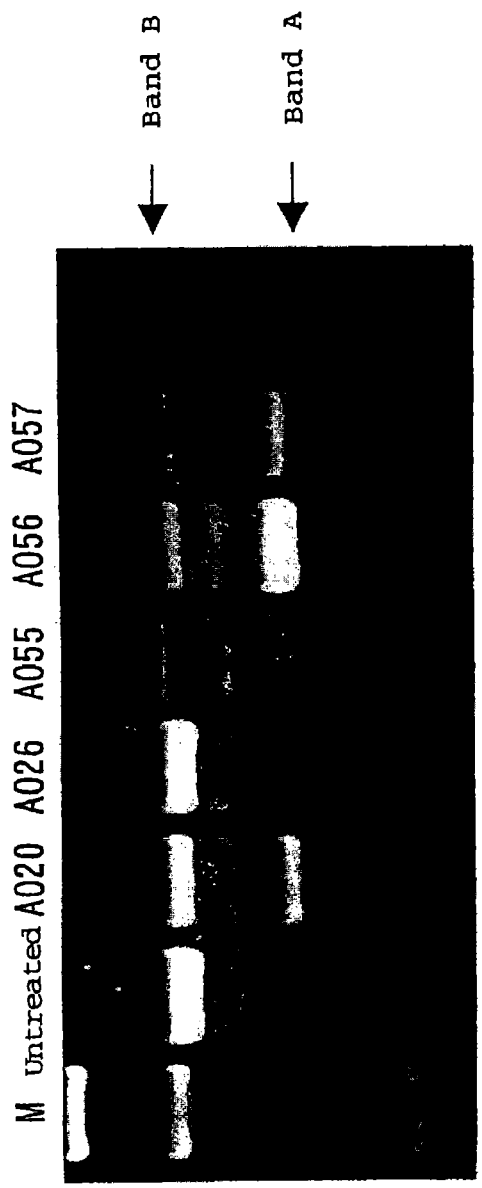
FIG. 4 shows the effects of the compounds of Examples 15-19 (AO20, AO26, AO55, AO56 and AO57) on exon 41 skipping.
Figure 5:
FIG. 5 shows the effects of the compounds of Examples 17-25 (AO55, AO56, AO57, AO76, AO77, AO78, AO79, AO80 and AO81) on exon 41 skipping.

The results of exon 41 skipping are shown in FIGS. 4 and 5. Exon 41 skipping occurred when the compounds of Examples 15 to 25 were used.

Figure 6:
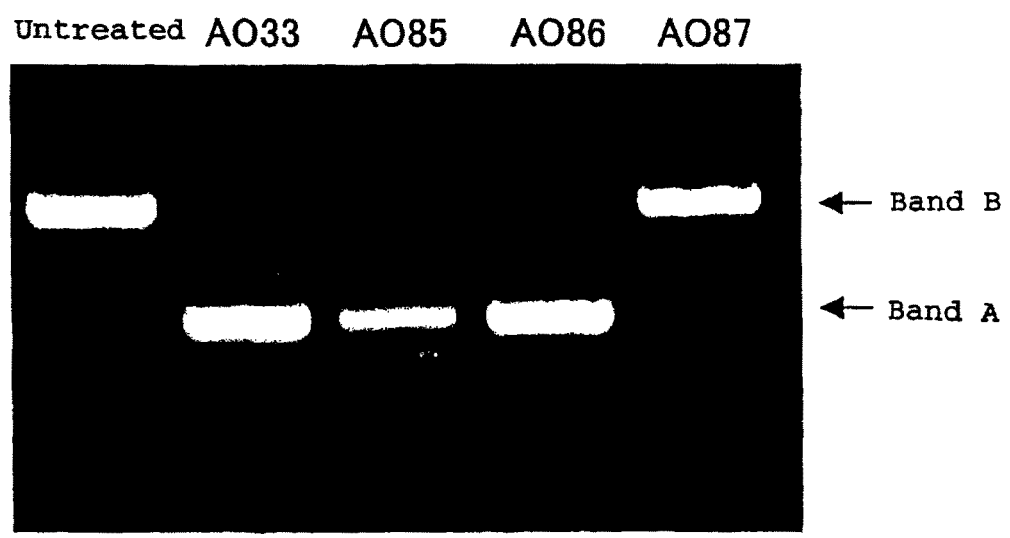
FIG. 6 shows the effects of the compounds of Examples 26-29 (AO33, AO85, AO86 and AO87) on exon 45 skipping.

The results of exon 45 skipping are shown in FIG. 6. Exon 45 skipping occurred when the compounds of Examples 26 to 29 were used.

Figure 7:
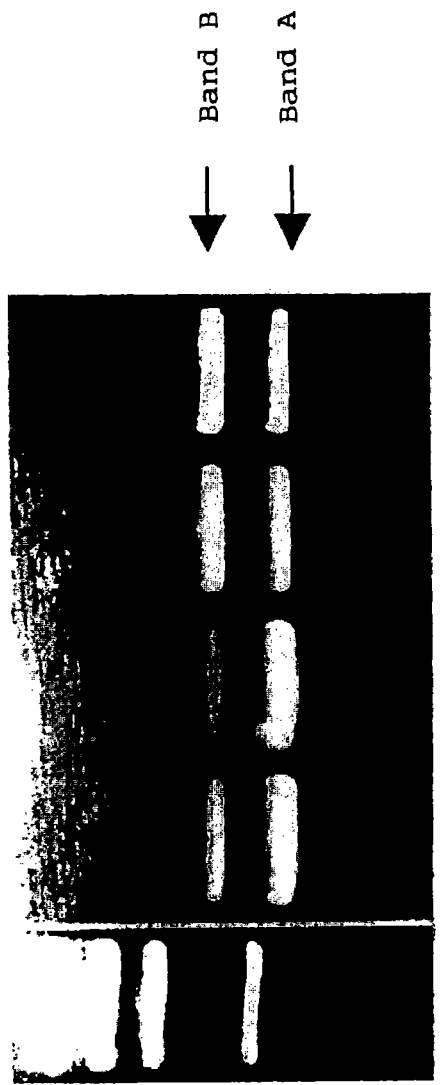
FIG. 7 shows the effects of the compounds of Examples 32-35 (AO23, AO27, AO28 and AO29) on exon 46 skipping.
Figure 8:
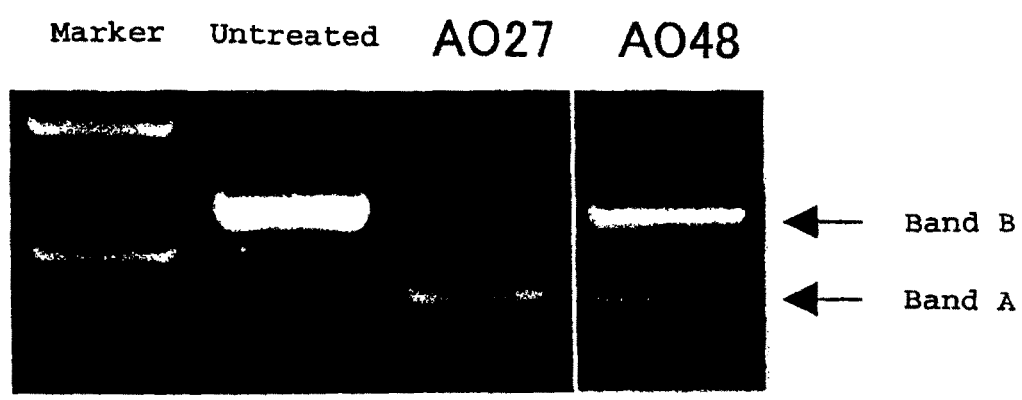
FIG. 8 shows the effects of the compounds of Examples 33 and 36 (AO27 and AO48) on exon 46 skipping.
Figure 9:
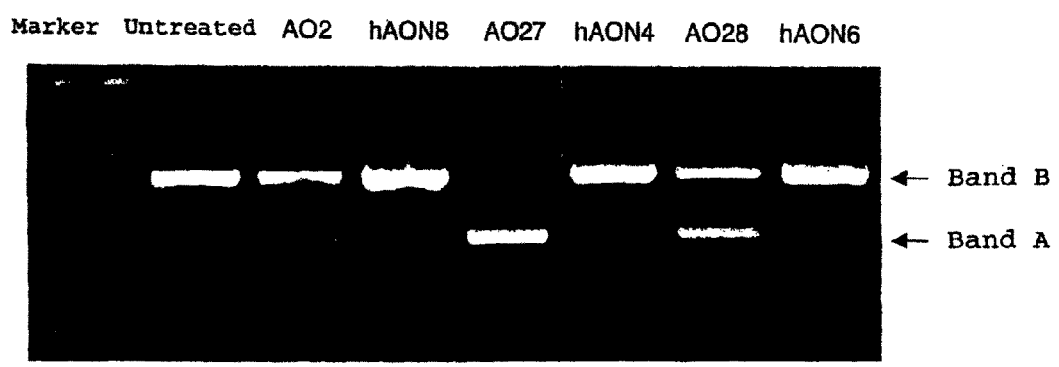
FIG. 9 shows the effects of the compounds of Examples 31, 33 and 34 and the compounds of Reference Examples 1-3 (AO2, AO27 and AO28; hAON4, hAON6 and hAON8) on exon 46 skipping.

The results of exon 46 skipping are shown in FIGS. 7, 8 and 9. Exon 45 skipping occurred when the compounds of Examples 31 to 36 were used. Further, compared to the compound of Reference Example 1 disclosed in van Deutekom, J. C. T. et al. (2001) Hum. Mol. Genet. 10, 1547-1554, the compound of Example 33 having the same nucleotide sequence showed more efficient exon 46 skipping. Compared to the compound of Reference Example 2 disclosed in van Deutekom, J. C. T. et al. (2001) Hum. Mol. Genet. 10, 1547-1554, the compound of Example 34 having the same nucleotide sequence also showed more efficient exon 46 skipping. Further, compared to the compound of Reference Example 2 disclosed in van Deutekom, J. C. T. et al. (2001) Hum. Mol. Genet. 10, 1547-1554, the compound of Example 34 having the same nucleotide sequence also showed more efficient exon 46 skipping. Further, compared to the compound of Reference Example 3 disclosed in van Deutekom, J. C. T. et al. (2001) Hum. Mol. Genet. 10, 1547-1554, the compound of Example 31 having the same nucleotide sequence also showed more efficient exon 46 skipping.

Figure 22:
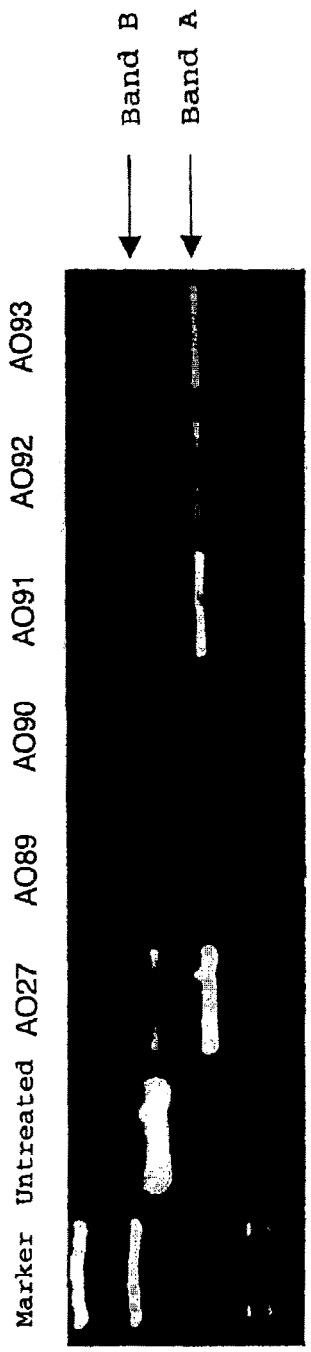
FIG. 22 shows the effects of the compounds of Examples 33, 37, 38, 39, 40 and 41 (AO27, AO89, AO90, AO91, AO92 and AO93) on exon 46 skipping.

FIG. 22 shows the results of exon 46 skipping. Exon 46 skipping occurred when the compounds of Examples 33 and 37-41 were used.

Test Example 3

Method of Analysis of the Exon Skipping Induction Ability by Antisense ENA

Preparation of Primary Culture of Myoblast Cells

A primary culture of myoblast cells was established as described below.
1. Muscle tissue samples taken from the rectus muscle of the thigh of Duchenne muscular dystrophy patients were cut into fine pieces and washed with PBS twice.
2. The muscle tissue from 1 above was treated with Difco Bacto™ tripton 250 (5% solution in PBS) at 37° C. for 30 min to thereby obtain free cells enzymatically.
3. The free cells from 2 above were washed with DMEM (containing 20% FBS) twice.
4. The cells from 3 above were suspended in DMEM (containing 20% FBS and 4% ultroser G).
5. The suspension cells from 4 were passed through a mesh (Becton Dickinson: cell strainer 35-2360) to recover only free cells.
6. The recovered cells from 5 above were seeded on gelatin-coated dishes.
7. The cells were cultured at 37° C. in an atmosphere of 5% $CO_2$ in air.

Induction of Differentiation

Differentiation of muscular cells was induced as described below.
1. Cultured cells obtained above were seeded on 6-well plates (gelatin coated). When cells became confluent, the medium was exchanged with DMEM (containing 2% horse serum (HS)).
2. After a 4 day cultivation, the cells were transfected with the compounds prepared in Examples (ENAs) as described below.

ENA Transfection

Myoblast cells were transfected with the compounds prepared in Examples (ENAs) as described below.

1. 200 pmol of each of the compounds prepared in Examples (10 μg/20 μl milliQ) was dissolved in 100 μl of Opti-MEM (GIBCO-BRL).
2. 6 μl of Plus reagent (GIBCO-BRL) was added to the solution from 1 above, which was then left at room temperature for 15 min.
3. In another tube, 8 μl of Lipofectamine (GIBCO-BRL) was dissolved in 100 μl of Opti-MEM.
4. After completion of the treatment of 2 above, the solution from 3 above was added to the solution from 2 above. The resultant solution was left at room temperature for another 15 min.
5. Myoblast cells 4 days after the start of the induction of differentiation were washed with PBS once. Then, 800 μl of Opti-MEM was added thereto.
6. After completion of the treatment of 4 above, the treated solution was added to the cells from 5 above.
7. The cells from 6 above were cultured at 37° C. in an atmosphere of 5% $CO_2$ in air for 3 hr. Then, 500 μl of DMEM (containing 6% HS) was added to each well.
8. Cells were cultured further.

RNA Extraction

RNA was extracted as described below.
1. ENA-transfected cells were cultured for 2 days and then washed with PBS once. To these cells, 500 μl of ISOGEN (Nippon Gene) was added.
2. The cells were left at room temperature for 5 min, followed by recovery of ISOGEN in each well into tubes.
3. RNA was extracted according to the protocol of ISOGEN (Nippon Gene).
4. Finally, RNA was dissolved in 20 μl of DEPW.

Reverse Transcription

Reverse transcription was performed as described below.
1. To 2 μg of RNA, DEPW (sterilized water treated with diethylpyrocarbonate) was added to make a 6 μl solution.
2. To the solution from 1 above, 2 μl of random hexamer (Invitrogen: 3 μg/μl product was diluted to 20-fold before use) was added.
3. The resultant solution was heated at 65° for 10 min.
4. Then, the solution was cooled on ice for 2 min.
5. To the above reaction solution, the following was added:

| | |
|---|---|
| MMLV-reverse transcriptase (Invitrogen: 200 U/μl) | 1 μl |
| Human placenta ribonuclease inhibitor (Takara: 40 U/μl) | 1 μl |
| DTT (attached to MMLV-reverse transcriptase) | 1 μl |
| Buffer (attached to MMLV-reverse transcriptase) | 4 μl |
| dNTPs (attached to Takara Ex Taq) | 5 μl |

6. The resultant solution was kept at 37° C. for 1 hr, and then heated at 95° C. for 5 min.
7. After the reaction, the solution was stored at −80° C.

PCR Reaction

PCR reaction was performed as described below.
1. The following components were mixed and then heated at 94° C. for 4 min.

| | |
|---|---|
| Reverse transcription product | 3 μl |
| Forward primer (10 pmol/μl) | 1 μl |
| Reverse primer (10 pmol/μl) | 1 μl |
| dNTP (attached to TAKARA Ex Taq) | 2 μl |
| Buffer (attached to TAKARA Ex Taq) | 2 μl |
| Ex Taq (TAKARA) | 0.1 μl |
| Sterilized water | 11 μl |

2. After the above-mentioned treatment at 94° C. for 4 min, 35 cycles of 94° C. for 1 min/60° C. for 1 min/72° C. for 3 min were performed.
3. Then, the reaction solution was heated at 72° C. for 7 min.

The nucleotide sequences of the forward and reverse primers used in the PCR reactions for detecting the skipping of exons 44, 50, 51, 53 and 55 are as described below.

```
Exon 44:
Forward:
                                    (SEQ ID NO: 79)
5'-TAGTCTACAACAAAGCTCAGGT-3' (exon 43)

Reverse:
                                    (SEQ ID NO: 80)
5'-CTTCCCCAGTTGCATTCAAT-3' (exon 45)

Exons 50 and 51:
Forward:
                                    (SEQ ID NO: 81)
5'-CAAGGAGAAATTGAAGCTCAA-3' (exon 48)

Reverse:
                                    (SEQ ID NO: 82)
5'-CGATCCGTAATGATTGTTCTAGC-3' (exon 52)

Exon 53:
Forward:
                                    (SEQ ID NO: 83)
5'-TGGACAGAACTTACCGACTGG-3' (exon 51)

Reverse:
                                    (SEQ ID NO: 84)
5'-GGCGGAGGTCTTTGGCCAAC-3' (exon 54)

Exon 55:
Forward:
                                    (SEQ ID NO: 85)
5'-AAGGATTCAACACAATGGCTGG-3' (exon 53)

Reverse:
                                    (SEQ ID NO: 86)
5'-GTAACAGGACTGCATCATCG-3' (exon 56)
```

3. The PCR product was analyzed by 2% agarose gel electrophoresis.

The resultant gel was stained with ethidium bromide. The resultant band (A) (where an exon was skipped) and band (B) (where an exon was not skipped) were visualized with a gel photographing device (Printgraph Model AE-6911FXFD; ATTO) and quantitatively determined with ATTO Densitograph ver.4.1 for the Macintosh. The values obtained were put into the formula A/(A+B)×100 to obtain skipping efficiency (%).
5. The band where skipping had occurred was cut out, and the PCR product was subcloned into pT7 Blue-T vector (Novagen), followed by sequencing reaction with Thermo Sequenase™ II dye terminator cycle sequencing kit (Amersham Pharmacia Biotec) and confirmation of the nucleotide sequence with ABI PRISM 310 Genetic Analyzer (Applied Biosystems). The reaction procedures were according to the manual attached to the kit.
[Results]

Figure 10:
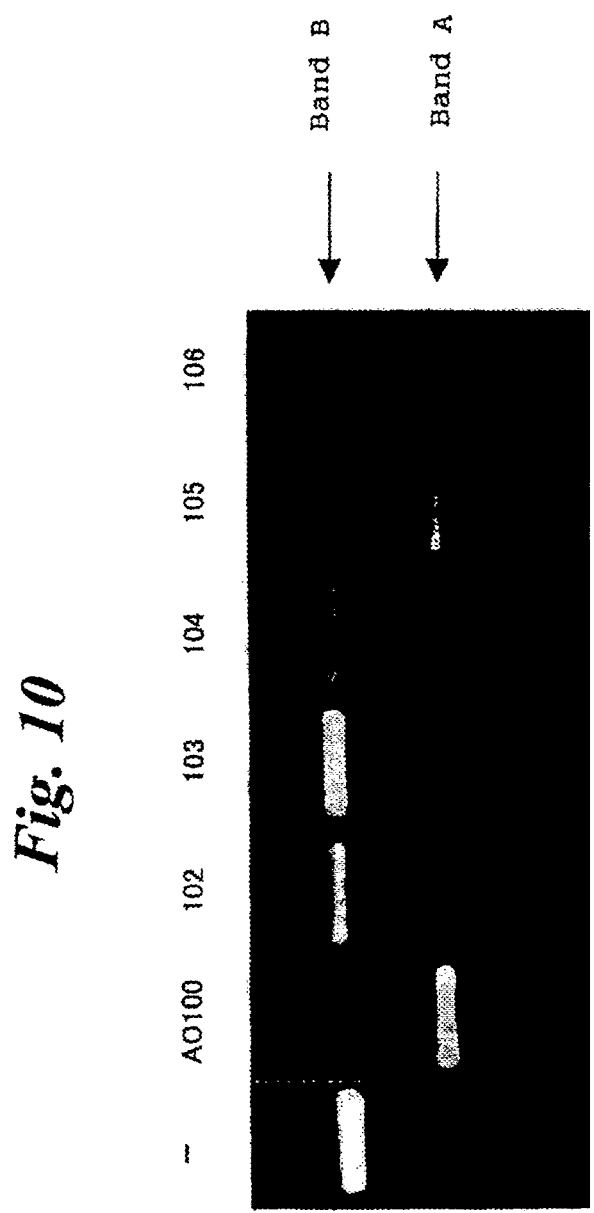
FIG. 10 shows the effects of the compounds of Examples 42-47 (AO100, AO102, AO103, AO104, AO105 and AO106) on exon 44 skipping.
Figure 11:
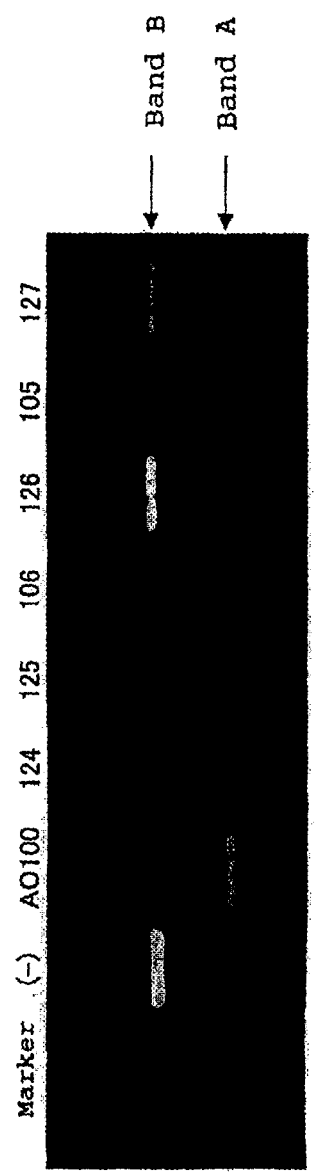
FIG. 11 shows the effects of the compounds of Examples 42, 62, 63, 47, 64, 46 and 65 (AO100, AO124, AO125, AO106, AO126, AO105 and AO127) on exon 44 skipping.

FIGS. 10 and 11 show examples of exon 44 skipping induced by compounds AO100, AO102-106 and AO124-127. As shown in these Figures, exon 44 skipping was observed when these compounds were used.

Figure 12:
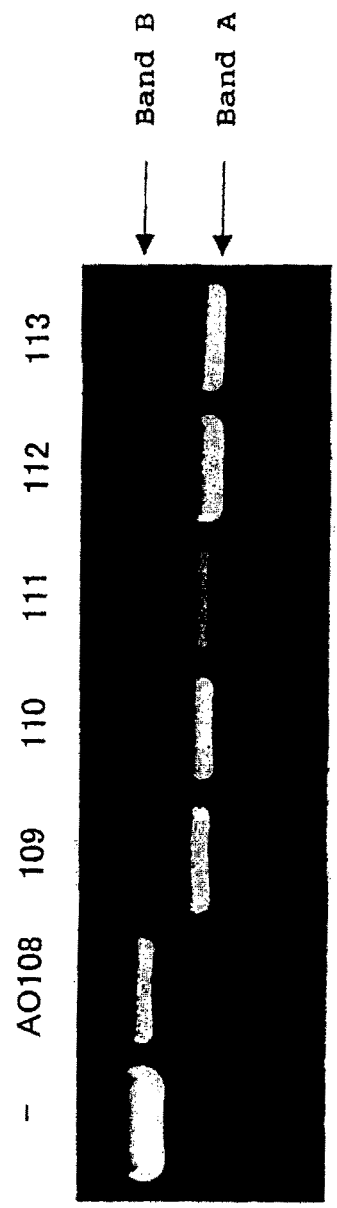
FIG. 12 shows the effects of the compounds of Examples 48-53 (AO108, AO109, AO110, AO111, AO112 and AO113) on exon 50 skipping.
Figure 13:
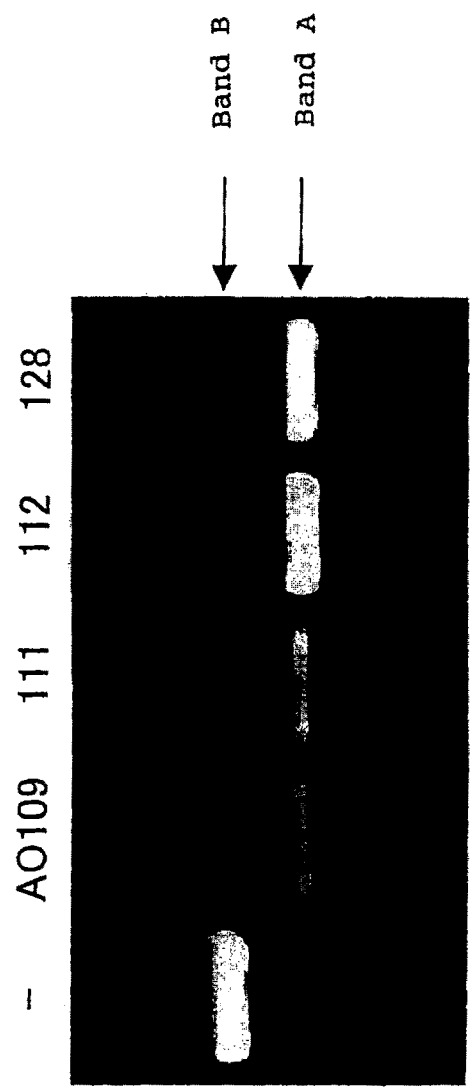
FIG. 13 shows the effects of the compounds of Examples 49, 51, 52 and 66 (AO109, AO111, AO112 and AO128) on exon 50 skipping.
Figure 14:
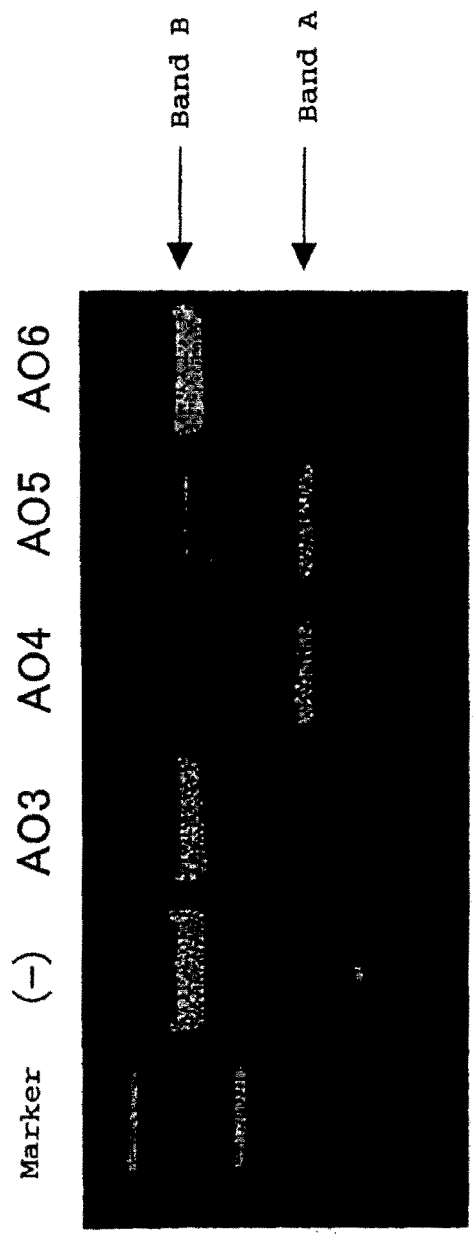
FIG. 14 shows the effects of the compounds of Examples 68-71 (AO3, AO4, AO5 and AO6) on exon 51 skipping.
Figure 15:
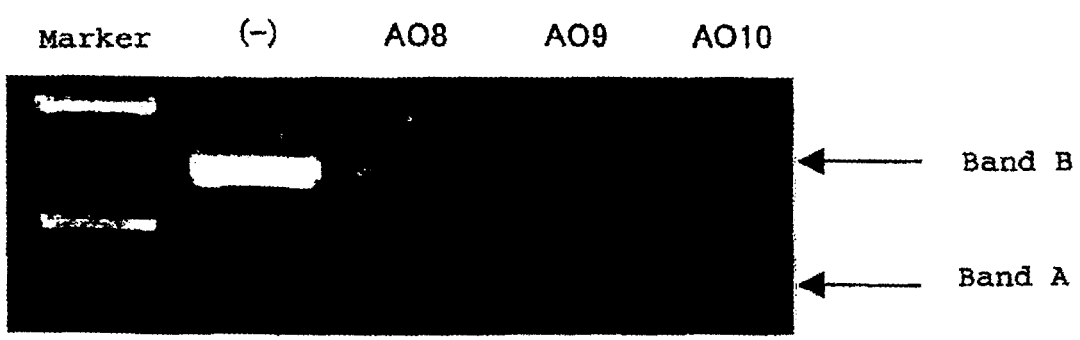
FIG. 15 shows the effects of the compounds of Examples 72-74 (AO8, AO9 and AO10) on exon 51 skipping.
Figure 16:
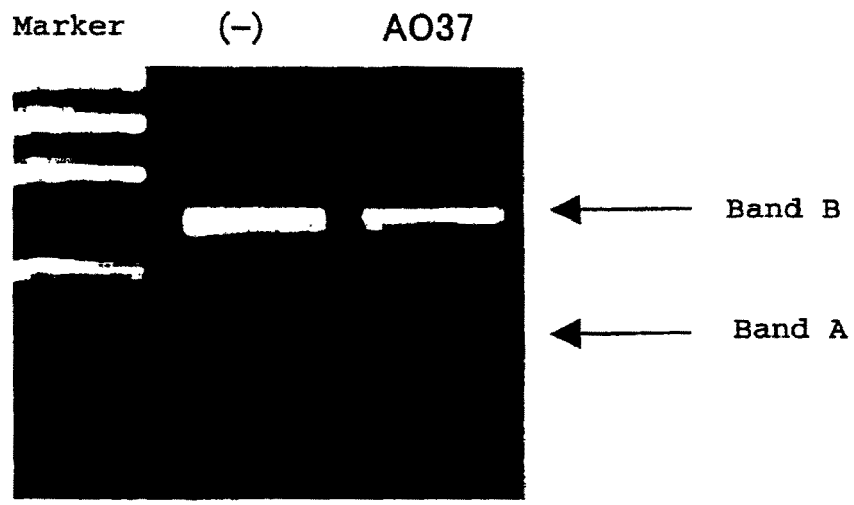
FIG. 16 shows the effect of the compound of Example 75 (AO37) on exon 51 skipping.
Figure 17:
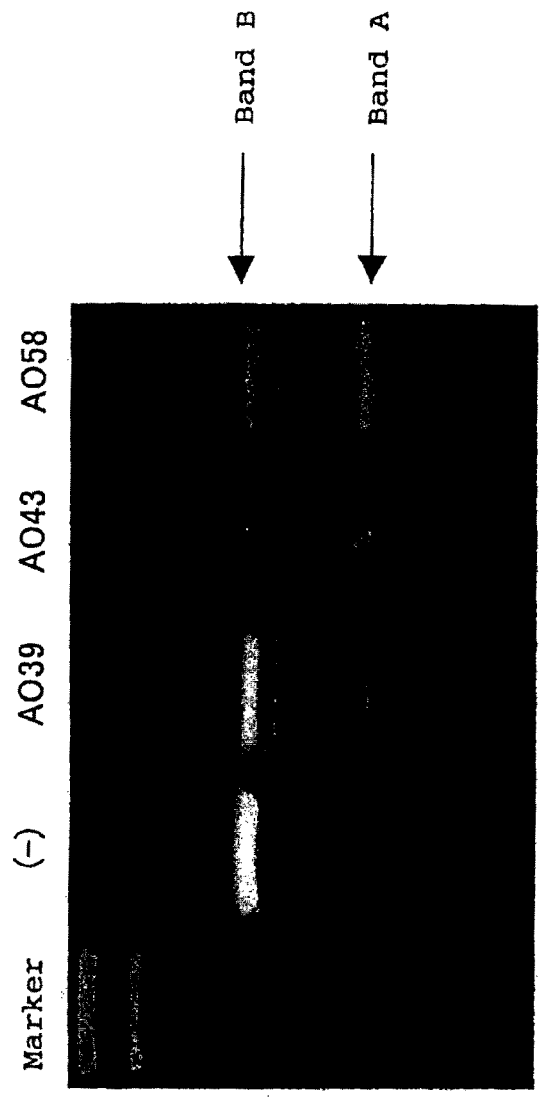
FIG. 17 shows the effects of the compounds of Examples 76-78 (AO39, AO43 and AO58) on exon 51 skipping.

FIGS. 12 and 13 show examples of exon 50 skipping induced by compounds AO108-113 and AO128. In FIG. 13, assay was performed under conditions that the concentration of the compounds was 40 pmol/ml. As shown in these Figures, exon 50 skipping was observed when these compounds were used.

FIGS. 14, 15, 16 and 17 shows examples of exon 51 skipping induced by compounds A03-6, AO8-10, AO37, AO39, AO43 and AO58. As shown in these Figures, exon 51 skipping was observed when these compounds were used.

Figure 18:
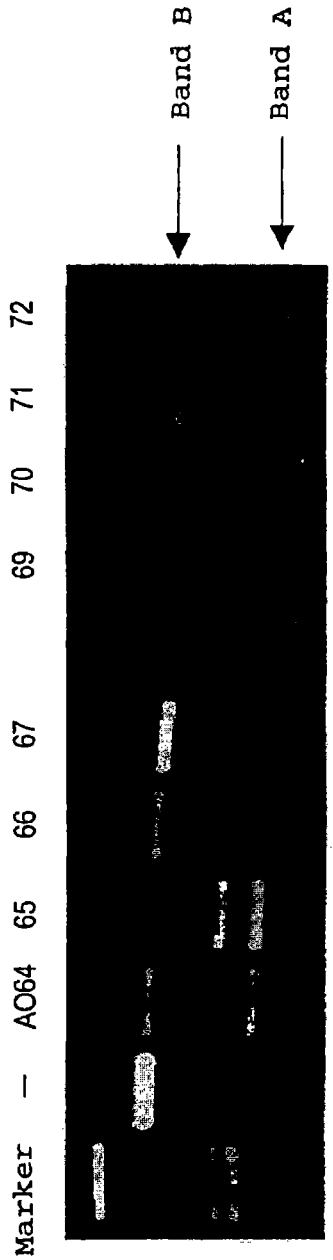
FIG. 18 shows the effects of the compounds of Examples 79-86 (AO64, AO65, AO66, AO67, AO69, AO70, AO71 and AO72) on exon 53 skipping.
Figure 19:
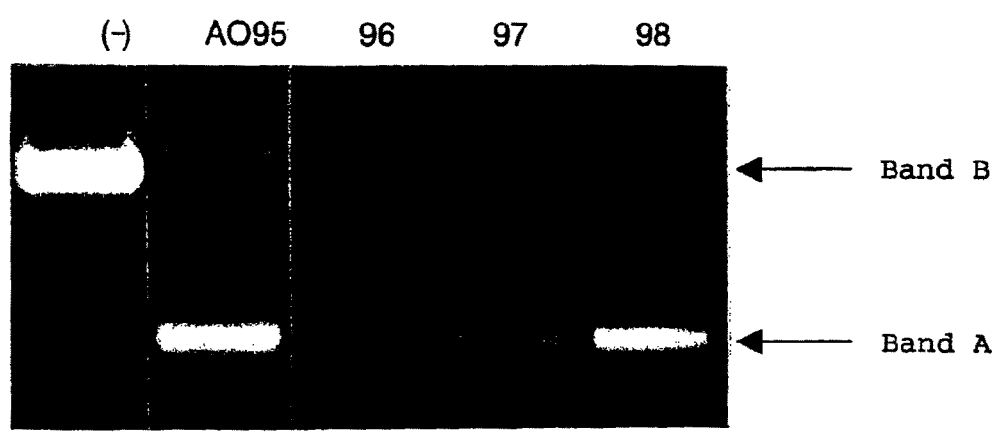
FIG. 19 shows the effects of the compounds of Examples 87-90 (AO95, AO96, AO97 and AO98) on exon 53 skipping.

FIGS. 18 and 19 show examples of exon 53 skipping induced by compounds A064-67, AO69-72 and AO95-98. As shown in these Figures, exon 53 skipping was observed when these compounds were used.

Figure 20:
FIG. 20 shows the effects of the compounds of Examples 54-61 (AO114, AO115, AO116, AO118, AO119, AO120, AO122 and AO123) on exon 55 skipping.
Figure 21:
FIG. 21 shows the effects of the compounds of Examples 54, 55 and 67 (AO114, AO115 and AO129) on exon 55 skipping.

FIGS. 20 and 21 show examples of exon 44 skipping induced by compounds A0114-116, AO118-120, AO122, AO123 and AO129. In FIG. 21, assay was performed under conditions that the concentration of the compounds was 100 pmol/ml. As shown in these Figures, exon 44 skipping was observed when these compounds were used.

Formulation Example 1

According to the following prescription, necessary amounts of base components are mixed and dissolved. To this solution, any one of the compounds of Examples 1 to 99 or a salt thereof is dissolved to prepare a solution of a specific volume. The resultant solution is filtered with a membrane filter 0.22 μm in pore size to thereby obtain a preparation for intravenous administration.

| | |
|---|---|
| Any one of the compounds of Examples 1 to 99 or a salt thereof | 500 mg |
| Sodium chloride | 8.6 g |
| Potassium chloride | 0.3 g |
| Calcium chloride | 0.33 g |
| Distilled water for injection | to give a total volume of 1000 ml |

Formulation Example 2

According to the following prescription, necessary amounts of base components are mixed and dissolved. To this solution, any one of the compounds of Examples 1 to 99 or a salt thereof is dissolved to prepare a solution of a specific volume. The resultant solution is filtered with a filter 15 nm in pore size (PLANOVE 15: Asahi Kasei) to thereby obtain a preparation for intravenous administration.

| | |
|---|---|
| Any one of the compounds of Examples 1 to 99 or a salt thereof | 100 mg |
| Sodium chloride | 8.3 g |
| Potassium chloride | 0.3 g |
| Calcium chloride | 0.33 g |
| Sodium hydrogenphosphate•12H$_2$O | 1.8 g |
| 1N HCl | appropriate amount (pH 7.4) |
| Distilled water for injection | to give a total volume of 1000 ml |

Formulation Example 3

According to the following prescription, necessary amounts of base components are mixed and dissolved. To this solution, any one of the compounds of Examples 1 to 99 or a salt thereof is dissolved to prepare a solution of a specific volume. The resultant solution is filtered with a filter 35 nm in pore size (PLANOVE 35: Asahi Kasei) to thereby obtain a preparation for intravenous administration.

| | |
|---|---|
| Any one of the compounds of Examples 1 to 99 or a salt thereof | 100 mg |

| | |
|---|---|
| Sodium chloride | 8.3 g |
| Potassium chloride | 0.3 g |
| Calcium chloride | 0.33 g |
| Glucose | 0.4 g |
| Sodium hydrogenphosphate•12H$_2$O | 1.8 g |
| 1N HCl | appropriate amount (pH 7.4) |
| Distilled water for injection | to give a total volume of 1000 ml |

All publications, patents and patent applications cited herein are incorporated herein by reference in their entity.

INDUSTRIAL APPLICABILITY

The compounds of the present invention and pharmacologically acceptable salts thereof have an effect of inducing skipping of exon 19, 41, 45, 46, 44, 50, 55, 51 or 53 of the dystrophin gene and thus useful as pharmaceuticals for treating muscular dystrophy.

SEQUENCE LISTING FREE TEXT

SEQ ID NO: 1 shows the nucleotide sequence of the oligonucleotide prepared in Example 1 (AO1).

SEQ ID NO: 2 shows the nucleotide sequence of the oligonucleotides prepared in Examples 2 and 14 (AO14 and AO24).

SEQ ID NO: 3 shows the nucleotide sequence of the oligonucleotide prepared in Example 3 (AO15).

SEQ ID NO: 4 shows the nucleotide sequence of the oligonucleotide prepared in Example 5 (AO18) and the oligonucleotide prepared in Example 7 (AO25).

SEQ ID NO: 5 shows the nucleotide sequence of the oligonucleotide prepared in Example 6 (AO19).

SEQ ID NO: 6 shows the nucleotide sequence of the oligonucleotide prepared in Example 4 (AO16).

SEQ ID NO: 7 shows the nucleotide sequence of the oligonucleotide prepared in Example 13 (AO17).

SEQ ID NO: 8 shows the nucleotide sequence of the forward primer used in Test Example 1.

SEQ ID NO: 9 shows the nucleotide sequence of the reverse primer used in Test Examples 1.

SEQ ID NO: 10 shows the nucleotide sequence of the oligonucleotides prepared in Examples 15 and 16 (AO20 and AO26).

SEQ ID NO: 11 shows the nucleotide sequence of the oligonucleotide prepared in Example 17 (AO55).

SEQ ID NO: 12 shows the nucleotide sequence of the oligonucleotides prepared in Examples 18, 20, 21 and 22 (AO56, AO76, AO77 and AO78).

SEQ ID NO: 13 shows the nucleotide sequence of the oligonucleotides prepared in Examples 19, 23, 24 and 25 (AO57, AO79, AO80 and AO81) and the oligonucleotide prepared in Example 21 (AO25).

SEQ ID NO: 14 shows the nucleotide sequence of the oligonucleotide prepared in Example 26 (AO33).

SEQ ID NO: 15 shows the nucleotide sequence of the oligonucleotides prepared in Examples 27 and 30 (AO85 and SO88).

SEQ ID NO: 16 shows the nucleotide sequence of the oligonucleotide prepared in Example 28 (AO86).

SEQ ID NO: 17 shows the nucleotide sequence of the oligonucleotide prepared in Example 29 (AO87).

SEQ ID NO: 18 shows the nucleotide sequence of the oligonucleotide prepared in Example 31 (AO2).

SEQ ID NO: 19 shows the nucleotide sequence of the oligonucleotides prepared in Examples 32 and 35 (AO23 and AO29).

SEQ ID NO: 20 shows the nucleotide sequence of the oligonucleotide prepared in Example 36 (AO48).

SEQ ID NO: 21 shows the nucleotide sequence of the oligonucleotides prepared in Examples 33, 37, 38, 39, 40 and 41 (AO27, AO89, AO90, SO91, AO92 and AO93).

SEQ ID NO: 22 shows the nucleotide sequence of the oligonucleotide prepared in Example 34 (AO28).

SEQ ID NO: 23 shows the nucleotide sequence of the oligonucleotide prepared in Reference Example 1.

SEQ ID NO: 24 shows the nucleotide sequence of the oligonucleotide prepared in Reference Example 2.

SEQ ID NO: 25 shows the nucleotide sequence of the oligonucleotide prepared in Reference Example 3.

SEQ ID NO: 26 shows the nucleotide sequence of the forward primer (for the PCR reaction for detecting exon 41 skipping) used in Test Example 2.

SEQ ID NO: 27 shows the nucleotide sequence of the reverse primer (for the PCR reaction for detecting exon 41 skipping) used in Test Example 2.

SEQ ID NO: 28 shows the nucleotide sequence of the forward primer (for the PCR reaction for detecting exon 45 and exon 46 skipping) used in Test Example 2.

SEQ ID NO: 29 shows the nucleotide sequence of the reverse primer (for the PCR reaction for detecting exon 45 and exon 46 skipping) used in Test Example 2.

SEQ ID NO: 30 shows the nucleotide sequence of the oligonucleotides prepared in Examples 42 and 94 (AO100 and AO134).

SEQ ID NO: 31 shows the nucleotide sequence of the oligonucleotide prepared in Example 43 (AO102).

SEQ ID NO: 32 shows the nucleotide sequence of the oligonucleotide prepared in Example 44 (AO103).

SEQ ID NO: 33 shows the nucleotide sequence of the oligonucleotide prepared in Example 45 (AO104).

SEQ ID NO: 34 shows the nucleotide sequence of the oligonucleotide prepared in Example 46 (AO105).

SEQ ID NO: 35 shows the nucleotide sequence of the oligonucleotide prepared in Example 47 (AO106).

SEQ ID NO: 36 shows the nucleotide sequence of the oligonucleotide prepared in Example 62 (AO124).

SEQ ID NO: 37 shows the nucleotide sequence of the oligonucleotide prepared in Example 63 (AO125).

SEQ ID NO: 38 shows the nucleotide sequence of the oligonucleotide prepared in Example 64 (AO126).

SEQ ID NO: 39 shows the nucleotide sequence of the oligonucleotide prepared in Example 65 (AO127).

SEQ ID NO: 40 shows the nucleotide sequence of the oligonucleotide prepared in Example 48 (AO108).

SEQ ID NO: 41 shows the nucleotide sequence of the oligonucleotides prepared in Examples 49 and 95 (AO109 and AO135).

SEQ ID NO: 42 shows the nucleotide sequence of the oligonucleotide prepared in Example 50 (AO110).

SEQ ID NO: 43 shows the nucleotide sequence of the oligonucleotide prepared in Example 51 (AO111).

SEQ ID NO: 44 shows the nucleotide sequence of the oligonucleotide prepared in Example 52 (AO112).

SEQ ID NO: 45 shows the nucleotide sequence of the oligonucleotide prepared in Example 53 (AO113).

SEQ ID NO: 46 shows the nucleotide sequence of the oligonucleotide prepared in Example 66 (AO128).

SEQ ID NO: 47 shows the nucleotide sequence of the oligonucleotides prepared in Examples 54 and 96 (AO114 and SO136).

SEQ ID NO: 48 shows the nucleotide sequence of the oligonucleotides prepared in Example 55 and 97 (AO115 and AO137).

SEQ ID NO: 49 shows the nucleotide sequence of the oligonucleotide prepared in Example 56 (AO116).

SEQ ID NO: 50 shows the nucleotide sequence of the oligonucleotide prepared in Example 57 (AO118).

SEQ ID NO: 51 shows the nucleotide sequence of the oligonucleotide prepared in Example 58 (AO119).

SEQ ID NO: 52 shows the nucleotide sequence of the oligonucleotide prepared in Example 59 (AO120).

SEQ ID NO: 53 shows the nucleotide sequence of the oligonucleotide prepared in Example 60 (AO122).

SEQ ID NO: 54 shows the nucleotide sequence of the oligonucleotide prepared in Example 61 (AO123).

SEQ ID NO: 55 shows the nucleotide sequence of the oligonucleotide prepared in Example 67 (AO129).

SEQ ID NO: 56 shows the nucleotide sequence of the oligonucleotide prepared in Example 68 (AO3).

SEQ ID NO: 57 shows the nucleotide sequence of the oligonucleotide prepared in Example 69 (AO4).

SEQ ID NO: 58 shows the nucleotide sequence of the oligonucleotide prepared in Example 70 (AO5).

SEQ ID NO: 59 shows the nucleotide sequence of the oligonucleotide prepared in Example 71 (AO6).

SEQ ID NO: 60 shows the nucleotide sequence of the oligonucleotide prepared in Example 72 (AO8).

SEQ ID NO: 61 shows the nucleotide sequence of the oligonucleotide prepared in Example 73 (AO9).

SEQ ID NO: 62 shows the nucleotide sequence of the oligonucleotide prepared in Example 74 (AO10).

SEQ ID NO: 63 shows the nucleotide sequence of the oligonucleotide prepared in Example 75 (AO37).

SEQ ID NO: 64 shows the nucleotide sequence of the oligonucleotide prepared in Example 76 (AO39).

SEQ ID NO: 65 shows the nucleotide sequence of the oligonucleotide prepared in Example 77 (AO43).

SEQ ID NO: 66 shows the nucleotide sequence of the oligonucleotide prepared in Example 78 (AO58).

SEQ ID NO: 67 shows the nucleotide sequence of the oligonucleotide prepared in Example 79 (AO64).

SEQ ID NO: 68 shows the nucleotide sequence of the oligonucleotide prepared in Example 80 (AO65).

SEQ ID NO: 69 shows the nucleotide sequence of the oligonucleotide prepared in Example 81 (AO66).

SEQ ID NO: 70 shows the nucleotide sequence of the oligonucleotide prepared in Example 82 (AO67).

SEQ ID NO: 71 shows the nucleotide sequence of the oligonucleotide prepared in Example 83 (AO69).

SEQ ID NO: 72 shows the nucleotide sequence of the oligonucleotide prepared in Example 84 (AO70).

SEQ ID NO: 73 shows the nucleotide sequence of the oligonucleotide prepared in Example 85 (AO71).

SEQ ID NO: 74 shows the nucleotide sequence of the oligonucleotide prepared in Example 86 (AO72).

SEQ ID NO: 75 shows the nucleotide sequence of the oligonucleotide prepared in Example 87 (AO95).

SEQ ID NO: 76 shows the nucleotide sequence of the oligonucleotide prepared in Example 88 (AO96).

SEQ ID NO: 77 shows the nucleotide sequence of the oligonucleotide prepared in Example 89 (AO97).

SEQ ID NO: 78 shows the nucleotide sequence of the oligonucleotides prepared in Examples 90 and 93 (AO98 and AO133).

SEQ ID NO: 79 shows the nucleotide sequence of the forward primer (for the PCR reaction for detecting exon 44 skipping) used in Test Example 3.

SEQ ID NO: 80 shows the nucleotide sequence of the reverse primer (for the PCR reaction for detecting exon 44 skipping) used in Test Example 3.

SEQ ID NO: 81 shows the nucleotide sequence of the forward primer (for the PCR reaction for detecting exon 50 and exon 51 skipping) used in Test Example 3.

SEQ ID NO: 82 shows the nucleotide sequence of the reverse primer (for the PCR reaction for detecting exon 50 and exon 51 skipping) used in Test Example 3.

SEQ ID NO: 83 shows the nucleotide sequence of the forward primer (for the PCR reaction for detecting exon 53 skipping) used in Test Example 3.

SEQ ID NO: 84 shows the nucleotide sequence of the reverse primer (for the PCR reaction for detecting exon 53 skipping) used in Test Example 3.

SEQ ID NO: 85 shows the nucleotide sequence of the forward primer (for the PCR reaction for detecting exon 55 skipping) used in Test Example 3.

SEQ ID NO: 86 shows the nucleotide sequence of the reverse primer (for the PCR reaction for detecting exon 55 skipping) used in Test Example 3.

SEQ ID NO: 87 shows the nucleotide sequence of the oligonucleotides prepared in Example 91 and 92 (AO131 and AO132).

SEQ ID NO: 88 shows the nucleotide sequence of the oligonucleotides prepared in Example 98 and 99 (AO139 and AO140).

The invention claimed is:

1. An oligonucleotide having the nucleotide sequence as shown in SEQ ID NO: 75 or 77 in the SEQUENCE LISTING, or a pharmacologically acceptable salt thereof, wherein at least one sugar constituting the oligonucleotide is modified and/or at least one phosphate constituting the oligonucleotide is modified.

2. The oligonucleotide of claim 1, wherein the oligonucleotide has the nucleotide sequence as shown in SEQ ID NO: 75 in the SEQUENCE LISTING, or a pharmacologically acceptable salt thereof, wherein at least one sugar constituting the oligonucleotide is modified and/or at least one phosphate constituting the oligonucleotide is modified.

3. The oligonucleotide of claim 1, wherein the oligonucleotide has the nucleotide sequence as shown in SEQ ID NO: 77 in the SEQUENCE LISTING, or a pharmacologically acceptable salt thereof, wherein at least one sugar constituting the oligonucleotide is modified and/or at least one phosphate constituting the oligonucleotide is modified.

4. The oligonucleotide or a pharmacologically acceptable salt thereof according to claim 1, wherein at least one of sugar constituting the oligonucleotide is modified, the sugar constituting the oligonucleotide is D-ribofuranose, and the modification of the sugar is modification of the hydroxyl group at position 2' of D-ribofuranose.

5. The oligonucleotide or a pharmacologically acceptable salt thereof according to claim 1, wherein the modification of the sugar is 2'-O-alkylation and/or 2'-O,4'-C-alkylenation of the D-ribofuranose.

6. The oligonucleotide or a pharmacologically acceptable salt thereof according to claim 1, wherein at least one of sugar constituting the oligonucleotide is modified, and said modification is selected from the group consisting of 2'-O-methylation of D-ribofuranose, 2'-O-aminoethylation of D-ribofuranose, 2'-O-propylation of D-ribofuranose, 2'-O-allylation of D-ribofuranose, 2'-O-methoxyethylation of D-ribofuranose, 2'-O-butylation of D-ribofuranose, 2'-O-pentylation of D-ribofuranose, 2'-O-propargylation of D-ribofuranose, 2'-O,4'-C-ethylenation of D-ribofuranose, 2'-O,4'-C-methylenation of D-ribofuranose, 2'-O,4'-C-propylenation of D-ribofuranose, 2'-O,4'-C-tetramethylation of D-ribofuranose, 2'-O,4'-C-pentamethylation of D-ribofuranose, 3'-deoxy-3'-amino-2'-deoxy-D-ribofuranose, and 3'-deoxy-3'-amino-2'-deoxy-2'-fluoro-D-ribofuranose.

7. The oligonucleotide or a pharmacologically acceptable salt thereof according to claim 1, wherein at least one of phosphate constituting the oligonucleotide is modified and the modification of the phosphate is thioation of the phosphate group.

8. The oligonucleotide or a pharmacologically acceptable salt thereof according to claim 1, wherein at least one sugar constituting the oligonucleotide is modified and at least one phosphate constituting the oligonucleotide is modified.

9. The oligonucleotide or a pharmacologically acceptable salt thereof according to claim 1, wherein at least one sugar constituting the oligonucleotide is modified.

10. The oligonucleotide or a pharmacologically acceptable salt thereof according to claim 1, wherein at least one phosphate constituting the oligonucleotide is modified.

11. An oligonucleotide having the nucleotide sequence as shown in SEQ ID NO: 23, 214, or 215 in the SEQUENCE LISTING, or a pharmacologically acceptable salt thereof, wherein at least one D-ribofuranose constituting the oligonucleotide is 2'-O,4'-C-ethylenated, wherein:

the oligonucleotide of SEQ ID NO: 23 has the structure of AO90 or AO91:

AO90: HO-$C^{e2p}$-$U^{mp}$-$G^{mp}$-$C^{e2p}$-$U^{mp}$-$U^{mp}$-$C^{e2p}$-$C^{e2p}$-$U^{mp}$-$C^{e2p}$-$C^{e2p}$-$A^{mp}$-$A^{mp}$-$C^{e2p}$-$C^{e2p}$-$CH_2CH_2OH$

AO91: HO-$C^{e2s}$-$U^{ms}$-$G^{ms}$-$C^{e2s}$-$U^{ms}$-$U^{ms}$-$C^{e2s}$-$C^{e2s}$-$U^{ms}$-$C^{e2s}$-$C^{e2s}$-$A^{ms}$-$A^{ms}$-$C^{e2s}$-$C^{e2s}$-$CH_2CH_2OH$ the oligonucleotide of SEQ ID NO: 214 has the structure of AO27, AO89, AO92, or AO93:

AO27: HO-$C^{e2p}$-$T^{e2p}$-$G^{e2p}$-$C^{e2p}$-$T^{e2p}$-$U^{mp}$-$C^{mp}$-$C^{mp}$-$U^{mp}$-$C^{mp}$-$C^{e2p}$-$A^{e2p}$-$A^{e2p}$-$C^{e2p}$-$C^{e2p}$-$CH_2CH_2OH$

AO89: HO-$C^{e2s}$-$T^{e2s}$-$G^{e2s}$-$C^{e2s}$-$T^{e2s}$-$U^{ms}$-$C^{ms}$-$C^{ms}$-$U^{ms}$-$C^{ms}$-$C^{e2s}$-$A^{e2s}$-$A^{e2s}$-$C^{e2s}$-$C^{e2s}$-$CH_2CH_2OH$

AO92: HO-$C^{e2p}$-$T^{e2p}$-$G^{mp}$-$C^{e2p}$-$T^{e2p}$-$U^{mp}$-$C^{mp}$-$C^{e2p}$-$U^{mp}$-$C^{mp}$-$C^{e2p}$-$A^{mp}$-$A^{mp}$-$C^{e2p}$-$C^{e2p}$-$CH_2CH_2OH$

AO93: HO-$C^{e2s}$-$T^{e2s}$-$G^{ms}$-$C^{e2s}$-$T^{e2s}$-$U^{ms}$-$C^{ms}$-$C^{e2s}$-$U^{ms}$-$C^{ms}$-$C^{e2s}$-$A^{ms}$-$A^{ms}$-$C^{e2s}$-$C^{e2s}$-$CH_2CH_2OH$ the oligonucleotide of SEQ ID NO: 215 has the structure of AO28:

AO28: HO-$G^{e2p}$-$T^{e2p}$-$T^{e2p}$-$A^{e2p}$-$T^{e2p}$-$C^{mp}$-$U^{mp}$-$G^{mp}$-$C^{mp}$-$U^{mp}$-$U^{mp}$-$C^{mp}$-$C^{mp}$-$U^{mp}$-$C^{mp}$-$C^{e2p}$-$A^{e2p}$-$A^{e2p}$-$C^{e2p}$-$C^{e2p}$-$CH_2CH_2OH$ wherein $A^{e2p}$, $G^{e2p}$, $C^{e2p}$, $T^{e2p}$, $A^{mp}$, $G^{mp}$, $C^{mp}$, $U^{mp}$, $A^{e2s}$, $G^{e2s}$, $C^{e2s}$, $T^{e2s}$, $A^{ms}$, $G^{ms}$, $C^{ms}$, and $U^{ms}$ have the following structures:

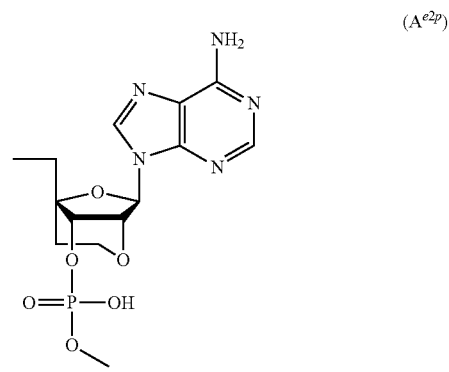

($A^{e2p}$)

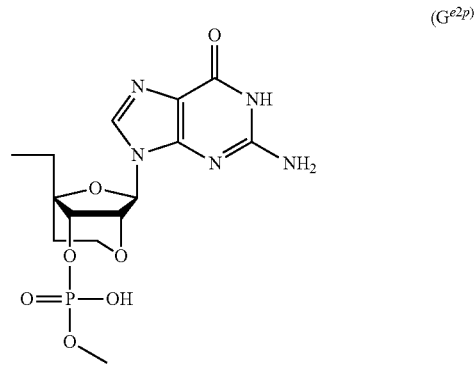

($G^{e2p}$)

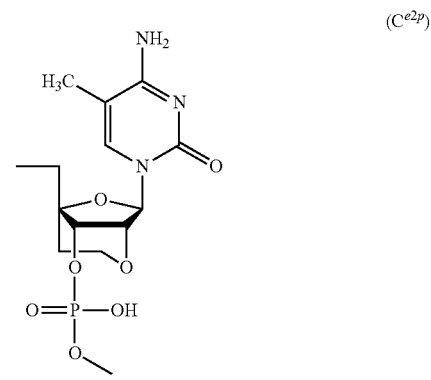

($C^{e2p}$)

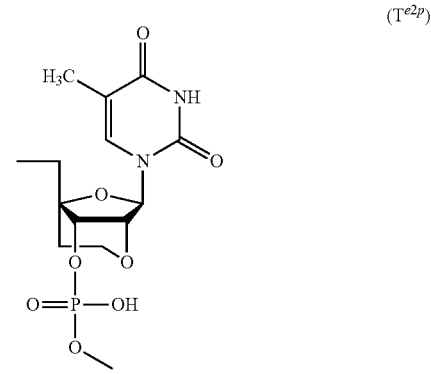

($T^{e2p}$)

363
-continued
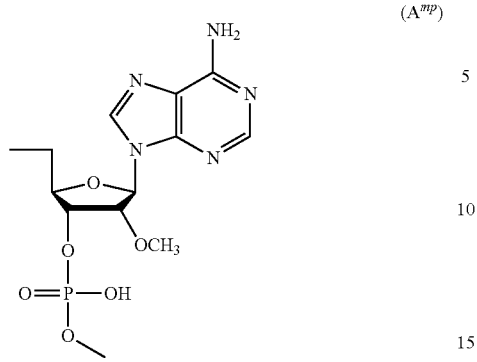
(A^mp)
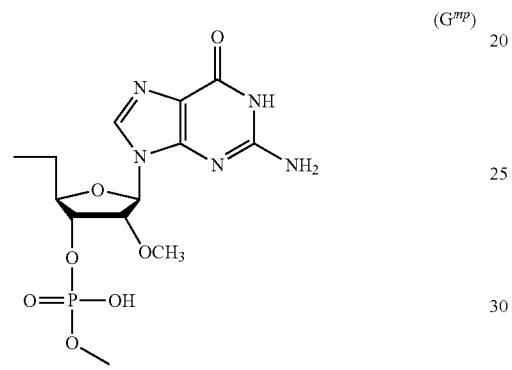
(G^mp)
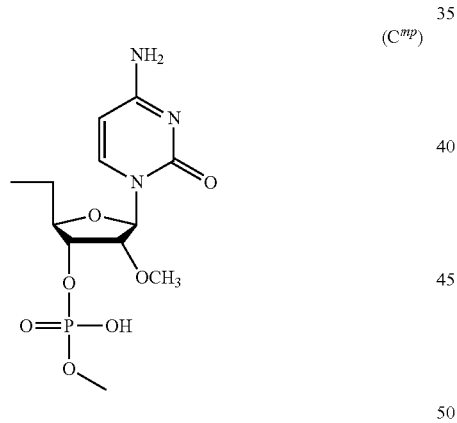
(C^mp)
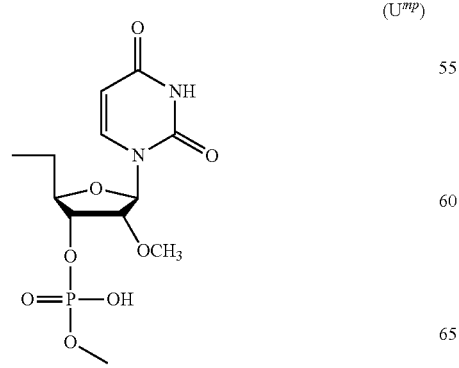
(U^mp)
364
-continued
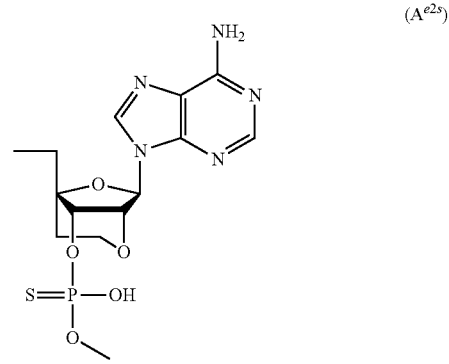
(A^e2s)
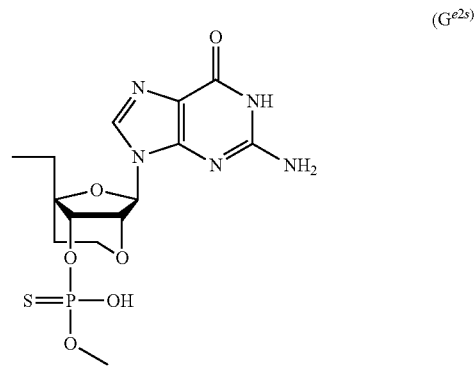
(G^e2s)
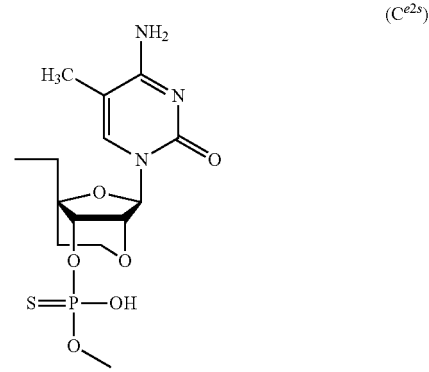
(C^e2s)
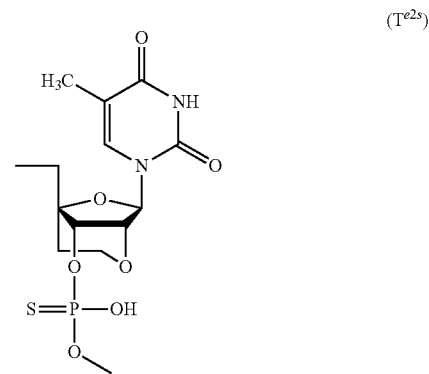
(T^e2s)

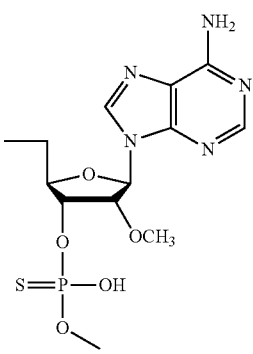
(A^{ms})

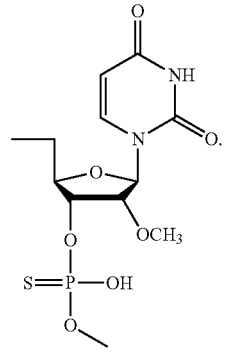
(U^{ms})

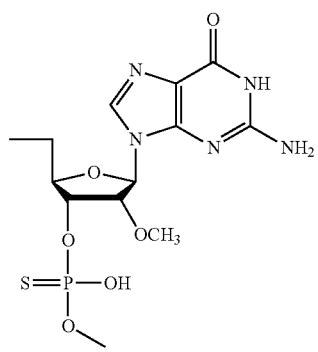
(G^{ms})

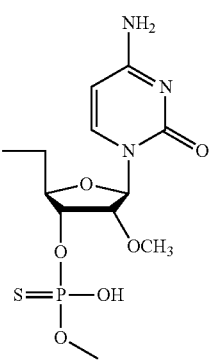
(C^{ms})

12. The oligonucleotide of claim 11, wherein the oligonucleotide has the nucleotide sequence AO90, or a pharmacologically acceptable salt thereof, wherein at least one D-ribofuranose constituting the oligonucleotide is 2'-O,4'-C-ethylenated.

13. The oligonucleotide of claim 11, wherein the oligonucleotide has the nucleotide sequence AO91, or a pharmacologically acceptable salt thereof, wherein at least one D-ribofuranose constituting the oligonucleotide is 2'-O,4'-C-ethylenated.

14. The oligonucleotide of claim 11, wherein the oligonucleotide has the nucleotide sequence AO27, or a pharmacologically acceptable salt thereof, wherein at least one D-ribofuranose constituting the oligonucleotide is 2'-O,4'-C-ethylenated.

15. The oligonucleotide of claim 11, wherein the oligonucleotide has the nucleotide sequence AO89, or a pharmacologically acceptable salt thereof, wherein at least one D-ribofuranose constituting the oligonucleotide is 2'-O,4'-C-ethylenated.

16. The oligonucleotide of claim 11, wherein the oligonucleotide has the nucleotide sequence AO92, or a pharmacologically acceptable salt thereof, wherein at least one D-ribofuranose constituting the oligonucleotide is 2'-O,4'-C-ethylenated.

17. The oligonucleotide of claim 11, wherein the oligonucleotide has the nucleotide sequence AO93, or a pharmacologically acceptable salt thereof, wherein at least one D-ribofuranose constituting the oligonucleotide is 2'-O,4'-C-ethylenated.

18. The oligonucleotide of claim 11, wherein the oligonucleotide has the nucleotide sequence AO28, or a pharmacologically acceptable salt thereof, wherein at least one D-ribofuranose constituting the oligonucleotide is 2'-O,4'-C-ethylenated.

* * * * *

UNITED STATES PATENT AND TRADEMARK OFFICE
CERTIFICATE OF CORRECTION

PATENT NO. : 9,657,050 B2  
APPLICATION NO. : 14/858404  
DATED : May 23, 2017  
INVENTOR(S) : Masafumi Matsuo et al.

Page 1 of 1

It is certified that error appears in the above-identified patent and that said Letters Patent is hereby corrected as shown below:

On the Title page

Item (73), the Assignees' Information is incorrect. Item (73) should read:  
--(73) Assignees: Daiichi Sankyo Company, Limited, Tokyo (JP);  
        Masafumi Matsuo, Kobe-shi (JP);  
        Yasuhiro Takeshima, Nishinomiya (JP)  
        Orphan Disease Treatment Institute Co., Ltd., Tokyo (JP)--

Signed and Sealed this  
Twenty-eighth Day of April, 2020

Andrei Iancu  
*Director of the United States Patent and Trademark Office*